(12) United States Patent
Chintamanani et al.

(10) Patent No.: US 9,677,082 B2
(45) Date of Patent: Jun. 13, 2017

(54) HAPLOID INDUCTION COMPOSITIONS AND METHODS FOR USE THEREFOR

(71) Applicant: Syngenta Participations AG, Basel (CH)

(72) Inventors: Satya Chintamanani, Slater, IA (US); Brent Delzer, Janesville, WI (US); Michael L Nuccio, Research Triangle Park, NC (US); Robert Arthur Dietrich, Research Triangle Park, NC (US); Suresh Babu Kadaru, Hydrabad (IN); Todd Lee Warner, Stanton, MN (US); William Paul Bullock, Slater, IA (US); Timothy Kelliher, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 350 days.

(21) Appl. No.: 14/212,504

(22) Filed: Mar. 14, 2014

(65) Prior Publication Data

US 2017/0067067 A1    Mar. 9, 2017

Related U.S. Application Data

(60) Provisional application No. 61/852,428, filed on Mar. 15, 2013.

(51) Int. Cl.
   *C12N 15/82* (2006.01)
   *C12Q 1/68* (2006.01)

(52) U.S. Cl.
   CPC ....... *C12N 15/8218* (2013.01); *C12Q 1/6895* (2013.01)

(58) Field of Classification Search
   CPC ................................................ C12N 15/8218

USPC ........................................................ 800/285
See application file for complete search history.

(56) References Cited

U.S. PATENT DOCUMENTS 7,411,117 B2 *  8/2008  Bohning ................. A01H 5/10
                                                          435/412

FOREIGN PATENT DOCUMENTS

WO          2012030893          3/2012

OTHER PUBLICATIONS

Thomas et al. 2001, The Plant Journal 25(4):417-425.*
1993 Hereditas 118:273-280.*
Colliver et al. Plant Molecular Biology 35:509-522.*
Kelliher et al., "Unresolved issues in pre-meiotic anther development", Frontiers in Plant Science, Plant Evolution and Development, published Jul. 21, 2014, vol. 5, Article 341, pp. 1-9.
Dong et al., Fine mapping of ghir1 influencing in vivo haploid induction in maize. Theor. Appl. Genet 126: 2013, pp. 1713-1720.

* cited by examiner

*Primary Examiner* — Li Zheng
(74) *Attorney, Agent, or Firm* — Christopher Leming

(57) ABSTRACT

Provided are expression cassettes; vectors; transgenic plant cells; plants, plant parts, and seeds; isolated polypeptides; amplicons and informative fragments of the presently disclosed nucleic acids; compositions that include amplification primer pairs; methods for producing plants that exhibit haploid induction (HI); methods for identifying the presence or absence of an allele associated with HI in a plant; methods for introgressing Haploid-inducing nucleotide sequences into plants; and methods for selecting parental plants predicted to produce progeny generations with plants that exhibit Haploid Induction trait.

2 Claims, 1 Drawing Sheet

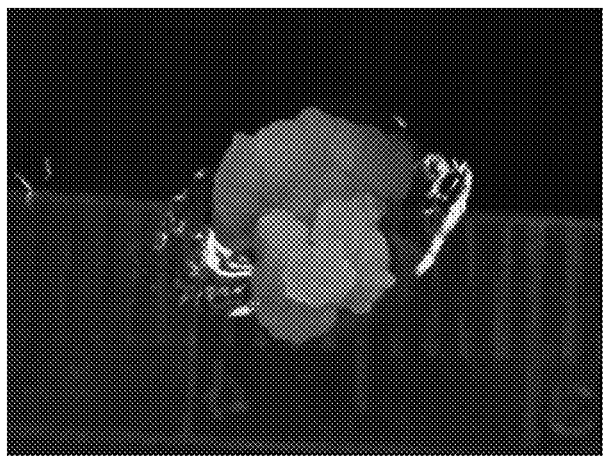

HAPLOID INDUCTION COMPOSITIONS AND METHODS FOR USE THEREFOR

STATEMENT OF PRIORITY

This application claims the benefit, under 35 U.S.C. §119(e), of U.S. Provisional Application No. 61/852,428 was filed on Mar. 15, 2013, the entire contents of which is incorporated by reference herein.

STATEMENT REGARDING ELECTRONIC FILING OF A SEQUENCE LISTING

A Sequence Listing in ASCII text format, submitted under 37 C.F.R. §1.821, entitled 80225_ST25.txt, 286,000 bytes in size, generated on Mar. 14, 2013 and filed via EFS-Web, is provided in lieu of a paper copy. This Sequence Listing is hereby incorporated herein by reference into the specification for its disclosures.

TECHNICAL FIELD

The presently disclosed subject matter relates to the diagnostic detection of haploid induction (HI) or its absence and/or presence in plants which are, or are not haploid inducers. More particularly, the presently disclosed subject matter relates to nucleic acids that can be employed for inducing HI in plants and/or the biological activities which can be modified in order to produce or prevent HI in either a plant that would otherwise exhibit HI or in a plant that would otherwise not exhibit HI. Even more particularly, the presently disclosed subject matter relates to a nucleic acid molecule that encodes a biologically active molecule as well as methods for using the same to regulate HI in plants.

BACKGROUND

Maize breeders have been crossing inbred parent lines, one acting as a male and one as a female to form hybrid seed. The process of developing inbred parent lines which are substantially homozygous usually required a hybrid cross to be selected and self-pollinated (selfed) for numerous generations to become nearly homozygous. This was a time consuming and expensive process. To shorten the time to develop homozygous inbreds in maize, maize breeders have been using a process of using a haploid inducer line to induce haploid seed on a hybrid parent. The chromosomes of the haploid plants are doubled to form double haploid homozygous inbred lines.

A high haploid induction rate allows a higher frequency of haploid seeds to be formed on the parent plant of interest. The parent plants can be pre-screened with genetic markers associated with desired traits or phenotypic observed traits to enrich the genetic potential of the parent plants. When these desired parent plants are pollinated by a haploid inducer that has a higher haploid induction rate, a higher potential of desired doubled haploids can be obtained with the desired genotype and phenotype.

Although the doubled haploid process resulted in faster production of homozygous inbreds, the volume of doubled haploid inbreds that could be produced was limited. The inducer lines had a low frequency of induction of haploids. A number of known haploid-inducing maize lines exist including but not limited to: stock 6, MHI (Moldovian Haploid Inducer), indeterminate gametophyte (ig) mutation, KEMS, RWK, ZEM, ZMS, KMS. The standard inducer lines such as Stock 6 were inducing only 1-3% haploid seeds. Induction of haploids was a rate limiting step in the process of producing doubled haploid lines.

Haploid induction (HI) is a class of plant phenomena characterized by loss of the male inducer chromosomes during embryo development. WO2012/030893 describes a slightly different region of chromosome (1) that is found responsible for haploid induction. The identified markers in the region responsible for haploid induction and increased haploid induction was described as being between 48,249, 509-51,199,249 which is associated with a public marker umc1169 that has the physical position of (60,213,661). This region apparently aligns with the Haploid Induction region in Stock 6. Dong et al. (2013) Theor. Appl. Genet. 126: 1713-1720 describe a QTL located in bin 1.04 which explains up to 66% of the genotypic variance for haploid induction rate.

Haploid induction has been observed in numerous plant species, such as sorghum, rice, and other grasses. The HI appears to be a result of rearrangements of, mutations in, and/or recombinations, insertion, or deletions within a region of chromosome 1. Purported HI-lines have been studied and roughly identified. However, experimental evidence demonstrating a causative genetic agent of HI in maize has not been presented. Nor have the markers listed herein that associate with this trait been previously identified.

The presently disclosed subject matter provides isolated cDNA. In some embodiments, the isolated cDNA are selected from the group consisting of: (a) a nucleic acid having at least 90% identity to SEQ ID NO: 33, SEQ ID NO: 37, SEQ ID NO: 52 or SEQ ID NO: 53, optionally wherein the percent identity is calculated over the entire length of SEQ ID NO: 33, SEQ ID NO: 37, SEQ ID NO: 52 or SEQ ID NO: 53; (b) a nucleic acid having at least 95% identity over nucleotides 91-1452 of SEQ ID NO: 33; (c) a nucleic acid that is the reverse complement of either of (a) or (b); and (d) a nucleic acid that encodes a polypeptide comprising an amino acid sequence that is at least 95% identical to SEQ ID NO: 54, or SEQ ID NO: 55, or SEQ ID NO: 56, or SEQ ID NO: 57 optionally wherein the percent identity is calculated over the entire length of SEQ ID NO: 54, or SEQ ID NO: 55, or SEQ ID NO: 56, or SEQ ID NO: 57.

In other embodiments, a synthetic hairpin nucleic acid construct comprising between 15 and 1000 nucleotides from SEQ ID NO. 33, 37, 52 or 53 and the antisense-complement thereof, such that the first and the second polynucleotide sequences hybridize when transcribed into a ribonucleic acid to form the hairpin-like double stranded ribonucleotide molecule. In further embodiments, the synthetic hairpin nucleic acid construct is selected from the group consisting of SEQ ID NO: 60 and SEQ ID NO: 61.

In other embodiments, an expression cassette for RNAi comprises a promoter operably linked to the synthetic hairpin. In further embodiments, the promoter is a constitutive promoter, optionally a maize ubiquitin-1 promoter, a rice actin-1 promoter, a rice ubiquitin-3 promoter, a rice alpha tubulin (tubA1) promoter, a cauliflower mosaic virus (CaMV) 35S promoter, a cestrum yellow leaf curling virus (CmYLCV) CMP promoter, a super MAS promoter, a sorghum ubiquitin-3 promoter, or a sugarcane ubiquitin-4 promoter. In other embodiments, the promoter is a stamen-, anther-, and/or pollen-specific promoter, optionally selected from the group consisting of SEQ ID NO: 58, a *Triticum aestivum* P19 promoter, a maize B200 promoter, a maize prCDPK-01 promoter, a maize prCDPK-02 promter, a rice alpha-N-acetylglucosaminidase (prOsANG) promoter, a rice MADS box gene promoter (optionally a prOsMADS1 promoter, a prOsMADS2 promoter, a prOsMADS6 promoter, a prOsMADS14 promoter, or a prOsMADS16 promoter), a rice anther specific-promoter (optionally a prRA8 promoter or a prOsG6 promoter). In other embodiments, the expression vector may optionally comprise a terminator. In further embodiments, the terminator may be SEQ ID NO: 59. In some embodiments consist of a plant comprising hairpin nucleic acid construct of the previous embodiments. This plant could be a monocot such as a maize plant.

Some embodiments consist of a method of creating a new haploid inducer plant with a silenced patatin-like phospholipase 2A, comprising transcribing a polynucleotide sequence capable of silencing the patatin-like phospholipase 2A, wherein said polynucleotide sequence is selected from the group consisting of: a polynucleotide sequence comprising the nucleic acid sequence set forth in SEQ ID NOs 33, 37, 52, 53 or the complement thereof, a functional fragment comprising at least 15 contiguous bases of any one of SEQ ID NOs 33, 37, 52, 53 or the complement thereof, a polynucleotide sequence having at least 95% sequence identity as determined using the BLASTN alignment tool to the nucleic acid sequence set forth in any one of SEQ ID NOs 33, 37, 52, 53 or the complement thereof, and a double-stranded ribonucleotide sequence produced from the expression of a polynucleotide sequence of any one of the above polynucleotide sequences, wherein silencing of the patatin-like phospholipase 2A creates a new haploid inducer plant.

Other embodiments are a plant made by the above method. The plant may be a maize plant or other monocot. Other embodiments are a method of inducing haploid embryos by using the pollen of the plant made by the above method to fertilize another plant, wherein the fertilization induces haploid embryos. Other embodiments are a method of identifying a maize plant that comprises a genotype associated with an increased haploid induction phenotype, comprising: isolating DNA from a maize plant, providing a reaction mixture comprising the DNA from a maize plant, the pair of primers comprising SEQ ID NO: 64 and SEQ ID NO 65 wherein the first primer is complementary to a sequence on the first strand of the target DNA and the second primer is complementary to a sequence on the second strand of the target DNA, Taq polymerase, and a plurality of free nucleotides comprising adenine, thymine, cytosine and guanine; heating the reaction mixture to a first predetermined temperature for a first predetermined time to separate the strands of the target DNA from each other; cooling the reaction mixture to a second predetermined temperature for a second predetermined time under conditions to allow the first and second primers to hybridize with their complementary sequences on the first and second strands of the target DNA, and to allow the Taq polymerase to extend the primers; and repeating steps (b) and (c) at least 20 times, wherein an amplification product of about 822 nucleotides indicates a maize plant that comprises a genotype associated with an increased haploid induction phenotype.

Some embodiments consist of an expression cassette for expression of a fertility restoring polypeptide in a plant, the expression cassette comprising an isolated nucleic acid of SEQ ID NO. 33 or 52 operably linked to a promoter that regulates transcription of the isolated nucleic acid of SEQ ID NO. 33 or 52 in a plant cell and/or tissue of interest, wherein the isolated cDNA of claim 1 encodes an amino acid sequence that is at least 95% identical to SEQ ID NO: 54 or 55, optionally wherein the percent identity is calculated over the entire length of SEQ ID NO: 54 or 55.

Other embodiments consist of a kit for detecting the presence of absence of a HI-inducing allele in a plant, the kit comprising one or more nucleic acid- and/or amino acid-based reagents derived from the maize HI locus or from a locus linked thereto wherein the one or more nucleic acid- and/or amino acid-based reagents are designed to be employed in a nucleic acid- and/or amino acid-based assay for the presence or absence in the plant of: a nucleic acid having at least 90% identity to SEQ ID NO: 33, SEQ ID NO: 37, SEQ ID NO: 52 or SEQ ID NO: 53, optionally wherein the percent identity is calculated over the entire length of SEQ ID NO: 33; a nucleic acid having at least 95% identity over nucleotides 91-1452 of SEQ ID NO: 33; a nucleic acid that is the reverse complement of either of (a) or (b); and/or a nucleic acid that encodes a polypeptide comprising an amino acid sequence that is at least 95% identical to SEQ ID NO: 54, SEQ ID NO: 55, SEQ ID NO: 56 or SEQ ID NO: 57 optionally wherein the percent identity is calculated over the entire length of SEQ ID NO: 54, SEQ ID NO: 55, SEQ ID NO: 56 or SEQ ID NO: 57, or nucleic acid comprising nucleotides 1230-1233 of SEQ ID NO: 53.

In some embodiments, the isolated nucleic acids are selected from the group consisting of: a sequence having at least 90% identity to the listed SEQ ID NOs which comprise at least one sequence evidencing an association with a haploid inducing trait by its presence or absence selected from the group consisting of genes identified as GRMZM2G305400, GRMZM2G082836, GRMZM2G382717, GRMZM2G120587, GRMZM2G471240, GRMZM2G866758, and GRMZM2G003530.

The presently disclosed subject matter also provides expression cassettes for expression of the gene products made by the gene which is absent in HI plants. In some embodiments, an expression cassette of the presently disclosed subject matter comprises a nucleic acid sequence as described herein as a synthetic hairpin nucleic acid construct comprising between 15 and 1000 nucleotides from SEQ ID NO: 33, SEQ ID NO: 37, SEQ ID NO: 52 or SEQ ID NO: 53 (such as, but not limited to SEQ ID NO: 60 or 61) operably linked to a promoter that regulates transcription of the isolated nucleic acid in a plant cell and/or tissue of interest, and/or an organelle or subcellular structure thereof. In some embodiments, the isolated nucleic acid present in the expression cassette encodes an amino acid sequence that is at least 95% identical to SEQ ID NO: 54, SEQ ID NO: 55, SEQ ID NO: 56 or SEQ ID NO: 57, optionally wherein the percent identity is calculated over the entire length of SEQ ID NO: 54, SEQ ID NO: 55, SEQ ID NO: 56 or SEQ ID NO: 57. In some embodiments, the promoter is a native promoters associated with the genes within this haploid induction region (such as, but not limited to SEQ ID NO: 58). In some embodiments, constitutive promoter, which can optionally be selected from the group consisting of the native promoter, a constitutive promoter such as ZmUbi1, ZmUbi58, ZmUbi361, SbUbiCh3, SbUbiCh4, a maize ubiquitin-1 promoter, a rice actin-1 promoter, a rice ubiquitin-3 promoter, a cauliflower mosaic virus (CaMV) 35S promoter, a sorghum ubiquitin-3 promoter, or a sugarcane ubiquitin-4 promoter, or a promoter that is pollen specific. Examples of pollen promoters are shown in the art in pollen-specific expression cassettes. Pollen-specific genes have been described for maize (Lopez I, Anthony, R. G., Maciver, S. K., Jaing, C.-J., Khan, S., Weeds, A. G., Hussey, P. J. (1996). Pollen specific expression of maize genes encoding actin depolymerizing factor-like proteins. Proc Natl Acad Sci USA 93:7415-7420.) Such information can be used to identify other maize pollen-specific genes, and promoters and produce pollen-specific expression cassettes. In some embodiments, the expression cassette further comprises a transcription terminator operably linked to the promoter and/or coding sequence. Some embodiments are a promoter for anther, stamen or pollen specific expression comprising SEQ ID NO:58.

In some embodiments, the plant cell and/or tissue of interest is selected from the group consisting of a stamen cell, a microspore, a meiotic cell, a cell that differentiates into a stamen cell or a progeny cell thereof, an anther cell, a cell that differentiates into an anther cell or a progeny cell thereof. In some embodiments, the organelle or subcellular structure of the plant cell and/or tissue of interest is a microspore. Thus, in some embodiments, the promoter is a stamen-, anther-, and/or pollen-specific promoter, which in some embodiments is selected from the group consisting of a *Triticum aestivum* P19 promoter, a maize B200 promoter, a maize prCDPK-01 and prCDPK-02 promoter, a rice α-N-acetylglucosaminidase (prOsANG) promoter, a rice MADS box gene promoter (including, but not limited to a prOsMADS1 promoter, a prOsMADS2 promoter, a prOsMADS6 promoter, prOsMADS7 promoter a prOsMADS14 promoter, or a prOsMADS16 promoter), a rice anther-specific promoter (such as, but not limited to a prRA8 promoter or a prOsG6 promoter), a rice stamen-specific promoter (such as, but not limited to the promoters disclosed in U.S. Pat. No. 5,639,948); and a corn stamen-specific promoter (such as, but not limited to the promoters disclosed in U.S. Pat. No. 5,589,610). In some embodiments, the promoter is a promoter that is transcriptionally active in a plant mitochondrion. Exemplary such promoters include, but are not limited to those disclosed in Fey & Maréchal-Drouard, 1999 and Binder et al., 1996.

In some embodiments, the expression cassette further comprises a transcription terminator, optionally a Nos or ags terminator.

In some embodiments, the expression cassette further comprises a targeting peptide (TP) coding sequence that is operably linked to and in frame with a sequence that encodes an amino acid sequence that is at least 95% identical to SEQ ID NO: 54, SEQ ID NO: 55, SEQ ID NO: 56 or SEQ ID NO: 57.

The presently disclosed subject matter also provides vectors comprising an expression cassette as disclosed herein.

The presently disclosed subject matter also provides transgenic plant cells comprising the presently disclosed expression cassettes, as well as plants, plant parts, and seeds comprising or derived from the presently disclosed transgenic plant cells.

The presently disclosed subject matter also provides isolated polypeptides comprising amino acid sequences that are at least 95% identical to SEQ ID NO: 54, SEQ ID NO: 55, SEQ ID NO: 56 or SEQ ID NO: 57. In some embodiments, wherein the percent identity is calculated over the entire length of SEQ ID NO: 54, SEQ ID NO: 55, SEQ ID NO: 56 or SEQ ID NO: 57. In some embodiments, the isolated polypeptides comprise amino acid sequences that comprise all or substantially all of amino acids 1-429 of SEQ ID NO: 54 locus.

The presently disclosed subject matter also provides subsequences, amplicons, and informative fragments of SEQ ID NO: 33, SEQ ID NO: 37, SEQ ID NO: 52 or SEQ ID NO: 53, as well as allelic variations thereof, wherein the subsequences, amplicons, informative fragments, and/or allelic variations can be used to identify the presence or absence of an allele associated with HI in a plant, or plant tissue, or plant cell.

The presently disclosed subject matter also provides compositions comprising amplification primer pairs capable of amplifying plant nucleic acid templates to generate marker amplicons, wherein the marker amplicons correspond to markers comprising informative subsequences of any of SEQ ID NO: 33, SEQ ID NO: 37, SEQ ID NO: 52 or SEQ ID NO: 53, or of the listed SEQ ID NOs. from this 0.6 MB region which comprise at least one sequence evidencing an association with a haploid inducing trait in this by its presence or absence selected from the group consisting of genes identified as GRMZM2G305400, GRMZM2G082836, GRMZM2G382717, GRMZM2G120587, GRMZM2G471240 (two), GRMZM2G003530, and GRMZM2G866758 (two) wherein the informative subsequences permit identification of the presence or absence of an allele associated with HI in plants. In some embodiments, the amplification primers are designed to amplify a subsequence of SEQ ID NO: 33, SEQ ID NO: 37, SEQ ID NO: 52 or SEQ ID NO: 53 (exemplary primers, but not limited to SEQ ID NO: 64, SEQ ID NO: 65, SEQ ID NO: 66 or SEQ ID NO: 67). The presently disclosed subject matter also provides methods for producing plants that exhibit a new or increased HI trait. In some embodiments, the methods comprise (a) transforming a plant cell with an expression cassette comprising a nucleic acid as disclosed herein to produce a transformed plant cell; and (b) generating a plant from the transformed plant cell.

The presently disclosed subject matter also provides methods for identifying the presence or absence of allele associated with HI in plants. In some embodiments, the methods comprise (a) obtaining a sample from the plant comprising genomic and/or nuclear DNA and/or an RNA product derived therefrom; (b) contacting the sample with a pair of primers that, when used in a nucleic acid amplification reaction with a nucleic acid sample from the plant, produces an amplicon that can be used to identify the presence or absence of an allele associated with HI; (c) amplifying a fragment from said sample using the primer pair of (b), wherein the primer pair is complementary and binds to the nucleotide sequence of (b); and (d) detecting an amplicon that can be used to identify the presence or absence of an allele associated with HI in the plant.

The presently disclosed subject matter also provides methods for introgressing HI-inducing nucleotide sequences or haplotypes into plants. In some embodiments, the methods comprise crossing a first plant with a second plant to produce a third plant, wherein the genome of the first plant or the second plant comprises a nucleic acid sequence (in some embodiments a recombinant nucleic acid sequence) encoding a HI-associated gene product of the presently disclosed subject matter and selecting those plants that do not exhibit production of the gene product, or a gene product at substantially reduced levels. In some embodiments, the methods further comprise assaying the genome of the third plant for the presence or absence of the nucleic acid sequence (in some embodiments, the recombinant nucleic acid sequence) encoding the HI-associated gene product. A HI-associated gene product, can be a negative or positive association. In this instance the association is a negative association, i.e. the presence of the gene product is associated with the absence of the haploid induction trait. In some embodiments, the recombinant nucleic acid comprises SEQ ID NO: 33, SEQ ID NO: 37, SEQ ID NO: 52 or SEQ ID NO: 53, and/or encodes a polypeptide that is at least 95% identical to SEQ ID NO: 54, SEQ ID NO: 55, SEQ ID NO: 56 or SEQ ID NO: 57. In some embodiments, the genome of the third plant that is assayed is the third plant's genome.

The presently disclosed subject matter also provides methods for selecting $F_0$ parental plants predicted to produce haploid inducing plants that exhibit inducible HI traits. In some embodiments, the methods comprise identifying in the genome of an $F_0$ plant the present or absence of a nucleic acid comprising a nucleotide sequence selected from the group consisting of: (a) a nucleic acid having at least 90% identity to SEQ ID NO: 33, SEQ ID NO: 37, SEQ ID NO: 52 or SEQ ID NO: 53, optionally wherein the percent identity is calculated over the entire length of SEQ ID NO: 33, SEQ ID NO: 37, SEQ ID NO: 52 or SEQ ID NO: 53; (b) a nucleic acid having at least 95% identity over nucleotides 1-1452 of SEQ ID NO: 33; (c) a nucleic acid that is the reverse complement of either of (a) or (b); and (d) a nucleic acid that encodes a polypeptide comprising an amino acid sequence that is at least 95% identical to SEQ ID NO: 54, SEQ ID NO: 55, SEQ ID NO: 56 or SEQ ID NO: 57, optionally wherein the percent identity is calculated over the entire length of SEQ ID NO: 54, SEQ ID NO: 55, SEQ ID NO: 56 or SEQ ID NO: 57.

In some embodiments, the methods comprise identifying in the genome of an $F_0$ plant the present or absence of a nucleic acid comprising a nucleotide sequence selected from the group consisting of the listed SEQ ID NOs. 3, 9-46 from this 0.6 MB region which comprise at least one sequence evidencing an association with a haploid inducing trait in this by its presence or absence selected from the group consisting of genes identified as GRMZM2G305400, GRMZM2G082836, GRMZM2G382717, GRMZM2G120587, GRMZM2G471240 (two), and GRMZM2G866758 (two) wherein the nucleic acid has at least 90% identity to the selected SEQ ID NO. optionally wherein the percent identity is calculated over the entire length of the selected SEQ ID NO.

Thus, it is an object of the presently disclosed subject matter to identify and/or introgress and/or provide nucleic acids for inducing and/or inhibiting the HI trait in a plant.

BRIEF DESCRIPTION OF THE FIGURES

FIG. 1 shows a Maize callus transformed with an *agrobacterium* binary vector carrying the RNAi expression cassette comprising SEQ ID NO: 61 are surviving selection indicating successful transformation

BRIEF DESCRIPTION OF THE SEQUENCE LISTING

SEQ ID NO: 1 is a cDNA nucleotide sequence from the maize NIL-genome of SEQ ID NO:3
SEQ ID NO: 2 is an amino acid sequence of a polypeptide encoded by SEQ ID NO: 1 which is a cDNA from the NIL-genome designated GRMZM2G062320-B
SEQ ID NO: 3 is the NIL-genome genomic nucleotide sequence
SEQ ID NO: 4 is the sequence of ZmABP2-GRMZM2G062320.
SEQ ID NOs: 5-8 are amino acid sequences for maize GRMZM2G062320-A, GRMZM2G062320-C, GRMZM2G062320-D, GRMZM2G062320-E
SEQ ID NO: 9 GRMZM2G305400 gDNA (from B73 genome)
SEQ ID NO: 10 GRMZM2G305400 cDNA (from B73 genome)
SEQ ID NO: 11 GRMZM2G082836 gDNA (from the B73 genome)
SEQ ID NO: 12 GRMZM2G082836 cDNA1 (from the B73 genome)
SEQ ID NO: 13 GRMZM2G082836 cDNA2 (from the B73 genome)
SEQ ID NO: 14 GRMZM2G082836 cDNA3 (from the B73 genome)
SEQ ID NO: 15 GRMZM2G082836 gDNA (from the NIL genome)
SEQ ID NO: 16 GRMZM2G082836 gDNA (from the Stock 6 genome)
SEQ ID NO: 17 GRMZM2G082836 gDNA (from the RWK genome)
SEQ ID NO: 18 GRMZM2G382717 gDNA (from B73 genome)
SEQ ID NO: 19 GRMZM2G382717 cDNA2 (from B73 genome)
SEQ ID NO: 20 GRMZM2G382717 gDNA (from NIL genome)
SEQ ID NO: 21 GRMZM2G382717 gDNA (from RWK genome)
SEQ ID NO: 22 GRMZM2G382717 gDNA (991832 from Stock 6 genome)
SEQ ID NO: 23 GRMZM2G382717 gDNA (989131 from Stock 6 genome)
SEQ ID NO: 24 GRMZM2G382717 protein coding sequence (from RWK genome)
SEQ ID NO: 25 GRMZM2G120587 gDNA (from the B73 genome)
SEQ ID NO: 26 GRMZM2G120587 cDNA1 (from the B73 genome)
SEQ ID NO: 27 GRMZM2G120587 cDNA2 (from the B73 genome)
SEQ ID NO: 28 GRMZM2G120587 cDNA3 (from the B73 genome)
SEQ ID NO: 29 GRMZM2G120587 GDNA (from the Stock 6 genome)
SEQ ID NO: 30 GRMZM2G120587 GDNA (from the RWK genome)
SEQ ID NO: 31 GRMZM2G120587 GDNA (from the Stock 6/RWK genome)
SEQ ID NO: 32 GRMZM2G471240 gDNA (from the B73 genome)
SEQ ID NO: 33 GRMZM2G471240 cDNA long splice variant (from the B73 genome)
SEQ ID NO: 34 GRMZM2G471240 gDNA (from the NIL genome)
SEQ ID NO: 35 GRMZM2G471240 gDNA (from the maize Stock 6 genome)
SEQ ID NO: 36 GRMZM2G471240 gDNA (from the maize RWK genome)
SEQ ID NO: 37 GRMZM2G471240 cDNA short splice variant (from the Stock6/RWK genome)
SEQ ID NO: 38 GRMZM5G866758 gDNA (from the B73 genome)
SEQ ID NO: 39 GRMZM5G866758 cDNA1 (from the B73 genome)
SEQ ID NO: 40 GRMZM5G866758 cDNA2 (from the B73 genome)
SEQ ID NO: 41 GRMZM5G866758 cDNA-1780 (from the B73 maize genome)
SEQ ID NO: 42 GRMZM5G866758 gDNA (from the NIL maize genome)
SEQ ID NO: 43 GRMZM5G866758 cDNA (from the NIL genome)
SEQ ID NO: 44 GRMZM5G866758 gDNA (from the Stock 6 genome)

SEQ ID NO: 45 GRMZM5G866758 gDNA (from the RWK genome)
SEQ ID NO: 46 GRMZM5G866758 gDNA (from the Stock 6/RWK genome)
SEQ ID NO: 47 GRMZM2G382717 cDNA1 (from B73 genome).
SEQ ID NO: 48 GRMZM2G003530 gDNA (from B73 genome).
SEQ ID NO: 49 GRMZM2G003530 gDNA (from NIL genome).
SEQ ID NO: 50 GRMZM2G003530 gDNA (from RWK genome).
SEQ ID NO: 51 GRMZM2G003530 gDNA (from Stock 6 genome).
SEQ ID NO: 52 GRMZM2G471240 cDNA short splice variant (from the B73 genome)
SEQ ID NO: 53 GRMZM2G471240 cDNA long splice variant (from the RWK genome)
SEQ ID NO: 54 is an amino acid sequence of a polypeptide encoded by SEQ ID NO: 33
SEQ ID NO: 55 is an amino acid sequence of a polypeptide encoded by SEQ ID NO: 52
SEQ ID NO: 56 is an amino acid sequence of a polypeptide encoded by SEQ ID NO: 37
SEQ ID NO: 57 is an amino acid sequence of a polypeptide encoded by SEQ ID NO: 53
SEQ ID NO: 58 is the promoter of the GRMZM2G471240 gene
SEQ ID NO: 59 is the terminator of the GRMZM2G471240 gene
SEQ ID NO: 60 is a synthetic hairpin designed to SEQ ID NO 33 nt 450-547 with 2 mismatches, a spacer sequence and the reverse compliment of SEQ ID NO 33 nt 450-547
SEQ ID NO: 61 is a synthetic hairpin designed to SEQ ID NO 33 nt 797-987 with 2 mismatches, a spacer sequence and the reverse compliment of SEQ ID NO 33 nt 797-987
SEQ ID NO: 62 is the reverse compliment of SEQ ID NO 33
SEQ ID NO: 63 is the reverse compliment of SEQ ID NO 52
SEQ ID NO: 64 is primer rwk.F1
SEQ ID NO: 65 is primer rwk.R1
SEQ ID NO: 66 is primer nil.F1
SEQ ID NO: 67 is primer nil.R1

DETAILED DESCRIPTION

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques and/or substitutions of equivalent techniques that would be apparent to one of skill in the art. While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. For example, the phrase "a cell" refers to one or more cells, and in some embodiments can refer to a tissue and/or an organ. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to all whole number values between 1 and 100 as well as whole numbers greater than 100.

Unless otherwise indicated, all numbers expressing quantities of ingredients, reaction conditions, and so forth used in the specification and claims are to be understood as being modified in all instances by the term "about". The term "about", as used herein when referring to a measurable value such as an amount of mass, weight, time, volume, concentration or percentage is meant to encompass variations of in some embodiments±20%, in some embodiments±10%, in some embodiments±5%, in some embodiments±1%, in some embodiments±0.5%, and in some embodiments±0.1% from the specified amount, as such variations are appropriate to perform the disclosed methods and/or employ the discloses compositions, nucleic acids, polypeptides, etc. Accordingly, unless indicated to the contrary, the numerical parameters set forth in this specification and attached claims are approximations that can vary depending upon the desired properties sought to be obtained by the presently disclosed subject matter.

As used herein, the term "allele" refers to a variant or an alternative sequence form at a genetic locus. In diploids, a single allele is inherited by a progeny individual separately from each parent at each locus. The two alleles of a given locus present in a diploid organism occupy corresponding places on a pair of homologous chromosomes, although one of ordinary skill in the art understands that the alleles in any particular individual do not necessarily represent all of the alleles that are present in the species.

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D (e.g., AB, AC, AD, BC, BD, CD, ABC, ABD, and BCD). In some embodiments, one of more of the elements to which the "and/or" refers can also individually be present in single or multiple occurrences in the combinations(s) and/or subcombination(s).

As used herein, the phrase "associated with" refers to a recognizable and/or assayable relationship between two entities. For example, the phrase "associated with HI" refers to a trait, locus, gene, allele, marker, phenotype, etc., or the expression thereof, the presence or absence of which can influence an extent and/or degree at which a plant or its progeny exhibits HI. As such, a marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with HI" refers to a marker whose presence or absence can be used to predict whether and/or to what extent a plant will display haploid induction.

The term "comprising", which is synonymous with "including", "containing", and "characterized by", is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, or ingredient not specifically recited. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter.

With respect to the terms "comprising", "consisting essentially of", and "consisting of", where one of these three terms is used herein, the presently disclosed and claimed subject matter can include in some embodiments the use of either of the other two terms. For example, if a subject matter relates in some embodiments to nucleic acids that encode polypeptides comprising amino acid sequences that are at least 95% identical to a SEQ ID NO: 55. It is understood that the disclosed subject matter thus also encompasses nucleic acids that encode polypeptides that in some embodiments consist essentially of amino acid sequences that are at least 95% identical to that SEQ ID NO: 55 as well as nucleic acids that encode polypeptides that in some embodiments consist of amino acid sequences that are at least 95% identical to that SEQ ID NO: 55. Similarly, it is also understood that in some embodiments the methods for the disclosed subject matter comprise the steps that are disclosed herein, in some embodiments the methods for the presently disclosed subject matter consist essentially of the steps that are disclosed, and in some embodiments the methods for the presently disclosed subject matter consist of the steps that are disclosed herein.

As used herein, the term "gene" refers to a hereditary unit including a sequence of DNA that occupies a specific location on a chromosome and that contains the genetic instruction for a particular characteristic or trait in an organism.

A "genetic map" is a description of genetic linkage relationships among loci on one or more chromosomes within a given species, generally depicted in a diagrammatic or tabular form. For each genetic map, distances between loci are measured by the recombination frequencies between them. Recombination events between loci can be detected using a variety of markers. A genetic map is a product of the mapping population, types of markers used, and the polymorphic potential of each marker between different populations. The order and genetic distances between loci can differ from one genetic map to another.

As used herein, the phrase "genetic marker" refers to a nucleic acid sequence (e.g., a polymorphic nucleic acid sequence) that has been identified as associated with a locus or allele of interest and that is indicative of the presence or absence of the locus or allele of interest in a cell or organism. Examples of genetic markers include, but are not limited to genes, DNA or RNA-derived sequences, promoters, any untranslated regions of a gene, microRNAs, siRNAs, QTLs, SNPs, transgenes, mRNAs, ds RNAs, transcriptional profiles, and methylation patterns.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) and/or haplotype(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome (in some embodiments, including the nuclear genome, the mitochondrial genome, plastid genome or all three). Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety, or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants can be grown, as well as plant parts, such as leafs, stems, pollen, or cells that can be cultured into a whole plant.

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the terms "informative fragment" and "informative subsequence" refer to nucleotide sequences comprising a fragment of a larger nucleotide sequence, wherein detecting of the presence of absence of the fragment allows for the detecting of the presence of absence of the larger nucleotide sequence. For example, an informative fragment of the nucleotide sequence of SEQ ID NO: 33 comprises a fragment of the nucleotide sequence of SEQ ID NO: 33 that permits the accurate identification of whether or not SEQ ID NO: 33 is present in a sample. This non HI locus lacks the 4 nucleotide insertion that is present in the HI germplasm as found in SEQ ID NO: 53 nucleotides 1230-1233. In some embodiments, an informative fragment of SEQ ID NO: 53 allows identification of the presence or absence of the HI locus. In some embodiments, informative fragments of SEQ ID NO: 53 containing nucleotides 1230-1233 allow identification of the presence or absence of the HI locus.

As used herein, the term "isolated" refers to a nucleotide sequence that is free of sequences that normally flank one or both sides of the nucleotide sequence in a plant genome. Thus, isolated nucleic acids include, without limitation, a recombinant DNA that exists as a separate molecule with no flanking sequences present, as well as a recombinant DNA that is incorporated into a vector, an autonomously replicating plasmid, or into the genomic DNA of a plant as part of a hybrid or fusion nucleic acid molecule.

As used herein, the term "linkage" refers to a phenomenon wherein alleles on the same chromosome tend to be transmitted together more often than expected by chance if their transmission were independent. Thus, two alleles on the same chromosome are said to be "linked" when they segregate from each other in the next generation in some embodiments less than 50% of the time, in some embodiments less than 25% of the time, in some embodiments less than 20% of the time, in some embodiments less than 15% of the time, in some embodiments less than 10% of the time, in some embodiments less than 9% of the time, in some embodiments less than 8% of the time, in some embodiments less than 7% of the time, in some embodiments less than 6% of the time, in some embodiments less than 5% of the time, in some embodiments less than 4% of the time, in some embodiments less than 3% of the time, in some embodiments less than 2% of the time, and in some embodiments less than 1% of the time.

As such, "linkage" typically implies and can also refer to physical proximity on a chromosome. Thus, two loci are linked if they are within in some embodiments 20 centiMorgans (cM), in some embodiments 15 cM, in some embodiments 12 cM, in some embodiments 10 cM, in some embodiments 9 cM, in some embodiments 8 cM, in some embodiments 7 cM, in some embodiments 6 cM, in some embodiments 5 cM, in some embodiments 4 cM, in some embodiments 3 cM, in some embodiments 2 cM, and in some embodiments 1 cM of each other. Similarly, a HI locus of the presently disclosed subject matter is linked to a marker (e.g., a genetic marker) if it is in some embodiments within 20, 15, 12, 10, 9, 8, 7, 6, 5, 4, 3, 2, or 1 cM of the marker.

Thus, the term "linkage" refers to the degree with which one marker locus is associated with another marker locus or some other locus (for example, a locus associated with HI). The linkage relationship between a molecular marker and a phenotype can be given as a "probability" or "adjusted probability." Linkage can be expressed as a desired limit or range. For example, in some embodiments, any marker is linked (genetically and physically) to any other marker when the markers are separated by less than about 50, 40, 30, 25, 20, or 15 map units (or cM).

As used herein, the term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and, by definition, are separated by less than 50 cM on the same chromosome). As used herein, linkage can be between two markers, or alternatively between a marker and a phenotype. A marker locus can be "associated with" (linked to) a trait, e.g., HI. The degree of linkage of a molecular marker to a phenotypic trait is measured, e.g., as a statistical probability of co-segregation of that molecular marker with the phenotype.

As used herein, the term "linkage equilibrium" describes a situation where two markers independently segregate, i.e., sort among progeny randomly. Markers that show linkage equilibrium are considered unlinked (whether or not they lie on the same chromosome). As such, the phrase "linkage disequilibrium" is defined as change from the expected relative frequency of gamete types in a population of many individuals in a single generation such that two or more loci act as genetically linked loci. If the frequency in a population of allele S is x, s is x', B is y, and b is y', then the expected frequency of genotype SB is xy, that of Sb is xy', that of sB is x'y, and that of sb is x'y', and any deviation from these frequencies is an example of disequilibrium. Linkage disequilibrium is most commonly assessed using the measure $r^2$, which is calculated using the formula described by Hill & Robertson, 1968. When $r^2=1$, complete linkage disequilibrium exists between the two marker loci, meaning that the markers have not been separated by recombination and have the same allele frequency. In some embodiments, values for $r^2$ above 0.33 indicate sufficiently strong linkage disequilibrium to be useful for mapping. See Ardlie et al., 2002. Hence, alleles are in linkage disequilibrium when $r^2$ values between pairwise marker loci are greater than or equal to about 0.33, 0.4, 0.5, 0.6, 0.7, 0.8, 0.9, or 1.0.

As used herein, the terms "marker", "genetic marker", and 'molecular marker" are used interchangeably to refer to an identifiable position on a DNA molecule (e.g., a chromosome or a nuclear genome) the inheritance of which can be monitored and/or a reagent that is used in methods for visualizing differences in nucleic acid sequences present at such identifiable positions on a DNA molecule. Thus, in some embodiments a marker comprises a known or detectable nucleic acid sequence. As such, a marker can comprise a nucleotide sequence that has been associated with an allele or alleles of interest and that is indicative of the presence or absence of the allele or alleles of interest in a cell or organism and/or to a reagent that is used to visualize differences in the nucleotide sequence at such an identifiable position or positions. A marker can be, but is not limited to, an allele, a gene, a haplotype, a restriction fragment length polymorphism (RFLP), a simple sequence repeat (SSR), random amplified polymorphic DNA (RAPD), cleaved amplified polymorphic sequences (CAPS; Rafalski & Tingey, 1993), an amplified fragment length polymorphism (AFLP; Vos et al., 1995), a single nucleotide polymorphism (SNP) (Brookes, 1993), a sequence-characterized amplified region (SCAR; Paran & Michelmore, 1993), a sequence-tagged site (STS; Onozaki et al., 2004), a single-stranded conformation polymorphism (SSCP; Orita et al., 1989), an inter-simple sequence repeat (ISSR; Blair et al., 1999), an inter-retrotransposon amplified polymorphism (IRAP), a retrotransposon-microsatellite amplified polymorphism (REMAP; Kalendar et al., 1999) or an RNA cleavage product (such as a Lynx tag). A marker can be present in genomic (including but not limited to nuclear genomic and/or 1 genomic) or expressed nucleic acids (e.g., ESTs). In some embodiments, a marker is an informative fragment of SEQ ID NO: 33, SEQ ID NO: 37, SEQ ID NO: 52 or SEQ ID NO: 53 that permits the specific identification of nucleic acids comprising or lacking SEQ ID NO: 33, SEQ ID NO: 37, SEQ ID NO: 52 or SEQ ID NO: 53 in samples.

The term marker can also refer to nucleic acids used as probes or primers (e.g., primer pairs) for use in amplifying, hybridizing to, and/or detecting nucleic acid molecules according to methods well known in the art. In some embodiments, a nucleic acid marker that can be employed to detect the presence or absence of SEQ ID NO: 33, SEQ ID NO: 37, SEQ ID NO: 52 or SEQ ID NO: 53 is a primer pair that comprises a forward primer that comprises a subsequence of nucleotides of SEQ ID NO: 33, SEQ ID NO: 37, SEQ ID NO: 52 or SEQ ID NO: 53 and a reverse primer that is the reverse complement of a subsequence of nucleotides of SEQ ID NO: 33, SEQ ID NO: 37, SEQ ID NO: 52 or SEQ ID NO: 53 and/or is an amplicon that is generated by using such a primer pair to amplify a subsequence of SEQ ID NO: 33, SEQ ID NO: 37, SEQ ID NO: 52 or SEQ ID NO: 53 (i.e., the subsequence of SEQ ID NO: 33, SEQ ID NO: 37, SEQ ID NO: 52 or SEQ ID NO: 53 that comprises nucleotides, optionally including 1, 2, 3, 4, 5, 6, 7, 8, 9, 10, or more nucleotides of SEQ ID NO: 33, SEQ ID NO: 37, SEQ ID NO: 52 or SEQ ID NO: 53 that are 5' to and/or 3' to nucleotides selected nucleotides from the positions listed in the Table on Fine Mapping in Example 3 and a part of SEQ ID NO: 1-47).

As used herein, the terms "marker probe" and "probe" refer to a nucleotide sequence or nucleic acid molecule that can be used to detect the presence or absence of sequence within SEQ ID NO: 33, SEQ ID NO: 37, SEQ ID NO: 52 or SEQ ID NO: 53 (e.g., a nucleic acid probe that is complementary to all of or a portion of the marker or marker locus, through nucleic acid hybridization). Marker probes comprising about 8, 10, 15, 20, 30, 40, 50, 60, 70, 80, 90, 100 or more contiguous nucleotides can be used for nucleic acid hybridization.

As used herein, the term "molecular marker" can be used to refer to a genetic marker, as defined above, or an encoded product thereof (e.g., a protein) used as a point of reference when identifying the presence/absence of a HI-associated locus. A molecular marker can be derived from genomic nucleotide sequences or from expressed nucleotide sequences (e.g., from an RNA, a cDNA, etc.). The term also refers to nucleotide sequences complementary to or flanking the marker sequences, such as nucleotide sequences used as probes and/or primers capable of amplifying the marker sequence. Nucleotide sequences are "complementary" when they specifically hybridize in solution (e.g., according to Watson-Crick base pairing rules). This term also refers to the genetic markers that indicate a trait by the absence of the nucleotide sequences complementary to or flanking the marker sequences, such as nucleotide sequences used as probes and/or primers capable of amplifying the marker sequence.

As used herein, the terms "nucleotide sequence", "polynucleotide", "nucleic acid sequence", "nucleic acid molecule", and "nucleic acid fragment" refer to a polymer of RNA or DNA that is single- or double-stranded, optionally containing synthetic, non-natural, and/or altered nucleotide bases. A "nucleotide" is a monomeric unit from which DNA or RNA polymers are constructed and consists of a purine or pyrimidine base, a pentose, and a phosphoric acid group. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

As used herein, the term "nucleotide sequence identity" refers to the presence of identical nucleotides at corresponding positions of two polynucleotides. Polynucleotides have "identical" sequences if the sequence of nucleotides in the two polynucleotides is the same when aligned for maximum correspondence (e.g., in a comparison window). Sequence comparison between two or more polynucleotides is generally performed by comparing portions of the two sequences over a comparison window to identify and compare local regions of sequence similarity. The comparison window is generally from about 20 to 200 contiguous nucleotides. The "percentage of sequence identity" for polynucleotides, such as about 50, 55, 60, 65, 70, 75, 80, 85, 90, 95, 98, 99 or 100 percent sequence identity, can be determined by comparing two optimally aligned sequences over a comparison window, wherein the portion of the polynucleotide sequence in the comparison window can include additions or deletions (i.e., gaps) as compared to the reference sequence for optimal alignment of the two sequences. In some embodiments, the percentage is calculated by: (a) determining the number of positions at which the identical nucleic acid base occurs in both sequences; (b) dividing the number of matched positions by the total number of positions in the window of comparison; and (c) multiplying the result by 100. Optimal alignment of sequences for comparison can also be conducted by computerized implementations of known algorithms, or by visual inspection. Readily available sequence comparison and multiple sequence alignment algorithms are, respectively, the Basic Local Alignment Search Tool (BLAST) and ClustalW/ClustalW2/Clustal Omega programs available on the Internet (e.g., the website of the EMBL-EBI). Other suitable programs include, but are not limited to, GAP, BestFit, Plot Similarity, and FASTA, which are part of the Accelrys GCG Package available from Accelrys, Inc. of San Diego, Calif., United States of America. See also Smith & Waterman, 1981; Needleman & Wunsch, 1970; Pearson & Lipman, 1988; Ausubel et al., 1988; and Sambrook & Russell, 2001.

One example of an algorithm that is suitable for determining percent sequence identity and sequence similarity is the BLAST algorithm, which is described in Altschul et al., 1990. In some embodiments, a percentage of sequence identity refers to sequence identity over the full length of one of the gDNA, cDNA, or the predicted protein sequences in the largest ORF of SEQ ID No: 33 being compared (e.g., the full length of any of SEQ ID NOs. 1-47 respectively). In some embodiments, a calculation to determine a percentage of nucleic acid sequence identity does not include in the calculation any nucleotide positions in which either of the compared nucleic acids includes an "N" (i.e., where any nucleotide could be present at that position).

The term "open reading frame" (ORF) refers to a nucleic acid sequence that encodes a polypeptide. In some embodiments, an ORF comprises a translation initiation codon, a translation termination (i.e., stop) codon, and the nucleic acid sequence there between that encodes the amino acids present in the polypeptide. The terms "initiation codon" and "termination codon" refer to a unit of three adjacent nucleotides ('codon') in a coding sequence that specifies initiation and chain termination, respectively, of protein synthesis (mRNA translation).

As used herein, the terms "phenotype," "phenotypic trait" or "trait" refer to one or more traits of a plant or plant cell. The phenotype can be observable to the naked eye, or by any other means of evaluation known in the art, e.g., microscopy, biochemical analysis, or an electromechanical assay. In some cases, a phenotype is directly controlled by a single gene or genetic locus (i.e., corresponds to a "single gene trait"). In the case of haploid induction use of color markers, such as R Navajo, and other markers including transgenes visualized by the presences or absences of color within the seed evidence if the seed is an induced haploid seed. The use of R Navajo as a color marker and the use of transgenes is well known in the art as means to detect induction of haploid seed on the female plant. In other cases, a phenotype is the result of interactions among several genes, which in some embodiments also results from an interaction of the plant and/or plant cell with its environment.

As used herein, the term "plant" can refer to a whole plant, any part thereof, or a cell or tissue culture derived from a plant. Thus, the term "plant" can refer to any of: whole plants, plant components or organs (e.g., leaves, stems, roots, etc.), plant tissues, seeds and/or plant cells.

A plant cell is a cell of a plant, taken from a plant, or derived through culture from a cell taken from a plant. Thus, the term "plant cell" includes without limitation cells within seeds, suspension cultures, embryos, meristematic regions, callus tissue, leaves, shoots, gametophytes, sporophytes, pollen, and microspores. The phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calli, and the like.

As used herein, the term "primer" refers to an oligonucleotide which is capable of annealing to a nucleic acid target (in some embodiments, annealing specifically to a nucleic acid target) allowing a DNA polymerase and/or reverse transcriptase to attach thereto, thereby serving as a point of initiation of DNA synthesis when placed under conditions in which synthesis of a primer extension product is induced (e.g., in the presence of nucleotides and an agent for polymerization such as DNA polymerase and at a suitable temperature and pH). In some embodiments, one or more pluralities of primers are employed to amplify plant nucleic acids (e.g., using the polymerase chain reaction; PCR).

As used herein, the term "probe" refers to a nucleic acid (e.g., a single stranded nucleic acid or a strand of a double stranded or higher order nucleic acid, or a subsequence thereof) that can form a hydrogen-bonded duplex with a complementary sequence in a target nucleic acid sequence. Typically, a probe is of sufficient length to form a stable and sequence-specific duplex molecule with its complement, and as such can be employed in some embodiments to detect a sequence of interest present in a plurality of nucleic acids.

As used herein, the terms "progeny" and "progeny plant" refer to a plant generated from a vegetative or sexual reproduction from one or more parent plants. In haploid induction the seed on the female parent is haploid, thus not a progeny of the inducing haploid line. The progeny of the haploid seed is what is the desired progeny. There is also the HI seed and subsequent plant and seed progeny of the haploid inducing plant. Both the haploid seed and the HI seed can be progeny. A progeny plant can be obtained by cloning or selfing a single parent plant, or by crossing two or more parental plants. For instance, a progeny plant can be obtained by cloning or selfing of a parent plant or by crossing two parental plants and include selfings as well as the $F_1$ or $F_2$ or still further generations. An $F_1$ is a first-generation progeny produced from parents at least one of which is used for the first time as donor of a trait, while progeny of second generation ($F_2$) or subsequent generations ($F_3$, $F_4$, and the like) are specimens produced from selfings, intercrosses, backcrosses, and/or other crosses of $F_1$s, $F_2$s, and the like. An $F_1$ can thus be (and in some embodiments is) a hybrid resulting from a cross between two true breeding parents (i.e., parents that are true-breeding are each homozygous for a trait of interest or an allele thereof), while an $F_2$ can be (and in some embodiments is) a progeny resulting from self-pollination of the $F_1$ hybrids.

As used herein, the phrase "recombination" refers to an exchange of DNA fragments between two DNA molecules or chromatids of paired chromosomes (a "crossover") over in a region of similar or identical nucleotide sequences. A "recombination event" is herein understood to refer in some embodiments to a meiotic crossover.

As used herein, the term "reference sequence" refers to a defined nucleotide sequence used as a basis for nucleotide sequence comparison. In some embodiments, any of SEQ ID NOs: 1 and 3 can serve as a reference sequence for comparing to other sequences obtained from plants.

As used herein, the term "regenerate", and grammatical variants thereof, refers to the production of a plant from tissue culture.

As used herein, the phrase "stringent hybridization conditions" refers to conditions under which a polynucleotide hybridizes to its target subsequence, typically in a complex mixture of nucleic acids, but to essentially no other sequences. Stringent conditions are sequence-dependent and can be different under different circumstances.

Longer sequences typically hybridize specifically at higher temperatures. An extensive guide to the hybridization of nucleic acids is found in Sambrook & Russell, 2001. Generally, stringent conditions are selected to be about 5-10° C. lower than the thermal melting point ($T_m$) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Exemplary stringent conditions are those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides).

Stringent conditions can also be achieved with the addition of destabilizing agents such as formamide. Additional exemplary stringent hybridization conditions include 50% formamide, 5×SSC, and 1% SDS incubating at 42° C.; or SSC, 1% SDS, incubating at 65° C.; with one or more washes in 0.2×SSC and 0.1% SDS at 65° C. For PCR, a temperature of about 36° C. is typical for low stringency amplification, although annealing temperatures can vary between about 32° C. and 48° C. (or higher) depending on primer length. Additional guidelines for determining hybridization parameters are provided in numerous references (see e.g., Ausubel et al., 1999).

As used herein, the term "trait" refers to a phenotype of interest, a gene that contributes to a phenotype of interest, as well as a nucleic acid sequence associated with a gene that contributes to a phenotype of interest. For example, a "HI trait" refers to a haploid induction phenotype as well as a gene that contributes to a haploid induction and a nucleic acid sequence (e.g., a HI-associated gene product) that is associated with the presence or absence of the haploid induction phenotype.

As used herein, the term "transgene" refers to a nucleic acid molecule introduced into an organism or one or more of its ancestors by some form of artificial transfer technique. The artificial transfer technique thus creates a "transgenic organism" or a "transgenic cell". It is understood that the artificial transfer technique can occur in an ancestor organism (or a cell therein and/or that can develop into the ancestor organism) and yet any progeny individual that has the artificially transferred nucleic acid molecule or a fragment thereof is still considered transgenic even if one or more natural and/or assisted breedings result in the artificially transferred nucleic acid molecule being present in the progeny individual.

Maize haploid inducer plants produce pollen which when crossed onto non-inducer germplasm results in the gynogenic development of haploid seeds. Unfortunately, this process often yields a low frequency of haploid kernels. Inefficient haploid induction frequency is a limiting factor in maize doubled haploid breeding programs. The present invention identifies a locus that identifies haploid induction in a plant; and a four nucleotide insertion at positions 1230-1233 of SEQ ID NO: 53 the presence or absence of which distinguishes haploid inducer germplasm from non-inducer germplasm. This locus or the presence or absence of the four nucleotide insertion at positions 1230-1233 of SEQ ID NO: 53 can be employed for selecting, and/or introgressing, and/or transforming the haploid inducing trait into plants.

More specifically, the present invention produces new maize haploid-inducing lines. A number of known haploid—inducing maize lines exist including but not limited to: stock 6, MHI (Moldavian Haploid Inducer), indeterminate gametophyte (ig) mutation, KEMS, ZEM, ZMS, KMS, RWS and RWK.—The present invention relates to a method of identifying, and/or selecting germplasm which can or cannot induce haploids. The present invention also relates to increasing and further development of the selected haploid inducing germplasm. The invention further relates to a method of improving haploid inducing germplasm to increase the induction of haploids on the seed producing parent.

The initial step in the production of haploid seeds from a hybrid or segregating maternal parent plant derives from the pollination with pollen from a haploid inducer on to the ear from a seed producing plant. A result of this hybridization process is the production of diploid and maternal haploid (1 n) kernels. The induced haploid (1 n) kernels are often distinguished from the diploid seed by the use of color markers which indicate embryo ploidy. The diploid seeds are generally discarded, while haploid kernels or embryos are often subjected to chromosome doubling processes to produce doubled haploid plants.

More specifically, the haploid genetic material is treated with one or more mitotic arrest agents to allow the haploid (1 n) chromosome complement in one or more cells to produce homolog-pairs. After the chemical treatment procedure, the chromosome doubling chemical(s) are removed. The now-doubled haploid maize is allowed to mature and the resulting doubled haploid seeds when planted will produce homozygous plants (also called inbred plant or lines) These inbred lines are the materials that breeders utilize to pursue their hybrid development programs.

The locus for the haploid induction trait was fine mapped. Although a major QTL on chromosome 1 responsible for haploid induction has been mapped and published, Dong et al. Theor. Appl. Genet (2013) 126: 1713-1720, the exact gene/genetic element responsible for the induction process has not been identified until now. The haploid induction locus is fine-mapped to be within a small region of 0.60 Mb (between the markers SM2363 (Chromosome 1, 67851018 nt Maize genome assembly version 3) and SM2712 (Chromosome 1, 68453157 nt Maize genome assembly version 3)). By comparing inducer and non-inducer germplasm, it was determined that a four nucleotide insertion present in haploid inducers which shifts the frame for amino acid coding of GRMZM2G471240 is not present in non-inducer germplasm. Therefore, the present invention has identified a gene with a frameshift mutation in inducer germplasm as being responsible for maize haploid induction. The candidate gene corresponding to gene model GRMZM2G471240 encodes a patatin-like phospholipase 2A.

Also notable are several secondary candidate genes identified as GRMZM2G305400, GRMZM2G082836, GRMZM2G382717, GRMZM2G120587, GRMZM2G062320, and GRMZM2G866758 that also may show differences between inducer and non-inducer lines. The secondary candidate genes may themselves be responsible for improved efficiency in HI. Crossing different HI inducers with these secondary candidate genes such as Stock 6 and RWK lines (each of which lack the candidate gene) can unexpectedly increase haploid induction, which may imply other genetic factors are also contributing to the HI trait. However, improved haploid induction germplasm can be difficult to maintain because it also results in significant seed abortion upon self-pollination and thus, makes HI line maintenance difficult.

DNA sequence was generated for each candidate gene from the two inducer lines and one non-inducer line. In addition, the public B73 genome data was used as a second non-inducer line. Gene model information was compared to EST/cDNA data to confirm the structure of each gene. The annotated sequence data were compared to catalog differences between the four alleles of each gene. The notable exceptions included GRMZM2G305400 which is only identified in the B73 genome and GRMZM2G062320 which is only detected in this study in the NIL and B73 genomes. PCR experiments show that it is present in RWK and Stock 6.

The sequence comparisons revealed that B73 and NIL alleles were similar to each other, and RWK and Stock 6 alleles were similar to each other. Most sequence differences were single nucleotide polymorphisms that do not alter protein coding sequence. There were some insertions and some deletions, most of which are in non-protein coding sequence.

The exceptional sequence difference identified by the method used to generate the sequence data is in GRMZM2G471240, which contains a four nucleotide insertion in RWK and Stock 6. GRMZM2G471240 (annotated as a patatin-like phospholipase 2A protein) has a frame-shift mutation in the RWK and Stock6 lines resulting from a four base pair insertion in the fourth (and last) exon. When the nucleotide sequence is translated, the mutation shifts the coding frame by one base pair, changing the amino acid (AA) identity for each codon after the mutation. This results in 20 incorrect AA followed by a new, premature stop codon. The entire protein lesion thus constitutes a 30 AA truncation of the protein from the C-terminus, in addition to 20 AA of incorrect sequence between the mutation and the premature stop codon.

The presently disclosed subject matter provides the isolated nucleic acids, the genomic sequence and the protein sequence, the presence or absence, showed an association with HI, as well as any subsequences and informative fragments therefrom. In some embodiments, The presently disclosed subject matter provides isolated cDNA selected from the group consisting of: (a) a nucleic acid having at least 90% identity to SEQ ID NO: 33, SEQ ID NO: 37, SEQ ID NO: 52 or SEQ ID NO: 53, optionally wherein the percent identity is calculated over the entire length of SEQ ID NO: 33, SEQ ID NO: 37, SEQ ID NO: 52 or SEQ ID NO: 53; (b) a nucleic acid having at least 95% identity over nucleotides 91-1452 of SEQ ID NO: 33; (c) a nucleic acid that is the reverse complement of either of (a) or (b); and (d) a nucleic acid that encodes a polypeptide comprising an amino acid sequence that is at least 95% identical to SEQ ID NO: 54, or SEQ ID NO: 55, or SEQ ID NO: 56, or SEQ ID NO: 57 optionally wherein the percent identity is calculated over the entire length of SEQ ID NO: 54, or SEQ ID NO: 55, or SEQ ID NO: 56, or SEQ ID NO: 57.

Comparisons of an amino acid sequence encoded thereby (i.e., SEQ ID NO: 54, SEQ ID NO: 55, SEQ ID NO: 56 and SEQ ID NO: 57) to sequences present in the GENBANK® biosequence database indicated the following this was a patatin-like phospholipase 2A protein. The table below lists gene identities in the interval shown in the tables below. This information is from chromosome 1, and lists a short description of the other encoded proteins from the genes within the haploid inducing locus.

TABLE SHOWING INFORMATION ON CHROMOSOME 1

| gene_id | transcript_start | transcript_end | Query length | Subject length | Score | Identity | Similarity | Align length | Short_description |
|---|---|---|---|---|---|---|---|---|---|
| GRMZM2G305400 | 67991172 | 67994092 | 308 | 362 | 385 | 33.3 | 53.33752 | 344 | Cyclin D2; 1 |
| GRMZM2G082836 | 68107606 | 68110989 | 202 | 205 | 729 | 71.2 | 83.33333 | 198 | GTP-binding protein 1 |
| GRMZM2G382717 | 68113455 | 68115168 | 396 | 464 | 489 | 38.77 | 53.17371 | 314 | Chaperone DnaJ-domain superfamily protein |
| GRMZM2G120587 | 68133178 | 68136953 | 458 | 461 | 1329 | 55 | 71.23894 | 452 | serine carboxypeptidase-like 51 |
| GRMZM2G471240 | 68240862 | 68242656 | 428 | 407 | 1049 | 51.5 | 72.36181 | 398 | phospholipase A 2A |
| GRMZM2G471240 | 68240862 | 68242656 | 401 | 407 | 961 | 50.15 | 70.0938 | 395 | phospholipase A 2A |
| GRMZM2G062320 | 68318898 | 68321409 | 335 | 334 | 1064 | 73.3 | 84.21053 | 285 | Phosphoglycerate mutase family protein |
| GRMZM5G866758 | 68430654 | 68436197 | 401 | 403 | 1678 | 80.4 | 90.45226 | 398 | acetoacetyl-CoA thiolase 2 |
| GRMZM5G866758 | 68430654 | 68436197 | 303 | 403 | 1248 | 78.4 | 89.40397 | 302 | acetoacetyl-CoA thiolase 2 |
| GRMZM2G003530 | 68435670 | 68439997 | 360 | 344 | 1063 | 60.5 | 76.41791 | 335 | P-loop containing nucleoside triphosphate hydrolases superfamily protein |
| GRMZM2G077991 | 68543246 | 68546264 | 94 | 95 | 424 | 79.7 | 91.48936 | 94 | Zinc-binding ribosomal protein family protein |
| GRMZM2G077991 | 68543694 | 68546264 | 94 | 95 | 424 | 79.7 | 91.48936 | 94 | Zinc-binding ribosomal protein family protein |
| GRMZM2G077991 | 68543805 | 68546269 | 147 | 95 | 419 | 79.5 | 91.39785 | 93 | Zinc-binding ribosomal protein family protein |
| GRMZM2G077960 | 68554980 | 68559182 | 438 | 428 | 1422 | 65.3 | 79.80998 | 421 | Protein phosphatase 2C family protein |
| GRMZM2G077897 | 68561209 | 68565155 | 784 | 807 | 1561 | 48.1 | 65.69848 | 723 | Plant protein of unknown function (DUF827) |
| GRMZM2G347583 | 68660278 | 68665995 | 1651 | 2156 | 1201 | 41.37 | 55.70954 | 1375 | |
| GRMZM2G173030 | 68668900 | 68671460 | 626 | 2156 | 858 | 35.6 | 48.30299 | 586 | |
| GRMZM2G022061 | 68876150 | 68882226 | 203 | 556 | 618 | 64.9 | 79.89691 | 194 | |
| GRMZM2G022061 | 68876150 | 68882226 | 322 | 556 | 1004 | 66 | 77.47748 | 333 | |
| GRMZM2G022061 | 68876150 | 68882226 | 142 | 556 | 547 | 79.6 | 89.84375 | 128 | |
| GRMZM2G022061 | 68876150 | 68882226 | 322 | 556 | 1004 | 66 | 77.47748 | 333 | |
| GRMZM2G022061 | 68876150 | 68882226 | 534 | 556 | 1802 | 67.7 | 79.81651 | 545 | |
| GRMZM2G340286 | 68928213 | 68929600 | 378 | 403 | 570 | 37.83 | 55.75713 | 407 | |
| GRMZM2G340279 | 68934652 | 68937080 | 746 | 937 | 3095 | 29.34 | 50.31745 | 2517 | Tetratricopeptide repeat (TPR)-like superfamily protein |
| GRMZM2G347808 | 69005208 | 69012612 | 589 | 455 | 1115 | 50.4 | 66.60178 | 423 | S-adenosyl-L-methionine-dependent methyltransferases superfamily protein |

RNA interference (RNAi) occurs when an organism recognizes double-stranded RNA (dsRNA) molecules and hydrolyzes them. The resulting hydrolysis products are small RNA fragments of about 19-24 nucleotides in length, called small interfering RNAs (siRNAs). The siRNAs then diffuse or are carried throughout the organism, including across cellular membranes, where they hybridize to mRNAs (or other RNAs) and cause hydrolysis of the RNA. Interfering RNAs are recognized by the RNA interference silencing complex (RISC) into which an effector strand (or "guide strand") of the RNA is loaded. This guide strand acts as a template for the recognition and destruction of the duplex sequences. This process is repeated each time the siRNA hybridizes to its complementary-RNA target, effectively preventing those mRNAs from being translated, and thus "silencing" the expression of specific genes from which the mRNAs were transcribed. Most plant miRNAs show extensive base pairing to, and guide cleavage of their target mRNAs (Jones-Rhoades et al. (2006) Annu. Rev. Plant Biol. 57, 19-53; Llave et al. (2002) Proc. Natl. Acad. Sci. USA 97, 13401-13406). In other instances, interfering RNAs may bind to target RNA molecules having imperfect complementarity, causing translational repression without mRNA degradation. The majority of the animal miRNAs studied so far appear to function in this manner.

Conveniently, the dsRNA can be produced from a single open reading frame in a recombinant host cell, wherein the sense and anti-sense sequences are flanked by an unrelated sequence which enables the sense and anti-sense sequences to hybridize to form the dsRNA molecule with the unrelated sequence forming a loop structure. Alternatively, the sense strand and antisense strand can be made without an open reading frame to ensure that no protein will be made in the transgenic host cell. The two strands can also be expressed separately as two transcripts, one encoding the sense strand and one encoding the antisense strand. RNA duplex formation can be initiated either inside or outside the cell. The dsRNA can be partially or fully double-stranded. The RNA can be enzymatically or chemically synthesized, either in vitro or in vivo.

The dsRNA need not be full length relative to either the primary transcription product or fully processed RNA. Generally, higher identity can be used to compensate for the use of a shorter sequence. Furthermore, the dsRNA can comprise single stranded regions as well, e.g., the dsRNA can be partially or fully double stranded. The double stranded region of the dsRNA can have a length of at least about 18 to about 25 base pairs, optionally a sequence of about 18 to about 50 base pairs, optionally a sequence of about 50 to about 100 base pairs, optionally a sequence of about 100 to about 200 base pairs, optionally a sequence of about 200 to about 500, and optionally a sequence of about 500 to about 1000 or more base pairs, up to molecule that is double stranded for its full length, corresponding in size to a full length target RNA molecule.

The dsRNA can contain known nucleotide analogs or modified backbone residues or linkages, which are synthetic, naturally occurring, and non-naturally occurring. Examples of such analogs include, without limitation, phosphorothioates, phosphoramidates, methyl phosphonates, chiralmethyl phosphonates and 2-O-methyl ribonucleotides.

As used herein, the term "specifically reduce the level of a target RNA and/or the production of a target protein encoded by the RNA", and variations thereof, refers to the sequence of a portion of one strand of the dsRNA being sufficiently identical to the target RNA such that the presence of the dsRNA in a cell reduces the steady state level and/or the production of said RNA. In many instances, the target RNA will be mRNA, and the presence of the dsRNA in a cell producing the mRNA will result in a reduction in the production of said protein. Preferably, this accumulation or production is reduced at least 10%, more preferably at least 50%, even more preferably at least 75%, yet even more preferably at least 95% and most preferably 100%, when compared to a wild-type cell.

The consequences of inhibition can be confirmed by examination of the outward properties of the cell or organism or by biochemical techniques such as, but not limited to, Northern hybridization, reverse transcription, gene expression monitoring with a microarray, antibody binding, enzyme linked immunosorbent assay (ELISA), Western blotting, radioimmunoassay (RIA), and other immunoassays.

MicroRNAs (miRNAs) are non-protein coding RNAs, generally of between about 18 to about 25 nucleotides in length (common(y about 20-24 nucleotides in length in plants). These miRNAs direct cleavage in trans of target transcripts, negatively regulating the expression of genes involved in various regulation and development pathways (Bartel, Cell, 116:281-297 (2004); Zhang et al. Dev. Biol. 289:3-16 (2006)). As such, miRNAs have been shown to be involved in different aspects of plant growth and development as well as in signal transduction and protein degradation. In addition, small endogenous mRNAs including miR-NAs may also be involved in biotic stress responses such as pathogen attack. Since the first miRNAs were discovered in plants (Reinhart et al. Genes Dev. 16:1616-1626 (2002), Park et al. Curr. Biol. 12:1484-1495 (2002)) many hundreds have been identified. Furthermore, many plant miRNAs have been shown to be highly conserved across very divergent taxa. (Floyd et al. Nature 428:485-486 (2004); Zhang et al. Plant J. 46:243-259 (2006)). Many microRNA genes (MI R genes) have been identified and made publicly available in a data base (miRBase; microma.sanger.ac.uk/sequences). miRNAs are also described in U.S. Patent Publications 2005/0120415 and 2005/144669A1, the entire contents of which are incorporated by reference herein.

Genes encoding miRNAs yield primary miRNAs (termed a "pri-miRNA") of 70 to 300 bp in length that can form imperfect stem-loop structures. A single pri-miRNA may contain from one to several miRNA precursors. In animals, pri-miRNAs are processed in the nucleus into shorter hairpin RNAs of about 65 nt (pre-miRNAs) by the RNaseIII enzyme Drosha and its cofactor DGCR8/Pasha. The pre-miRNA is then exported to the cytoplasm, where it is further processed by another RNaseIII enzyme, Dicer, releasing a miRNA/miRNA* duplex of about 22 nt in size. In contrast to animals, in plants, the processing of pri-miRNAs into mature miRNAs occurs entirely in the nucleus using a single RNaseIII enzyme, DCL1 (Dicer-like 1). (Zhu. Proc. Natl. Acad. Sci. 105:9851-9852 (2008)). Many reviews on microRNA biogenesis and function are available, for example, see, Bartel Cell 116:281-297 (2004), Murchison et al. Curr. Opin. Cell Biol. 16:223-229 (2004), Dugas et al. Curr. Opin. Plant Biol. 7:512-520 (2004) and Kim Nature Rev. Mol. Cell Biol. 6:376-385 (2005).

The term "plant microRNA precursor molecule" as used herein describes a small (~70-300 nt) non-coding RNA sequence that is processed by plant enzymes to yield a ~19-24 nucleotide product known as a mature microRNA sequence. The mature sequences have regulatory roles through complementarity to messenger RNA. The term "artificial plant microRNA precursor molecule" describes the non-coding miRNA precursor sequence prior to processing that is employed as a backbone sequence for the delivery of a siRNA molecule via substitution of the endogenous native miRNA/miRNA* duplex of the miRNA precursor molecule with that or a non-native, heterologous miRNA (amiRNA/amiRNA*; e.g. siRNA/siRNA*) that is then processed into the mature miRNA sequence with the siRNA sequence.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

As used herein, "complementary" polynucleotides are those that are capable of base pairing according to the standard Watson-Crick complementarity rules. Specifically, purines base pair with pyrimidines to form a combination of guanine paired with cytosine (G:C) and adenine paired with either thymine (A:T) in the case of DNA, or adenine paired with uracil (A:U) in the case of RNA. For example, the sequence "A-G-T" binds to the complementary sequence "T-C-A." It is understood that two polynucleotides may hybridize to each other even if they are not completely complementary to each other, provided that each has at least one region that is substantially complementary to the other.

The terms "complementary" or "complementarity," as used herein, refer to the natural binding of polynucleotides under permissive salt and temperature conditions by base-pairing. Complementarity between two single-stranded molecules may be "partial," in which only some of the nucleotides bind, or it may be complete when total complementarily exists between the single stranded molecules. The degree of complementarity between nucleic acid strands has significant effects on the efficiency and strength of hybridization between nucleic acid strands.

As used herein, the terms "substantially complementary" or "partially complementary" mean that two nucleic acid sequences are complementary at least about 50%, 60%, 70%, 80% or 90% of their nucleotides. In some embodiments, the two nucleic acid sequences can be complementary at least at 85%, 90%, 95%, 96%, 97%, 98%, 99% or more of their nucleotides. The terms "substantially complementary" and "partially complementary" can also mean that two nucleic acid sequences can hybridize under high stringency conditions and such conditions are well known in the art In some embodiments, the dsRNA molecule can comprise, consist essentially of or consist of from at least 18 to about 25 consecutive nucleotides (e.g. 18, 19, 20, 21, 22, 23, 24 or 25) to at least about 400 consecutive nucleotides. In some embodiments the dsRNA molecule can comprise, consist essentially of or consist of about 500, or about 50 or about 543 consecutive nucleotides. Additional nucleotides can be added at the 3' end, the 5' end or both the 3' and 5' ends to facilitate manipulation of the dsRNA molecule but that do not materially affect the basic characteristics or function of the dsRN A molecule in RNA interference (RNAi).

In some embodiments, the portion of the mRNA polynucleotide transcribable from a GRMZM2G471240 gene that the antisense strand is complementary to comprises at least 18 consecutive nucleotides of SEQ ID NO:33, SEQ ID NO:37, SEQ ID NO:52 or SEQ ID NO:53. In other embodiments, the portion of mRNA comprises, consists essentially of or consists of at least from 19, 20 or 21 consecutive nucleotides to at least 400 consecutive nucleotides of SEQ ID NO:33, SEQ ID NO:37, SEQ ID NO:52 or SEQ ID NO:53. In other embodiments, the portion of mRNA comprises, consists essentially of or consists of at least about 500, or at least about 98 or at least about 185 consecutive nucleotides of SEQ ID NO:33.

In other embodiments, the portion of the mRNA polynucleotide that is complementary to the antisense strand of a dsRNA of the invention comprises any 19-mer subsequence of SEQ ID NO:33 (GRMZM2G471240) consisting of N to N±18 nucleotides, wherein N is nucleotide 1 to 1452 of SEQ ID NO:33. In other words, the portion of the mRNA that is targeted comprises any of the 1452 19 consecutive nucleotide subsequences (i.e. 19-mer) of SEQ ID NO:33, for example, bases 1-19 (5'-AGTTCATCACTAATCACAC-3'), bases 2-20 (5'-GTTCATCACTAATCACACT-3'), bases 3-21 (5'-TTCATCACTAATCACACTT-3') and so forth to bases 1434-1452 (5'-AAAACATAAAAATATATAT-3').

In other embodiments, the nucleotide sequence of the antisense strand can consist essentially of the nucleotide sequence of any 19-mer subsequence of SEQ ID NO:62 consisting of N to N+18 nucleotides, wherein N is nucleotide 1 to nucleotide 1452 of SEQ ID NO:62. In other words, the antisense strand consists essentially of the nucleotide sequence of any of the 1452 19 consecutive nucleotide subsequences (i.e. 19-mer) of SEQ NO:62, for example, bases 1-19 (5'-ATATATATTTTTATGTTTT-3'), bases 2-20 (5'-TATATATTTTTATGTTTTA-3'), bases 3-21 (5'-ATAT-ATTTTTATGTTTTAT-3') and so forth to bases 1434-1452 (5'-GTGTGATTAGTGATGAACT-3').

It would be understood that the deletion of the one nucleotide or the addition of up to six nucleotides do not materially affect the basic characteristics or function of the double stranded RNA molecule of the invention. Such additional nucleotides can be nucleotides that extend the complementarity of the antisense strand along the target sequence and/or such nucleotides can be nucleotides that facilitate manipulation of the RNA molecule or a nucleic acid molecule encoding the RNA molecule, as would be known to one of ordinary skill in the art. For example, a TT overhang at the 3; end may be present, which is used to stabilize the siRNA duplex and does not affect the specificity of the siRNA.

In some embodiments of this invention, the antisense strand of the double stranded RNA molecule can be fully complementary to the target RNA polynucleotide or the antisense strand can be substantially complementary or partially complementary to the target RNA polynucleotide. By substantially or partially complementary is meant that the antisense strand and the target RNA polynucleotide can be mismatched at about 1, 2, 3, 4, 5, 6, 7, 8, 9, or 10 nucleotide pairings. Such mismatches can be introduced into the antisense strand sequence, e.g., near the 3' end, to enhance processing of the double stranded RNA molecule by Dicer, to duplicate a pattern of mismatches in a siRNA molecule inserted into a chimeric nucleic acid molecule or artificial microRNA precursor molecule of this invention, and the like, as would be known to one of skill in the art. Such modification will weaken the base pairing at one end of the duplex and generate strand asymmetry, therefore enhancing the chance of the antisense strand, instead of the sense strand, being processed and silencing the intended gene (Geng and Ding "Double-mismatched siRNAs enhance selective gene silencing of a mutant ALS-causing Allelel" Acta Pharmacol. Sin. 29:211-216 (2008); Schwarz et al. "Asymmetry in the assembly of the RNAi enzyme complex" Cell 115:199-208 (2003)). Other such mismatches can be introduced into the antisense strand due to eliminating fortuitous open reading frames created in making dsRNA encoding expression cassettes. Such open reading frames are eliminated by making point mutations in the dsRNA encoding nucleotide sequence thus creating some mismatches in the dsRNA compared to the target gene. In some embodiments of this invention, the dsRNA molecule of the invention is a short hairpin RNA (shRNA) molecule. Expression of shRNA in cells is typically accomplished by delivery of plasmids or recombinant vectors, for example in transgenic plants such as transgenic corn.

The invention encompasses a nucleic acid molecule encoding at least one strand of a dsRNA molecule of the invention. The invention further encompasses a nucleic acid construct comprising at least one strand of a dsRNA molecule of the invention or comprising the nucleic acid molecule encoding the at least one strand of a dsRNA molecule of the invention. In one embodiment of the invention, the nucleic acid molecule encodes a short hairpin RNA. In another embodiment, the nucleic acid molecule that encodes the short hairpin RNA comprises SEQ ID NO:62 or SEQ ID NO:63

The invention further encompasses chimeric nucleic acid molecules comprising an antisense strand of a dsRNA of the invention operably linked with a plant microRNA precursor molecule. In some embodiments, the chimeric nucleic acid molecule comprises an antisense strand having the nucleotide sequence of any of the 19-mer subsequences of SEQ ID NO:33, SEQ ID NO:37, SEQ ID NO:52 or SEQ ID NO:53 operably linked with a plant microRNA precursor molecule. In some embodiments, the plant microRNA precursor molecule is a maize microRNA precursor.

In some embodiments, the invention encompasses an artificial plant microRNA precursor molecule comprising an antisense strand of a dsRNA molecule of the invention. In other embodiments, the artificial plant microRNA precursor molecule comprises an antisense strand having the nucleotide sequence of any of the 19-mer subsequences of SEQ ID NO:62, or SEQ ID NO:63. The use of artificial plant microRNAs to deliver a nucleotide sequence of interest (e.g an artificial miRNA; siRNA/siRNA*) into a plant is known in the art (see, e.g., Schwab et al. 2006. The Plant Cell 18:1121-1133 and Examples section herein). In the invention, the artificial microRNAs are chimeric or hybrid molecules, having a plant microRNA precursor backbone and an insect (i.e. animal) siRNA sequence inserted therein. As would be understood by one of ordinary skill in the art, it is typically desirable to maintain mismatches that normally occur in the plant microRNA precursor sequence in any nucleotide sequence that is substituted into the plant microRNA precursor backbone. In still other embodiments, the artificial plant microRNA precursor comprises portions of a corn microRNA precursor molecule. Any corn microRNA (miRNA) precursor is suitable for the compositions and methods of the invention. Nonlimiting examples include miR156, miR159, miR160, miR162, miR164, miR166, miR167, miR168, miR169, miR171, miR172, miR319, miR390, miR393, miR394, miR395, miR396, miR397, miR398, miR399, miR408, miR482, miR528, miR529, miR827, miR1432, as well as any other plant miRNA precursors now known or later identified.

In some embodiments, the invention encompasses nucleic acid constructs, nucleic acid molecules or recombinant vectors comprising at least one strand of a dsRNA molecule of the invention, or comprising a chimeric nucleic acid molecule of the invention, or comprising an artificial plant microRNA of the invention. In some embodiments the nucleic acid construct comprises a nucleic acid molecule of the invention. In other embodiments, the nucleic acid construct is a recombinant expression vector.

In some embodiments, the invention encompasses compositions comprising two or more dsRNA molecules of the invention wherein the two or more RNA molecules each comprise a different antisense strand. In some embodiments the two or more dsRNA molecules are present on the same nucleic acid construct, on different nucleic acid constructs or any combination thereof. In other embodiments, the composition comprises an RNA molecule comprising an antisense strand consisting essentially of the nucleotide sequence of SEQ ID NO:62 and an RNA molecule comprising an antisense strand consisting essentially of the nucleotide sequence of SEQ ID NO:63. In other embodiments, the composition comprises two or more nucleic acid constructs, two or more nucleic acid molecules, two or more chimeric nucleic acid molecules, two or more artificial plant microRNA precursors of the invention, wherein the two or more nucleic acid constructs, two or more nucleic acid molecules, two or more chimeric nucleic acid molecules, or two or more artificial plant microRNA precursors, each comprise a different antisense strand.

RNA interference (RNAi) can be used to produce genetically modified plants that are tolerant or resistant to abiotic and biotic stresses. In the past decade, RNAi has been described and characterized in organisms as diverse as plants, fungi, nematodes, hydra, and humans. Zamore and Haley (2005) Science 309, 1519-24. RNA interference in plants is commonly referred to as post-transcriptional gene silencing or RNA silencing and is referred to as quelling in fungi. The process of post-transcriptional gene silencing is thought to be an evolutionarily conserved cellular defense mechanism used to prevent the expression of foreign genes and is commonly shared by diverse flora and phyla. Fire (1999) Trends Genet. 15, 358-363.

RNA interference occurs when an organism recognizes double-stranded RNA molecules and hydrolyzes them. The resulting hydrolysis products are small RNA fragments of 19-24 nucleotides in length, called small interfering RNAs (siRNAs) or microRNAs (miRNAs). The siRNAs then diffuse or are carried throughout the organism, including across cellular membranes, where they hybridize to mRNAs (or other RNAs) and cause hydrolysis of the RNA. Most plant miRNAs show extensive base pairing to, and guide cleavage of their target mRNAs, Jones-Rhoades et al. (2006) Annu Rev. Plant Biol 57, 19-53; Llave et al. (2002) Proc. Natl. Acad., Sci. USA 97, 13401-10406. In other instances, interfering RNAs may bind to target RNA molecules having imperfect complementarity, causing translational repression without mRNA degradation.

The mode of action for silencing a plant gene generally includes a double stranded RNA (dsRNA) that associates with a dicer enzyme that cuts the dsRNA into ds fragments 19-24 bps in length (siRNA). There may be more than one dicer enzyme, depending on the organism. Meister and Tuschl, 2004). The siRNA is typically degraded into two single stranded RNAs (ssRNAs), referred to as the passenger strand and the guide strand. A RNA-interference silencing complex (RISC complex) loads the guide strand. The RISC complex associates with a target mRNA that has partial or complete homology to the guide strand. The catalytic RISC component agronaute causes cleavage of the target mRNA preventing it from being used as a translation template. Ahlquist P (2002) RNA-dependent RNA polymerases, viruses, and RNA silencing, Science 296 (5571): 1270-3. The RNAi pathway is exploited in plants by using recombinant technology, which entails transforming a plant with a vector comprising DNA that when expressed produces a dsRNA homologous or nearly homologous to a gene target. The gene target can be homologous to a endogenous plant gene or an insect gene. If the target is an insect gene, the insect eats the plant thereby ingesting the dsRNA, at which the RNAi RISC complex of the insect causes cleavage and targeting of the homologous mRNA, causing disruption of a vital insect process.

To date, plant recombinant technology is the vehicle for delivering gene silencing of target genes, either endogenous plant target genes or target genes of a plant pest organism. In general, a plant is transformed with DNA that is incorporated into the plant genome, and when expressed produces a dsRNA that is complementary to a gene of interest, which can be an endogenous plant gene or an essential gene of a plant pest. Plant recombination techniques to generate transgene and beneficial plant traits require significant investments in research and development, and pose significant regulatory hurdles. Methods and formulations for delivering dsRNA into plant cells by exogenous application to exterior portions of the plant, such as leaf, stem, and/or root surfaces for regulation of endogenous gene expression are not known in the art. Such methods and formulations represent a significant development for gene silencing technology. Known methods for delivering exogenous dsRNA into plant cells are via particle bombardment or viral RNA infection through wounding the plant tissue (e.g. tobacco and rice leaf tissues). Application by spray or brush of RNA molecules, or other non-tissue evasive techniques, resulting in assimilation of the exogenous RNA molecules into plant tissue, thereby causing endogenous and/or pest gene silencing, has not been reported.

The present invention is directed to methods and formulations to incorporate exogenous RNA, by application to external tissue surface(s) of plants, into the plant cells causing silencing of plant endogenous target gene(s) or of the target genes of plant pests.

The present invention is not directed to any particular RNAi mechanism or mode of action of gene silencing, and should not be construed as limited to any such mechanisms, known or unknown.

The terms "silencing" and "suppression" are used interchangeably to generally describe substantial and measurable reductions of the amount of the target mRNA available in the cell for binding and decoding by ribosomes. The transcribed RNA can be in the sense orientation to effect what is referred to as co-suppression, in the anti-sense orientation to effect what is referred to as anti-sense suppression, or in both orientations producing a double-stranded RNA to effect what is referred to as RNA interference. A "silenced" gene includes within its definition a gene that is subject to silencing or suppression of the mRNA encoded by the gene.

MicroRNAs are encoded by genes that are transcribed but not translated into protein (non-coding DNA), although some miRNAs are encoded by sequences that overlap protein-coding genes. By way of background, miRNAs are processed from primary transcripts known as pri-miRNAs to short stem loop structures called pre-miRNAs that are further processed by action of dicer enzyme(s) creating functional siRNAs/miRNAs. Typically, a portion of the precursor miRNA is cleaved to produce the final miRNA molecule. The stem-loop structures may range from, for example, about 50 to about 80 nucleotides, or about 60 nucleotides to about 70 nucleotides (including the miRNA residues, those pairing to the miRNA, and any intervening segments). The secondary structure of the stem-loop structure is not fully base-paired; mismatches, bulges, internal loops, non-WatsonCrick base pairs (i.e., G-U wobble base pairs), and other features are frequently observed in pre-miRNAs and such characteristics are thought to be important for processing. Mature miRNA molecules are partially complementary to one or more mRNA molecules, and they function to regulate gene expression. siRNAs of the present invention have structural and functional properties of endogenous miRNAs (e.g., gene silencing and suppressive functions). Thus, in various aspects of the invention, siRNAs of the invention can derived from miRNAs, from target gene sequence information, or can be produced synthetically based on predictive models known in the art. The phrases "target-specific small interfering RNAs," "target-specific siRNAs," "target-specific microRNAs," "target-specific miRNAs," "target-specific amiRNAs," and "target-specific nucleotide sequence" refer to interfering RNAs that have been designed to selectively hybridize with nucleic acids in a target organism, but not in a non-target organism, such as a host organism (the organism expressing or producing the miRNA) or a consumer of the host organism, Consequently, "target-specific siRNAs" only produce phenotypes in target organisms and do not produce phenotypes in non-target organisms. In the present invention, the target-specific siRNAs selectively hybridize to nucleic acids that are endogenous to the host organism, which are plants. MicroRNAs (miRNAs) are non-protein coding RNAs, generally of between about 19 to about 25 nucleotides (commonly about 20-24 nucleotides in plants). miRNAs direct cleavage in trans of target transcripts, regulating the expression of genes involved in various regulation and development pathways (Bartel, Cell, 116:281-297 (2004); Zhang et al, Dev. Biol. 289:3-16 (2006)). miRNAs have been shown to be involved in different aspects of plant growth and development as well as in signal transduction and protein degradation. In addition, growing evidence indicates that small endogenous mRNAs including miRNAs may also be involved in biotic stress responses such as parasite attack. Since the first miRNAs were discovered in plants (Reinhart et al. Genes Dev. 16:1616-1626 (2002), Park et al. Curr. Biol. 12:1484-1495 (2002)), many hundreds have been identified. Further, many plant miRNAs have been shown to be highly conserved across very divergent taxa. (Floyd et al. Nature 428:485-486 (2004); Zhang et al. Plant J. 46:243-259 (2006)). Many microRNA genes (MIR genes) have been identified and made publicly available in a database ("miRBase," available on line at microrna.sanger.ac.uk/sequences). miRNAs are also described in U.S. Patent Publications 2005/0120415 and 2005/144669A1, the entire contents of which are incorporated by reference herein.

Further encompassed within the presently disclosed subject matter are expression cassettes according to the embodiments of the presently disclosed subject matter as well as expression vectors comprising the same. Also encompassed are plant cells comprising expression cassettes according to the present disclosure, and plants comprising these plant cells. In some embodiments, the plant is a dicot. In some embodiments, the plant is a monocot. In some embodiments, the monocot is a cereal. The plant can be, for example, rice, maize, grass, wheat, maize, barley, brome, oats, rye, millet, sorghum, triticale, secale, einkorn, spelt, emmer, teff, milo, flax, gramma grass, Tripsacum, or teosinte.

Thus, the compositions of the presently disclosed subject matter can comprise nucleic acid sequences for transformation and expression in a plant of interest. The expression is of the primary candidate gene and HI trait is desired the expression may also be for down regulated expression or induced expression in some or all of the female portion of the plant and no expression in the male flowering plant parts. The nucleic acid sequences can be present in DNA constructs or expression cassettes. "Expression cassette" as used herein means a nucleic acid molecule capable of directing expression of a particular nucleotide sequence, or iRNA in an appropriate host cell, comprising a promoter operatively linked to the sequence of interest (e.g., a sequence encoding a gene product or iRNA associated with HI) which is optionally also operatively linked to termination signals. It also typically comprises sequences required for proper translation of the nucleotide sequence. The coding region usually codes for a protein of interest but can also code for a functional RNA of interest, for example antisense RNA or a nontranslated RNA such as, but not limited to a siRNA, in the sense or antisense direction. The expression cassette comprising the nucleotide sequence of interest can be chimeric, meaning that at least one of its components is heterologous with respect to at least one of its other components. The expression cassette can also be one that is naturally occurring but has been obtained in a recombinant form useful for heterologous expression. In some embodiments, the expression cassette is heterologous with respect to the host (i.e., the particular DNA sequence of the expression cassette, or a subsequence thereof, does not occur naturally in the host cell and must have been introduced into the host cell or an ancestor of the host cell by a transformation event). The expression of the nucleotide sequence in the expression cassette can be under the control of a constitutive promoter, a tissue specific promoter, and/or an inducible promoter that initiates transcription only when the host cell is exposed to some particular external stimulus, a minimal promoter, etc. Additionally, the promoter can also be specific to a particular cell type, tissue, organ, and/or stage of development. In some embodiments, an expression cassette is present in a vector that permits replication of the expression cassette in a host cell.

The present presently disclosed subject matter encompasses the transformation of plants with expression cassettes capable of expressing a polynucleotide of interest (e.g., a polynucleotide encoding a gene product or iRNA associated with HI) alone or in combination with one or more additional nucleic acid molecules encoding polypeptides that confer desirable traits. However, if the polynucleotide is the primary gene, GRMZM2G062320, it may be preferred that the cassette is adapted to down regulate or knock out the gene in nonhaploid inducing material. Or expressed in an inducible matter so that the pollen used to self the HI plant is expressing the gene product that occurs in B73 and other non haploid inducing material. In some embodiments, the expression cassette includes at least the following basic elements oriented in the 5'-3' direction of transcription: a transcriptional and translational initiation region (i.e., a promoter) and a polynucleotide of interest. The expression cassette can optionally comprise a transcriptional and translational termination region (e.g., termination region) functional in plants. In some embodiments, the expression cassette comprises a selectable marker gene to allow for selection for stable transformants.

In some embodiments, the regulatory sequences of the expression construct are operably linked to the polynucleotide of interest. By "operably linked" is intended a functional linkage between a first sequence (e.g., a promoter) and a second sequence (e.g., a coding sequence), wherein the first sequence influences a biological event (e.g., transcription, transcription, replication, etc.) that occurs with respect to the second sequence. Generally, operably linked means that the nucleotide sequences being linked are contiguous in a single molecule.

Any promoter capable of driving expression in the plant of interest can be used in the practice of the presently disclosed subject matter. In some embodiments, the expression cassette is expressed throughout the plant. In some embodiments, the expression cassette is expressed in a specific location and/or tissue of a plant, or at a certain time during the development of the plant. In some embodiments, the location and/or tissue includes, but is not limited to, anther, ovule, plastid, pollen, mitochondrion, chloroplast, epidermis, root, vascular tissue, meristem, cambium, cortex, pith, leaf, flower, and combinations thereof. In another embodiment, the location and/or tissue is a seed.

The promoter can be native or analogous, or can be heterologous or exogenous, to the plant or plant cell in which it is intended to be active. The terms "heterologous" and "exogenous" when used herein to refer to a nucleic acid sequence (e.g., a DNA or RNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, in some embodiments the terms refer to a DNA segment that is foreign or heterologous to the cell, or homologous to the cell but in a position within the host cell nucleic acid in which the element is not ordinarily found. In some embodiments, an exogenous DNA segment is expressed to yield an exogenous polypeptide in a cell or tissue type of interest. In some embodiments, a heterologous or exogenous nucleic acid is referred to herein as a transgene.

A "homologous" nucleic acid (e.g., DNA) sequence is a nucleic acid (e.g., DNA or RNA) sequence that is naturally associated with a host cell into which it is introduced. As such, and by way of example and not limitation, a nucleic acid that is derived from (i.e., isolated from with or without subsequent modification) a plant cell or tissue could be considered a homologous nucleic acid when reintroduced into a plant cell or tissue of the same species, but could be considered heterologous or exogenous when introduced into a cell or tissue of a plant other than the plant species from which it was derived. In some embodiments, a homologous nucleic acid can also be referred to herein as a heterologous or a transgene when the homologous nucleic acid is operatively linked to a nucleotide sequence to which it is not naturally operatively linked.

The choice of promoters to be included depends in some embodiments upon several factors, including, but not limited to, efficiency, selectability, inducibility, desired expression level, and/or cell- or tissue-preferential and/or -specific expression. It is a routine matter for one of skill in the art to modulate the expression of a sequence by appropriately selecting and positioning promoters and other regulatory regions relative to that sequence. The promoters that are used for expression of the transgene(s) can be in some embodiments a strong plant promoter, in some embodiments a viral promoter, and in some embodiments a chimeric promoter comprising such basic transcriptional regulatory elements such as but not limited to a TATA box from any gene (or synthetic, based on analysis of plant gene TATA boxes), optionally fused to the region 5' to the TATA box of plant promoters (which direct tissue and temporally appropriate gene expression), optionally fused to one or more enhancers (such as the 35S enhancer, FMV enhancer, CMP enhancer, etc.).

For example, the selection of the promoter used in expression cassettes can determine the spatial and temporal expression pattern of the transgene in the transgenic plant. Selected promoters can express transgenes in specific cell types and/or in specific tissues or organs, and the selection can reflect the desired location for accumulation of the gene product. Alternatively, the selected promoter can drive expression of the gene under various inducing conditions. Promoters vary in their strength; i.e., their abilities to promote transcription. Depending upon the host cell system utilized, any one of a number of suitable promoters can be used, including the gene's native promoter. The following are non-limiting examples of promoters that can be used in expression cassettes.

Promoters which are directing expression of the gene are referred to herein as "constitutive" promoters and are active under most environmental conditions and states of development or cell differentiation. Examples of constitutive promoters include the 1'- or 2'-promoter derived from T-DNA of *Agrobacterium tumefaciens*, and other transcription initiation regions from various plant genes known to those of ordinary skill in the art. Such genes include, but are not limited to, the inducible promoters of AP2 gene; ACT11 from *Arabidopsis* (Huang et al., 1996); Cat3 from *Arabidopsis* (GENBANK® Accession No. U43147; Zhong et al., 1996); the gene encoding stearoyl-acyl carrier protein desaturase from *Brassica napus* (GENBANK® Accession No. X74782; Solocombe et al., 1994); GPc1 from maize (GENBANK® Accession No. X15596; Martinez et al., 1989); and Gpc2 from maize (GENBANK® Accession No. U45855; Manjunath et al., 1997). Additional non-limiting examples of constitutive promoters include, for example, the core promoter of the Rsyn7 promoter and other constitutive promoters disclosed in PCT International Patent Application Publication No. WO 1999/43838 and U.S. Pat. No. 6,072,050; various ubiquitin promoters (see e.g., U.S. Pat. Nos. 5,641,876 and 8,168,859; Christensen et al., 1989; Christensen et al., 1992; Wei et al., 2003; Lu et al., 2008); the core CaMV 35S promoter (Odell et al., 1985; Benfey & Chua, 1990); the CaMV 19S promoter; the figwort mosaic virus (FMV) promoter; the rice actin-1 promoter (McElroy et al., 1990); the rice alpha tubulin (tubA1) promoter (Fiume et al., 2004); pEMU (Last et al., 1991); the Cestrum yellow leaf curling virus (CmYLCV) CMP promoter (Hohn et al., 2007; U.S. Pat. No. 7,166,770); the MAS promoter (Velten et al., 1984); the Super MAS promoter (Ni et al., 1995; Lee et al., 2007); the ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142; and 6,177,611.

The present invention shows a frame shift mutation in GRMZM2G471240 in the Haploid inducing material, thus RNAi silencing of GRMZM2G471240 will create a HI line. The silencing can be accomplished in numerous ways including expression of a hairpin or artificial mircoRNA to target GRMZM2G471240. The down regulated expression transformants will allow various types of germplasm to act as HI lines.

It should also be possible to compensate the defect in a HI line. Transgenic material with the non haploid inducing sequence when expressed (SEQ ID NO: 33) should if joined with an inducible promoter make the HI line switchable between being a HI line and a non HI line. Therefore, transformation methods, cassettes, vectors and transgenic plant with the non HI sequence are described herein.

Appropriate plant or chimeric promoters are useful for applications such as expression of transgenes and/or other heterologous or homologous nucleic acids in certain tissues, while minimizing expression (including but not limited to a level of expression that is below detection using routine techniques) in other tissues, in some embodiments such as but not limited to seeds and/or female reproductive tissues. In some embodiments, expression of a nucleic acid designed to silence a gene product associated with HI of the current presently disclosed subject matter can optionally be localized to seed, or fruit tissues and preferably no expression in the anther or pollen or very downregulated expression if this gene product is present at all in the anther or pollen. The data suggests that expression of the expression is most likely important in early reproductive structures, particularly female structures. Exemplary cell type- or tissue-preferential (in some embodiments, tissue-specific) promoters drive expression preferentially (or in some embodiments essentially specifically) in the target tissue, but can also lead to some expression in other cell types or tissues as well. Methods for identifying and characterizing promoter regions in plant genomic DNA include, for example, those described in the following references: Green et al., 1988; Bustos et al., 1989; Jordano et al., 1989; Meier et al., 1991; and Zhang et al., 1996.

Alternatively, the plant promoter can direct expression of the nucleic acid molecules of the presently disclosed subject matter in a specific tissue or can be otherwise under more precise environmental or developmental control. Examples of environmental conditions that can effect transcription by inducible promoters include anaerobic conditions, elevated temperature, or the presence of light. Such promoters are referred to herein as "inducible", "cell type-specific", or "tissue-specific" promoters. Those of ordinary skill in the art will recognize that a tissue-specific promoter can drive expression of operatively linked sequences in tissues other than the target tissue. Thus, as used herein a "tissue-specific" promoter is one that drives expression preferentially in the target tissue, but can also lead to some expression in other tissues as well.

Examples of promoters under developmental control include promoters that initiate transcription preferentially or exclusively in certain tissues, such as pollen, anthers, fruit, seeds, or flowers. Promoters that direct expression of nucleic acids in pollen, anthers, and the like and possibly in ovules, flowers, or seeds are particularly useful in the presently disclosed subject matter. As used herein a seed-specific promoters are active in cells destined to produce the ovule and tend to direct expression specifically or preferentially in the seed tissues. And reproduction specific promoters are promoters that are active in cells destined to produce the male parts such as the anther, pollen and microspores and the female parts such as the ovule, silks, embryo, and seed. And male Reproductive specific promoters are promoters that are active in cells destined to produce the male parts like pollen.

Seed specific promoters can be, for example, ovule-specific, embryo-specific, endosperm-specific, integument-specific, seed coat-specific, or some combination thereof. Examples include a promoter from the ovule-specific BEL1 gene described in Reiser et al., 1995 (GENBANK® Accession No. U39944). Non-limiting examples of seed specific promoters are derived from the following genes: MAC1 from maize (Sheridan et al., 1996); Cat3 from maize (GENBANK® Accession No. L05934; Abler et al., 1993); the gene encoding oleosin 18 kD from maize (GENBANK® Accession No. J05212; Lee & Huang, 1994); vivparous-1 from *Arabidopsis* (GENBANK® Accession No. U93215); the gene encoding oleosin from *Arabidopsis* (GENBANK® Accession No. Z17657); Atmycl from *Arabidopsis* (Urao et al., 1996); the 2s seed storage protein gene family from *Arabidopsis* (Conceicao et al., 1994); the gene encoding oleosin 20 kD from *Brassica napus* (GENBANK® Accession No. M63985); napA from *Brassica napus* (GENBANK® Accession No. J02798; Josefsson et al., 1987); the napin gene family from *Brassica napus* (Sjodahl et al., 1995); the gene encoding the 2S storage protein from *Brassica napus* (Dasgupta et al., 1993); the genes encoding oleosin A (GENBANK® Accession No. U09118) and oleosin B (GENBANK® Accession No. U09119) from soybean; and the gene encoding low molecular weight sulfur rich protein from soybean (Choi et al., 1995). Additional cell type- and/or tissue-specific promoters include, but are not limited to the *Triticum aestivum* pistil specific P19 promoter (see Japanese Patent Application JP 2001512988-A/13); the maize silk promoter prB200 (see Japanese Patent Application JP 001512988-A/13), the maize prCDPK-01 and prCDPK-02 promoters (Estruch et al., 1994); the rice α-N-acetylglucosaminidase (prOsANG) promoter (U.S. Pat. No. 7,550,578); the rice MADS box gene promoters prOsMADS1, prOsMADS2, prOsMADS6, prOsMADS7, prOsMADS14; and prOsMADS16 (U.S. Patent Application Publication Nos. 2007/0006344, 2010/0205692 A1, and 2012/0021506 A1); the rice anther-specific promoter prRA8 (see Japanese Patent Application JP 2001512988-A/13); the rice prOsG6 promoter (Tsuchiya et al., 1994); the whole seed-specific promoter disclosed in U.S. Patent Application Publication No. 2012/0036595; and the endosperm promoter disclosed in U.S. Patent Application Publication No. 2012/0036593.

Additional promoters that can be employed with the presently disclosed subject matter include, but are not limited to those described in U.S. Pat. No. 7,151,201; the PsEND1 promoter described in Roque et al., 2007; the corn stamen-specific promoters described in PCT International Patent Application Publication No. WO 1992/013957; and the APETALA3 promoter described in U.S. Pat. No. 7,253,340.

In some embodiments, an inducible promoter might be desired. Inducible promoters drive transcription in response to external stimuli such as chemical agents or environmental stimuli. For example, inducible promoters can confer transcription in response to hormones such as gibberellic acid or ethylene, or in response to light, heat or drought.

In some embodiments, an expression construct further comprises a transcription terminator operably linked to the nucleic acid of interest. These are responsible for the termination of transcription beyond the transgene and/or correct mRNA polyadenylation. A variety of transcriptional terminators are available for use in expression cassettes. The termination region can be native with respect to the transcriptional initiation region/promoter (i.e., the promoter and transcription terminator can be derived from the same genetic locus), can be native with the operably linked DNA sequence of interest, can be native with the plant host, and/or can be derived from another source (e.g., can be foreign or heterologous to the promoter, the DNA sequence of interest, the plant host, or any combination thereof). Exemplary transcriptional terminators are those that are known to function in plants and include the CAMV 35S terminator, the tml terminator, the nopaline synthase (Nos) terminator, and the pea rbcs E9 terminator. These can be used in both monocotyledons and dicotyledons. In addition, a gene's native transcription terminator can be used.

In some embodiments, an expression cassette comprises a selectable marker gene for the selection of transformed cells.

Additionally, various sequences have been found to enhance gene expression from within the transcriptional unit, and in some embodiments these sequences are used in conjunction with the nucleic acids of the presently disclosed subject matter to increase their expression in transgenic plants. For example, certain intron sequences have been shown to enhance expression, particularly in monocotyledonous cells. For example, the introns of the maize Adh1 gene have been found to significantly enhance the expression of the wild type gene under its cognate promoter when introduced into maize cells. Intron 1 was found to be particularly effective and enhanced expression in fusion constructs with the chloramphenicol acetyltransferase gene (Callis et al., 1987). In the same experimental system, the intron from the maize bronze 1 gene had a similar effect in enhancing expression of an operably linked nucleic acid sequence. Intron sequences have been routinely incorporated into plant transformation vectors, typically within the non-translated leader.

Expression constructs of the presently disclosed subject matter can also comprise a leader sequence and/or a sequence allowing for inducible expression of the polynucleotide of interest. See e.g., Guo et al., 2003; Chen et al., 2003 for examples of sequences allowing for inducible expression.

A number of non-translated leader sequences derived from viruses are also known to enhance expression of operably linked nucleic acid sequences, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (see e.g., Gallie et al., 1987; Skuzeski et al., 1990). Other leader sequences known in the art include, but are not limited to, picornavirus leaders (e.g., the EMCV leader (the encephalomyocarditis 5'-non-coding region); Elroy-Stein et al., 1989); potyvirus leaders (e.g., the Tobacco Etch Virus (TEV) leader; Allison et al., 1986); the Maize Dwarf Mosaic Virus (MDMV) leader (see GENBANK® Accession No. NC_003377); the human immunoglobulin heavy-chain binding protein (BiP) leader (Macejak & Samow, 1991); the untranslated leader from the coat protein mRNA of alfalfa mosaic virus (AMV RNA 4; Jobling & Gehrke, 1987); the tobacco mosaic virus leader (TMV) leader (Gallie et al., 1989); and the Maize Chlorotic Mottle Virus (MCMV) leader (Lommel et al., 1991). See also, Della-Cioppa et al., 1987.

Alternatively or in addition, an expression construct of the present invention can include a presequence that directs the localization polypeptide encoded by the expression construct to an organelle within a plant cell. A nucleotide sequence encoding a presequence can be introduced in frame at the 5' end of a coding sequence in order to target the polypeptide encoded by the presequence/coding sequence hybrid to the target area. In some embodiments, the coding sequence encodes a subsequence or the entire sequence set forth in SEQ ID NO: 54. In some embodiments 454 amino acids of SEQ ID NO: 54 or a subsequence thereof that comprised amino acids non HI trait or or less consecutive amino acids or more consecutive amino acids or an amino acid sequence that is 95% identical thereto can be fused to any presequence using standard molecular cloning techniques.

The transformation of non HI; or HI germplasm can include transformants in monocots and dicots which may be for example orthologs. Species that have orthologues to this sequence can readily be employed in the transformation process these include but are not limited to the species: sorghum bicolor, maize, wheat, millet, *Setaria Italica, Oryza brachyantha, Oryza indica, Oryza glaberrima, Hordeum vulgare, Oryza sativa, Solanum lycopersicum* (tomato), and brachypodium distachyon.

In some embodiments, the presently disclosed subject matter provides markers for detecting and/or assaying for the presence or absence of gene products associated with HI in a plant cell or other source of biomolecules. In some embodiments, a marker is intended to detect the presence of a nucleic acid molecule that includes the deletion junction where the maize HI sequences show an insertion in the sequence in SEQ ID NO. 53 to allow for the specific detection of the presence or absence of a chimeric nucleic acid comprising SEQ ID NO: 33, SEQ ID NO: 37, SEQ ID NO: 52 or SEQ ID NO: 53 in a sample. The number of nucleotides 5' and/or 3' of the deletion junction that allow for specific detection of the presence of absence of a chimeric nucleic acid comprising SEQ ID NO: 53 in a sample can vary based on the identification method employed, but can be in some embodiments at least about 5 nucleotides, in some embodiments at least about 10 nucleotides, in some embodiments at least about 15 nucleotides, in some embodiments at least about 20 nucleotides, in some embodiments at least about 25 nucleotides, and in some embodiments at least about 50 nucleotides 5' and/or 3' to the insertion junction on either side of nucleotides 1230-1233 in SEQ ID NO: 53 should have fit within the HI Locus and does appear in the non HI locus at this position. In some embodiments, an informative fragment of SEQ ID NO: 33, SEQ ID NO: 37, SEQ ID NO: 52 or SEQ ID NO: 53 can be a marker as defined herein below. A marker which tracks the lesion which causes the phenotype will be superior to any marker which is meerly linked because the marker to the causative lesion will never disassociate from the phenotype. Linked markers can and become disassociated by a recombination event.

The presently disclosed subject matter also provides reagents for use in detecting and/or assaying for the presence of gene products associated with HI in a plant cell or other source of biomolecules. Such reagents can include in some embodiments an amplification primer pair capable of amplifying a plant nucleic acid template to generate a marker amplicon, wherein the marker amplicon corresponds to a marker comprising an informative subsequence of SEQ ID NO: 33, SEQ ID NO: 37, SEQ ID NO: 52 or SEQ ID NO: 53, wherein the informative subsequence permits identification of the presence or absence of an allele associated with HI in a plant. By way of example and not limitation, such a amplification primer pair can be designed with a forward primer that is located 5' to the fusion junction and a reverse primer that is located 3' to the fusion junction present in SEQ ID NO: 53. Such an amplification primer pair would not be expected to amplify a gene product derived from a wildtype maize non HI locus.

In some embodiments, one or more amplification primer pairs of the presently disclosed subject matter are provided in the form of a kit, wherein the kit further comprises one or more positive and/or negative amplification primer pairs (such as but not limited to an amplification primer pair designed to amplify a wild type (HI) gene product), instructions for employing the amplification primer pairs, and/or one or more additional reagents necessary for performing an amplification reaction (e.g., a DNA polymerase, a reverse transcriptase, a buffer solution, etc.).

Thus, in some embodiments, a method for detecting and/or assaying for the presence of gene products associated with HI in a plant cell or other source of biomolecules can employ the polymerase chain reaction (PCR) using appropriately designed primers to detect the presence in a plant cell or other source of biomolecules of a gene product associated with HI (including, but not limited to a gene product comprising SEQ ID NO: 33, SEQ ID NO: 37, SEQ ID NO: 52 or SEQ ID NO: 53 or an informative fragment thereof. It is understood that other molecular biological techniques can also be employed for this purpose including, but not limited to TAQMAN® assays, KASPAR™ assays, ILLUMINA® GOLDENGATE® assays, etc.

In some embodiments, the presently disclosed subject matter provides methods for diagnostic determination of whether a plant having such DNA will or will not exhibit HI and/or producing plants that exhibit HI. In some embodiments, the methods comprise (a) transforming a plant cell with an expression cassette as disclosed herein to produce a transformed plant cell; and (b) generating a plant from the transformed plant cell.

In some embodiments, a plant cell is stably transformed with an expression cassette of the presently disclosed subject matter. "Stable transformation" or "stably transformed" is intended to mean that a polynucleotide, for example, an expression cassette as described herein, introduced into a plant integrates into the genome of the plant and is capable of being inherited by the progeny thereof, more particularly, by the progeny of multiple successive generations.

Numerous transformation vectors available for plant transformation are known to those of ordinary skill in the plant transformation arts, and the nucleic acids pertinent to the presently disclosed subject matter can be used in conjunction with any such vectors. The selection of a vector will depend upon the transformation technique to be employed and the target species for transformation. For certain target species, different antibiotic or herbicide selection markers might be preferred. Selection markers used routinely in transformation include the nptII gene, which confers resistance to kanamycin and related antibiotics (Viera & Messing, 1982; Bevan et al., 1983); the pat and bar genes, which confer resistance to the herbicide glufosinate (also called phosphinothricin; see White et al., 1990; Spencer et al., 1990; and U.S. Pat. Nos. 5,561,236 and 5,276,268); the hph gene, which confers resistance to the antibiotic hygromycin (Blochinger & Diggelmann, 1984), and the dhfr gene, which confers resistance to methatrexate (Bourouis & Jarry, 1983); the EPSPS gene, which confers resistance to glyphosate (U.S. Pat. Nos. 4,940,935 and 5,188,642); the glyphosate N-acetyltransferase (GAT) gene, which also confers resistance to glyphosate (Castle et al., 2004; U.S. Patent Application Publication Nos. 2005/0060767, 2005/0246798, and 2007/0004912); and the mannose-6-phosphate isomerase gene, which provides the ability to metabolize mannose (U.S. Pat. Nos. 5,767,378 and 5,994,629), the gene encoding a mutant D-amino acid oxidase which can be derived from *Rhodotorula gracilis*, with a lysine at position 58 rather than a phenylalanine which interacts with D-phosphinothricin to produce a toxin (U.S. Pat. No. 7,939,709).

Thus, in some embodiments the presently disclosed subject matter relates to inducing HI in a plant. In some embodiments, a general technique for producing plants that exhibit HI comprises transforming a plant cell with an expression cassette to produce a transformed plant cell, wherein the expression cassette encodes an RNAi construct targeted to a gene associated with HI; and (b) generating a plant from the transformed plant cell. After a plant cell is transformed with an expression vector or expression cassette encodes an RNAi construct targeted to a gene associated with HI, a whole plant or plant tissue can be regenerated, if desired. Methods for regeneration of plants are also well known in the art. For example, Ti plasmid vectors have been utilized for the delivery of foreign DNA, as well as direct DNA uptake, liposomes, electroporation, microinjection, and microprojectiles. In addition, bacteria from the genus *Agrobacterium* can be utilized to transform plant cells. Below are descriptions of representative techniques for transforming both dicotyledonous and monocotyledonous plants, as well as a representative plastid transformation technique.

Many vectors are available for transformation using *Agrobacterium tumefaciens*. These typically carry at least one T-DNA border sequence and include vectors such as pBIN19

(Bevan, 1984). For the construction of vectors useful in *Agrobacterium* transformation, see e.g., U.S. Patent Application Publication No. 2006/0260011. See also Lee & Glevin, 2008.

Transformation without the use of *Agrobacterium tumefaciens* circumvents the requirement for T-DNA sequences in the chosen transformation vector and consequently vectors lacking these sequences can be utilized in addition to vectors such as the ones described above which contain one or more T-DNA sequences. Transformation techniques that do not rely on *Agrobacterium* include transformation via particle bombardment, protoplast uptake (e.g., PEG and electroporation), whiskering, and microinjection. The choice of vector depends largely on the chosen selection for the species being transformed. For the construction of such vectors, see e.g., U.S. Patent Application Publication No. 2006/0260011.

For expression of a nucleotide sequence of the presently disclosed subject matter in plant plastids, plastid transformation vector pPH143 (PCT International Patent Application Publication No. WO 1997/32011, example 36) can be used. The nucleotide sequence is inserted into pPH143 thereby replacing the PROTOX coding sequence.

Transformation techniques for dicotyledons are well known in the art and include *Agrobacterium*-based techniques and techniques that do not require *Agrobacterium*. Non-*Agrobacterium* techniques involve the uptake of exogenous genetic material directly by protoplasts or cells. This can be accomplished by PEG or electroporation mediated uptake, particle bombardment-mediated delivery, and/or microinjection. Examples of these techniques are described by Paszkowski et al., 1984; Potrykus et al., 1985; Reich et al., 1986; and Klein et al., 1987. In each case the transformed cells are regenerated to whole plants using standard techniques known in the art.

*Agrobacterium*-mediated transformation is a preferred technique for transformation of dicotyledons because of its high efficiency of transformation and its broad utility with many different species. *Agrobacterium* transformation typically involves the transfer of the binary vector carrying the foreign DNA of interest (e.g., pCIB200 or pCIB2001) to an appropriate *Agrobacterium* strain which may depend of the complement of vir genes carried by the host *Agrobacterium* strain either on a co-resident Ti plasmid or chromosomally (e.g., strain CIB542 for pCIB200 and pCIB2001 (Uknes et al., 1993). The transfer of the recombinant binary vector to *Agrobacterium* is accomplished by a triparental mating procedure using *E. coli* carrying the recombinant binary vector, a helper *E. coli* strain which carries a plasmid such as pRK2013 and which is able to mobilize the recombinant binary vector to the target *Agrobacterium* strain. Alternatively, the recombinant binary vector can be transferred to *Agrobacterium* by DNA transformation (Hofgen & Willmitzer, 1988).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. Variations of this technique are disclosed in U.S. Pat. Nos. 4,945,050, 5,036,006, and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium, or a bacteriophage, each containing DNA sought to be introduced) can also be propelled into plant cell tissue.

Transformation of most monocotyledon species has now also become routine. Exemplary techniques include direct gene transfer into protoplasts using PEG or electroporation techniques, and particle bombardment into callus tissue. Transformations can be undertaken with a single DNA species or multiple DNA species (i.e., co-transformation), and both of these techniques are suitable for use with the presently disclosed subject matter. Co-transformation can have the advantage of avoiding complete vector construction and of generating transgenic plants with unlinked loci for the gene of interest and the selectable marker, thereby permitting the removal of the selectable marker in subsequent generations, should this be regarded desirable. However, a disadvantage of the use of co-transformation can be the less than 100% frequency with which separate DNA species are integrated into the genome (Schocher et al. Biotechnology 4: 1093-1096 (1986)).

European Patent Applications EP 0 292 435 and EP 0 392 225, and PCT International Patent Application Publication No. WO 1993/07278 describe techniques for the preparation of callus and protoplasts from an elite inbred line of maize, transformation of protoplasts using PEG or electroporation, and the regeneration of maize plants from transformed protoplasts. Gordon-Kamm et al., 1990) and Fromm et al., 1990 have published techniques for transformation of A188-derived maize line using particle bombardment. Furthermore, PCT International Patent Application Publication No. WO 1993/07278 and Koziel et al., 1993 describe techniques for the transformation of elite inbred lines of maize by particle bombardment. This technique utilizes immature maize embryos of 1.5-2.5 mm length excised from a maize ear 14-15 days after pollination and a BIOLISTIC® PDS-1000/He (Bio-Rad Laboratories, Hercules, Calif., United States of America) device for bombardment.

Transformation of rice can also be undertaken by direct gene transfer techniques utilizing protoplasts or particle bombardment. Protoplast-mediated transformation has been described for Japonica-types and Indica-types (Zhang et al., 1988; Shimamoto et al., 1989; Datta et al., 1990). Both types are also routinely transformable using particle bombardment (Christou et al., 1991). Furthermore, PCT International Patent Application Publication No. WO 1993/21335 describes techniques for the transformation of rice via electroporation.

European Patent Application EP 0 332 581 describes techniques for the generation, transformation and regeneration of *Pooideae* protoplasts. These techniques allow the transformation of *Dactylis* and wheat. Furthermore, wheat transformation has been described by Vasil et al., 1992 using particle bombardment into cells of type C long-term regenerable callus, and also by Vasil et al., 1993 and Weeks et al., 1993 using particle bombardment of immature embryos and immature embryo-derived callus. An exemplary technique for wheat transformation, however, involves the transformation of wheat by particle bombardment of immature embryos and includes either a high sucrose or a high maltose step prior to gene delivery. Prior to bombardment, any number of embryos (0.75-1 mm in length) are plated onto MS medium with 3% sucrose (Murashige & Skoog, 1962) and 3 mg/l 2,4-D for induction of somatic embryos, which is allowed to proceed in the dark. On the chosen day of bombardment, embryos are removed from the induction medium and placed onto the osmoticum (i.e., induction medium with sucrose or maltose added at the desired concentration, typically 15%). The embryos are allowed to plasmolyze for 2-3 hours and are then bombarded. Twenty embryos per target plate is typical, although not critical. An appropriate gene-carrying plasmid (such as pCIB3064 or pSOG35) is precipitated onto micrometer size gold particles using standard procedures. Each plate of embryos is shot with the DuPont BIOLISTICS® helium device using a burst pressure of about 1000 psi using a standard 80 mesh screen. After bombardment, the embryos are placed back into the dark to recover for about 24 hours (still on osmoticum). After 24 hours, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Transformation of monocotyledons using *Agrobacterium* has also been described. See e.g., PCT International Patent Application Publication No. WO 1994/00977 and U.S. Pat. No. 5,591,616. See also Negrotto et al., Plant Cell Reports 19: 798-803 (2000), incorporated herein by reference.

For example, rice (*Oryza sativa*) can be used for generating transgenic plants. Various rice cultivars can be used (Hiei et al., 1994; Dong et al., 1996; Hiei et al., 1997). Also, the various media constituents described below can be either varied in quantity or substituted. Embryogenic responses are initiated and/or cultures are established from mature embryos by culturing on MS-CIM medium (MS basal salts, 4.3 g/liter; B5 vitamins (200×), 5 ml/liter; Sucrose, 30 g/liter; proline, 500 mg/liter; glutamine, 500 mg/liter; casein hydrolysate, 300 mg/liter; 2,4-D (1 mg/ml), 2 ml/liter; adjust pH to 5.8 with 1 N KOH; PHYTAGEL™ plant tissue culture reagent, 3 g/liter). Either mature embryos at the initial stages of culture response or established culture lines are inoculated and co-cultivated with the *Agrobacterium tumefaciens* strain LBA4404 (*Agrobacterium*) containing the desired vector construction. *Agrobacterium* is cultured from glycerol stocks on solid YPC medium (100 mg/L spectinomycin and any other appropriate antibiotic) for about 2 days at 28° C. *Agrobacterium* is resuspended in liquid MS-CIM medium. The *Agrobacterium* culture is diluted to an $OD_{600}$ of 0.2-0.3 and acetosyringone is added to a final concentration of 200 µM. Acetosyringone is added before mixing the solution with the rice cultures to induce *Agrobacterium* for DNA transfer to the plant cells. For inoculation, the plant cultures are immersed in the bacterial suspension. The liquid bacterial suspension is removed and the inoculated cultures are placed on co-cultivation medium and incubated at 22° C. for two days. The cultures are then transferred to MS-CIM medium with Ticarcillin (400 mg/liter) to inhibit the growth of *Agrobacterium*. For constructs utilizing the PMI selectable marker gene (Reed et al., 2001), cultures are transferred to selection medium containing Mannose as a carbohydrate source (MS with 2% Mannose, 300 mg/liter Ticarcillin) after 7 days, and cultured for 3-4 weeks in the dark. Resistant colonies are then transferred to regeneration induction medium (MS with no 2,4-D, 0.5 mg/liter IAA, 1 mg/liter zeatin, 200 mg/liter timentin, 2% Mannose, and 3% Sorbitol) and grown in the dark for 14 days. Proliferating colonies are then transferred to another round of regeneration induction media and moved to the light growth room. Regenerated shoots are transferred to GA7 containers with GA7-1 medium (MS with no hormones and 2% Sorbitol) for 2 weeks and then moved to the greenhouse when they are large enough and have adequate roots. Plants are transplanted to soil in the greenhouse (To generation) grown to maturity, and the $T_1$ seed is harvested.

The plants obtained via transformation with a nucleic acid sequence of interest in the presently disclosed subject matter can be any of a wide variety of plant species, including those of monocots and dicots. The plants used in the methods of the presently disclosed subject matter are in some embodiments selected from the list of agronomically important target crops set forth elsewhere herein. The expression of a nucleic acid of the presently disclosed subject matter in combination with other characteristics important for production and quality can be incorporated into plant lines through breeding. Breeding approaches and techniques are known in the art. See e.g., Welsh, 1981; Wood, 1983; Mayo, 1987; Singh, 1986; and Wricke & Weber, 1986.

For the transformation of plastids, seeds of *Nicotiana tabacum* c.v. "Xanthienc" are germinated seven per plate in a 1" circular array on T agar medium and bombarded 12-14 days after sowing with 1 µm tungsten particles (M10, Biorad Laboratories, Hercules, Calif., United States of America) coated with DNA from plasmids pPH143 and pPH145 essentially as described in Svab & Maliga, 1993. Bombarded seedlings are incubated on T medium for two days after which leaves are excised and placed abaxial side up in bright light (350-500 µmol photons/$m^2$/s) on plates of RMOP medium (see Svab et al., 1990) containing 500 µg/ml spectinomycin dihydrochloride (Sigma, St. Louis, Mo., United States of America). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (see Sambrook & Russell, 2001). BamHI/EcoRI-digested total cellular DNA (Mettler, 1987) is separated on 1% Tris-borate (TBE) agarose gels, transferred to nylon or nitrocellulose membranes, and probed with $^{32}$P-labeled random-primed DNA sequences corresponding to a 0.7 kb BamHI/HindIII DNA fragment from pC8 containing a portion of the rps 7/12 plastid targeting sequence. Homoplasmic shoots are rooted aseptically on spectinomycin-containing MS/IBA medium (McBride et al., 1994) and transferred to the greenhouse.

To test the haploid induction capacity of newly created lines, the pollen from each line is to be crossed onto an ear to induce fertilization, and the resulting progeny of the cross subjected to ploidy analysis. Ploidy analysis can be defined in this case as any experimental test where the ploidy level of an individual plant is determined. In crosses between two non-inducing lines, the resulting progeny should be almost exclusively diploid, or 2N. However, if a haploid induction line is the male parent, the resulting progeny will be a mixed population of haploids (1N), diploids (2N), aneuploids (somewhere between 1N and 2N), and chimeras (containing tissues with mixed ploidy). The determination of haploid induction capacity can be made binary by setting a cutoff value for the haploid induction rate, which is defined as the number of haploid embryos over the total number of viable embryos. The rate should be at least greater than 0.5%, and for high stringency, a good cutoff off is greater than 1% haploids. This is because a natural 'background' haploid induction rate of around 0.1% exists in maize. Because haploidy is only induced through the male parent during in vivo maize haploid induction, the female simply serves as a "tester" and thus, the female germplasm could be any number of lines. The female tester could be the inducer line itself (and the cross would thus be a self hybridization), or the tester could be any inbred, hybrid, or backcrossed maize line. The ploidy analysis can involve different methods, as described below.

One method of plant ploidy analysis is to evaluate the phenotypic characteristics of the plant, paying attention to those characteristics associated with haploidy, including but not limited to short plant stature, altered phylotaxy, smaller leaf width, low overall body mass, and male sterility. Plants could be given a score on each characteristic and then the scores could be added together and compared to known haploid and diploid controls. In another embodiment, the embryos resulting from a haploid induction cross may be extracted mechanically from immature kernels anytime between day 9 and day 20 after pollination, and then subjected to ploidy analysis by a ploidy analyzer (Partec) which uses DAPI stain combined with flow cytometry to quantify the total DNA amount per cell. In one embodiment, embryonic and/or scutellar tissue is used for processing; in another embodiment, adult plant tissues including roots, leaves, stems, or flowers are used. In one embodiment, the selected tissues are chopped up with a razor blade, incubated in an extraction buffer, filtered through a nylon mesh filter and then incubated in a DAPI stain before loading into the ploidy analyzer. In another embodiment, embryonic or adult tissue including those described above is first digested into protoplasts using a combination of cellulose and maceroenzyme in a buffer solution, then filtered and incubated in DAPI.

In yet another method of ploidy analysis, microscopic imaging of mature, juvenile, or embryonic plant tissues can be used to identify the ploidy by counting the number of chromosomes in certain cells that are undergoing mitosis. The DNA in this case may be stained with DAPI or any other common DNA stain such as propidium iodide. In maize a diploid plant will have 20 chromosomes per cell while a haploid plant will have 10 per cell. In such an approach, the embryos can be incubated on media for anywhere from zero to fourteen days, during which many embryos may germinate and grow small rootlets.

Alone or in combination with any of the ploidy analysis methods described above, the putative novel haploid induction line may be first crossed to a marker line, including but not limited to lines that contain the R1-navajo (R1-nj) or R1-scutellum2 (R1-Scm2) markers, or any line having DNA that encode for protein products that confer a visual identifier, such as a color visible to the human eye (e.g. anthocyanin) or a fluorescence-based marker visible only via fluorescent microscopy. Such markers, having been introgressed into the putative haploid inducer line, can serve as evidence of the existence of the paternal genome in progeny indicating a diploid state, with absence indicating a haploid state. The presence or absence of the marker may be detected using a visual test or microscopy.

The presently disclosed subject matter also provides methods for identifying the presence or absence of an allele associated with HI in a plant. In some embodiments, the methods comprise (a) obtaining a sample from the plant comprising genomic and/or nuclear DNA and/or an RNA product derived therefrom; (b) contacting the sample with a pair of primers that, when used in a nucleic-acid amplification reaction with a nucleic acid sample from the plant, produces an amplicon that can be used to identify the presence or absence of an allele associated with HI; (c) amplifying a fragment from said sample using the primer pair of (b), wherein the primer pair is complementary and binds to the nucleotide sequence of (b); and (d) detecting an amplicon that can be used to identify the presence or absence of an allele associated with HI in the plant.

The presently disclosed subject matter also provides methods for introgressing HI-inducing nucleotide sequences into plants. In some embodiments, the methods comprise crossing a first plant with a second plant to produce a third plant, wherein the genome of the first plant or the second plant comprises a recombinant nucleic acid sequence encoding a HI-associated gene product of the presently disclosed subject matter. In some embodiments, the methods further comprise assaying the genome of the third plant for the presence of the recombinant nucleic acid sequence encoding the HI-associated gene product. In some embodiments, the recombinant nucleic acid comprises (a) a nucleic acid having at least 90% identity to SEQ ID NO: 33, optionally wherein the percent identity is calculated over the entire length of SEQ ID NO: 33; (b) a nucleic acid having at least 95% identity over nucleotides 91-1452 of SEQ ID NO: 33; (c) a nucleic acid that is the reverse complement of either of (a) or (b); (d) a nucleic acid that encodes a polypeptide comprising an amino acid sequence that is at least 95% identical to SEQ ID NO: 54, SEQ ID NO: 55, SEQ ID NO: 56 or SEQ ID NO: 57 optionally wherein the percent identity is calculated over the entire length of SEQ ID NO: 54, SEQ ID NO: 55, SEQ ID NO: 56 or SEQ ID NO: 57 respectively; and, (e) a sequence having at least 90% identity to SEQ ID NO: 32, optionally wherein the percent identity is calculated over the entire length of SEQ ID NO: 32; (f) a sequence having at least 95% identity over nucleotides 1-1795 of SEQ ID NO: 32; (g) a nucleic acid sequence that is the reverse complement of either of (e) or (f). In some embodiments, the recombinant nucleic acid encodes an amino acid sequence that comprises all or substantially all of amino acids 1-454 of SEQ ID NO: 54.

The presently disclosed subject matter also provides methods for selecting $F_0$ parental plants that are predicted to produce subsequent (e.g., $F_1$, $F_2$, $F_3$, etc.) generations with plants that exhibit HI. In some embodiments, the methods comprise identifying in the absence of sequence in the genome of an $F_0$ plant a nucleic acid comprising a sequence selected from the group consisting of The presently disclosed subject matter also provides kits for detecting the presence or absence of a HI-inducing allele in a plant. In some embodiments, the kits comprise one or more nucleic acid- and/or amino acid-based reagents derived from the maize HI locus or from a locus linked thereto, wherein the one or more nucleic acid- and/or amino acid-based reagents are designed to be employed in a nucleic acid- and/or amino acid-based assay for the presence or absence in the plant (a) a nucleic acid having at least 90% identity to SEQ ID NO: 33, optionally wherein the percent identity is calculated over the entire length of SEQ ID NO: 33; (b) a nucleic acid having at least 95% identity over nucleotides 91-1452 of SEQ ID NO: 33; (c) a nucleic acid that is the reverse complement of either of (a) or (b); (d) a nucleic acid that encodes a polypeptide comprising an amino acid sequence that is at least 95% identical to SEQ ID NO: 54, SEQ ID NO: 55, SEQ ID NO: 56 or SEQ ID NO: 57 optionally wherein the percent identity is calculated over the entire length of SEQ ID NO: 54, SEQ ID NO: 55, SEQ ID NO: 56 or SEQ ID NO: 57 respectively; and, (e) a sequence having at least 90% identity to SEQ ID NO: 32, optionally wherein the percent identity is calculated over the entire length of SEQ ID NO: 32; (f) a sequence having at least 95% identity over nucleotides 1-1795 of SEQ ID NO: 32; (g) a nucleic acid sequence that is the reverse complement of either of (e) or (f). In some embodiments, the recombinant nucleic acid encodes an amino acid sequence that comprises all or substantially all of amino acids 1-454 of SEQ ID NO: 54.

In some embodiments, the one or more nucleic acid- and/or amino acid-based reagents derived from the maize HI locus or from a locus linked thereto comprise one or more oligonucleotide primers that are diagnostic of the presence in the plant of in the plant of the nucleic acid having at (a) a nucleic acid having at least 90% identity to SEQ ID NO: 33, optionally wherein the percent identity is calculated over the entire length of SEQ ID NO: 33; (b) a nucleic acid having at least 95% identity over nucleotides 91-1452 of SEQ ID NO: 33; (c) a nucleic acid that is the reverse complement of either of (a) or (b); (d) a nucleic acid that encodes a polypeptide comprising an amino acid sequence that is at least 95% identical to SEQ ID NO: 54, SEQ ID NO: 55, SEQ ID NO: 56 or SEQ ID NO: 57 optionally wherein the percent identity is calculated over the entire length of SEQ ID NO: 54, SEQ ID NO: 55, SEQ ID NO: 56 or SEQ ID NO: 57 respectively; and, (e) a sequence having at least 90% identity to SEQ ID NO: 32, optionally wherein the percent identity is calculated over the entire length of SEQ ID NO: 32; (f) a sequence having at least 95% identity over nucleotides 1-1795 of SEQ ID NO: 32; (g) a nucleic acid sequence that is the reverse complement of either of (e) or (f). In some embodiments, the recombinant nucleic acid encodes an amino acid sequence that comprises all or substantially all of amino acids 1-454 of SEQ ID NO: 54.

As used herein, a "nucleic acid- or amino acid-based reagent" of the presently disclosed subject matter refers to any nucleic acid, peptide, or polypeptide that can be used to detect the presence or absence of SEQ ID NO: 33, SEQ ID NO: 37, SEQ ID NO: 52 or SEQ ID NO: 53 or an informative fragment thereof in a plant in any type of assay. By way of example and not limitation, a nucleic acid-based reagent of the presently disclosed subject matter can be an oligonucleotide primer pair that is designed to flank the deletion junction such that an amplification product will occur only if (a) a nucleic acid having at least 90% identity to SEQ ID NO: 33, optionally wherein the percent identity is calculated over the entire length of SEQ ID NO: 33; (b) a nucleic acid having at least 95% identity over nucleotides 91-1452 of SEQ ID NO: 33; (c) a nucleic acid that is the reverse complement of either of (a) or (b); (d) a nucleic acid that encodes a polypeptide comprising an amino acid sequence that is at least 95% identical to SEQ ID NO: 54, SEQ ID NO: 55, SEQ ID NO: 56 or SEQ ID NO: 57 optionally wherein the percent identity is calculated over the entire length of SEQ ID NO: 54, SEQ ID NO: 55, SEQ ID NO: 56 or SEQ ID NO: 57 respectively; and, (e) a sequence having at least 90% identity to SEQ ID NO: 32, optionally wherein the percent identity is calculated over the entire length of SEQ ID NO: 32; (f) a sequence having at least 95% identity over nucleotides 1-1795 of SEQ ID NO: 32; (g) a nucleic acid sequence that is the reverse complement of either of (e) or (f). In some embodiments, the recombinant nucleic acid encodes an amino acid sequence that comprises all or substantially all of amino acids 1-454 of SEQ ID NO: 54.

Similarly, an amino acid-based reagent of the presently disclosed subject matter can be, but is not limited to, an antibody that binds to a polypeptide having SEQ ID NO: 54, SEQ ID NO: 55, SEQ ID NO: 56 or SEQ ID NO: 57 or an informative fragment thereof. In some embodiments, an antibody that binds to both a polypeptide of SEQ ID NO: 54, SEQ ID NO: 55, SEQ ID NO: 56 or SEQ ID NO: 57 and a maize HI gene product can be employed, wherein in an appropriate assay (e.g., a Western blot or an SDS-PAGE gel), the polypeptide of SEQ ID NO: 54, SEQ ID NO: 55, SEQ ID NO: 56 or SEQ ID NO: 57 and its absence or presence shows the maize HI gene product can be distinguished. In some embodiments, the kit further comprises a set of instructions for performing an assay with the nucleic acid- or amino acid-based reagent. In some embodiments, the kit further comprises one or more additional reagents that can be employed in the performance of the assay with the nucleic acid- or amino acid-based reagent.

EXAMPLE

The following Examples provide illustrative embodiments of the presently disclosed subject matter. In light of the present disclosure and the general level of skill in the art, those of skill will appreciate that the following examples are intended to be exemplary only and that numerous changes, modifications, and alterations can be employed without departing from the scope of the presently disclosed subject matter.

Example 1

QTL Mapping Material Choices

Two mapping populations involving a haploid inducer inbred (RWK) and two non-inducer inbreds (NP2391, NP2460) were generated. RWK was selected because of its high haploid induction ability compared to stock 6. The two non-inducer lines were selected due to existence of extensive data relevant to them. The recombinant inbred populations were backcross populations (BC1) such that the theoretical allele content was 75% RWK and 25% NP2391 for the first population (138 RILs, Recombinant Inbred Lines) and 75% RWK and 25% NP2460 for the second population (123 RILs). The mapping populations were self-pollinated two generations to make the BC1F3. The subsequent BC1F4 plants were testcrossed onto eight plants in two tester rows. The testcrosses were harvested and bulk shelled. Approximately 500 kernels of testcross seed were planted for each entry to observe the number of haploid and diploid plants and thereby determine the haploid induction rate of each recombinant inbred entry within that population.

QTL analysis was performed for both the populations using a version of "QTL Cartographer" software by combining the testcross induction rates with the SNP genotyping data of RILs. QTLs were declared when the LOD score is higher than 2. In total about ~70% variation in haploid induction rate was explained by QTL Bin 1.04. A number of other QTLs were also detected but these accounted for less of the variation. The two important values in QTL studies are the LOD (logarithm of odds) and the $R^2$. A high LOD value represents greater statistical evidence for the present of a QTL, and a higher $R^2$ indicates that the particular QTL has more effect on the trait of interest. The major QTL detected was on Chromosome 1, in a somewhat different region of Chromosome 1 than what was previously indicated by a patent application publication. Additional information about the fine mapping is provided in the subsequent examples.

| Breeding - Mapping Strategy | | |
|---|---|---|
| Season | What | Result |
| Year 0 | F1 | Two non-inducers inbreds (NP2391; P2460) were crossed with RWK |
| Year 0 | F1 -> BC1 | Both F1 backcrossed to RWK |
| Year 1 | BC1F1 -> BC1F2 | |
| Year 1 | BC1F2 -> BC1F3 | |
| Year 1 | BC1F4 testcrosses made X 2 testers | Two mapping Populations x two testers |
| Year 1 | BC1F4 testcrosses phenotyped | QTL Bin 1.04 identified, ~70% variation explained |
| Year 1 | BC2 made | |
| Year 2 | BC3 made | |
| Year 2 | BC3F2 made | |
| Year 2 | BC3F3 testcrosses made X 2 testers | Two fine mapping Populations X two testers |
| Year 3 | BC3F3 testcrosses phenotyped | First fine mapping completed |
| Year 3 | BC3F4 testcrosses made X 2 testers | |
| Year 3 | BC3F4 testcrosses phenotyped | Second fine mapping completed |
| Year 4 | BC3F5 testcrosses made X 2 testers | |
| Year 5 | BC3F5 testcrosses phenotyped | Fine mapping completed |
| Year 5 | RWK, RWK-NIL, Stock 6 gemones sequences | Annotations |

Example 2

Development of Near Isogenic Lines

To accurately position and fine-map the QTL for Haploid induction, near isogenic lines (NIL's) are created by back-crossing to RWK for three generations and followed by selfing for another 3 generations. During this process several NIL's were created in RWK background with regions from NP2391 and NP2460 in the target QTL region. This particular strategy was utilized to create NIL's because, haploid induction efficiency can change with the background and also to keep the rest of the RWK genome mostly uniform while focusing on the small non-inducer chromosome regions that were back-crossed into RWK.

Example 3

Fine Mapping

When the experiment was initiated, the haploid induction locus was localized in a region of 3.3 MB containing approximately 90 putative genes within that interval. The fine mapping process reduced the haploid induction locus to a 0.88 MB region with twenty five annotated genes. Additional fine mapping reduced the haploid induction locus to a 0.60 region. The BC3F3 plants described in the above examples, which were heterozygous at the region of interest were selfed to create additional recombinations. These BC3F4 recombinants were testcrossed with two different testers and phenotypic information was gathered by measuring their haploid induction (HI) ability. The genotypic information from this localized haploid induction region and the phenotypic information taken concerning these line's haploid induction ability were correlated to fine-map the haploid induction locus to a 0.60 MB region with fewer than 7 annotated genes.

| | | | TABLE ON FINE MAPPING | | | |
|---|---|---|---|---|---|---|
| Old interval | New Confidence interval | Refined interval | Gene_ID | transcript_start | transcript_end | transcript_strand |
| x | x | x | GRMZM2G305400 | 67991172 | 67994092 | −1 |
| x | x | x | GRMZM2G082836 | 68107606 | 68110989 | 1 |
| x | x | x | GRMZM2G382717 | 68113455 | 68115168 | −1 |
| x | x | x | GRMZM2G120587 | 68133178 | 68136953 | −1 |
| x | x | x | GRMZM2G471240 | 68240862 | 68242656 | 1 |
| x | x | x | GRMZM2G471240 | 68240862 | 68242656 | 1 |
| x | x | x | GRM2M2G062320 | 68318898 | 68321409 | 1 |
| x | x | | GRMZM5G866758 | 68430654 | 68436197 | 1 |
| x | x | | GRMZM5G866758 | 68430654 | 68436197 | 1 |
| x | x | | GRMZM2G003530 | 68435670 | 68439997 | −1 |
| x | | | GRMZM2G077991 | 68543246 | 68546264 | −1 |
| x | | | GRMZM2G077991 | 68543694 | 68546264 | −1 |
| x | | | GRMZM2G077991 | 68543805 | 68546269 | −1 |
| x | | | GRMZM2G077960 | 68554980 | 68559182 | 1 |
| x | | | GRMZM2G077897 | 68561209 | 68565155 | −1 |
| x | | | GRMZM2G347583 | 68660278 | 68665995 | 1 |
| x | | | GRMZM2G173030 | 68668900 | 68671460 | 1 |
| x | | | GRMZM2G022061 | 68876150 | 68882226 | 1 |
| x | | | GRMZM2G022061 | 68876150 | 68882226 | 1 |
| x | | | GRMZM2G022061 | 68876150 | 68882226 | 1 |
| x | | | GRMZM2G022061 | 68876150 | 68882226 | 1 |
| x | | | GRMZM2G022061 | 68876150 | 68882226 | 1 |
| x | | | GRMZM2G340286 | 68928213 | 68929600 | 1 |
| x | | | GRMZM2G340279 | 68934652 | 68937080 | −1 |
| x | | | GRMZM2G347808 | 69005208 | 69012612 | 1 |

Example 4

Markers for Refining Fine Mapping

The Table shown in example four shows the marker or locus name on the far left of the table. The limiting factor for further refining the locus was the availability of markers and not the maize line recombinants. Thus additional taqman assays were developed for gathering genotypic information from the haploid induction region. The Table shows the SNPs and their map positions. Each of these markers identifies an allele. The desirable nucleotides for a haploid inducing allele in the RWK (haploid inducing line) are also listed. These markers can be utilized in a marker assisted breeding program to select for or against the haploid induction ability in germplasm.

MARKER TABLE

| Marker or Locus Name | Chromosome | Map Position | RWK Allele |
|---|---|---|---|
| SM0262A | 1 | 45441103 | G/G |
| SM0390D | 1 | 45514003 | G/G |
| SM0657AQ | 1 | 56221199 | A/A |
| SM0103A | 1 | 60144794 | A/A |
| SM2317 | 1 | 60806574 | G/G |
| SM2318 | 1 | 60808690 | A/A |
| SM2315 | 1 | 60834691 | A/A |
| SM2322 | 1 | 61019467 | G/G |
| SM1994CQ | 1 | 61940683 | C/C |
| SM1994AQ | 1 | 61948232 | A/A |
| SM2014DQ | 1 | 62141179 | A/A |
| SM2014CQ | 1 | 62141297 | G/G |
| SM1208A | 1 | 62890212 | C/C |
| SM1208BQ | 1 | 62890343 | C/C |
| SM2332 | 1 | 62890343 | C/C |
| SM2331 | 1 | 62918261 | C/C |
| SM2542 | 1 | 65086371 | A/A |
| SM2543 | 1 | 65086379 | A/A |
| SM2547 | 1 | 65086882 | C/C |
| SM2548 | 1 | 65087687 | G/G |
| SM2359 | 1 | 65222457 | C/C |
| SM2366 | 1 | 65223245 | C/C |
| SM2333 | 1 | 65657736 | G/G |
| SM2338 | 1 | 66955942 | C/C |
| SM2340 | 1 | 67130654 | G/G |
| SM2339 | 1 | 67130683 | A/A |
| SM2356 | 1 | 67645465 | A/A |
| SM2357 | 1 | 67645486 | G/G |
| SM2361 | 1 | 67850657 | G/G |
| SM2363 | 1 | 67851018 | A/A |
| SM2587 | 1 | 68128675 | A/A |
| SM2589 | 1 | 68128928 | G/G |
| SM2593 | 1 | 68129217 | G/G |
| SM2594 | 1 | 68129237 | C/C |
| SM2602 | 1 | 68130522 | A/A |
| SM2607 | 1 | 68424731 | A/A |
| SM2608 | 1 | 68428500 | A/A |
| SM2365 | 1 | 68431623 | G/G |
| SM2362 | 1 | 68431768 | C/C |
| SM2712 | 1 | 68453157 | A/A |
| SM2709 | 1 | 68454360 | G/G |
| SM2706 | 1 | 68455010 | A/A |
| SM2710 | 1 | 68565361 | C/C |
| SM2707 | 1 | 68658060 | G/G |
| SM2550 | 1 | 68670604 | C/C |
| SM2551 | 1 | 68670713 | C/C |
| SM2708 | 1 | 68678452 | A/A |
| SM2610 | 1 | 69012158 | A/A |
| SM2613 | 1 | 69158347 | A/A |
| SM2552 | 1 | 69543214 | A/A |
| SM2553 | 1 | 69587711 | G/G |
| SM2554 | 1 | 69881293 | C/C |
| SM2556 | 1 | 69887955 | A/A |
| SM2557 | 1 | 69889226 | G/G |
| SM2558 | 1 | 70155695 | A/A |
| SM2616 | 1 | 70158847 | A/A |
| SM2617 | 1 | 70159265 | A/A |
| SM2559 | 1 | 70162230 | A/A |
| SM2621 | 1 | 70164485 | A/A |
| SM2624 | 1 | 70213152 | A/A |
| SM2626 | 1 | 70244705 | A/A |
| SM2560 | 1 | 70251144 | A/A |
| SM2628 | 1 | 70347954 | A/A |
| SM2629 | 1 | 70512212 | G/G |
| SM2013BQ | 1 | 71020438 | C/C |
| SM2573 | 1 | 71066077 | C/C |
| SM2575 | 1 | 71541039 | A/A |
| SM2576 | 1 | 71590349 | A/A |
| SM2579 | 1 | 71794881 | G/G |
| SM2580 | 1 | 71794974 | C/C |
| SM2581 | 1 | 72013466 | A/A |
| SM2347 | 1 | 72233113 | G/G |
| SM2349 | 1 | 72233448 | G/G |
| SM2368 | 1 | 73246562 | G/G |
| SM2352 | 1 | 73379493 | A/A |
| SM2369 | 1 | 73380804 | C/C |
| SM2351 | 1 | 73635946 | G/G |
| SM2354 | 1 | 73966550 | G/G |
| SM2353 | 1 | 73966557 | G/G |
| SM2345 | 1 | 73967645 | A/A |
| SM0118A | 1 | 75203350 | G/G |
| SM0251A | 1 | 82575679 | G/G |
| SM0241C | 1 | 147159831 | A/A |
| SM0201B | 1 | 178008426 | A/A |
| SM1990AQ | 1 | 184012848 | G/G |
| SM0376B | 1 | 195332392 | G/G |

Example 5

New Interval Developed with Fine Mapping

As indicated in Example 4, the limiting factor for further refinement of the haploid induction QTL region was resolved with the development of additional markers for the haploid induction region on Chromosome 1. The recombinants were screened with these newly developed markers. The original haploid induction locus was reduced from a starting interval containing ~64 genes, which was then reduced its size to 17-25 genes. Further fine mapping resolved the region to 0.60 MB with 8 genes in the interval. The eight genes include two genes GRMZ2G471240, and GRMZ2G866758 which appear twice because expression data suggests alternative transcripts. Each of the genes are listed in the Table below and are identified by the public Gene ID with the transcript start and end identified. The new refined haploid induction locus is indicated in the new confidence level. With the data from a single recombinant, a subset of approximately 8 genes were identified to be highly likely to have impact on the haploid induction trait. These are indicated by the highlighted section of the third column from the left of the Haploid Interval Table below.

Table Describing Haploid Induction QTL Interval

| New Confidence interval | Refined interval | Sequencing data analysis | gene_id |
|---|---|---|---|
| x | x | Appears to be missing from all three lines | GRMZM2G305400 |

Table Describing Haploid Induction QTL Interval

| New Confidence interval | Refined interval | Sequencing data analysis | gene_id |
|---|---|---|---|
| x | x | NIL and B73 gDNAs align in coding region. RWK/Stock 6 gDNAs are very similar. All protein coding sequences appear similar. | GRMZM2G082836 |
| x | x | NIL/B73 are identical. RWK differs at several bases and three AA residues. It also has a 21 base insert just downstream of the stop codon. Stock 6 data not so good at amino terminus, but suggests it's similar to RWK at the carboxy terminus. | GRMZM2G382717 |
| x | x | Stock 6, RWK and NIL differ from B73 outside protein coding region. RWK and Stock 6 have 2 additional amino acids | GRMZM2G120587 |
| x | x | NIL and B73 are virtually identical. Stock 6 and RWK are identical and a frame shift results in 20 incorrect AA followed by a new, premature stop codon | GRMZM2G471240 |
|  | x |  | GRMZM2G471240 |
| x | x | Not present in Stock 6/RWK. NIL/B73 are virtually identical. Some evidence this is a transcribed gene. | GRMZM2G062320 |
|  | x | NIL and B73 are virtually identical. Stock 6 and RWK are identical. The pairs differ slightly at the protein level and outside the coding region. | GRMZM5G866758 |
| x |  |  | GRMZM5G866758 |
| x |  | NIL is 97-98% identical to B73; RWK/Stock 6 95-99% similar to B73. Adjacent to GRMZM5G866758 but transcribed from opposite strand. All 4 encode the same protein. | GRMZM2G003530 |

Example 6

Sequence Analysis of Inducer and Non-Inducer Genomes

The maize haploid induction locus was understood to be present in a 2.2 Mb QTL located on Chromosome 1. This QTL represents approximately 70% of the variation associated with the haploid induction trait, and is therefore required for haploid induction. To date, no one has identified the genetic element responsible for haploid induction. As indicated in the earlier examples the haploid induction QTL was fine-mapped to reduce its size to 0.60 Mb In order to further identify the genes in this Haploid Induction region, the genomes of two haploid inducer lines, Stock 6 and RWK, and an RWK-NIL line were sequenced. Stock 6 is a maize haploid inducer line which is available from the Maize Genetics Stock Center in Champaign Ill. RWK is a maize line which is a haploid inducer line available from the University of Hohenhiem in Germany. B73 is a stiff stalk maize line produced and is broadly available from many sources including the Iowa State University in Ames, Iowa Genomic DNA from the leaf tissue of RWK, RWK-NIL, and Stock 6, was prepared and fragmented to produce two short-insert paired end (SIPE) libraries and one long-insert paired end (LIPE) library. Sufficient DNA sequence data were generated for 50× coverage of each genome, as indicated in the table below. The raw data were trimmed and compiled into sequence contigs. B73 sequence data for the Haploid Induction QTL on Chromosome 1 was used as a scaffold to enrich and refine contigs corresponding to this region from each genome.

Sequence Coverage

|  | SIPE data | | LIPE data | | | | |
|---|---|---|---|---|---|---|---|
|  | total Mb | Coverage | total Mb | coverage | total cov | % SIPE | % LIPE |
| Stock6 | 185,117 | 74.0 | 47,301 | 18.9 | 93.0 | 80% | 20% |
| NIL | 117,060 | 46.8 | 17,649 | 7.1 | 53.9 | 87% | 13% |
| RNK | 215,666 | 86.3 | 28,108 | 11.2 | 97.5 | 88% | 12% |

Total = total Mb of sequence data
coverage = average depth of sequence coverage (based on maize genome estimate of 2.5 Gb)
SIPE = short insert paired end library data (average insert size ~330 bp)
LIPE = long insert paired end library data (average insert size ~5000 bp)
Sequencing target was >=50× coverage, >=10% of data from LIPE reads The contigs were assembled and analyzed. The process produced ~300 contigs. These were then BLASTed against the 25 genes found within the HI interval. The candidate sequence from each line was annotated and compared. Expression was verified by cDNA/EST analysis, and the annotation was verified by cDNA/gDNA alignment. The differences between the lines were noted and distinguished. (see Tables in earlier examples.)

Example 7

Sequence Analysis of Inducer and Non-Inducer Genomes

The assembled Stock 6, RWK and NIL (RWK-NIL) sequence contigs were compared to corresponding B73 sequence data. Gene models for each candidate gene were confirmed with additional sequence data from public and proprietary databases. The sequence data for each gene in the reduced HI interval were compared.

Structural Variants in Haploid Induction Interval

| Gene | structural variants? | # SNPs altering protein sequence | annotation |
|---|---|---|---|
| GRMZM2G120587 | No | 3 | Serine carboxypeptidase |
| GRMZM2G471240 | No | 4 | Patatin-like phospholipase |
| GRMZM2G062320 | Yes | 1 | Histidine phosphatase superfamily, Phosphoglycerate mutase family |
| AC213048.3 | No | 0 | pseudogene/hypothetical protein |
| GRMZM5G866758 | Yes | 2 | acetyl-CoA acetyltransferase, cytosolic 1 [Zea mays] |
| GRMZM2G003530 | Yes | 2 | Putative uncharacterized protein |
| GRMZM2G077991 | Yes | 2 | Ribosomal protein L37e |
| GRMZM2G077960 | No | 0 | Protein phosphatase 2C family protein |

Structural Variants in Haploid Induction Interval

| Gene | structural variants? | # SNPs altering protein sequence | annotation |
|---|---|---|---|
| GRMZM2G077897 | No | 15 | Plant protein of unknown function, paramyosin, |
| GRMZM2G347583 | No | 2 | uncharacterized protein |
| GRMZM2G173030 | No | 0 | hypothetical protein |
| GRMZM2G031591 | Yes | 0 | hypothetical protein |
| GRMZM2G070462 | Yes | 0 | FHA domain-containing protein |
| GRMZM2G022061 | No | 5 | hypothetical protein LOC100279962 (LOC100279962 |
| GRMZM2G340286 | No | 4 | uncharacterized protein |
| GRMZM2G340279 | Yes | 8 | pentatricopeptide repeat-containing protein |
| GRMZM2G347808 | No | 4 | uncharacterized protein |

The experiment did not find DNA sequence evidence that GRMZM2G305400 is present in the Stock 6, RWK or Nil genomes.

The gene GRMZM2G062320 is encoding a phosphoglycerate mutase and is absent in RWK and Stock 6 but present in NIL and B73. This result will be tested by PCR. This gene product has expression in most plant tissues and stages of development. The gene product can be classified as a phosphoglycerate mutase and has sequence that places it in the histidine phosphatase superfamily.

We noted that other genes in the refined HI interval differ in sequence between the various genomes we examined. GRMZM2G471240 encodes a phospholipase that is exclusively expressed in meiotic anthers, and has a four nucleotide insertion resulting in 20 incorrect AA followed by a new, premature stop codon.

GRMZM2G120587 encodes a serine carboxypeptidase-like 51 (SCPL51) that is expressed in anthers and is a good candidate for a haploid induction because proteolysis has been shown to contribute towards centromere-specific localization of CENH3 proteins. The proteins encoded by RWK and Stock 6 have 2 additional amino acids.

GRMZM2G305400 encodes a cyclin and this gene was not present in the inducers or NIL, but it was present in B73.

GRMZM2G082836 gDNAs in Stock 6 and RWK are more similar to each other, and the GRMZM2G082836 gDNAs in NIL and B73 gene are more similar to each other. However the GRMZM2G082836 protein coding sequences of Stock 6, RWK, NIL and B73 are identical. This gene encodes a GTP-binding protein 1.

GRMZM2G382717 gDNAs in the NIL and B73 lines are identical. Sequence coverage for Stock 6 was not complete, but the available data align precisely to the RWK sequence data. RWK differs from NIL/B73 at several bases and at three amino acids, and there is an additional 21 base pair insertion in RWK downstream of the translation stop codon. This gene encodes a chaperone DnaJ-domain superfamily protein.

GRMZM5G866758 gDNAs from the B73 and NIL lines are virtually identical. GRMZM5G866758 gDNAs from the inducer lines, RWK and Stock 6, are identical. The data indicate some sequence differences between RWK/stock 6 and B73/NIL at the protein level and outside the protein coding sequence. This gene encodes an acetoacetyl-CoA thiolase 2.

Example 8

A Method to Knock Out GRMZM2G062320 Expression in Pollen

Any unique GRMZM2G062320 transcript sequence ranging from 200-500 contiguous bases can be used to make an RNAi molecule targeting this gene. Sequences comprising the double stranded RNA can separate by an intron, or other DNA strand that doesn't constrain formation of the GRMZM2G062320 double-strand RNA. Any number of constitutive promoters could be selected. A short list of some constitutive promoters include ZmUbi1, ZmUbi158, ZmUbi361, SbUbiCh3, SbUbiCh4. Pollen specific: Pollen-specific genes have been described for maize (Lopez I, Anthony, R. G., Maciver, S. K., Jaing, C.-J., Khan, S., Weeds, A. G., Hussey, P. J. (1996) Pollen specific expression of maize genes encoding actin depolymerizing factor-like proteins. Proc Natl Acad Sci USA 93:7415-7420.) Such information can be used to identify other maize pollen-specific genes and produce pollen-specific expression cassettes. A general expression cassette design strategy is given in U.S. Pat. No. 8,129,588. Use of the NOS, AGS terminator components in the design is optional. The gene regulatory sequences are derived from the ZmABP2 gene (Lopez I, Anthony, R. G., Maciver, S. K., Jaing, C.-J., Khan, S., Weeds, A. G., Hussey, P. J. (1996) Pollen specific expression of maize genes encoding actin depolymerizing factor-like proteins. Proc Natl Acad Sci USA 93:7415-7420.).

Example 9

Example Demonstrating Conservation of GRMZM2G062320 Protein Sequence in Maize Syngenta's Maize Solexa Association panel is a collection of RNA-seq data derived from 790 lines. Lines in this collection were chosen based on their phenotypic and genotypic diversity from a larger collection of maize germplasm. Seedling leaf tissue was used to generate the data. The largest open reading frame for each cDNA was translated to the encoded protein for each line. The proteins were then compared to establish diversity across all lines. This evidence shows that there are five GRMZM2G062320 variants in this collection. Sequence analysis of these 790 diverse maize lines showed that version A, SEQ ID NO: 5 is present in 784 lines, version B, SEQ ID NO: 2 is present in 3 lines and versions C SEQ ID NO: 6, D SEQ ID NO: 7, and E SEQ ID NO: 8 are present in one line each. The protein sequences are derived from RNA-seq data. The evidence suggests the GRMZM2G062320 protein is highly conserved.

```
>SEQ ID NO: 5 GRMZM2G062320-A
MAGAISHHALAFSQSHWCSAKNSRFGKRTGNARLVYLKGRCGSGSRKLGL

MWASSSQSSVMEPTHLPSDGNSSHTPKKSSESALILIWHGESLWNEKNLF

TGCIDVPLTPKGVEEAIEAGKRICNIPIDVIYTSSLICAQMTAMLAMMQH

RRKKIPVITHNESEQAHRWSQIYSEETMKQSIPVITAWQLNERMYGELQG

LNKQETVDRFGKEQVHEWHRSYDIPPPNGESLEKCAERAVAYFKDQIIPQ

LVAGKHVMVAAHGNSLRSIIMHLDKLTSQKVISLELSTGIPMLYIFKEGK

FIRRGTPVGPSEASVYAYTRTKRFAEHITFQNKLA

>SEQ ID NO: 2 GRMZM2G062320-B
```

-continued

```
MAGAISHHALAFSQSHWCSAKNSRFGKRTGNARLVYLKGRCGSGSRKLGL

MWASSSQSSVMEPTHLPSDGNSSHTPKKSSESALILIWHGESLWNEKNLF

PGCIDVPLTPKGVEEAIEAGKRICNIPIDVIYTSSLICAQMTAMLAMMQH

RRKKILVITHNESEQAHRWSQIYSEETMKQSIPVITAWQLNERMYGELQG

LNKQETVDRFGKEQVHEWRRSYDIPPPNGESLEKCAERAVAYFKDQIIPQ

LVAGKHVMVAAHGNSLRSIIMHLDKLTSQKVISLELSTGIPMLYIFKEGK

FIRRGTPVGPSEASVYAYTRTKRFAEHITFQNKLA

>SEQ ID NO: 6 GRMZM2G062320-C
MAGAISHHALAFSQSHWCSAKNSRFGKRTGNARLVYLKGRCGSGSRKLGL

MWASSSQSSVMEPTHLPSDGNSSHTPKKSSESALILIWHGESLWNEKNLF

PGCIDVPLTPKGVEEAIEAGKRICNIPIDVIYTSSLICAQMTAMLAMMQH

RRKKIPVITHNESEQAHRWSQIYSEETMKQSIPVITAWQLNERMYGELQG

LNKQETVDRFGKEQVHEWHRSYDIPPPNGESLEKCAERAVAYFKDQIIPQ

LVAGKHVMVAAHGNSLRSIIMHLDKLTSQKVISLELSTGIPMLYIFKEGK

FIRRGTPVGPSEASVYAYTRTKRFAEHITFQNKLA

>SEQ ID NO: 7 GRMZM2G062320-D
MAGAISHHALAFSQSHWCSAKNSRFGKRTGNARLVYLKGRCGSGSRKLGL

MWASSSQSSVMEPTHLPSDGNSSHTPKKSSESALILIWHGESLWNEKNLF

TGCIDVPLTPKGVEEAIEAGKRICNIPIDVIYTSSLICAQMTSMLAMMQH

RRKKIPVITHNESEQAHRWSQIYSEETMKQSIPVITAWQLNERMYGELQG

LNKQETVDRFGKEQVHEWHRSYDIPPPNGESLEKCAERAVAYFKDQIIPQ

LVAGKHVMVAAHGNSLRSIIMHLDKLTSQKVISLELSTGIPMLYIFKEGK

FIRRGTPVGPSEASVYAYTRTKRFAEHITFQNKLA

>SEQ ID NO: 8 GRMZM2G062320-E
MAGAISHHALAFSQSHWCSAKNSRFGKRTGNARLVYLKGRCGSGSRKLGL

MWASSSQSSVMEPTHLPSDGNSSHTPKKSSESALILIWHGESLWNEKNLF

TGCIDVPLTPKGVEEAIEAGKRICNIPIDVIYTSSLICAQMTSMLAMMQH

RRKKIPVITHNESEQAHRWSQIYSEETMKQSIPVITAWQLNERMYGELQG

LNKQETVDRFGKEQVHEWRRSYDIPPPNGESLEKCAERAVAYFKDQIIPQ

LVAGKHVMVAAHGNSLRSIIMHLDKLTSQKVISLELSTGIPMLYIFKEGK

FIRRGTPVGPSEASVYAYTRTKRFAEHITFQNKLA
```

Example 10

PCR Experiments to Determine the Presence or Absence of GRMZM2G062320 in the Haploid Inducer Lines These pairs worked as expected on NIL, RWK, and Stock6 DNA: NIL gDNA only amplified the NIL primer pair. RWK and Stock6 gDNA only amplified the RWK/Stock6 primer pair, which specifically detects the frameshift allele. The PCR products were sequenced and the sequences were identical to that from whole genome sequencing. The primer pairs are "nil.F1/R1" and "rwk.F1/R1".

Three PCR reactions spanning all but the first two exons of the gene model amplified in RWK and Stock6, and the amplicons had the correct size PCR gel band. These bands were excised from the gel, sub-cloned and sequenced, and were found to be nearly identical in sequence to the B73 and NIL amplicons, except for a few single nucleotide polymorphisms (SNPs). These SNPs may represent normal genetic drift because none of them caused non-conservative amino acid substitutions. The 5' end of the gene model could not be detected by PCR in RWK, Stock6, or NIL DNA samples. After multiple rounds of PCR and primer redesign, the 5' end was never amplified or cloned in any of the lines. Overall, this data contradicts the genome assemblies, suggesting that at least part of the gene model exists in RWK and Stock6 inducers.

One primer pair, designed to amplify a ~400 bp amplicon spanning exons 6-8, not only amplified in all lines tested, but the DNA sequence also matched B73 with 100% nucleotide identity. This primer pair was used to query a panel of high, low, and non-inducer maize plants. The high inducers all give greater than 7% haploid embryos upon outcrossing through the male (>7% haploid induction rate (HIR)). The low inducers have a HIR between 1 and 3%, and the non-inducers have a HIR of <0.1%. All of the high and low inducer lines were derived from the original Stock6 line, and thus it is assumed that the lesion responsible for haploid induction should be present in all high and low inducers, and absent in non-inducers.

When the exon 6-8 PCR primers were tested on these DNA samples, a band of the correct size and sequence was found in 9/9 non-inducers, 8/12 high inducers, and 6/7 low inducers. No band was present in 4/12 high inducers and 1/7 low inducers (Table 1). This indicates that, contrary to the sequencing data, this gene does exist in RWK and Stock6, but in various other induction lines, there may be presence/absence variation but it does not correlate with induction capacity. This makes it difficult to explain how GRMZM2G062320 is responsible for haploid induction.

| GRMZM2G062320<br>PCR test for presence of amplicon exon 6-8 | Induction Rate | Band present? |
|---|---|---|
| Controls: | | |
| Stock 6 (low) | 2.50% | + |
| RWK (high) | 12% | + |
| RWK-NIL (non) | <1% | + |
| High Inducers: | | |
| ZMS | 7% | − |
| Z19-PR | 7% | − |
| RWS-Z86 | 10% | + |
| K13 | 9% | + |
| (ID3002/Z22)B > 29-5 > 2-5-1-B- | 7% | − |
| Z-19-//AF4031PR//Z-19-)1-1-2-3-1-3-B- | 9.5% | + |
| ZR86 | 12% | + |
| ZR53 | 12% | − |
| ZR75 | 13% | + |
| (Z21/RWS)B(GS)-75-1-2-3-B- | ~8% | + |
| AX5707 inducer-good | ~9% | + |
| Poor Inducers: | | |
| Stock6 R1-nj | 2.5% | + |
| (Z21/RWS//[RWS]B$)33-5- | <2% | + |
| (K-13-/(ZMS/SEW-PR)B > 2 > B-9//K-13-)2-4-1- | <2% | + |
| (K-13-/(ZMS/SEW-PR)B > 2 > B-9//K-13-)6-1-2- | <2% | + |
| (ZMS/SEW-PR)B > 2 > B-7-2-1-2- | <2% | − |
| AX5707 inducer-low | ~3% | + |
| Non-inducers: | | |
| Stock6 R1-nj B1Pl1 | <0.1% | + |
| (Z-21-/AF4031PR//Z-21-1-B-)1-1-1-1-B- | <0.1% | + |
| FF6096 | <0.1% | + |
| ID5829 | <0.1% | + |
| XO5744 | <0.1% | + |
| ID3002 | <0.1% | + |

-continued

| GRMZM2G062320 PCR test for presence of amplicon exon 6-8 | Induction Rate | Band present? |
|---|---|---|
| AF4031PR | <0.1% | + |
| AX5707 | <0.1% | + |

Example 11

PCR Experiments to Determine the Presence or Absence of GRMZM2G471240 in the Haploid Inducer Lines In order to develop a PCR test that would distinguish between RWK/Stock6 and NIL haplotypes, two primer pairs were designed: one pair should amplify the RWK/Stock6 frame-shift allele, while the other should amplify the B73/NIL allele.

```
For STOCK6/RWK allele (mutant, frameshift allele):
rwk.F1
TACGCCGTGCGCTAACATA rwk.R1
GTACCTCGCTCCCTGTCTCC SIZE: 822 bp FOR B73/RWK-NIL
nil.F1
GTACGCCGTGCGCTAACA nil.R1
TCGTACCTCCCTGTCTCCAC

SIZE: 821
```

Use: In a PCR reaction, these would be used at 500 nMol final concentration. The reaction may also contain:
1×PCR reaction buffer
200 uM of dNTPs (dATP, dCTP, dGTP, and dTTP)
<250 ng of genomic DNA
deionized water
Taq enzyme (1 unit—many different types available—usually 0.2 uL or 0.5 uL depending on the units/uL
magnesium chloride or magnesium sulfate (1 mM)
Reaction volume: 25 or 50 uL
recommended reaction:
1. 95 degrees C. 3'
2. 95 degrees C. 30" (denature)
3. 62 degrees C. 30" (anneal)
4. 72 degrees C. 1' (extend)
5. Repeat steps 2-4, 35 times
6. 72 degrees C., 10" (final extension)
7. 4 degrees C., forever These pairs worked as expected on NIL, RWK, and Stock6 DNA, NIL gDNA only amplified the NIL primer pair. RWK and Stock6 gDNA only amplified the RWK/Stock6 primer pair, which specifically detects the frame-shift allele. The PCR products were sequenced and the sequences were identical to that from whole genome sequencing. SNPs that were identified in the whole genome sequencing were confirmed in the PCR products (data not shown). The primer pairs are "nil.F1/R1" and "rwk.F1/R1". Detecting the Frame-Shift Mutation in the Panel of Inducer Lines:

The "rwk.F1/R1" and "nil.F1/R1" primer pairs were used to genotype the panel of high, low, and non-inducers. The data indicates that the frame-shift allele correlates with induction capacity. 14/14 high and 7/7 low inducers amplified the RWK/Stock6 allele, but not the NIL allele, while 9/9 non-inducers amplified the NIL allele, but not the RWK/Stock6 allele (Table 2).

| GRMZM2G471240 | Induction Rate | RWK amplicon | NIL amplicon |
|---|---|---|---|
| Controls: | | | |
| Stock 6 (low) | 2.50% | + | − |
| RWK (high) | 12% | + | − |
| RWK-NIL (non) | <1% | − | + |
| Good Inducers: | | | |
| ZMS | 7% | + | − |
| Z19-PR | 7% | + | − |
| Z22 | 7% | | |
| Z21 | 7% | | |
| RWS-Z86 | 10% | + | − |
| K13 | 9% | + | − |
| (ID3002/Z22)B > 29-5 > 2-5-1-B- | 7% | + | − |
| Z-19-//AF4031PR//Z-19-)1-1-2-3-1-3-B- | 9.5% | + | − |
| ZR86 | 12% | + | − |
| ZR53 | 12% | + | − |
| ZR75 | 13% | + | − |
| (Z21/RWS)B(GS)-75-1-2-3-B- | ~8% | + | − |
| AX5707 inducer-good | ~9% | + | − |
| Poor Inducers: | | | |
| Stock6 R1-nj | 2.5% | + | − |
| (Z21/RWS//[RWS]B$)33-5- | <2% | + | − |
| (K-13-/(ZMS/SEW-PR)B > 2 > B-9//K-13-)2-4-1- | <2% | + | − |
| (K-13-/(ZMS/SEW-PR)B > 2 > B-9//K-13-)6-1-2- | <2% | + | − |
| (ZMS/SEW-PR)B > 2 > B-7-2-1-2- | <2% | + | − |
| AX5707 inducer-low | ~3% | + | − |
| Non-inducer Lines and Donors: | | | |
| Stock6 R1-nj B1Pl1 | <0.1% | − | + |
| (Z-21-/AF4031PR//Z-21-1-B-)1-1-1-1-B- | <0.1% | − | + |
| FF6096 | <0.1% | − | + |
| ID5829 | <0.1% | − | + |
| XO5744 | <0.1% | − | + |
| ID3002 | <0.1% | − | + |
| AF4031PR | <0.1% | − | + |
| AX5707 | <0.1% | − | + |

Example 12

A Method to Knock Out GRMZM2G471240 Expression

Any unique GRMZM2G471240 transcript sequence ranging from 200-1000 contiguous bases can be used to make an RNAi molecule targeting this gene. Sequences comprising the double stranded RNA can separate by an intron, or other DNA strand that doesn't constrain formation of the GRMZM2G471240 double-strand RNA. Any number of constitutive promoters could be selected. A short list of some constitutive promoters include ZmUbi1, ZmUbi158, ZmUbi361, SbUbiCh3, SbUbiCh4. Pollen specific: Pollen-specific genes have been described for maize (Lopez I, Anthony, R. G., Maciver, S. K., Jaing, C.-J., Khan, S., Weeds, A. G., Hussey, P. J. (1996) Pollen specific expression of maize genes encoding actin depolymerizing factor-like proteins. Proc Natl Acad Sci USA 93:7415-7420.) Such information can be used to identify other maize pollen-specific genes and produce pollen-specific expression cassettes. An effective expression cassette to accomplish this in pollen is shown in FIG. 1. A general expression cassette design strategy is given in U.S. Pat. No. 8,129,58. Use of the NOS, AGS terminator components in the design is optional. The gene regulatory sequences are derived from the ZmABP2 gene (Lopez I, Anthony, R. G., Maciver, S. K., Jaing, C.-J., Khan, S., Weeds, A. G., Hussey, P. J. (1996) Pollen specific expression of maize genes encoding actin depolymerizing factor-like proteins. Proc Natl Acad Sci USA 93:7415-7420.). Expression constructs have been built comprising The promoter of GRMZM2G471240 as in SEQ ID NO: 58 operably linked to the hairpin construct in SEQ ID NO: 60 operably linked to the terminator of SEQ ID NO:59. Another construct was made with The promoter of GRMZM2G471240 as in SEQ ID NO: 58 operably linked to the hairpin construct in SEQ ID NO: 61 operably linked to the terminator of SEQ ID NO:59.

Example 13

Generation of Transgenic Maize Plants

Transformation of immature maize embryos is performed essentially as described in Negrotto et al., Plant Cell Reports 19:798-803 (2000). Various media constituents described therein can be substituted.

Agrobacterium strain LBA4404 (Invitrogen) containing the plant transformation plasmid is grown on YEP (yeast extract (5 g/L), peptone (10 g/L), NaCl (5 g/L), 15 g/l agar, pH 6.8) solid medium for 2 to 4 days at 28° C. Approximately 0.8×109 Agrobacteria are suspended in LS-inf media supplemented with 100 μM acetosyringone (As) (LSAs medium) (Negrotto et al., Plant Cell Rep 19:798-803 (2000)). Bacteria are pre-induced in this medium for 30-60 minutes. Immature embryos from maize line, A188, or other suitable maize genotypes are excised from 8-12 day old ears into liquid LS-inf+100 μM As (LSAs). Embryos are vortexed for 5 seconds and rinsed once with fresh infection medium. Infection media is removed and Agrobacterium solution is then added and embryos are vortexed for 30 seconds and allowed to settle with the bacteria for 5 minutes. The embryos are then transferred scutellum side up to LSAs medium and cultured in the dark for two to three days. Subsequently, between 20 and 25 embryos per petri plate are transferred to LSDc medium supplemented with cefotaxime (250 mg/l) and silver nitrate (1.6 mg/l) (Negrotto et al., Plant Cell Rep 19:798-803 (2000)) and cultured in the dark for 28° C. for 10 days.

Immature embryos producing embryogenic callus are transferred to LSD1M0.5S medium (LSDc with 0.5 mg/l 2,4-D instead of Dicamba, 10 g/l mannose, 5 g/l sucrose and no silver nitrate). The cultures are selected on this medium for 6 weeks with a subculture step at 3 weeks. Surviving calli are transferred either to LSD1M0.5S medium to be bulked-up or to Reg1 medium (as described in Negrotto et al., Plant Cell Rep 19:798-803 (2000)). Calli transformed with an agrobacterium binary vector carrying the RNAi expression cassette comprising or SEQ ID NO: 61 are surviving selection indicating successful transformation. See FIG. 1. An agrobacterium binary vector carrying the RNAi expression cassette comprising or SEQ ID NO: 60 will be transformed into maize. Following culturing in the light (16 hour light/8 hour dark regiment), green tissues will be transferred to Reg2 medium without growth regulators (as described in Negrotto et al., Plant Cell Rep 19:798-803 (2000)) and incubated for 1-2 weeks. Plantlets will be transferred to Magenta GA-7 boxes (Magenta Corp, Chicago Ill.) containing Reg3 medium (as described in Negrotto et al. (2000)) and grown in the light. Plants that are PCR positive for PMI and negative for Spectinomycin will be transferred to soil and grown in the greenhouse.

Example 14

Haploid Induction

T0 transgenic plants expressing an RNAi construct which silences GRMZM2G471240 will be tested for haploid induction capacity. The pollen from each plant is to be crossed onto an ear to induce fertilization, and the resulting progeny of the cross subjected to ploidy analysis. Ploidy analysis can be defined in this case as any experimental test where the ploidy level of an individual plant is determined. In crosses between two non-inducing lines, the resulting progeny should be almost exclusively diploid, or 2N. However, if a haploid induction line is the male parent, the resulting progeny will be a mixed population of haploids (1N), diploids (2N), aneuploids (somewhere between 1N and 2N), and chimeras (containing tissues with mixed ploidy). The determination of haploid induction capacity can be made binary by setting a cutoff value for the haploid induction rate, which is defined as the number of haploid embryos over the total number of viable embryos. The rate should be at least greater than 0.5%.

REFERENCES

All references listed below, as well as all references cited in the instant disclosure, including but not limited to all patents, patent applications and publications thereof, scientific journal articles, and database entries (e.g., GEN-BANK® database entries and all annotations available therein) are incorporated herein by reference in their entireties to the extent that they supplement, explain, provide a background for, or teach methodology, techniques, and/or compositions employed herein.

Abler et al. (1993) Isolation and characterization of a genomic sequence encoding the maize Cat3 catalase gene. *Plant Mol Biol* 22: 1031-1038.

Allison et al. (1986) The nucleotide sequence of the coding region of tobacco etch virus genomic RNA: evidence for the synthesis of a single polyprotein. *Virology* 154:9-20.

Ardlie et al. (2002) Patterns of linkage disequilibrium in the human genome. *Nature Reviews Genetics* 3:299-309.

Ausubel et al. (1988) *Current Protocols in Molecular Biology*, John Wiley & Sons, New York, N.Y., United States of America.

Barret P, Brinkmann M, Beckert M. 2008. A major locus expressed in the male gametophyte with incomplete penetrance is responsible for in situ gynogenesis in maize. *Theoretical and Applied Genetics* 117, 581-594.

Benfey & Chua (1990) The Cauliflower Mosaic Virus 35S Promoter: Combinatorial Regulation of Transcription in Plants. *Science* 250: 959-966.

Bennett M D, Finch R A, Barclay I R. 1976. The time rate and mechanism of chromosome elimination in Hordeum hybrids. *Chromosoma* 54, 175-200.

Bevan (1984) Binary *Agrobacterium* vectors for plant transformation. *Nucl Acids Res* 12:8711-8721.

Bevan et al. (1983) A chimeric antibiotic resistance gene as a selectable marker for plant cell transformation. *Nature* 304:184-187.

Binder et al. (1996) Regulation of gene expression in plant nuclear. *Plant Mol Biol* 32:303-314.

Birchler J A. 1993. Dosage analysis of maize endosperm development. *Annual Review of Genetics* 27, 181-204.

Birchler J A, Gao Z, Sharma A, Presting G G, Han F. 2011. Epigenetic aspects of centromere function in plants. *Current Opinion in Plant Biology* 14, 217-222.

Blair et al. (1999) Inter-simple sequence repeat (ISSR) amplification for analysis of microsatellite motif frequency and fingerprinting in rice (*Oryza sativa* L.). *Theor Appl Genet* 98:780-792.

Blochinger & Diggelmann (1984) Hygromycin B phosphotransferase as a selectable marker for DNA transfer experiments with higher eucaryotic cells. *Mol Cell Biol* 4:2929-2931.

Bourouis & Jarry (1983) Vectors containing a prokaryotic dihydrofolate reductase gene transform Drosophila cells to methotrexate-resistance. *EMBO J* 2:1099-1104.

Braun & Schmitz (1999) The protein-import apparatus of plant nuclear. *PLANTA* 209:267-274.

Brookes (1994) The essence of SNPs. *Gene* 234:177-186.

Bustos et al. (1989) Regulation of beta-glucuronidase expression in transgenic tobacco plants by an A/T-rich, cis-acting sequence found upstream of a French bean beta-phaseolin gene. *Plant Cell* 1:839-854.

Callis et al. (1987) Introns increase gene expression in cultured maize cells. *Genes Develop* 1:1183-1200.

Castle et al. (2004) Discovery and directed evolution of a glyphosate tolerance gene. *Science* 304:1151-1154.

Chalyk, S. T., 1994 Properties of maternal haploid maize plants and potential application to maize breeding. *Euphytica* 79: 13-18.

Chalyk, S. T., A. Baumann, G. Daniel, and J. Eder, 2003 Aneuploidy as a possible cause of haploid-induction in maize. Maize Genet. Newsl. 77: 29-30.

Chang, M., and E. H. Coe, 2009 Doubled haploids, pp. 127-142 in Molecular Genetic Approaches to Maize Improvement, edited by A. L. Kritz and B. Larkins Springer-Verlag, Berlin.

Chase (2007) Haploid induction: a window to the world of plant 1—nuclear interactions. *Trends in Genetics* 23:81-90.

Chase, S. S., 1952 Monoploids in maize, pp. 389-399 in Heterosis, edited by J. W. Gowen. Iowa State College Press, Ames, Iowa.

Chen et al. (2003) Temporal and spatial control of gene silencing in transgenic plants by inducible expression of double-stranded RNA. *Plant J* 36:731-740.

Choi et al. (1995) Tissue-specific and developmental regulation of a gene encoding a low molecular weight sulfur-rich protein in soybean seeds. *Mol Gen Genet* 246:266-268.

Christensen et al. (1989) Sequence analysis and transcriptional regulation by heat shock of polyubiquitin transcripts from maize. *Plant Mol Biol* 12:619-632.

Christensen et al. (1992) Maize polyubiquitin genes: structure, thermal perturbation of expression and transcript splicing, and promoter activity following transfer to protoplasts by electroporation. *Plant Mol Biol* 18:675-689.

Christou et al. (1991) Production of Transgenic Rice (*Oryza Sativa* L.) plants from agronomically important Indica and Japonica varieties via electric discharge particle acceleration of exogenous DNA into immature zygotic embryos. *Nature Biotechnol* 9:957-962.

Coe, E. H., 1959 A line of maize with high haploid frequency. Am. Nat. 93: 381-382.

Conceicao et al. (1994) A cotyledon regulatory region is responsible for the different spatial expression patterns of *Arabidopsis* 2S albumin genes. *Plant* 5:493-505.

Dasgupta et al. (1993) Cloning and sequencing of 5' flanking sequence from the gene encoding 2S storage protein, from two *Brassica* species. *Gene* 133:301-302.

Datta et al. (1990) Genetically engineered fertile Indica-rice recovered from protoplasts. *Nature Biotechnol* 8:736-740.

Deimling, S., F. K. Röber, and H. H. Geiger, 1997 Methodology and genetics of in vivo haploid induction in maize. Vortr. Pflanzenzüchtg. 38: 203-224.

Della-Cioppa et al. (1987) Protein trafficking in plant cells. *Plant Physiol* 84:965-968.

Dong et al. (1996) Characterization of rice transformed via an *Agrobacterium*-mediated inflorescence approach. *Molecular Breeding* 2:267-276.

Dong et al. (2013) Fine mapping of qhir1 influencing in vivo haploid induction in maize. Theor. Appl. Genet. 126: 1713-1720.

Dunwell J M. 2010. Haploids in flowering plants: origins and exploitation. *Plant Biotechnology Journal* 8, 377-424.

Eldar, A., V. K. Chary, P. Xenopoulos, M. E. Fontes, O. C. Losón et al., 2009 Partial penetrance facilitates developmental evolution in bacteria. Nature 460: 510-514.

Elroy-Stein et al. (1989) Cap-independent translation of mRNA conferred by encephalomyocarditis virus 5' sequence improves the performance of the vaccinia virus/bacteriophage T7 hybrid expression system. *Proc Natl Acad Sci USA* 86:6126-6130.

Estruch et al. (1994) Cloning and characterization of a maize pollen-specific calcium-dependent calmodulin-independent protein kinase. *Proc Natl Acad Sci USA* 91:8837-8841.

European Patent Applications EP 0 292 435; EP 0 332 581; EP 0 392 225.

Evans M M S. 2007. The indeterminate gametophyte 1 gene of maize encodes a LOB domain protein required for embryo sac and leaf development. *The Plant Cell* 19, 46-62.

Fey & Maréchal-Drouard (1999) Compilation and analysis of plant nuclearl promoter sequences: An illustration of a divergent evolution between monocot and dicot nuclear. *Biochem Biophys Res Commun* 256:409-414.

Fiume et al. (2004) Introns are key regulatory elements of rice tubulin expression. *Planta* 218: 693-703.

Fischer E. 2004. Molecular genetic studies on the occurrence of paternal DNA transmission during in vivo haploid induction in maize (Zea mays) [in German]. Dissertation, University of Hohenheim.

Fromm et al. (1990) Inheritance and expression of chimeric genes in the progeny of transgenic maize plants. *Nature Biotechnol* 8:833-839.

Gallie et al. (1987) A comparison of eukaryotic viral 5'-leader sequences as enhancers of mRNA expression in vivo. *Nucl Acids Res* 15:8693-8711.

Gallie et al. (1989) Eukaryotic viral 5'-leader sequences act as translational enhancers in eukaryotes and prokaryotes. In: *Molecular Biology of RNA*, Cech (ed.). UCLA Symposia on Molecular and Cellular Biology, New Series, Alan R. Liss, Inc., New York, N.Y., Volume 92, pp. 237-256.

Geiger, H. H., 2009 Doubled haploids, pp. 641-657 in Maize Handbook, Vol. 2, edited by J. L. Bennetzen, and S. Hake. Springer, N.Y.

GENBANK® Accession Nos. EF115541; NC_007579.

GENBANK® Accession Nos. J02798; J05212; L05934; M63985; NC_003377; U09118; U09119; U39944; U43147; U45855; U93215; X15596; X74782; YP_398418; YP_398423; Z17657.

Gordon-Kamm et al. (1990) Transformation of maize cells and regeneration of fertile transgenic plants. *Plant Cell* 2:603-618.

Green et al. (1988) Binding site requirements for pea nuclear protein factor GT-1 correlate with sequences required for light-dependent transcriptional activation of the rbcS-3A gene. *EMBO J* 7:4035-4044.

Guo et al. (2003) A chemical-regulated inducible RNAi system in plants. *Plant J* 34:383-392.

Hanson & Bentolila (2004) Interactions of nuclearl and nuclear genes that affect male gametophyte development. *Plant Cell* 16 Suppl:S154-169

Hedgcoth et al. (2002) A chimeric open reading frame associated with haploid induction in alloplasmic wheat with *Triticum timopheevi* nuclear is present in several *Triticum* and *Aegilops* species, maize, and rye. *Curr Genet* 41:357-365.

Hiei et al. (1994) Efficient transformation of rice (*Oryza sativa* L.) mediated by *Agrobacterium* and sequence analysis of the boundaries of the T-DNA. *Plant J*6:271-282.

Hiei et al. (1997) Transformation of rice mediated by *Agrobacterium tumefaciens*. *Plant Mol Biol* 35:205-218.

Hill & Robertson (1968) Linkage disequilibrium in finite populations. Theor. Appl. Genet. 38, 226-231. *Theor Appl Genet* 38:226-231.

Hofgen & Willmitzer (1988) Storage of competent cells for Agrobacterium transformation. *Nucl Acids Res* 16:9877.

Huang et al. (1996) The *Arabidopsis* ACT11 actin gene is strongly expressed in tissues of the emerging inflorescence, pollen, and developing ovules. *Plant Mol Biol* 33:125-139.

Huang et al. (2009) Refining the Definition of Plant Nnuclearl Presequences through Analysis of Sorting Signals, N-Terminal Modifications, and Cleavage Motifs. *Plant Physiol* 150:1272-128.

Japanese Patent Application JP 2001512988-A/13.

Jing et al. (2012) A male sterility-associated cytotoxic protein ORF288 in *Brassica juncea* causes aborted pollen development. *J Exp Biol* 63:1285-1295.

Jobling & Gehrke (1987) Enhanced translation of chimaeric messenger RNAs containing a plant viral untranslated leader sequence. *Nature* 325:622-625.

Jordano et al. (1989) A sunflower helianthinin gene upstream sequence ensemble contains an enhancer and sites of nuclear protein interaction. *Plant Cell* 1:855-866.

Josefsson et al. (1987) Structure of a gene encoding the 1.7 S storage protein, napin, from *Brassica napus*. *J Biol Chem* 262:12196-1201.

Kalendar et al. (1999) IRAP and REMAP: two new retrotransposon-based DNA fingerprinting techniques. *Theor Appl Genet* 98:704.

Kermicle J L. 1969. Androgenesis conditioned by a mutation in maize. *Science* 166, 1422-1424.

Klein et al. (1987) High-velocity microprojectiles for delivering nucleic acids into living cells. *Nature* 327:70-73.

Koziel et al. (1993) Field performance of elite transgenic maize plants expressing an insecticidal protein derived from *Bacillus thuringiensis*. *Nature Biotechnol* 11:194-200.

Lashermes, P., and M. Beckert, 1988 Genetic control of maternal haploidy in maize (Zea mays L.) and selection of haploid inducing lines. Theor. Appl. Genet. 76: 405-410.

Last et al. (1991) Emu: an improved promoter for gene expression in cereal cells. *Theor Appl Genet* 81:581-588.

Lee & Gelvin (2008) T-DNA Binary vectors and systems. *Plant Physiol* 146:325-332.

Lee & Huang (1994) Genes encoding oleosins in maize kernel of inbreds Mo17 and B73. *Plant Mol Biol* 26:1981-1987.

Lee et al. (2007) Novel Plant Transformation Vectors Containing the Superpromoter. *Plant Physiol* 1294-1300.

Lommel et al. (1991) Identification of the maize chlorotic mottle virus capsid protein cistron and characterization of its subgenomic messenger RNA. *Virology* 181:382-385.

Lu et al. (2008) Activity of the 5' regulatory regions of the rice polyubiquitin rubi3 gene in transgenic rice plants as analyzed by both GUS and GFP reporter genes. *Plant Cell Rep* 27:1587-600.

Li L, Xu X, Jin W, Chen S. 2009. Morphological and molecular evidences for DNA introgression in haploid induction via a high oil inducer CAUHOI in maize. *Planta* 230, 367-376.

Macejak & Samow (1991) Internal initiation of translation mediated by the 5' leader of a cellular mRNA. *Nature* 353:90-94.

Manjunath et al. (1997) Molecular characterization and promoter analysis of the maize cytosolic glyceraldehyde 3-phosphate dehydrogenase gene family and its expression during anoxia. *Plant Mol Biol* 33:97-112.

Martinez et al. (1989) Structure, evolution and anaerobic regulation of a nuclear gene encoding cytosolic glyceraldehyde-3-phosphate dehydrogenase from maize. *J Mol Biol* 208:551-565.

Mayo (1987) *The Theory of Plant Breeding, Second Edition*, Clarendon Press, Oxford, United Kingdom.

McBride et al. (1994) ontrolled expression of plastid transgenes in plants based on a nuclear DNA-encoded and plastid-targeted T7 RNA polymerase. *Proc Natl Acad Sci USA* 91:7301-7305.

McElroy et al. (1990) Isolation of an efficient actin promoter for use in rice transformation. *Plant Cell* 2:163-171.

Meier et al. (1991) Elicitor-inducible and constitutive in Vivo DNA footprints indicate novel cis-acting elements in the promoter of a parsley gene encoding pathogenesis-related protein 1. *Plant Cell* 3:309-316.

Mettler (1987) A simple and rapid method for miniprepararion of DNA from tissue cultured plant cells. *Plant Mol Biol Reporter* 5:346-349.

Murashige & Skoog (1962) A revised medium for rapid growth and bioassays with tobacco tissue cultures. *Physiologia Plantarum* 15:473-497.

Nanda, D. K., and S. S. Chase, 1966 An embryo marker for detecting monoploids of maize (Zea mays L.). Crop Sci. 6: 213-215.

Needleman & Wunsch (1970) A general method applicable to the search for similarities in the amino acid sequence of two proteins. *J Mol Biol* 48:443-453.

Negrotto et al. (2000) The use of phosphomannose-isomerase as a selectable marker to recover transgenic maize plants (Zea mays L.) via *Agrobacterium* transformation. *Plant Cell Reports* 19:798-803.

Neuffer M G, Sheridan W F. 1980. Defective kernel mutants of maize. I. Genetic and lethality studies. *Genetics* 95, 929-944.

Ni et al. (1995) Strength and tissue specificity of chimeric promoters derived from the octopine and mannopine synthase genes. *Plant J* 7:661-676.

Odell et al. (1985) Identification of DNA sequences required for activity of the cauliflower mosaic virus 35S promoter. *Nature* 313:810-812.

Onozaki et al. (2004) A RAPD-derived STS marker is linked to a bacterial wilt (*Burkholderia caryophylli*) resistance gene in carnation. *Euphytica* 138:255-262.

Orita et al. (1989) Detection of polymorphisms of human DNA by gel electrophoresis as single-strand conformation polymorphisms. *Proc Natl Acad Sci USA* 86:2766.

Paran & Michelmore (1993) Development of reliable PCR-based markers linked to downy mildew resistance genes in lettuce. *Theon Appl Genet* 85:985-993.

Paszkowski et al. (1984) Direct gene transfer to plants. *EMBO J* 3:2717-2722.

PCT International Patent Application Publication Nos. WO 1992/013957; WO 1993/07278; WO 1993/21335; WO 1994/00977; WO 1997/32011; WO 1999/043838.

Pearson & Lipman (1988) Improved tools for biological sequence comparison. *Proc Natl Acad Sci USA* 85:2444-2448.

Potrykus et al. (1985) Molecular and general genetics of a hybrid foreign gene introduced into tobacco by direct gene transfer. *Mol Gen Genet* 199:169-177.

Prigge V, Melchinger A E. 2012. Production of haploids and doubled haploids in maize. *Methods in Molecular Biology* 877, 161-172.

Prigge, V., and A. E. Melchinger, 2012 Production of haploids and doubled haploids in maize, Plant Cell Culture Protocols, Ed. 3, edited by V. M. Loyola-Vargas and N. Ochoa-Alejo. Humana Press-Springer Verlag, Totowa, N.J, (in press).

Prigge, V., C. Sánchez, B. S. Dhillon, W. Schipprack, J. L. Araus et al., 2011 Doubled haploids in tropical maize. I. Effects of inducers and source germplasm on in vivo haploid induction rates. Crop Sci. 51: 1498-1506.

Prigge V, Xu X, Li L, Babu R, Chen S, Atlin G N, Melchinger A E. 2012. New insights into the genetics of in vivo induction of maternal haploids, the backbone of doubled haploid technology in maize. *Genetics* 190, 781-793.

Rafalski & Tingey (1993) Genetic diagnostics in plant breeding: RAPDs, microsatellites and machines. *Trends Genet* 9:275-280.

Ravi, M., and S. W. L. Chan, 2010 Haploid plants produced by centromere-mediated genome elimination. Nature 464: 615-619

Reed et al. (2001) Phosphomannose isomerase: an efficient selectable marker for plant transformation. *In Vitro Cell Dev Biol-Plant* 37:127-132.

Reich et al. (1986) Efficient transformation of alfalfa protoplasts by the intranuclear microinjection of Ti plasmids. *Nature Biotechnol* 4:1001-1004.

Reiser et al. (1995) he BELL1 Gene Encodes a Homeodomain Protein Involved in Pattern Formation in the *Arabidopsis* Ovule Primordium. *Cell* 83:735-742.

Riker, F. K., G. A. Gordillo, and H. H. Geiger, 2005 In vivo haploid induction in maize: performance of new inducers and significance for doubled haploid lines in hybrid breeding. Maydica 50: 275-283

Roque et al. (2007) The PsENDJ promoter: a novel tool to produce genetically engineered male-sterile plants by early anther ablation. *Plant Cell Reports* 26:313-325.

Sambrook & Russell (2001) *Molecular Cloning: A Laboratory Manual* (3$^{rd}$ ed.), Cold Spring Harbor Library Press, Cold Spring Harbor, N.Y., United States of America.

Sarkar K, Coe E. 1966. A genetic analysis of the origin of maternal haploids in maize. *Genetics* 54,453-464.

Schocher et al. (1986) Co-transformation of unlinked foreign genes into plants by direct gene transfer. *Nature Biotechnol* 4:1093-1096.

Sheridan et al. (1996) The mac 1 Gene: Controlling the Commitment to the Meiotic Pathway in Maize. *Genetics* 142:1009-1020.

Shimamoto et al. (1989) Fertile transgenic rice plants regenerated from transformed protoplasts. *Nature* 338:274-276.

Singh, (1986) *Breeding for Resistance to Diseases and Insect Pests*, Springer-Verlag, New York, N.Y., United States of America.

Sjodahl et al. (1995) Deletion analysis of *Brassica napus* cruciferin gene cm 1 promoter in transformed tobacco: promoter activity during early and late stages of embryogenesis is influenced by cis-acting elements in partially separate regions. *Planta* 197:264-274.

Sjoling & Glaser (1998) Nnuclearl targeting peptides in plants. *Trends Plant Sci* 3:136-140.

Skuzeski et al. (1990) Analysis of leaky viral translation termination codons in vivo by transient expression of improved beta-glucuronidase vectors. *Plant Mol Biol* 15:65-79.

Smith & Waterman (1981) "Comparison of biosequences. *Adv Appl Math* 2: 482-489.

Solocombe et al. (1994) Temporal and tissue-specific regulation of a *Brassica napus* stearoyl-acyl carrier protein desaturase gene. *Plant Physiol* 104:1167-1176.

Song & Hedgcoth (1994) A chimeric gene (orf256) is expressed as protein only in cytoplasmic male-sterile lines of wheat. *Plant Mol Biol* 26:535-539.

Spencer et al. (1990) Bialaphos selection of stable transformants from maize cell cultures. *Theor Appl Genet* 79:625-631.

Svab & Maliga, (1993) High-frequency plastid transformation in tobacco by selection for a chimeric aadA gene. *Proc Natl Acad Sci USA* 90:913-917.

Svab et al. (1990) Stable transformation of plastids in higher plants. *Proc Natl Acad Sci USA* 87:8526-8530.

Tsuchiya et al. (1994) Molecular characterization of rice genes specifically expressed in the anther tapetum. *Plant Mol Biol* 26:1737-1746.

U.S. Patent Application Publication Nos. 2005/0060767; 2005/0246798; 2006/0260011; 2007/0004912; 2007/0006344; 2010/0205692; 2012/0021506; 2012/0036593.

U.S. Pat. Nos. 4,945,050; 4,940,935; 5,036,006; 5,100,792; 5,188,642; 5,268,463; 5,276,268; 5,399,680; 5,466,785; 5,569,597; 5,561,236; 5,589,610; 5,591,616; 5,604,121; 5,608,142; 5,608,144; 5,608,149; 5,639,948; 5,641,876; 5,659,026; 5,767,378; 5,994,629; 6,072,050; 6,177,611; 7,151,201; 7,166,770; 7,253,340; 7,550,578; 8,168,859.

Uknes et al. (1993) Regulation of pathogenesis-related protein-1a gene expression in tobacco. *Plant Cell* 5:159-169.

Urao et al. (1996) Molecular cloning and characterization of a gene that encodes a MYC-related protein in *Arabidopsis*. *Plant Mol Biol* 32:571-576.

Vasil et al. (1992) Herbicide resistant fertile transgenic wheat plants obtained by microprojectile bombardment of regenerable embryogenic callus. *Nature Biotechnol* 10:667-674.

Vasil et al. (1993) Rapid production of transgenic wheat plants by direct bombardment of cultured immature embryos. *Nature Biotechnol* 11:1553-1558.

Velten et al. (1984) Isolation of a dual plant promoter fragment from the Ti plasmid of *Agrobacterium tumefaciens*. *EMBO J* 3:2723-2730.

Viera & Messing (1982) The pUC plasmids, an M13mp7-derived system for insertion mutagenesis and sequencing with synthetic universal primers. *Gene* 19:259-268.

Vos et al. (1995) AFLP: a new technique for DNA fingerprinting. *Nucleic Acids Res* 23:4407-4414.

Weeks et al. (1993) Rapid production of multiple independent lines of fertile transgenic wheat (*Triticum aestivum*). *Plant Physiol* 102:1077-1084.

Wei et al. (2003) Comparative expression analysis of two sugarcane polyubiquitin promoters and flanking sequences in transgenic plants. *J Plant Physiol* 160:1241-1251.

Welsh (1981) *Fundamentals of Plant Genetics and Breeding*, John Wiley & Sons, New York, N.Y., United States of America.

White et al. (1990) A cassette containing the bar gene of *S. hygroscopicus*: a selectable marker for plant transformation. *Nucl Acids Res* 18:1062.

Wood (ed) (1983) *Crop Breeding*, American Society of Agronomy, Madison, Wis., United States of America.

Wricke & Weber (1986) *Quantitative Genetics and Selection Plant Breeding*, Walter de Gruyter and Co., Berlin, Germany.

Yang et al. (2010) Nnuclearlly-targeted expression of a haploid induction-associated orf220 gene causes male sterility in *Brassica juncea*. *BMC Plant Biol* 10:231.

Zhang & Glaser (2002) Interaction of plant nuclearl and chloroplast signal peptides with the Hsp70 molecular chaperone. *Trends Plant Sci* 7:14-21.

Zhang, Z. L., F. Z. Qiu, Y. Z. Liu, K. J. Ma, Z. Y. Li et al., 2008 Chromosome elimination and in vivo haploid induction by stock 6-derived inducer line in maize (Zea mays L.). Plant Cell Rep. 27: 1851-1860.

Zhang et al. (1988) Transgenic rice plants produced by electroporation-mediated plasmid uptake into protoplasts. *Plant Cell Rep* 7:379-384.

Zhang et al. (1996) DNA sequences that activate isocitrate lyase gene expression during late embryogenesis and during postgerminative growth. *Plant Physiol* 110:1069-1079.

Zhong et al. (1996) The circadian clock gates expression of two *Arabidopsis catalase* genes to distinct and opposite circadian phases. *Mol Gen Genet* 251:196-203.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. Method of creating a new haploid inducer maize plant with a silenced patatin-like phospholipase 2A, comprising transcribing a polynucleotide sequence capable of silencing the patatin-like phospholipase 2A in maize, wherein said polynucleotide sequence comprises a first sequence selected from the group consisting of:
   a) a polynucleotide sequence comprising the nucleic acid sequence set forth in SEQ ID NO: 37 or the complement thereof,
   b) a functional fragment comprising at least 22 contiguous bases of SEQ ID NO: 37 or the complement thereof, and
   c) a polynucleotide sequence having at least 95% sequence identity as determined using the BLASTN alignment tool to the nucleic acid sequence set forth in SEQ ID NO: 37 or the complement thereof,
   and a second sequence that is the complement of the first sequence, wherein the polynucleotide sequence expresses a double-stranded ribonucleotide sequence which silences the patatin-like phospholipase 2A when contacted with a maize plant and thus creates a new haploid inducer maize plant.

2. The method of claim 1, wherein the contacting is achieved by transforming the plant with a polynucleotide sequence which when expressed produces a double-stranded ribonucleotide sequence capable of silencing the patatin-like phospholipase 2A.

* * * * *

SEQUENCE LISTING

```
<160> NUMBER OF SEQ ID NOS: 66

<210> SEQ ID NO 1
<211> LENGTH: 1302
<212> TYPE: DNA
<213> ORGANISM: Zea mays

<400> SEQUENCE: 1
cccgctacct gttcaccgcg cgccagcgaa acctccgcac gcccactgcc catctgttcc      60
ccgtgcgcca gcgaaacatc cgcacgcccg cggcccgcct gttcccgcg catcccgctg      120 cacgacttct gctaccgcaa cggccaccca cgcacgcccg cctgttcacc gcgcatcccg      180
ctgacctccc cttcacgctc gcacacgctc cgttccccca ccccaccgca atccccgacg      240
aactcattac cagtagaatc agttactaac tgcttttctt tttcttggat tagaatggct      300
ggggctatct ctcaccatgc gctagcattt tcacaatccc actggtgcag tgcgaagaac      360
tctagattcg gaaagaggac gggcaatgct cgcctggttt atctaaaagg aagatgtggt      420
tcaggcagca gaaaactggg tttgatgtgg gcctcgagct cgcagtcttc tgtcatggag      480
ccgacgcacc taccatctga tggcaacagc agccacaccc caaaaaaatc aagtgaaagc      540
gctcttatat tgatttggca tggtgaatcc ctgtggaacg agaaaaatct atttcctggc      600
tgcatcgatg taccctgac accgaagggt gttgaggagg ccattgaggc aggtaaaagg      660
atatgcaata tcccaatcga tgtgatatat acttcatcac tgatttgtgc tcagatgacc      720
gcaatgcttg ccatgatgca gcatcgacgc aagaagatcc tagttatcac gcataatgag      780
agtgaacaag ctcacaggtg gagtcagata tacagtgagg agacaatgaa acagtccatt      840
cctgtcatca cagcttggca attgaatgaa cggatgtatg gtgagctaca aggccttaac      900
aagcaagaaa ctgtagatcg atttggcaaa gaacaagttc atgagtggcg ccgcagttat      960
gatattcctc cgccaaatgg agaaagtcta gagaagtgtg ctgagagagc tgttgcttat     1020
ttcaaagatc agattattcc acaacttgtg gctggaaaac atgtgatggt tgctgcacat     1080
gggaattcac ttcgttcaat tataatgcat ctggacaaat taacttctca gaaggtaata     1140
agccttgagc tgtctactgg cattcccatg ctttacatat tcaaagaggg aaagtttatt     1200
cgacgtggga ctccagtagg accttcggag gccagtgttt atgcttatac caggaccaaa     1260
cgatttgctg agcacattac atttcagaac aaattggcct ag                        1302
```

<210> SEQ ID NO 2
<211> LENGTH: 335
<212> TYPE: PRT
<213> ORGANISM: Zea mays

<400> SEQUENCE: 2

```
Met Ala Gly Ala Ile Ser His His Ala Leu Ala Phe Ser Gln Ser His
1               5                   10                  15

Trp Cys Ser Ala Lys Asn Ser Arg Phe Gly Lys Arg Thr Gly Asn Ala
            20                  25                  30

Arg Leu Val Tyr Leu Lys Gly Arg Cys Gly Ser Gly Ser Arg Lys Leu
        35                  40                  45

Gly Leu Met Trp Ala Ser Ser Gln Ser Ser Val Met Glu Pro Thr
    50                  55                  60

His Leu Pro Ser Asp Gly Asn Ser Ser His Thr Pro Lys Lys Ser Ser
65                  70                  75                  80

Glu Ser Ala Leu Ile Leu Ile Trp His Gly Glu Ser Leu Trp Asn Glu
                85                  90                  95

Lys Asn Leu Phe Pro Gly Cys Ile Asp Val Pro Leu Thr Pro Lys Gly
            100                 105                 110

Val Glu Glu Ala Ile Glu Ala Gly Lys Arg Ile Cys Asn Ile Pro Ile
        115                 120                 125

Asp Val Ile Tyr Thr Ser Ser Leu Ile Cys Ala Gln Met Thr Ala Met
130                 135                 140

Leu Ala Met Met Gln His Arg Arg Lys Lys Ile Leu Val Ile Thr His
145                 150                 155                 160

Asn Glu Ser Glu Gln Ala His Arg Trp Ser Gln Ile Tyr Ser Glu Glu
                165                 170                 175

Thr Met Lys Gln Ser Ile Pro Val Ile Thr Ala Trp Gln Leu Asn Glu
            180                 185                 190

Arg Met Tyr Gly Glu Leu Gln Gly Leu Asn Lys Gln Glu Thr Val Asp
        195                 200                 205

Arg Phe Gly Lys Glu Gln Val His Glu Trp Arg Arg Ser Tyr Asp Ile
    210                 215                 220

Pro Pro Pro Asn Gly Glu Ser Leu Glu Lys Cys Ala Glu Arg Ala Val
225                 230                 235                 240

Ala Tyr Phe Lys Asp Gln Ile Ile Pro Gln Leu Val Ala Gly Lys His
                245                 250                 255

Val Met Val Ala Ala His Gly Asn Ser Leu Arg Ser Ile Ile Met His
            260                 265                 270

Leu Asp Lys Leu Thr Ser Gln Lys Val Ile Ser Leu Glu Leu Ser Thr
        275                 280                 285

Gly Ile Pro Met Leu Tyr Ile Phe Lys Glu Gly Lys Phe Ile Arg Arg
    290                 295                 300

Gly Thr Pro Val Gly Pro Ser Glu Ala Ser Val Tyr Ala Tyr Thr Arg
305                 310                 315                 320

Thr Lys Arg Phe Ala Glu His Ile Thr Phe Gln Asn Lys Leu Ala
                325                 330                 335
```

<210> SEQ ID NO 3
<211> LENGTH: 2992
<212> TYPE: DNA
<213> ORGANISM: Zea mays

<400> SEQUENCE: 3

```
ttcaaccacc aaaatcaatt aggaaaaggt gtaagcctat ttcccttcca ggaggcgtac      60
gtgagaggga gaggtgaaaa ggaacaacgc gtataccaga taaggtccca cagcctaagt    120
aggtagcctt ctgatatctc tactaactat taaggagaga gtgtagactg cccccgctcc    180
ctacccaacg ccccccgcta cctgttcacc gcgcgccagc gaaacctccg cacgcccact    240
gcccatctgt tccccgtgcg ccagcgaaac atccgcacgc ccgcggcccg cctgttcccc    300
gcgcatcccg ctgcacgact tctgctaccg caacggccac ccccgcacgc ccgcctgttc    360
accgcgcatc ccgctgacct ccccttcacg ctcgcacacg ctccgttccc ccaccccacc    420
gcaatccccg acgctataag agcggtaacc aactccatct ccctggtgcc acgcattgtt    480
gagttcttaa ggtgcgtttc gttgaggact tgttcatttt tgttggtcat gtattccatt    540
ttactgctct accattttgt ggaataaagg gaggaatgtt tcactagaa gagttcatca    600
atcttatgtt ggtttcttgg atcagttttg ctctatggct aaatggtcga attgagccta    660
tttcattata aagttagcga gcgaataatt gttcagcctc ttcctagaac tcattaccag    720
tagaatcagt tactaactgc ttttcttttt cttggattag aatggctggg gctatctctc    780
accatgcgct agcatttttca caatcccact ggtgcagtgc gaagaactct agattcggaa    840
agaggacggg caatgctcgc ctggtttatc taaaaggaag atgtggttca ggcagcagaa    900
aactgggttt gatgtgggcc tcgagctcgc agtcttctgt catggagccg acgcacctac    960
catctgatgg caacagcagc cacaccccaa aaaaatcaag taattttaac gacctcctat   1020
ggtggttatt tgttttaat ttgagaaaac tatccatttg acacatttaa ctttgggctt    1080
ctcagaattt ggggcatata ataagatctg ctaatctgtt atctctatgt cgttgtaggt   1140
gaaagcgctc ttatattgat ttggcatggt gaatccctgt ggaacgagaa aaatctattt   1200
actggctgca tcgatgtacc cctgacaccg aagggtgttg aggaggccat tgaggcaggt   1260
aaaaggatat gcaatatccc aatcgatgtg atatatactt catcactgat ttgtgctcag   1320
atgaccgcaa tgcttgccat gatgcagcat cgacgcaaga aggtttgtgt ctttcctttg   1380
aaattccagt aatttcttct agcatttgta tgaacttgcc ggagaaatca tgctttgctg   1440
gtgatatatg tatttataga tcccagttat cacgcataat gagagtgaac aagctcacag   1500
gtggagtcag atatacagtg aggagacaat gaaacagtcc attcctgtca tcacagcttg   1560
gcaattgaat gaacggatgt aatactttct ccatactctt tgatttgcta attactccct   1620
ctgtctcaaa atagtattaa ttttagctct tgatttttat gtctatattc aaatagatga   1680
tgataaatct agattctaga cacaaatata aacatatac atcaagtatt atatgaatct   1740
attaatttac taagaccaat tttaatttgg gacagaggga gtatacgatt ataatagttg   1800
tttgactgtg cttctcttta aatatcccctt gacatttcta ggtatggtga gctacaaggc   1860
cttaacaagc aagaaactgt agatcgattt ggcaaagaac aagttcatga gtggcaccgc   1920
agttatgata ttcctccgcc aaatggagaa agtctagaga agtgtgctga gagagctgtt   1980
gcttatttca aagatcaggc acatctagca aggccacttt acactaattg aaagatacac   2040
tttttacttg ggttattggt cttgctgcag tattggtatg catgctaaag gttattcttg   2100
aatcgatgaa ttcctctact atgggatgca gaaatgcatg tgcttagttt tctttctatt   2160
gtgctagctc atatcaaatt tataacctga attttttatt tatgttcgac tctaaaaaac   2220
agtttttct agctcgattt gacctatagt aattttccg taatagatta ttccacaact    2280
tgtggctgga aaacatgtga tggttgctgc acatgggaat tcacttcgtt caattataat   2340
```

| | |
|---|---|
| gcatctggac aaattaactt ctcagaaggt aattcactgt cgttttgtc tttccatcaa | 2400 |
| aaaggactcg gctaaacaga acatgtagca ttatgttaag tttgggagtg agcctttcgt | 2460 |
| cccttcaggt aataagcctt gagctgtcta ctggcattcc catgctttac atattcaaag | 2520 |
| agggaaagtt tattcgacgt gggactccag taggaccttc ggaggccagt gtttatgctt | 2580 |
| ataccagggt aagattcttt cccccacatg ttctaccata ggacgatact ccagtttaca | 2640 |
| aaccttatct gtacagacca aacgatttgc tgagcacatt acatttcaga acaaattggc | 2700 |
| ctagaagata agggtgttt ggtttgagaa atcactctat tcaaaatgag atggtgtatc | 2760 |
| atgggtccat ttctcaaatt tggtgggatg accctattcc tcatattagt actaactagg | 2820 |
| tgagtgtccg tgcgttgcaa cgggaacata taataacatg ataacttata tacaaaatgt | 2880 |
| gtcttatatt gttataagaa aatgtttcat aatctatttg tgatcctggc catacataaa | 2940 |
| ttttgttatt ttaatttaac tgtttcacta ctacattgaa atcatcagta tc | 2992 |

<210> SEQ ID NO 4
<211> LENGTH: 6916
<212> TYPE: DNA
<213> ORGANISM: Artificial Sequence
<220> FEATURE:
<223> OTHER INFORMATION: Synthetic

<400> SEQUENCE: 4

| | |
|---|---|
| cctcgggacc cttgtcgcgt tgttcgttcc attgccgcat cacctccttt ctcatcgtgc | 60 |
| attacgaggt cttcaagggg cttttggtca tcagccggga gcgcctccat cgccggcttg | 120 |
| atgatgttgg tagtggagat cttggtgtga tccttaaaac cggccattta tgggccgatt | 180 |
| tttagcagat ctagacacct attccccagc ggagtcgcca aaagtatgtt gacgcttttt | 240 |
| cggagcgcca atcactcaag aagaaccggc ggcggtgccc tctgcacagg ggcggacgct | 300 |
| ccgcgcgcag gggccggacg ctccgcggcc tggtgcgagg cggcggcgct ctctggttag | 360 |
| acgcggacgg tgcgcggcac agggccggac ggtgcgcgac ctagtgcagg agcacgggtt | 420 |
| ccctgcctga cggccggacg ctccgcgctc tagggccgga cggtgcgcgc gtgcgcaggg | 480 |
| gcggcggaag atcgccggcg cgcgcctgga tctcgctccc ggagggagcc cgtcggggag | 540 |
| gagagatcct aggagttgtc taggctcggg ccggccgacc tagactcctc taatcgacgt | 600 |
| agagtcgagg agaggcagag aatttgggga ttggaatact aaactagggc taaactagaa | 660 |
| ctagactaga actactccta attgtgctga aaataaatgc gagatagaag ttgtattggt | 720 |
| tcgattgttg ggggtcaatc ggccgtagcc cttcatctat ataaagggga ggtctggatc | 780 |
| cgtttccaac tgatttccga gttaatcccg cggttttagg taacaaatcc cgcgagaaac | 840 |
| taggaacccct aactgactct cgcacgcgc cgaccgtccg cgccaccacc gcggacggtc | 900 |
| ccgaccgcgg agcgtccggc ctcggggccg gagcgtccgc acggtcattt tgggttcgaa | 960 |
| cagagtccca acgaggttag taaatgtagt gatgaaatta agttttgtac gaagtttgta | 1020 |
| aatttaagga cctgttttac ataactattg gagaagagtt ttctctgaaa aattcttaaa | 1080 |
| tttatattta gggagttgtt tatataacta ttggcatttg agatgctcta aggaagcgaa | 1140 |
| ggaaataact tggcggcgat cctagtcgac aaccgttgaa ttcgtgagaa tcaatcattc | 1200 |
| tgtaggagta aaaaaataaa ataaaatatg catttcctcg ttcctatacg cttaaattag | 1260 |
| acgaccctgg actggaacca ggaactagga aggggcaccg atgtcatttg cgaagcaaca | 1320 |
| acaacatgcg tgaggacgac caagtcaaac gttgcgtcgc gttgcctcgc cggcgggccg | 1380 |
| gtcccaccaa gacgtggcgc catgcaagtg cgtcgtcgac cctcttctct ctctctcttg | 1440 |

```
tagtcttgtt cctgttatct ctctcggctg tccgctgccc cgtgatctga gcgcgtttct    1500
ctcccgtcct ctcttctccc tctcccgcaa caaacacctg ctatccggtc tccctctccc    1560
ctgccatctc tctctagcgc attgctagcg cgagcgcaga aggcacacac gtagagcctt    1620
ggtgatacct cctcctcctc ctcctcctcc tcctgatctc ctctcctcct ccggcctccg    1680 tataccctata actaaaagat gatcatcgtg cgatgcaggc gaactcgtcg tccgaaaacc    1740
atggatccaa ctcattacca gtagaatcag ttactaactg ctttctttt tcttggatta    1800 gaatggctgg ggctatctct caccatgcgc tagcattttc acaatcccac tggtgcagtg    1860
cgaagaactc tagattcgga agaggacgg gcaatgctcg cctggtttat ctaaaaggaa    1920
gatgtggttc aggcagcaga aaactgggtt tgatgtgggc ctcgtgctcg cagtcttctg    1980
tcatggagcc gacgcaccta ccatctgatg gcaacagcag ccacacccca aaaaaatcaa    2040
gtgaaagcgc tcttatattg atttggcatg gtgaatccct gtggaacgag aaaaatctat    2100
ttcctggctg catcgatgta ccctgacac cgaagggtgt tgaggaggcc attgaggcag    2160
gtaaaaggat atgcaatatc ccaatcgatg tgatatatac ttcatcactg atttgtgctc    2220
agatgaccgc aatgcttgcc atgatgcact cgagaaatct gaagaagaga catcagtagg    2280
aaaaccatga aacaactcac caagtgataa actttgata aattcattca aaagtatcat    2340
gttctacgtg attcgcttgt atgccaaatt atctaaatat tagtaagaat taactactcg    2400
gacgatcatc agcaaatgaa aatgaaacag cacaccaatt gagactgatc agatcagaaa    2460
ccagaaaaac atctcaacat ggataaattc atcagcaata ctgtagcatt gatatatttg    2520
tgtttcttga agaaagaca tcaaagaaac tttgcaatta tgtagtattg tttattttc    2580 tgttacaaac ttaatcaact gacatgtaat gtgtctctat tgtcagttca agtattagac    2640
tatccattgt caccttttaa atgtaccttt actgtcagcg tacgagataa agttggccga    2700
ttgaattcta agctactata aaagcaactt tattatatag acatggcaaa caatcgttaa    2760
caaactgttt ttctttttga ttgattagga cttggaaaca cactgaacat gatcaaagtc    2820
acaaaagtca cttggttgcc tagtctgaca gcaagcgcag gtgtaaattc agaatgatag    2880
tgaaccaaaa ctcatctgct tccagtacca aattcgtcag aaggcagaac ggaggcataa    2940
gcacaaaggg catgctcacc cgagtcgagt gcatcatggc aagcattgcg gtcatctgag    3000
cacaaatcag tgatgaagta tatatcacat cgattgggat attgcatatc cttttacctg    3060
cctcaatggc ctcctcaaca cccttcggtg tcaggggtac atcgatgcag ccaggaaata    3120 gattttctc gttccacagg gattcaccat gccaaatcaa tataagagcg ctttcacttg    3180
atttttttgg ggtgtggctg ctgttgccat cagatggtag gtgcgtcggc tccatgacag    3240
aagactgcga gcacgaggcc cacatcaaac ccagttttct gctgcctgaa ccacatcttc    3300
cttttagata aaccaggcga gcattgcccg tcctctttcc gaatctagag ttcttcgcac    3360
tgcaccagtg ggattgtgaa aatgctagcg catggtgaga gatagcccca gccattctaa    3420
tccaagaaaa agaaaagcag ttagtaactg attctactgg taatgagttg gatctccatg    3480
ggagctctcg tcatcgtcct actatcaagc aacacgatcg accaccacct cgattatata    3540
tgcatcatta gtatcgtt tattaatttc agacccaccc actgctaacc acatcgtcca    3600
cgagagatta tattcatccg tggactacgc tctcgatctt acaatttgaa acctttctat    3660
tttcctaatt actatgtatt ccaggttcat tttgattgtg accattcttc agttcttct    3720 gtaaggatcg gagcatatta tatactctat gtggctatgc caattatatt gttgggtata    3780
```

```
agaatgcatt ttgtttctgt aatacggaaa aatatatttt ctttaagcaa caacaaggta      3840
aaaacttgcc tcgttgcata ttttcttat gtcaatctcc ttttgttcgt tgtatgatcc       3900
tctgtttgga aactgaatac tgatcgaaca actgatcagg agttaaaaca tattgtaaat      3960
atatataaaa acttgctgtg tacaactctt ctttattgta taagtttctt gaggtaaccg      4020
aaatagatag taaatcccaa tacaaataga ttcctccgtt actaactaat ctgaacataa      4080
atgctaataa aaaagtata aatttctatc tgcgtatgta ccttgacctt accttattc         4140 tattaactcc tgattttcta ttcagatttt gaacggtctg ttacttcctt tctattctgt      4200
tctggtttcg tcgtcgtttg tttccgaacg gtctgctact tctgattttc tatttgttct      4260
tacgtttggt tttgccgttc tagtttcttg cgttttcca tataaatata gaaacacaaa        4320
ataaatgtaa tgttgtagat acttgaacta tcgatctttt cctttaaaaa atgatattgc      4380
taccactaat gtagttttaa ttaggaacaa aacttacaac caatgatcaa ctaatgaacc      4440
ggtctagaac agtctatatg gacatggtga gcaagcgtac gtaattccgg accgcgcggg      4500
cggccgcact agtcccgggc ccatcgatga tatcagatct ggttctatag tgtcacctaa      4560
atcgtatgtg tatgatacat aaggttatgt attaattgta gccgcgttct aacgacaata     4620
tgtccatatg gtgcactctc agtacaatct gctctgatgc cgcatagtta agccagcccc     4680
gacacccgcc aacacccgct gacgcgccct gacgggcttg tctgctcccg gcatccgctt     4740
acagacaagc tgtgaccgtc tccgggagct gcatgtgtca gaggttttca ccgtcatcac    4800
cgaaacgcgc gagacgaaag ggcctcgtga tacgcctatt tttataggtt aatgtcatga    4860
taataatggt ttcttagacg tcaggtggca cttttcgggg aaatgtgcgc ggaacccta     4920 tttgtttatt tttctaaata cattcaaata tgtatccgct catgagacaa taaccctgat    4980
aaatgcttca ataatattga aaaggaaga gtatgagtat tcaacatttc cgtgtcgccc    5040
ttattccctt ttttgcggca ttttgccttc ctgtttttgc tcacccagaa acgctggtga    5100
aagtaaaaga tgctgaagat cagttgggtg cacgagtggg ttacatcgaa ctggatctca    5160
acagcggtaa gatccttgag agttttcgcc ccgaagaacg ttttccaatg atgagcactt    5220
ttaaagttct gctatgtggc gcggtattat cccgtattga cgccgggcaa gagcaactcg    5280
gtcgccgcat acactattct cagaatgact tggttgagta ctcaccagtc acagaaaagc    5340
atcttacgga tggcatgaca gtaagagaat tatgcagtgc tgccataacc atgagtgata    5400
acactgcggc caacttactt ctgacaacga tcggaggacc gaaggagcta accgcttttt    5460
tgcacaacat gggggatcat gtaactcgcc ttgatcgttg ggaaccggag ctgaatgaag    5520
ccataccaaa cgacgagcgt gacaccacga tgcctgtagc aatggcaaca acgttgcgca    5580
aactattaac tggcgaacta cttactctag cttcccggca acaattaata gactggatgg    5640
aggcggataa agttgcagga ccacttctgc gctcggccct tccggctggc tggtttattg    5700
ctgataaatc tggagccggt gagcgtgggt ctcgcggtat cattgcagca ctggggccag    5760
atggtaagcc ctcccgtatc gtagttatct acacgacggg gagtcaggca actatggatg    5820
aacgaaatag acagatcgct gagataggtg cctcactgat taagcattgg taactgtcag    5880
accaagttta ctcatatata ctttagattg atttaaaact tcattttta tttaaaagga      5940 tctaggtgaa gatcctttt gataatctca tgaccaaaat cccttaacgt gagttttcgt      6000
tccactgagc gtcagacccc gtagaaaaga tcaaaggatc ttcttgagat cctttttttc    6060
tgcgcgtaat ctgctgcttg caaacaaaaa aaccaccgct accagcggtg gtttgtttgc    6120
cggatcaaga gctaccaact ctttttccga aggtaactgg cttcagcaga gcgcagatac    6180
```

```
caaatactgt tcttctagtg tagccgtagt taggccacca cttcaagaac tctgtagcac    6240
cgcctacata cctcgctctg ctaatcctgt taccagtggc tgctgccagt ggcgataagt    6300
cgtgtcttac cgggttggac tcaagacgat agttaccgga taaggcgcag cggtcgggct    6360
gaacgggggg ttcgtgcaca cagcccagct tggagcgaac gacctacacc gaactgagat    6420
acctacagcg tgagctatga aaagcgcca cgcttcccga agggagaaag cggacaggt     6480
atccggtaag cggcagggtc ggaacaggag agcgcacgag ggagcttcca ggggaaacg    6540
cctggtatct ttatagtcct gtcgggtttc gccacctctg acttgagcgt cgattttgt    6600
gatgctcgtc aggggggcgg agcctatgga aaaacgccag caacgcggcc tttttacggt    6660
tcctggcctt tgctggcct tttgctcaca tgttctttcc tgcgttatcc cctgattctg    6720
tggataaccg tattaccgcc tttgagtgag ctgataccgc tcgccgcagc cgaacgaccg    6780
agcgcagcga gtcagtgagc gaggaagcgg aagagcgccc aatacgcaaa ccgcctctcc    6840
ccgcgcgttg gccgattcat taatgcaggt taacctggct tatcgaaatt aatacgactc    6900
actataggga gaccgg                                                    6916

<210> SEQ ID NO 5
<211> LENGTH: 335
<212> TYPE: PRT
<213> ORGANISM: Zea mays

<400> SEQUENCE: 5

Met Ala Gly Ala Ile Ser His His Ala Leu Ala Phe Ser Gln Ser His
1               5                   10                  15

Trp Cys Ser Ala Lys Asn Ser Arg Phe Gly Lys Arg Thr Gly Asn Ala
            20                  25                  30

Arg Leu Val Tyr Leu Lys Gly Arg Cys Gly Ser Gly Ser Arg Lys Leu
        35                  40                  45

Gly Leu Met Trp Ala Ser Ser Gln Ser Ser Val Met Glu Pro Thr
    50                  55                  60

His Leu Pro Ser Asp Gly Asn Ser Ser His Thr Pro Lys Lys Ser Ser
65                  70                  75                  80

Glu Ser Ala Leu Ile Leu Ile Trp His Gly Glu Ser Leu Trp Asn Glu
                85                  90                  95

Lys Asn Leu Phe Thr Gly Cys Ile Asp Val Pro Leu Thr Pro Lys Gly
            100                 105                 110

Val Glu Glu Ala Ile Glu Ala Gly Lys Arg Ile Cys Asn Ile Pro Ile
        115                 120                 125

Asp Val Ile Tyr Thr Ser Ser Leu Ile Cys Ala Gln Met Thr Ala Met
    130                 135                 140

Leu Ala Met Met Gln His Arg Arg Lys Lys Ile Pro Val Ile Thr His
145                 150                 155                 160

Asn Glu Ser Glu Gln Ala His Arg Trp Ser Gln Ile Tyr Ser Glu Glu
                165                 170                 175

Thr Met Lys Gln Ser Ile Pro Val Ile Thr Ala Trp Gln Leu Asn Glu
            180                 185                 190

Arg Met Tyr Gly Glu Leu Gln Gly Leu Asn Lys Gln Glu Thr Val Asp
        195                 200                 205

Arg Phe Gly Lys Glu Gln Val His Glu Trp Arg Ser Tyr Asp Ile
    210                 215                 220

Pro Pro Pro Asn Gly Glu Ser Leu Glu Lys Cys Ala Glu Arg Ala Val
225                 230                 235                 240
```

```
Ala Tyr Phe Lys Asp Gln Ile Ile Pro Gln Leu Val Ala Gly Lys His
                245                 250                 255

Val Met Val Ala Ala His Gly Asn Ser Leu Arg Ser Ile Ile Met His
            260                 265                 270

Leu Asp Lys Leu Thr Ser Gln Lys Val Ile Ser Leu Glu Leu Ser Thr
        275                 280                 285

Gly Ile Pro Met Leu Tyr Ile Phe Lys Glu Gly Lys Phe Ile Arg Arg
    290                 295                 300

Gly Thr Pro Val Gly Pro Ser Glu Ala Ser Val Tyr Ala Tyr Thr Arg
305                 310                 315                 320

Thr Lys Arg Phe Ala Glu His Ile Thr Phe Gln Asn Lys Leu Ala
                325                 330                 335

<210> SEQ ID NO 6
<211> LENGTH: 335
<212> TYPE: PRT
<213> ORGANISM: Zea mays

<400> SEQUENCE: 6

Met Ala Gly Ala Ile Ser His His Ala Leu Ala Phe Ser Gln Ser His
1               5                   10                  15

Trp Cys Ser Ala Lys Asn Ser Arg Phe Gly Lys Arg Thr Gly Asn Ala
            20                  25                  30

Arg Leu Val Tyr Leu Lys Gly Arg Cys Gly Ser Gly Ser Arg Lys Leu
        35                  40                  45

Gly Leu Met Trp Ala Ser Ser Gln Ser Ser Val Met Glu Pro Thr
    50                  55                  60

His Leu Pro Ser Asp Gly Asn Ser Ser His Thr Pro Lys Lys Ser Ser
65                  70                  75                  80

Glu Ser Ala Leu Ile Leu Ile Trp His Gly Glu Ser Leu Trp Asn Glu
                85                  90                  95

Lys Asn Leu Phe Pro Gly Cys Ile Asp Val Pro Leu Thr Pro Lys Gly
            100                 105                 110

Val Glu Glu Ala Ile Glu Ala Gly Lys Arg Ile Cys Asn Ile Pro Ile
        115                 120                 125

Asp Val Ile Tyr Thr Ser Ser Leu Ile Cys Ala Gln Met Thr Ala Met
    130                 135                 140

Leu Ala Met Met Gln His Arg Arg Lys Lys Ile Pro Val Ile Thr His
145                 150                 155                 160

Asn Glu Ser Glu Gln Ala His Arg Trp Ser Gln Ile Tyr Ser Glu Glu
                165                 170                 175

Thr Met Lys Gln Ser Ile Pro Val Ile Thr Ala Trp Gln Leu Asn Glu
            180                 185                 190

Arg Met Tyr Gly Glu Leu Gln Gly Leu Asn Lys Gln Glu Thr Val Asp
        195                 200                 205

Arg Phe Gly Lys Glu Gln Val His Glu Trp Arg Ser Tyr Asp Ile
    210                 215                 220

Pro Pro Pro Asn Gly Glu Ser Leu Glu Lys Cys Ala Glu Arg Ala Val
225                 230                 235                 240

Ala Tyr Phe Lys Asp Gln Ile Ile Pro Gln Leu Val Ala Gly Lys His
                245                 250                 255

Val Met Val Ala Ala His Gly Asn Ser Leu Arg Ser Ile Ile Met His
            260                 265                 270

Leu Asp Lys Leu Thr Ser Gln Lys Val Ile Ser Leu Glu Leu Ser Thr
```

```
            275                 280                 285

Gly Ile Pro Met Leu Tyr Ile Phe Lys Glu Gly Lys Phe Ile Arg Arg
            290                 295                 300

Gly Thr Pro Val Gly Pro Ser Glu Ala Ser Val Tyr Ala Tyr Thr Arg
305                 310                 315                 320

Thr Lys Arg Phe Ala Glu His Ile Thr Phe Gln Asn Lys Leu Ala
                325                 330                 335

<210> SEQ ID NO 7
<211> LENGTH: 335
<212> TYPE: PRT
<213> ORGANISM: Zea mays

<400> SEQUENCE: 7

Met Ala Gly Ala Ile Ser His His Ala Leu Ala Phe Ser Gln Ser His
1               5                   10                  15

Trp Cys Ser Ala Lys Asn Ser Arg Phe Gly Lys Arg Thr Gly Asn Ala
            20                  25                  30

Arg Leu Val Tyr Leu Lys Gly Arg Cys Gly Ser Gly Ser Arg Lys Leu
        35                  40                  45

Gly Leu Met Trp Ala Ser Ser Gln Ser Ser Val Met Glu Pro Thr
    50                  55                  60

His Leu Pro Ser Asp Gly Asn Ser Ser His Thr Pro Lys Lys Ser Ser
65                  70                  75                  80

Glu Ser Ala Leu Ile Leu Ile Trp His Gly Glu Ser Leu Trp Asn Glu
                85                  90                  95

Lys Asn Leu Phe Thr Gly Cys Ile Asp Val Pro Leu Thr Pro Lys Gly
            100                 105                 110

Val Glu Glu Ala Ile Glu Ala Gly Lys Arg Ile Cys Asn Ile Pro Ile
        115                 120                 125

Asp Val Ile Tyr Thr Ser Ser Leu Ile Cys Ala Gln Met Thr Ser Met
    130                 135                 140

Leu Ala Met Met Gln His Arg Arg Lys Lys Ile Pro Val Ile Thr His
145                 150                 155                 160

Asn Glu Ser Glu Gln Ala His Arg Trp Ser Gln Ile Tyr Ser Glu Glu
                165                 170                 175

Thr Met Lys Gln Ser Ile Pro Val Ile Thr Ala Trp Gln Leu Asn Glu
            180                 185                 190

Arg Met Tyr Gly Glu Leu Gln Gly Leu Asn Lys Gln Glu Thr Val Asp
        195                 200                 205

Arg Phe Gly Lys Glu Gln Val His Glu Trp His Arg Ser Tyr Asp Ile
    210                 215                 220

Pro Pro Pro Asn Gly Glu Ser Leu Glu Lys Cys Ala Glu Arg Ala Val
225                 230                 235                 240

Ala Tyr Phe Lys Asp Gln Ile Ile Pro Gln Leu Val Ala Gly Lys His
                245                 250                 255

Val Met Val Ala Ala His Gly Asn Ser Leu Arg Ser Ile Ile Met His
            260                 265                 270

Leu Asp Lys Leu Thr Ser Gln Lys Val Ile Ser Leu Glu Leu Ser Thr
        275                 280                 285

Gly Ile Pro Met Leu Tyr Ile Phe Lys Glu Gly Lys Phe Ile Arg Arg
    290                 295                 300

Gly Thr Pro Val Gly Pro Ser Glu Ala Ser Val Tyr Ala Tyr Thr Arg
305                 310                 315                 320
```

```
Thr Lys Arg Phe Ala Glu His Ile Thr Phe Gln Asn Lys Leu Ala
                325                 330                 335

<210> SEQ ID NO 8
<211> LENGTH: 335
<212> TYPE: PRT
<213> ORGANISM: Zea mays

<400> SEQUENCE: 8

Met Ala Gly Ala Ile Ser His His Ala Leu Ala Phe Ser Gln Ser His
1               5                   10                  15

Trp Cys Ser Ala Lys Asn Ser Arg Phe Gly Lys Arg Thr Gly Asn Ala
            20                  25                  30

Arg Leu Val Tyr Leu Lys Gly Arg Cys Gly Ser Gly Ser Arg Lys Leu
        35                  40                  45

Gly Leu Met Trp Ala Ser Ser Gln Ser Ser Val Met Glu Pro Thr
    50                  55                  60

His Leu Pro Ser Asp Gly Asn Ser Ser His Thr Pro Lys Lys Ser Ser
65                  70                  75                  80

Glu Ser Ala Leu Ile Leu Ile Trp His Gly Glu Ser Leu Trp Asn Glu
                85                  90                  95

Lys Asn Leu Phe Thr Gly Cys Ile Asp Val Pro Leu Thr Pro Lys Gly
            100                 105                 110

Val Glu Glu Ala Ile Ala Gly Lys Arg Ile Cys Asn Ile Pro Ile
        115                 120                 125

Asp Val Ile Tyr Thr Ser Ser Leu Ile Cys Ala Gln Met Thr Ser Met
130                 135                 140

Leu Ala Met Met Gln His Arg Arg Lys Lys Ile Pro Val Ile Thr His
145                 150                 155                 160

Asn Glu Ser Glu Gln Ala His Arg Trp Ser Gln Ile Tyr Ser Glu Glu
                165                 170                 175

Thr Met Lys Gln Ser Ile Pro Val Ile Thr Ala Trp Gln Leu Asn Glu
            180                 185                 190

Arg Met Tyr Gly Glu Leu Gln Gly Leu Asn Lys Gln Glu Thr Val Asp
        195                 200                 205

Arg Phe Gly Lys Glu Gln Val His Glu Trp Arg Arg Ser Tyr Asp Ile
    210                 215                 220

Pro Pro Pro Asn Gly Glu Ser Leu Glu Lys Cys Ala Glu Arg Ala Val
225                 230                 235                 240

Ala Tyr Phe Lys Asp Gln Ile Ile Pro Gln Leu Val Ala Gly Lys His
                245                 250                 255

Val Met Val Ala Ala His Gly Asn Ser Leu Arg Ser Ile Ile Met His
            260                 265                 270

Leu Asp Lys Leu Thr Ser Gln Lys Val Ile Ser Leu Glu Leu Ser Thr
        275                 280                 285

Gly Ile Pro Met Leu Tyr Ile Phe Lys Glu Gly Lys Phe Ile Arg Arg
    290                 295                 300

Gly Thr Pro Val Gly Pro Ser Glu Ala Ser Val Tyr Ala Tyr Thr Arg
305                 310                 315                 320

Thr Lys Arg Phe Ala Glu His Ile Thr Phe Gln Asn Lys Leu Ala
                325                 330                 335

<210> SEQ ID NO 9
<211> LENGTH: 4921
<212> TYPE: DNA
<213> ORGANISM: Zea mays
```

<400> SEQUENCE: 9

```
attgctataa gtataataat atctaagaga tggaagaaga ctggccggcc gggtagtgac      60
aataatgaat gaccaacggc agaaaagttg gtgcgaagat gttttaggtg aatgcaagtc     120
acaaaaggaa aaggctggca tctcgaatag aactcctata ccacggatca agaaacaatt     180
aaaaccatac ataattgtcg gagtaatatg ctaatcctag taattttagt cacatcattg     240
gaggtccttc gttccattca attttttttc tttcttcatg aacatttgtt caagatttat     300
ctcccacatg tttcaaagca tgcattattt attattattg gcaaatttca tgatctttca     360
aaagatatct cttgggcctg gcatggatat gctctatctc tagtaagtaa ttggctctgc     420
aataatgagt tggatattgc cacgaagaac cacgccttgc ttggaagaaa cttgatgaat     480
gccaaatctt gctcttttc aacatgttga tttaggaaat tatttggcaa ccaaacataa      540
tgtgactaga attagcacac ttctaatgac aaaaatataa tcacatttct gcgcgcacaa     600
aatatttgct tgccaaaatg caatcatgtt ttgatgtaca gttcgataga cattgaaaaa     660
gaatgcattt aggaaccttt tagtaccact ttgatcaatt tctgccatct acacgtcaaa     720
ctagataaaa agaataatgg cagccacatc ctacagaaaa aaaagacat atcaagaatt      780
caacttaatt tcagaatata caagatttca tagtgacctt taacattgat ttttcgactc     840
acatcttata gcgggtgaa gcagtatata aagaattcc acaaaaaaat ctacaacagc       900
cataagcatt aattacacat aaacgctcac caccctataa aacacccaga ccttcacatt    960
tcttcttcag acctccaaca agcagcagat agatagagaa atgaagagat agattagagt    1020
taccatcata tccccaacaa tggcatagcc aacaagttgg atccttcgga ccctgtagct    1080
cctggtccat gaattgccaa gagaacacct tttagttcct ttgagcaacc tcgatctcgc    1140
catggggttc cgctgtggcc gtgcctcctc ttcgctgctg tgtgaagagg acgtggccgg    1200
catgtttgga tgcaatgggc acgacgacga agaggtgggg cttctggtgt tggggatgga    1260
cacgactttt gctgcgctgc catcacagag cgacgaggtc gtagcatccc tgatggagaa    1320
ggagaaggag cagctgcata gcgttgcgac gggggattac ctccagaggc tgagcagtgg    1380
aggactggag tcatcttgta ggattgccgc cattgattgg ataaaaaagg tttctgcttc    1440
tccatccata ctatatagta tgtatatgat ttctcgcgca tcgatcctag ttagaatctc    1500
atgtttctgt gttttgcagc aaaatgcaat ttatttgact ccaagtttga cttaaacttc    1560
agtttgttca aaaaaaaaaa gtttgcccct gcttgaccaa aacctcgttt tgcatatata    1620
gataaatata tagttactga aatgtgtact acttgtctct tacatgtgta ttaattgcag    1680
gcccaggctt atcacgactt tggaccgttg tctgcttatc ttgctgttaa ctaccttgat    1740
agggtcctct ccacaaatca agtcccagtg agttctacaa atgtacccaa cttgtttatt    1800
cttttttcta catgtccaat cagcatgtgg ttgtcagagg tctttgcctc tccctctcta    1860
gaaaacctta tggcatgttt ggttcagcgg cggaccagga actaaagaca gcctatgcga    1920
gattataagt gtcaataact atagctaatt tcatataaaa aaatacatgc atatttggat    1980
ttgagatgca ctttcgtccg atcagtagat aaggtcattt ggtttaggat catgagttga    2040
gttaggactt agcactattg gaatcgagct cttttgtcaat tgtctgaagc actcggcaaa    2100
gctgggaaaa cactcgacga cgtctttgcc gagtgtagca ctcggcaaag agagctcggc    2160
gaacagtata tcgacacggc ttcttttgccg agtattttt atcgggcact cgacaaagac    2220
tttgccgagt gtcactcggt actcggcaaa gaaaagtcgc cgtcaaggcg accggaaacg    2280
```

```
gagacagcgc ctttgccgag tgttctaggt gacactcggc aaagagatta cctttgtcga   2340
gtgtccgcca gtctacactc gccaaagggg ctaccagcgg acccctttgt cagtttcttt   2400
gccgagtgcg ctagaaggca ctcggcaaag cttgcttctt tgtcgagtgc caaggccaca   2460
gcactcggca aataagcttt accggtgccc aggaatggca ctcggcaaaa tgttctttat   2520
cgagtgtcag gcgataggac actcggcaaa gtagcttctt tgccgaatgc caaagcctag   2580
cgttcggcat agataacagc cgtcagctat agacggctgc tgacggttct ttgcctagca   2640
ccgaattgtg tcgagtgttt ggcactcgac aaagtagtct ttgccactac tttgccgagt   2700
gtctttctgt gccgagagtc ctattatcgg caaacgcgat cgttatcgag agtgaaactt   2760
tgtcgagtgt ggcactcggc aaagaagtgt cgagtgcccg ataaaaaaca cttggcaaag   2820
agccaaattc cgatagcgta gcattcgtgc agccgtacgt tagaattgga cagacgaggg   2880
atgtgactgt gctcggctgt ccagctata tcctgcaacc aaacacaacc ttacattttg   2940
atggggcaca aatcttatgt gagtttcttg gtgtaggctg atgctgacca ccagccctgg   3000
atgccacagc tgctgtccgt tgcttgccta accattgcag ccaagatgga ggagaccgtg   3060
gttcctcgcc gtctggacat ccatcagaat caggtggaca aaattggata tatagtacag   3120
tttcacgttt gagttcacca aatctttatc tttattatat atatatatat gtcacaggtt   3180
ctcagcgaga agtacagatt cgatttagat gctattcaga ggatggagat ttacattcta   3240
gactctctga attggaggat gcaagctgtg acgccattct cttacatcaa ctatttcgtg   3300
gacaagttca ctgatgggaa gccgctaagt tgcggattca tttctcggtg caccgagatc   3360
atacttggca gtcttgaagg tacatcagat tacttcatgc atgagcgagc gaatcggact   3420
tacccgcctt ttccattcga taagcaattg ttactatgtg attggaacat gcatctaaat   3480
agatgtctgt gtgcatttga tttgcagcaa cgaagctcct acagttcagg ccttctgaga   3540
tggcagcagc agtggttctg tcagcagctg ctgagtctca agtcattgcc ttcagcggcg   3600 ctctttttagc ttctaatatc cttgtcaata aggtgtagat cctctctctc tatgaaggtt   3660
tagtattttt tttaatgtac gtatttacat ttctaggaaa atgtaaggag atgccatgaa   3720
gcattgcaag aagtgggatt agtgaagaag aaaacagact acagtgcgag tccatctcgc   3780
gtgctagatg cctcatgctt cagcttcaag actgacgata accagacagc cggttcatcc   3840
caatcccaag caaacaacaa tggcaactac aaccaggctt actctccagc tagcaagagg   3900
acaaggctag acatctagac tcaatcagga aaaattgcat gagatcatag acgtacacat   3960
atacacacaa gttttcttta gataaaggat acataaagtt aaatttgatt ctggctacat   4020
ttctgagtac gtgcttctca actcagaaga gttcataggg aacattatac atgcatgcat   4080
gctaacaggc aaaagaaggc tgaattatta agagcaatcc tatttatttc ctcctttgtt   4140
cctttgttaa cttttttcttt cttcttgtct actttaaatc atggcattag caaagacatt   4200
tgcgtgtatg ggacaggtga tgcaatgata caacataaaa gaaggctagg cattgttttc   4260
aacataagca gaggtaatct cgtttcagga aaaaatgag cgccaggaac tttgatatct   4320
gatcaaggga gaagcaaagt tagttgttgt gggaatctgt ggctgagttc ttggttctcg   4380
atttcttgtt tgtttgtttg tctgtgatga atattttca gatttattca atgaactgac   4440
catgttatgc tatagagcaa gtacaacaat aggttctaag caggataaat gatgaggtac   4500
aggagagaga agatgagaga gaggataagc gagctataaa cttacaacca tctaagactt   4560
agatataaga ataaaaaaac tttgagagag acaaatgagt tatgtattag tagtgaacgg   4620
ttaactatta tgtagatgga ctaagagata ggacgcaaat agccaatagt cagctatatt   4680
```

```
attagcctcg ctcttattca gcacccgggc aattttatcg tccaaatttg ttagcatgca   4740
tgctacttct tatagaatga atattagata tgcattaggc ttcacatcct attcaaaata   4800
aggtgctaga ggccttaaaa tttaagtgtt ttagatgagt tccatggatg aatcttagtt   4860
gcgccataca tataattaat ttaaaacaca caaaaaaaac actagccata tacttactat   4920
g                                                                  4921

<210> SEQ ID NO 10
<211> LENGTH: 1071
<212> TYPE: DNA
<213> ORGANISM: Zea mays

<400> SEQUENCE: 10
atgaagagat agattagagt taccatcata tccccaacaa tggcatagcc aacaagttgg     60
atccttcgga ccctgtagct cctggtccat gaattgccaa gagaacacct tttagtttct    120
ttgagcaacc tcgatctcgc catggggttc cgctgtggcc gtgcctcctc ttcgctgctg    180
tgtgaagagg acgtggccgg catgtttgga tgcaatgggc acgacgacga agaggtgggg    240
cttctggtgt tggggatgga cacgactttt gctgcgctgc catcacagag cgacgaggtc    300
gtagcatccc tgatggagaa ggagaaggag cagctgcata gcgttgcgac ggggggattac    360 ctccagaggc tgagcagtgg aggactggag tcatcttgta ggattgccgc cattgattgg    420
ataaaaaagg cccaggctta tcacgacttt ggaccgttgt ctgcttatct tgctgttaac    480
taccttgata gggtcctctc cacaaatcaa gtcccagtga gttctacaaa taagtacaga    540
ttcgatttag atgctattca gaggatggag atttacattc tagactctct gaattggagg    600
atgcaagctg tgacgccatt ctcttacatc aactatttcg tggacaagtt cactgatggg    660
aagccgctaa gttgcggatt catttctcgg tgcaccgaga tcatacttgg cagtcttgaa    720
gcaacgaagc tcctacagtt caggccttct gagatggcag cagcagtggt tctgtcagca    780
gctgctgagt ctcaagtcat tgccttcagc ggcgctcttt tagcttctaa tatccttgtc    840
aataaggaaa atgtaaggag atgccatgaa gcattgcaag aagtgggatt agtgaagaag    900
aaaacagact acagtgcgag tccatctcgc gtgctagatg cctcatgctt cagcttcaag    960
actgacgata accagacagc cggttcatcc caatcccaag caaacaacaa tggcaactac   1020
aaccaggctt actctccagc tagcaagagg acaaggctag acatctagac t           1071

<210> SEQ ID NO 11
<211> LENGTH: 5918
<212> TYPE: DNA
<213> ORGANISM: Zea mays

<400> SEQUENCE: 11
ttggtagtgg aattagctag ctaacaaata actatctaac tattaactaa tttaccaaaa     60
atagctaata gttgaactat taactaaagt gtttggatgt ctcaactaat tttagctact    120
aactattagc tctagtgcat tcaaacaccc cttaagtgaa tgtcatggta tgggctgaca    180
tttcgagagg tggagagtgt catggtatgg gctgccatgt gggccgagag tccgagaccg    240
ggctaaatga gctgggctga ataggactga ctgcaggtag aaaggcaagc gcaacatttg    300
gcaccgttag ctctccacta aacttgtcag atgcaataat ttatgttttt attaatggca    360
aagccctcct gccagccagt gccttccttc cgggtcaacc actggtacag tcacatcacg    420
aattcccact ggcagtacga taacctcact gagcggtagg gcctcccgtc ccagaatcct    480
```

```
gcaggaccca tcgatcatgg ccccacgggt cctgctcctg cgtgggttcc aattccaagt    540
cgcccaccgt gacgcccatc gagtcaaccg aacccaagcc gtgtggcgac tggcgaggcg    600
agtgccccag ttcctaactc cggtgggcgc gctcccaccg ccgcgcggct caaaacccgc    660
cctcagcctc ccgcgctcca gtccacacgg gagcgggtgg tgtcgtctga agcggcgcga    720
tcaaggagtc ttcgggcgct ccggtgagct atctagatct caacatcctc tcccctctgt    780
agtctgtagt tgtactctcc cgcccgatgg ttcagttaag ttatatcctc tccccttatt    840
tttactcggt cgataccatt tcgttgtgga ttgggcgccc ccgcaggttg aaatgctgcc    900
catcatgctg cggccctgta ctatgaggat ggttctagtt ttgcgtctgg caatttgggg    960
cgtacatgct tttggctgcg tactgttact gatcggagaa aatgtttgta acgtatgatt   1020 cgttttcag gacgtaacgt gctggcggtt gcttatctcc ggatgtatat ataagcggaa    1080
atgttctcct tgttctatgg cctgtggaag tatgtgttcg ccaaggacga gttccgtgtt   1140
ctgattcttg tgttgacag agctggcaag acggtagctg ctagctccca gccttcatat    1200
atatatttcc ctttctgaac tagaaattga tgatacttac ctgtacacga tgtttctgga   1260
accgttgcca tagactttgc tggagaagtt gaaatcgata tatctcaagg gggaaggact   1320
tccgcctgac cgtgtcgttc caacagttgg gctcaacatt ggccgcatcg aagacgcaaa   1380
ggcaaaactt gttttctggg atctaggtgg tcaggtaaga acgtttacgt acgtagtaaa   1440
gtgagccttc tgttgccgtg gcaccaccct acgatcgttg atatttgagt cttgtcagtt   1500
tggtgctata tcagggtttc taatgcctgg gaaatacatg tcataaattc aaattactag   1560
gatgtggttg ctttagttat taacctagca tcttttttgcg ttccagcaga atatatataa   1620
tctagttata tggaatgctc aatagaattt tcagaaagca aagatatgct ctgttggcta   1680
acattcacag tactcaatag aattgtttac tagtagaaca gcatcagctt ctctgctatg   1740
ttataagaat tagtgtaaaa ctaacttcag tatcactgct tgctagtatg ataattaagc   1800
ttccatgcca agttcagtat ttcttacaca cttgcctgct tggcaggtta gcctacgaac   1860
aatctgggag aaatactatg aagaggccca tgccataatg tacgttattg acgctgccac   1920
agcatcgtca tttgaagatt ccaaatctgc tctgggtaag gttcttattt gtgttaatta   1980
taaactactc cctccattcc aaattataag acattttggc ctttttctta gataaataaa   2040
ttttgctatg gacttaaata ttatttatat atatatatat atatatataa aatgtcctgg   2100
tacatagtta aaacattata tcttaaaaag ctaaacatt gtcttataac ttggaacaag    2160
ggagtactgg tttgtttcta ttgctagatc ttccgagaag atgcattgcc tctctggtaa   2220
atgggatgag aactcattct agctagagaa cctaacctaa atttcttact tcagagaagg   2280
ttattcgcca tgaacatctg agaggagcac cactcttgat agttgcaaac aaacaggtga   2340
agggtttact tccactttct atattttgta ccacagtaca taattatgat tgaaagattc   2400
agtgcttaca ataaagttgc catcgtagta aaataaagat tttgtttttg tcatgtgccc   2460
atgctgtgag gcatacaaat ctaaattcct acgttgcaaa gcgcctatgc gccattgcga   2520
ggttgaatac cagatgtagt ttggccaatt gtgatgtaca gatgtgccac attgacaatt   2580
gacacgcagt ttaaaggaga gtcagactac tagtttttc attgcccaac atataccttt    2640
ggccacttat tgaaaatgtg agagatcatt tgagtttgaa cagtaagttt tgtgagatat   2700 catttattt agtaatcatg cacacatgtc tagaattgtg aaatgcacaa taaagacgca    2760
aactcccacg agcatgcagg tacacccgat tgaggattct cagcgaatgt tccagtttcg   2820
agaatcaaac aacatataac aatgatgaat ttttaaatc aattaaaact tcctgaaaag    2880
```

```
atcacatgga aaccaatgac tacatgcact gtctgtttct gttaagctgg gtacacatta    2940
ttctatcaaa ttgtttatta tttacctctt gttctcatgt ttggagggtg cttctggatt    3000
tcttttggca ggatttacct ggagccattg atgaggaaga attggctaaa tttctgcata    3060
aagaactgga tgagaggcca tatacatttc aggctgtatc tgcatatgat gggtgagcgc    3120
agaaactcaa ctggttcctg aggaaatttg actcgccatg aaaaaaaatg acaattttac    3180
tcaaagatac aaaaaattca cacattcgtc tgttatattg tttcctgggt gcatgaaact    3240
caactggttc gtgaggaaat ttgactcgcc atgaaaaaaa tgacaatttt actcaaagat    3300
acaaaaaatt cacacattcg tctgttatat tgtttcctgg gtgcatgata ttctaaagat    3360
ctgttatatt gtttaaatgt gacaccggct cttgcagcag ggggatcaaa tctggcatag    3420
actggctggt ggaacaaatg gaaaaaagca aacgtaccga gacactgcag gctcgtgctg    3480
gcgtagctgg acaaatttag aatggggtga atttgttaaa gaacaaagca ttggatagga    3540
cggcttcctt cgtatcgcgt aagcagccat ttgctgcatt ccgggattat cgttccaggt    3600
cgcccagagt gctgcaagaa atgtttggct ggttgctcct gtggtggtgg tgattggtga    3660
ggcgattcgt ttggtattat tgaggttgca ttcatatgta cctaaaggtc gcaagcatac    3720
atgtctatat gatgcttttc aattttcgta gcaaactagt agcttcaata cagaggatca    3780
aagagagccg tgttctttaa cttgtttgtg ataaaaaaaa aggaagaaag gaaagcgaag    3840
aaggaattat tggtgcatct gaaagtcttt attgcatatg tctaaaccat tttaaccgat    3900
gctggatgag cttttcttcg caccgatgtt acatctagtc tatcatatgt atcctcgttt    3960
catactcgca ccgatgttac atctagtcta tcatatgtat cctcgtttca tactcgatcc    4020
ttttttatgg ccaaactcca acacaacata tacatttctg tagcgcatac gtattgaaca    4080
tgtctttttt agactaacat tctgcaccga acaatatagc agatcgaatt gtcatcctat    4140
aaagattatt tttaactttt gtggtatcct attgtcatat ttattgaggt tgcattcata    4200
tgtacctaaa ggtcgcaagc atacatgtct atatgatgct tttcaatttt cgtagcaaac    4260
tagtagcttc aatacagagg atcaaagaga gccgtgttct ttaacttgtt tgtgataaaa    4320
aaaaaggaag aaaggaaagc gaagaaggaa ttattggtgc atctgaaagt ctttattgca    4380
tatgtctaaa ccattttaac cgatgctgga tgagcttttc ttcgcaccga tgttacatct    4440
agtctatcat atgtatcctc gtttcatact cgcaccgatg ttacatctag tctatcatat    4500
gtatcctcgt ttcatactcg atccttttt atggccaaac tccaacacaa catatacatt    4560
tctgtagcgc atacgtattg aacatgtctt ttttagacta acattctgca ccgaacaata    4620
tagcagatcg aattgtcatc ctataaagat tcttttttaac ttttgtggta tcctattgtc    4680
atatagaaca tcaaatgttt ggcgccacct catccttttga ctaataccttt tatcactatc    4740 tctacgtagc ctttcgtagc atagatccta aatatctatg catagatcct aaatatctat    4800
gcatagatcc taaatatcta agatgtcct ttcagaacac tacttgattt ttcaaactaa    4860
catgtctttc ctcatatgta gtagcataga ttctaaatat ctaaagatgt ccttccggac    4920
actacttgat ttttcaaact aacatgtctt cctcatatg tagtagtgtt gaaatcacat    4980
cttttatatt caatttgagt tctactgatc gagtccaaaa tcgtccaaaa cctttaaact    5040
ctagaatctc ccacgacaac tctagttttc catttactcg tgcttagctt tcatcaacta    5100
acactacatc cataaaaaca tatgttaaga gatcccttg tgatcttatc catagactca    5160
aagctaattt ttttatgtag tcatattcta atcggaaagt cacatgtgtc tccatcatt    5220
```

| | |
|---|---|
| attcaaacat attcataaca ttgttgttgg aactttgctt cctcaaaaaa tagggataaa | 5280 |
| aaaaacagta aaaggaattg gcccttcagg ctagggctgc tgatatcccc actaagctgg | 5340 |
| gccaatcggc caagaaactt tgcttcattc agggcatggt atggacaacc cactgcgggt | 5400 |
| tgccaaacaa aggagttagt aagaaaccac aaaatgctta gtctgagctt tgaagagttc | 5460 |
| tacttggtga gtaaaacagt taatcttaac tactgcttgg ctaagataag atgttagtca | 5520 |
| aaagaattct gtagatgtgc aatctcaaac caatctgcct ttgcatcatt tagaaaactg | 5580 |
| ctttaaaatt cgaaatattt tgcttaccat agctcatagc acagaagaat attatagaac | 5640 |
| aaaccaaggc aagtgacttt ctgaaacaca gttttcaaga acaggttcag attaaactag | 5700 |
| ataacaggat gccagcgttg gtaataagtg tactccccaa gagaagtcgc tgttttgttc | 5760 |
| tatctcaatg aaaaataacg acacgaaaat gaactatggc cgtctgcatt aatatggata | 5820 |
| ctcagcaaaa atggacatga gtaactcaaa atcgtcaatt gcttgctatg ttaggcaccc | 5880 |
| aagtcaatga tttctattcc atgctatcac aaagatta | 5918 |

<210> SEQ ID NO 12
<211> LENGTH: 1288
<212> TYPE: DNA
<213> ORGANISM: Zea mays
<400> SEQUENCE: 12

| | |
|---|---|
| ttccaagtcg cccaccgtga cgcccatcga gtcaaccgaa cccaagccgt gtggcgactg | 60 |
| gcgaggcgag tgccccagtt cctaactccg gtgggcgcgc tcccaccgcc gcgcggctca | 120 |
| aaacccgccc tcagcctccc gcgctccagt ccacacggga gcgggtggtg tcgtctgaag | 180 |
| cggcgcgatc aaggagtctt cgggcgctcc ggacgtaacg tgctggcggt tgcttatctc | 240 |
| cggatgtata tataagcgga aatgttctcc ttgttctatg gcctgtggaa gtatgtgttc | 300 |
| gccaaggacg agttccgtgt tctgattctt ggtgttgaca gagctggcaa gacgactttg | 360 |
| ctggagaagt tgaaatcgat atatctcaag ggggaaggac ttccgcctga ccgtgtcgtt | 420 |
| ccaacagttg ggctcaacat tggccgcatc gaagacgcaa aggcaaaact tgttttctgg | 480 |
| gatctaggtg gtcaggttag cctacgaaca atctgggaga aatactatga agaggcccat | 540 |
| gccataatgt acgttattga cgctgccaca gcatcgtcat ttgaagattc caaatctgct | 600 |
| ctggagaagg ttattcgcca tgaacatctg agaggagcac cactcttgat agttgcaaac | 660 |
| aaacaggatt tacctggagc cattgatgag gaagaattgg ctaaatttct gcataaagaa | 720 |
| ctggatgaga ggccatatac atttcaggct gtatctgcat atgatggcag ggggatcaaa | 780 |
| tctggcatag actggctggt ggaacaaatg gaaaaaagca aacgtaccga gacactgcag | 840 |
| gctcgtgctg gcgtagctgg acaaatttag aatggggtga atttgttaaa gaacaaagca | 900 |
| ttggatagga cggcttcctt cgtatcgcgt aagcagccat ttgctgcatt ccgggattat | 960 |
| cgttccaggt cgcccagagt gctgcaagaa atgtttggct ggttgctcct gtggtggtgg | 1020 |
| tgattggtga ggcgattcgt ttggtattat tgaggttgca ttcatatgta cctaaaggtc | 1080 |
| gcaagcatac atgtctatat gatgcttttc aattttcgta gcaaactagt agcttcaata | 1140 |
| cagaggatca aagagagccg tgttctttaa cttgtttgtg ataaaaaaaa aggaagaaag | 1200 |
| gaaagcgaag aaggaattat tggtgcatct gaaagtcttt attgcatatg tctaaaccat | 1260 |
| tttaaccgat gctggatgag ctttctctt | 1288 |

<210> SEQ ID NO 13
<211> LENGTH: 979

```
<212> TYPE: DNA
<213> ORGANISM: Zea mays

<400> SEQUENCE: 13
aatcgagtca accgaaccca agccgtgtgg cgactggcga ggcgagtgcc ccagttccta    60
actccggtgg gcgcgctccc accgccgcgc ggctcaaaac ccgccctcag cctcccgcgc   120
tccagtccac acgggagcgg gtggtgtcgt ctgaagcggc gcgatcaagg agtcttcggg   180
cgctccggac gtaacgtgct ggcggttgct tatcaccgga tatatatata taagcggaaa   240
tgttctcctt gttctatggc ctgtggaagt atgtgttcgc caaggacgag ttccgtgttc   300
tgattcttgg tgttgacaga gctggcaaga cgactttgct ggagaagttg aaatcgatat   360
atctcaaggg ggaaggactt ccgcctgacc gtgtcgttcc aacagttggg ctcaacattg   420
gccgcatcga agacgcaaag gcaaaacttg ttttctggga tctaggtggt caggttagcc   480
tacgaacaat ctgggagaaa tactatgaag aggcccatgc cataatgtac gttattgacg   540
ctgccacagc atcgtcattt gaagattcca aatctgctct ggagaaggtt attcgccatg   600
aacatctgag aggagcacca ctcttgatag ttgcaaacaa acaggattta cctggagcca   660
ttgatgagga agaattggct aaatttctgc ataaagaact ggatgagagg ccatatacat   720
ttcaggctgt atctgcatat gatgggtgag cgcagaaact caactggttc ctgaggaaat   780
ttgactcgcc atgaaaaaaa atgacaattt tactcaaaga tacaaaaaat tcacacattc   840
gtctgttata ttgtttcctg ggtgcatgaa actcaactgg ttcgtgagga aatttgactc   900
gccatgaaaa aaatgacaat tttactcaaa gatacaaaaa attcacacat tcgtcaaaaa   960
aaaaaaaaaa aaaaaaaa                                                 979

<210> SEQ ID NO 14
<211> LENGTH: 1305
<212> TYPE: DNA
<213> ORGANISM: Zea mays

<400> SEQUENCE: 14
aaccgaaccc aagccgtgtg gcgactggcg aggcgagtgc cccagttcct aactccggtg    60
ggcgcgctcc accgtcgcg cggctcaaaa cccgccctca gcctcccgcg ctccagtcca   120
cacgggagcg gtggtgtcg tctgaagcgg cgcgatcaag gagtcttcgg gcgctccgga   180
cgtaacgtgc tggcggttgc ttatcaccgg atatatatat ataagcggaa atgttctcct   240
tgttctatgg cctgtggaag tatgtgttcg ccaaggacga gttccgtgtt ctgattcttg   300
gtgttgacag agctggcaag acgactttgc tggagaagtt gaaatcgata tatctcaagg   360
gggaaggact tccgcctgac cgtgtcgttc aacagttggg ctcaacatt ggccgcatcg   420
aagacgcaaa ggcaaaactt gttttctggg atctaggtgg tcaggttagc ctacgaacaa   480
tctgggagaa atactatgaa gaggcccatg ccataatgta cgttattgac gctgccacag   540
catcgtcatt tgaagattcc aaatctgctc tggagaaggt tattcgccat gaacatctga   600
gaggagcacc actcttgata gttgcaaaca acaggattt acctggagcc attgatgagg   660
aagaattggc taaatttctg cataaagaac tggatgagag gccatataca tttcaggctg   720
tatctgcata tgatgggagg gggatcaaat ctggcataga ctggctggtg aacaaatgg   780
aaaaaagcaa acgtaccgag acactgcagg ctcgtgctgg cgtagctgga caaatttaga   840
atggtaagct tgcagctgcg accggatgaa tttgttaaaa gaacaaagca ttggatagga   900
cggcttcctt cgtatcgcgt aagcagccat ttgctggatt acaggattga tcgttccagg   960
```

```
ccgcccagag tgctgcaaga aatgtttggc tggttgctcc tgtggtggtg gtgattggtg    1020
aggcgattcg tttggtatta gaggttgcat tcatatgtac ctaaaggtca cgagcataca    1080
tgtctatatg atgcttttca attttcgtag caaactagta gcttcaacac agaggatcaa    1140
agagagccgt gttctttaac ttgtttgtga taaaaaaaag gaagaaagga aagcgaagaa    1200
ggaatcactg gtgcatctga aagtctttat tggatatgtc taaaccattt caactgatgc    1260
tggataagtt tttcttaaaa aaaaaaaata aaaaaaaaaa aaaaa                    1305
```

<210> SEQ ID NO 15
<211> LENGTH: 3993
<212> TYPE: DNA
<213> ORGANISM: Zea mays
<220> FEATURE:
<221> NAME/KEY: misc_feature
<222> LOCATION: (2094)..(2094)
<223> OTHER INFORMATION: n is a, c, g, or t

<400> SEQUENCE: 15

```
tgaaaatata tattgaataa cttttaacgg cttttagtgg tttccatcaa acggttttta      60 gcttttaac atctcacagc ccacagtaac ttttttccaca gctcacaacc tatagcagct     120
tttttcacag ccacatccca actaaaaaga ccctaagtga atgtcatggt atgggctgac     180
atttcgagag gtggacaaat ggagaatggc atgatatggg ctgccatgtg ggccgagggt     240
ctgagaccgg gctaaatgag ctgggctgaa gaggactgac tgtaggtaga aaggcaagcg     300
caacatttgg caccgttagc tctccactaa acttgtcaga tgcaataatt tatgtttttt     360
aaatggcaaa gccctcctgc cagccagtgc cttccttccg ggtcaaccac tggtaccgtc     420
acatcacgaa ttcccactgg cagtacgata acctcactga gcggtagggc ctcccgtccc     480
agaatcctgc aggacccatc gatcatgccc cacgggtcc tgctcctgcg tgggttccaa      540
ttccaagtcg cccaccgtga cgcccatcga gtcaaccgaa cccaagccgt gtggcgactg     600
gcgaggcgag tgccccagtt cctaactccg gtgggcgcgc tcccaccgcc gcgcggctca     660
aaacccgccc tcagcctccc gcgctccagt ccacacggga gcgggtggtg tcgtctgaag     720
cggcgcgatc aaggagtctt cgggcgctcc ggtgagctat ctagatctca acatcctctc     780
ccctctgtag tctgtagttg tactctcccg cccgatggtt cagttaagtt atatcctctc     840 cccttattt  tactcggtcg ataccatttc gttgtggatt gggcgccccc gcaggttgaa     900
atgctgccca tcatgctgcg gccctgtact atgaggatgg ttctagtttt gcgtctggca     960
atttggggcg tacatgcttt tggctgcgta ctgttactga tcggagaaaa tgtttgtaac    1020
gtatgattcg ttttttcagga cgtaacgtgc tggcggttgc ttatctccgg atgtatatat    1080
aagcggaaat gttctccttg ttctatggcc tgtggaagta tgtgttcgcc aaggacgagt    1140
tccgtgttct gattcttggt gttgacagag ctggcaagac ggtagctgct agctcccagc    1200
cttcatatat atatttccct ttctgaacta gaaattgatg atacttaccct gtacacgatg    1260 tttctggaac cgttgccata gactttgctg gagaagttga aatcgatata tctcaagggg    1320
gaaggacttc cgcctgaccg tgtcgttcca acagttgggc tcaacattgg ccgcatcgaa    1380
gacgcaaagg caaaacttgt tttctgggat ctaggtggtc aggtaagaac gtttacgtac    1440
gtagtaaagt gagccttctg ttgccgtggc accaccctac gatcgttgat atttgagtct    1500
tgtcagtttg gtgctatatc agggtttcta atgcctggga aatacatgtc ataaattcaa    1560
attactagga tgtggttgct ttagttatta acctagcatc ttttttgcgtt ccagcagaat    1620 atatataatc tagttatatg gaatgctcaa tagaattttc agaaagcaaa gatatgctct    1680
```

```
gttggctaac attcacagta ctcaatagaa ttgtttacta gtagaacagc atcagcttct    1740
ctgctatgtt ataagaatta gtgtaaaact aacttcagta tcactgcttg ctagtatgat    1800
aattaagctt ccatgccaag ttcagtattt cttacacact tgcctgcttg gcaggttagc    1860
ctacgaacaa tctgggagaa atactatgaa gaggcccatg ccataatgta cgttattgac    1920
gctgccacag catcgtcatt tgaagattcc aaatctgctc tgggtaaggt tcttatttgt    1980
gttaattata aactactccc tccattccaa attataagac attttggcct tttttctaga    2040
taaataaatt ttgctatgga cttaaatatt atttatatat atatatatat atantatata    2100
tatatatata tataaaatgt cctggtacat agttaaaaca ttatatctta aaaagctaaa    2160
acattgtctt ataacttgga acaagggagt actggtttgt ttctattgct agatcttccg    2220
agaagatgca ttgcctctct ggtaaatggg atgagaactc attctagcta gagaacctaa    2280
cctaaatttc ttacttcaga gaaggttatt cgccatgaac atctgagagg agcaccactc    2340
ttgatagttg caaacaaaca ggtgaagggt ttacttccac tttctatatt ttgtaccaca    2400
gtacataatt atgattgaaa gattcagtgc ttacaataaa gttgccatcg tagtaaaata    2460
aagattttgt ttttgtcatg tgcccatgct gtgaggcata caaatctaaa ttcctacgtt    2520
gcaaagcgcc tatgcgccat tgcgaggttg aataccagat gtagtttggc caattgtgat    2580
gtacagatgt gccacattga caattgacac gcagtttaaa ggagagtcag actactagtt    2640
ttttcattgc ccaacatata cctttggcca cttattgaaa atgtgagaga tcatttgagt    2700
ttgaacagta agttttgtga gatatcattt tatttagtaa tcatgcacac atgtctagaa    2760
ttgtgaaatg cacaataaag acgcaaactc ccacgagcat gcaggtacac ccgattgagg    2820
attctcagcg aatgttccag tttcgagaat caaacaacat ataacaatga tgaattttt     2880 aaatcaatta aaacttcctg aaaagatcac atggaaacca atgactacat gcactgtctg    2940
tttctgttaa gctgggtaca cattattcta tcaaattgtt tattatttac ctcttgttct    3000
catgtttgga gggtgcttct ggatttcttt tggcaggatt tacctggagc cattgatgag    3060
gaagaattgg ctaaatttct gcataaagaa ctggatgaga ggccatatac atttcaggct    3120
gtatctgcat atgatgggtg agcgcagaaa ctcaactggt tcctgaggaa atttgactcg    3180
ccatgaaaaa aaatgacaat tttactcaaa gatacaaaaa attcacacat tcgtctgtta    3240 tattgttttcc tgggtgcatg aaactcaact ggttcgtgag gaaatttgac tcgccatgaa    3300
aaaaatgaca tttttactca agatacaaa aaattcacac attcgtctgt tatattgttt    3360
cctgggtgca tgatattcta aagatctgtt atattgttta aatgtgacac cggctcttgc    3420
agcaggggga tcaaatctgg catagactgg ctggtggaac aaatggaaaa aagcaaacgt    3480
accgagacac tgcaggctcg tgctggcgta gctggacaaa tttagaatgg ggtgaatttg    3540
ttaaagaaca aagcattgga taggacggct tccttcgtat cgcgtaagca gccatttgct    3600
gcattccggg attatcgttc caggtcgccc agagtgctgc aagaaatgtt tggctggttg    3660
ctcctgtggt ggtggtgatt ggtgaggcga ttcgtttggt attattgagg ttgcattcat    3720
atgtacctaa aggtcgcaag catacatgtc tatatgatgc ttttcaattt tcgtagcaaa    3780
ctagtagctt caatacagag gatcaaagag agccgtgttc tttaacttgt ttgtgataaa    3840
aaaaaaggaa gaaaggaaag cgaagaagga attattggtg catctgaaag tctttattgc    3900
atatgtctaa accatttaa ccgatgctgg atgagctttt cttcgcaccg atgttacatc     3960
tagtctatca tatgtatcct cgtttcatac tcg                                 3993
```

<210> SEQ ID NO 16
<211> LENGTH: 6492
<212> TYPE: DNA
<213> ORGANISM: Zea mays

<400> SEQUENCE: 16

| | | | | | |
|---|---|---|---|---|---:|
| cgaagaacaa | ggaaagcact | tgtccatcaa | ttgcacttga | gtagcaaagg | tttcaggttg | 60 |
| tcggtgctga | catctcttct | actctgttaa | gaccaggcta | aggggtgtt | tgaatgcact | 120 |
| agaactaata | gttagttggc | taaaaattgg | tagtggaatt | agctagctaa | caataacta | 180 |
| tctaactatt | aactaatta | ccaaaaatag | ctaatagttg | aactattaac | taaagtgttt | 240 |
| ggatgtctca | actaatttta | gctactaact | attagctcta | gtgcattcaa | acacccctta | 300 |
| agtgaatgtc | atggtatggg | ctgacatttc | gagaggtgga | gagtgtcatg | gtatgggctg | 360 |
| ccatgtgggc | cgagagtccg | agaccgggct | aaatgagctg | ggctgaatag | gactgactgc | 420 |
| aggtagaaag | gcaagcgcaa | catttggcac | cgttagctct | ccactaaact | tgtcagatgc | 480 |
| aataatttat | gttttatta | atggcaaagc | cctcctgcca | gccagtgcct | tccttccggg | 540 |
| tcaaccactg | gtacagtcac | atcacgaatt | cccactggca | gtacgataac | ctcactgagc | 600 |
| ggtagggcct | cccgtcccag | aatcctgcag | gacccaccga | tcatagcccc | acgggtcctg | 660 |
| ctcctgcgtg | ggttccagtt | ccaagtcgcc | caccgtgacg | cccatcgagt | caaccgaacc | 720 |
| caagccgtgt | ggcgactggc | gaggcgagtg | ccccagttcc | taactccggt | gggcgcgctc | 780 |
| ccaccgccgc | gcggctcaaa | acccgccctc | agcctcccgc | gctccagtcc | acgggagc | 840 |
| gggtggtgtc | gtctgaagcg | gcgcgatcaa | ggagccttcg | agcgctccgg | tgagctatct | 900 |
| agatctcaac | atcctctccc | ctctgtagtc | tgtagttgta | ctctcccgcc | cgatggttca | 960 |
| gttaagttat | atcctctccc | cttatttta | ctcggtcgat | accatttcgt | tgtggattga | 1020 |
| aatgctgcgg | ccctgtacta | tgaggatggt | tcctagtttt | gcgtctggca | atttggggcg | 1080 |
| tacatgcttt | tggctgcgta | ctgttactga | tcggagaaaa | tgtttgtaac | gtatgattcg | 1140 |
| tttttcagga | cgtaacgtgc | tggcggttgc | ttatcgccgg | atatatatat | ataagcggaa | 1200 |
| atgttctcct | tgttctatgg | cctgtggaag | tatgtgttcg | ccaaggacga | gttccgtgtt | 1260 |
| ctgattcttg | gtgttgacag | agctggcaag | acggtagctg | ctagctccca | gccttcatat | 1320 |
| atatatattt | ccctttctga | actagaaatt | gatgaaactt | acctgtacac | aatgtttctg | 1380 |
| gaaccgttgc | catagacttt | gctggagaag | ttgaaatcga | tatatctcaa | gggggaagga | 1440 |
| cttccgcctg | accgtgtcgt | tccaacagtt | gggctcaaca | ttggccgcat | cgaagacgca | 1500 |
| aaggcaaaac | ttgttttctg | ggatctaggt | ggtcaggtaa | gaacgtttac | gtacgtagta | 1560 |
| aagtgagcct | tctgttgccg | tggcaccacc | ctacgatcgt | tgatatttga | gtcttgtcag | 1620 |
| tttggtgcta | tatcagggtt | tctaatgcct | gggaaataca | tgtcataaaa | tcaaattact | 1680 |
| aggatgtggt | tgctttagtt | attaacctag | catcttttg | cgttccagca | gaatatatat | 1740 |
| aatctagtta | tatggaatgc | tcaatagaat | tttcagaaag | caaagatatg | ctctgttggc | 1800 |
| taacattcac | agtactcaat | agaattgggt | ggctagtaga | acagcatcag | cttctctgct | 1860 |
| atgttataag | aattagtgta | aaactaactt | cagtatcact | gcttgctagt | atgataatta | 1920 |
| agcttccatg | ccaagttcag | tatttcttac | acacttgcct | gcttggcagg | ttagcctacg | 1980 |
| aacaatctgg | gagaaatact | atgaagaggc | ccatgccata | atgtacgtta | ttgacgctgc | 2040 |
| cacagcatcg | tcatttgaag | attccaaatc | tgctttgggt | aaggttctta | tttgtgtcaa | 2100 |
| ttataaacta | cgccatccat | tccaaattat | aagacatttt | ggcctttttc | tagataaata | 2160 |

```
aattttgcta tggacttaaa tattaaaaat atatataatg tcctggtaca tagttaaaac      2220
aatatatcta gaaaagctaa acatcgtcct tataacttgg aacagaggga gtactggttt      2280
gtttctattg ctagatcttt ccagaagatg caatgcctct ctggtaaatg ggatgagaac      2340
tcattctaga gaacctaacc taaatttctt acttcagaga aggttattcg ccatgaacat      2400
ctgagaggag caccactctt gatagttgca acaaacagg tgaagggttt acttccactt       2460
tctatatttt gtaccacagt acataattat gattgaaaga tttagtgctt acaataaagt      2520
tgccatcgta gttaaaataa agattttgtt tttgtcatgt gcacatgctg tgaggcatac      2580
aaatataaat tcctacgttg caaagcgcct atgcgccatt gcgaggttga ataccagatg      2640
tagtttttaa atcaattaaa acttcctgaa aagatcacat ggaaaccaat gactacatgc      2700
actgtctgtt tctgttaagc tgggtacaca ttattctatc aaattgttta ttatttacct      2760
ctagcttgtt ctcatgtttg gagggtgctt ctggatttct tttggcagga tttacctgga      2820
gccattgatg aggaagaatt ggctaaattt ctgcataaag aactggatga gaggacatat      2880
acatttcagg ctgtatctgc atatgatggg tgagcgcaga aactcaactg gttcctgagg      2940
aaatttgact cgccatgaaa aaatgacaa ttttactcaa agatacaaaa aaattcacac        3000
attcgtctgt tatattgttt cctgggtgca tgatattcta aagatctgtt atattgttta      3060
aatgtgacac cggctcttgc aggaggggga tcaaatctgg catagactgg ctggtggaac      3120
aaatggaaaa aagcaaacgt accgagacac tgcaggctcg tgctggcgta gctggacaaa      3180
tttagaatgg ggtgaatttg ttaaagaaca aagcattgga taggaccgct tccttcgtat      3240
cgcgtaagca gccatttgct gcattccggg attatcgttc caggtcgccc agagtgctgc      3300
aagaaatgtt tggctggttg ctcctgtggt ggtggtgatt ggtgaggcga ttcgtttggt      3360
attattgagg ttgcattctt atgtacctaa aggtcgcaag catacatgtt tatatgatgc      3420
ttttcaattt tcgtagcaaa ctagtagctt caatacagag gatcaaagag agccgtgttc      3480
tttaacttgt ttgtgataaa aaaaaggaag aaaggaaagc gaagaaggaa ttattggtgc      3540
atctgaaagt cttattgat atgtctaaac catttcaacc gatgttggat gaggttttct      3600
tcgcaccggt gttacatcta gtctatcata tgtatcgtcg tttcatactc gatccttttt      3660
tatggccaaa ctccaacaca acatatgcat ttctgtagcg catatgtatt gaacatgtct      3720
tttttagact aacattttgc accgaacaac atagcagatc gaattgtcat cctataaaac      3780 ttcttttaa cttttgtggt atcctattgt catatagaat atcaaatgtt tggcgctacc       3840
tcatccattg actaatacct ttatcaatat ctctacgtag catagatcct aaatatctaa      3900
agatgtcctt catggacact acttgatttt tcaaactaac atgtctttcc taatatgtag      3960
tagcatagat cctaaatatc taagatgtc cttcctggac actacttgat ttttcaaact       4020
aacatgtctt tcctcatatg tagtagtgtt gaaatcacat cttttatatt caatttgagt      4080
tctactgatc gagtccaaaa tcgtccaaaa cctttaaact ctagaatctc ccaccacaac      4140
tctagttttc tatttactcg tgcttagctt tcatcaacta acactacatc cataaaaaac      4200
atatgttaag agatatccct ttgtgatctt atccatagac tcagctaatt ttttatgtag      4260
tcatattcta atcgaaaagt cacatgtgtc tccatcattt attcaaacat attcataaca      4320
ttgttgttgg aactttgctt cctcaaaaaa cagggataaa aacagtaaa aggaattggc       4380 ccttcaggct agagctgctg atatccccac taagctgggc caatcggcca agaaactttg      4440
cttcattcag ggcatgatat ggacaaccca ctgcggattg ccaaacaaag aagttagtaa      4500
```

```
gaaaccacaa aatgcttagt ctgagctttg aagagttcta cttggtgagt aaaacagtta    4560
atcttaacta ctgcttggct aagataagat gttagctaaa agaattctgt agatgtgcaa    4620
tctcaaacca atctgccttt gcatcattta gaaaactgct ttaaaattcg aaatattttg    4680
cttacaatag ctcatagcac agaagaatat tatagaacaa accaaggcaa gtgactttct    4740
gaaacacagt tttcaagaac aggttcagat taaactagat aacaggatgc cagcgttggt    4800
aataagtcta ctccccaaga gaagtcactg ttttgttctt tctcaatgaa aaataacgac    4860
acaaaaatga actatggccg tctgcattaa tatggatacg cagcaaaaat ggacatgagt    4920
aactcaaaat cgtcaagtgc ttgctatgtt aagcacccaa gtcaatgatt tatattccat    4980
gatatcgcaa agattatcta taacaagttc tgagtgtgtt tcaaacatta aatgatccat    5040
gaaaggtaag cacttgtatt tagcggacag tactagtctg ctgtgggatt aacccatttt    5100
ttatggttct cgatggcctt ttgcttcaag ataatatctg atccaattaa tagacaaaat    5160
cacaagtaat ctttgttaca tgtcatcatc gaatcctatc ttctgtagga gcaaacttaa    5220
acggtgacat atcaagcaac actatgagaa ttcatgtgta tctgataaag gatcattcac    5280
ttcacatgta gacatatatg actacaaaag tggtatgaat attgttaaca gaatcaatgg    5340
aaaatggaat atatctcatt aggtaacata tggaattgta agcaggctat aaaaaatcag    5400
aggtattaag tatcaattca gacagcagaa tgatgcaatg atcacaacca agtcaacaag    5460
ttatcataac taagattagt cctttttgtag ccaaagaagt ttaccgaact cagaaagcag    5520
aacataattc acttacttga tctcaacaac attttgtgtc accatgccag gaagaaacca    5580
gaagtggcat ggtaagcatt gccagtccaa ccagacctct gtgaagcatt atcccatcac    5640
tggaaacctc cacaaagcgt gtttgctaag gcaaatggca tgtatctcca tctaatgaac    5700
atacaaattt tgccctgcct gatgttaagt aactacaggt accaggtaga ctacaagtct    5760
acaactacaa cattacataa cagggatgga acaattacac tcaaatgaac acttgaacag    5820
caagagccag tctctgagac atctgcttcg gcctggctaa tcatagcccc agtaaaccat    5880
aacaacagtt aaatcatccg tccaagattg tccaccctca agaagtgcat gttgtgcaaa    5940
ttccccaata tatcctcaga tgcatcaaca tcgatatgaa agttgctgat atcttcaact    6000
ccgccagcac cgctaacatt aaccctacca gtgccatctg tagcatgtgc tgcctcatt    6060 atgttaattc tcctcacctc ctcggccctt ccatctccag cgttctcatc cccagcccag    6120
ccttcctgcc cgagcatcga agaatcaatg ccactctcca caccaagaga acgtctcctg    6180
agccctaccc cgaccttctt gcgggccgtc gtcttcttga tcctacctct agaagagcca    6240
ccacgagcac tgtcattctg tggctgccta ccaccatggt ttccgtgact cctaccacca    6300
ccaccttggc cactgggagc cgtgttccaa ggaaacatct tgtagaatgg cttccagttg    6360
gcacccaggt cggccgcgtt gggaaatccg aggggggaaga accccaggc gcagtggtac    6420 atttcagtgc ccggcacaac ggtgggtggg gtcgggagct cagaagccac gaatccgcgg    6480
cggcagcccg cg                                                       6492

<210> SEQ ID NO 17
<211> LENGTH: 10054
<212> TYPE: DNA
<213> ORGANISM: Zea mays

<400> SEQUENCE: 17
tttggatgtc tcaactaatt ttagctacta actattagct ctagtgcatt caaacacccc      60
ttaagtgaat gtcatggtat gggctgacat ttcgagaggt ggagagtgtc atggtatggg     120
```

```
ctgccatgtg ggccgagagt ccgagaccgg gctaaatgag ctgggctgaa taggactgac    180
tgcaggtaga aaggcaagcg caacatttgg caccgttagc tctccactaa acttgtcaga    240
tgcaataatt tatgttttta ttaatggcaa agccctcctg ccagccagtg ccttccttcc    300
gggtcaacca ctggtacagt cacatcacga attcccactg gcagtacgat aacctcactg    360
agcggtaggg cctcccgtcc cagaatcctg caggacccac cgatcatagc cccacgggtc    420
ctgctcctgc gtgggttcca gttccaagtc gcccaccgtg acgcccatcg agtcaaccga    480
acccaagccg tgtggcgact ggcgaggcga gtgccccagt cctaactcc ggtgggcgcg     540
ctcccaccgc cgcgcggctc aaaacccgcc ctcagcctcc cgcgctccag tccacacggg    600
agcgggtggt gtcgtctgaa gcggcgcgat caaggagcct tcgagcgctc cggtgagcta    660
tctagatctc aacatcctct cccctctgta gtctgtagtt gtactctccc gcccgatggt    720
tcagttaagt tatatcctct ccccttattt ttactcggtc gataccattt cgttgtggat    780
tgaaatgctg cggccctgta ctatgaggat ggttcctagt tttgcgtctg caatttggg     840
gcgtacatgc ttttggctgc gtactgttac tgatcggaga aaatgtttgt aacgtatgat    900
tcgttttttca ggacgtaacg tgctggcggt tgcttatcgc cggatatata tatataagcg   960
gaaatgttct ccttgttcta tggcctgtgg aagtatgtgt tcgccaagga cgagttccgt   1020
gttctgattc ttggtgttga cagagctggc aagacggtag ctgctagctc ccagccttca   1080
tatatatata tttcccttc tgaactagaa attgatgaaa cttacctgta cacaatgttt    1140
ctggaaccgt tgccatagac tttgctggag aagttgaaat cgatatatct caaggggggaa  1200
ggacttccgc ctgaccgtgt cgttccaaca gttgggctca acattggccg catcgaagac   1260
gcaaaggcaa aacttgtttt ctgggatcta ggtggtcagg taagaacgtt tacgtacgta   1320
gtaaagtgag ccttctgttg ccgtggcacc accctacgat cgttgatatt tgagtcttgt   1380
cagtttggtg ctatatcagg gtttctaatg cctgggaaat acatgtcata aaatcaaatt   1440
actaggatgt ggttgcttta gttattaacc tagcatcttt ttgcgttcca gcagaatata   1500
tataatctag ttatatggaa tgctcaatag aattttcaga aagcaaagat atgtctgtt    1560
ggctaacatt cacagtactc aatagaattg ggtggctagt agaacagcat cagcttctct   1620
gctatgttat aagaattagt gtaaaactaa cttcagtatc actgcttgct agtatgataa   1680
ttaagcttcc atgccaagtt cagtatttct tacacacttg cctgcttggc aggttagcct   1740
acgaacaatc tgggagaaat actatgaaga ggcccatgcc ataatgtacg ttattgacgc   1800
tgccacagca tcgtcatttg aagattccaa atctgctttg ggtaaggttc ttatttgtgt   1860
caattataaa ctacgccatc cattccaaat tataagacat tttggccttt ttctagataa   1920
ataaattttg ctatggactt aaatattaaa aatatatata atgtcctggt acatagttaa   1980
aacaatatat ctagaaaagc taaaacatcg tcttataact tggaacagag ggagtactgg   2040
tttgttttcta ttgctagatc tttccagaag atgcaatgcc tctctggtaa atgggatgag  2100
aactcattct agagaaccta acctaaattt cttacttcag agaaggttat tcgccatgaa   2160
catctgagag gagcaccact cttgatagtt gcaaacaaac aggtgaaggg tttacttcca   2220
cttttctatat tttgtaccac agtacataat tatgattgaa agatttagtg cttacaataa   2280
agttgccatc gtagttaaaa taagattttt gttttttgtca tgtgcacatg ctgtgaggca   2340
tacaaatata aattcctacg ttgcaaagcg ccctatgcgcc attgcgaggt tgaataccag   2400
atgtagtttt taaatcaatt aaaacttcct gaaaagatca catggaaacc aatgactaca   2460
```

```
tgcactgtct gtttctgtta agctgggtac acattattct atcaaattgt ttattattta    2520
cctctagctt gttctcatgt ttggagggtg cttctggatt tcttttggca ggatttacct    2580
ggagccattg atgaggaaga attggctaaa tttctgcata agaactgga tgagaggaca    2640 tatacatttc aggctgtatc tgcatatgat gggtgagcgc agaaactcaa ctggttcctg    2700
aggaaatttg actcgccatg aaaaaaatga caattttact caaagataca aaaaaattca    2760
cacattcgtc tgttatattg tttcctgggt gcatgatatt ctaaagatct gttatattgt    2820
ttaaatgtga caccggctct tgcaggaggg ggatcaaatc tggcatagac tggctggtgg    2880
aacaaatgga aaaagcaaa cgtaccgaga cactgcaggc tcgtgctggc gtagctggac    2940
aaatttagaa tggggtgaat tgttaaaga acaaagcatt ggataggacc gcttccttcg    3000
tatcgcgtaa gcagccattt gctgcattcc gggattatcg ttccaggtcg cccagagtgc    3060
tgcaagaaat gtttggctgg ttgctcctgt ggtggtggtg attggtgagg cgattcgttt    3120
ggtattattg aggttgcatt cttatgtacc taaaggtcgc aagcatacat gtttatatga    3180
tgcttttcaa ttttcgtagc aaactagtag cttcaataca gaggatcaaa gagagccgtg    3240
ttctttaact tgtttgtgat aaaaaaaagg aagaaggaa agcgaagaag gaattattgg    3300
tgcatctgaa agtctttatt gatatgtcta aaccatttca accgatgttg gatgaggttt    3360
tcttcgcacc ggtgttacat ctagtctatc atatgtatcg tcgtttcata ctcgatcctt    3420
ttttatggcc aaactccaac acaacatatg catttctgta gcgcatatgt attgaacatg    3480
tcttttttag actaacatt tgcaccgaac aacatagcag atcgaattgt catcctataa    3540
aacttctttt taacttttgt ggtatccat tgtcatatag aatatcaaat gtttggcgct    3600
acctcatcca ttgactaata cctttatcaa tatctctacg tagcatagat cctaaatatc    3660
taaagatgtc cttcatggac actacttgat ttttcaaact aacatgtctt tcctaatatg    3720
tagtagcata gatcctaaat atctaaagat gtccttcctg gacactactt gattttcaa    3780 actaacatgt ctttcctcat atgtagtagt gttgaaatca catcttttat attcaatttg    3840
agttctactg atcgagtcca aaatcgtcca aaacctttaa actctagaat ctcccaccac    3900
aactctagtt ttctatttac tcgtgcttag ctttcatcaa ctaacactac atccataaaa    3960
aacatatgtt aagagatatc cctttgtgat cttatccata gactcagcta atttttatg    4020 tagtcatatt ctaatcgaaa agtcacatgt gtctccatca tttattcaaa catattcata    4080
acattgttgt tggaactttg cttcctcaaa aaacagggat aaaaaacagt aaaaggaatt    4140
ggcccttcag gctagagctg ctgatatccc cactaagctg gccaatcgg ccaagaaact    4200 ttgcttcatt cagggcatga tatggacaac ccactgcgga ttgccaaaca agaagttag    4260 taagaaacca caaatgctt agtctgagct ttgaagagtt ctacttggtg agtaaaacag    4320
ttaatcttaa ctactgcttg gctaagataa gatgttagct aaaagaattc tgtagatgtg    4380
caatctcaaa ccaatctgcc tttgcatcat ttagaaaact gctttaaaat tcgaaatatt    4440
ttgcttacaa tagctcatag cacagaagaa tattatagaa caaaccaagg caagtgactt    4500
tctgaaacac agttttcaag aacaggttca gattaaacta gataacagga tgccagcgtt    4560
ggtaataagt ctactcccca agagaagtca ctgtttttgt ctttctcaat gaaaaataac    4620
gacacaaaaa tgaactatgg ccgtctgcat taatatggat acgcagcaaa aatggacatg    4680
agtaactcaa aatcgtcaag tgcttgctat gttaagcacc caagtcaatg atttatattc    4740
catgatatcg caaagattat ctataacaag ttctgagtgt gtttcaaaca ttaaatgatc    4800
catgaaaggt aagcacttgt atttagcgga cagtactagt ctgctgtggg attaacccat    4860
```

-continued

```
tttttatggt tctcgatggc cttttgcttc aagataatat ctgatccaat taatagacaa   4920
aatcacaagt aatctttgtt acatgtcatc atcgaatcct atcttctgta ggagcaaact   4980
taaacggtga catatcaagc aacactatga gaattcatgt gtatctgata aaggatcatt   5040
cacttcacat gtagacatat atgactacaa aagtggtatg aatattgtta acagaatcaa   5100
tggaaaatgg aatatatctc attaggtaac atatggaatt gtaagcaggc tataaaaaat   5160
cagaggtatt aagtatcaat tcagacagca gaatgatgca atgatcacaa ccaagtcaac   5220
aagttatcat aactaagatt agtccttttg tagccaaaga agtttaccga actcagaaag   5280
cagaacataa ttcacttact tgatctcaac aacattttgt gtcaccatgc caggaagaaa   5340
ccagaagtgg catggtaagc attgccagtc aaccagacc  tctgtgaagc attatcccat   5400
cactggaaac ctccacaaag cgtgtttgct aaggcaaatg gcatgtatct ccatctaatg   5460
aacatacaaa ttttgccctg cctgatgtta agtaactaca ggtaccaggt agactacaag   5520
tctacaacta caacattaca taacagggat ggaacaatta cactcaaatg aacacttgaa   5580
cagcaagagc cagtctctga gacatctgct tcggcctggc taatcatagc cccagtaaac   5640
cataacaaca gttaaatcat ccgtccaaga ttgtccaccc tcaagaagtg catgttgtgc   5700
aaattcccca atatatcctc agatgcatca acatcgatat gaaagttgct gatatcttca   5760
actccgccag caccgctaac attaacccta ccagtgccat ctgtagcatg tgctgcctca   5820
tttatgttaa ttctcctcac ctcctcggcc cttccatctc cagcgttctc atccccagcc   5880
cagccttcct gcccgagcat cgaagaatca atgccactct ccacaccaag agaacgtctc   5940
ctgagcccta ccccgacctt cttgcgggcc gtcgtcttct tgatcctacc tctagaagag   6000
ccaccacgag cactgtcatt ctgtggctgc ctaccaccat ggtttccgtg actcctacca   6060
ccaccacctt ggccactggg agccgtgttc caaggaaaca tcttgtagaa tggcttccag   6120
ttggcaccca ggtcggccgc gttgggaaat ccgaggggga agaaccccca ggcgcagtgg   6180
tacatttcag tgcccggcac aacggtgggt ggggtcggga gctcagaagc cacgaatccg   6240
cggcggcagc ccgcgttggg gcacttgagg gcgcgcccga tcaggctgcg cgggtactgg   6300
tgcacgtagc agcagaaggg gcacgccgtc cagaactccg gggtgtccga ggcgggagcg   6360
gccgcggcgg gatactggga ggagtaaggg gtaccagtgg cgggatcggc gggcggcggg   6420
gggcggcgag agggatccga gaggaaggcg taggcgtcgt tgacgaggcg gagcgccatc   6480
tcggctcccg ggtgcgggtt gctggggccg aggaggagcg cgaggcggcg gaaggcgcgg   6540
gacacgcgcg cctggtcggg gctgactccg ggcggcagct ggaggatggc gagcgggtcc   6600
ggctggcccg aggggcccat gaactgggaa gcgaggagga cgtcggcgac ggcgaggagc   6660
tcgtcaacgc cagcgaggag cgggttcgcc tccatcgacc gctccgcgaa gcgcttgcag   6720
ccgacgaggt cgcgcgccgc gaggagcttc tcggcgatct ccagccagcg ctccgcctgc   6780
gcggggccgt cgctggcgcc tccgccgccc cgctcacgc  tcccgccggt ggagaagtcc   6840
atggtttggg ggaggaaaag gtggatgctg tcggaggcag ctggtttggt tttggggagg   6900
gggaagatcc tgctgcccga ggggctcttg actggcgact gtctgtcagt ccgagagtat   6960
tttgttgggc agcacattta ttttaaggac aactgtgatt atacgttttc aacttcgtga   7020
attattgatt acgaaaatta aaaatgaggg gtaaaatcat aattgtaagg gaagagaagg   7080
atatactcaa aattaatctg aaaataatat taaacttttt atggttaatt gtgattatag   7140
ccttctctca ctttacaatt gtgattttac cccttatttt tatttttaat cactaattct   7200
```

```
gattttatt aacgttgata aggcggtgca aacaacggct ttgttttcaa aacagagggg      7260
taacaaagtt aaaaagaag ggataaaatc acaattaaaa tattagaaaa gggtataatc      7320
acaattatcc cttgatttta ttaggctctc tccaatcatt ctccatctca aatcccacat      7380 ttggacttc tattcatatt taaatatcct catcttcact attattccc tattttacct      7440 cctctccaag catccctcta ttcagctctc cctttaccct ttaactaagc tatttgactt      7500
ttctacatca gtttttagag ttttaatat ttataatatc ataatacaca ttgtcactta      7560
accaaactta tagcagatta attttatagt taaaaacact aattagtgaa gagtagggtt      7620
ctatctttct cgttttacaa ggtgtttcc ttctctcacc ctacaagagg gaggagaggg      7680
acctgttgaa gctctctcga tgtacgaaat caccgaatac gtcgtgaagg ggagggaaa      7740 ggatccgttg gagagcgtct tatagcctgt tagcttcgaa ttaaagtcag ttgtttagat      7800
tattgtagct gcaattcaca gagaccaaaa cactacagaa atagtaaaag ccgtttcgaa      7860
ttaaaaccaa gggaacgggc tattagtttt cccatatgca aacataccag accattgtag      7920
cgccccaccg cagagcaagt tttgcataca atcaatgtat aattggacta ccaaaaacca      7980
taaaaaattc taaaaatata taaatataat ttattgttta ctttattaga ttataaaatt      8040
ttaagtttaa atttatacaa tagtaaaaga aaaaatatat tcaattagat aaaaaaatt      8100 ccctcaattc cgtaaaataa ggcctgcatt ttaaaaaaa aagactcaat gttttaaaac      8160
ttttgactag taattcagcc aaaagcatat attttagtat atacatgtta tatacttgat      8220
ttgtattcaa aaattacttt aatttaatgc tcgttatgtt tttattgata gcatattttg      8280 aaataaaacaa atagtcaaag tttcgctcca aagactgtac caaaaatata taccttgtta      8340
tataagatga atgaattata tattaacata gcataaatca atctaggatc ttaaatatga      8400
tatattgata aagtaaataa tatatatgta taatttttta aatattttg tgactttga      8460 tagttggatt gtatagaatg tttggttgca caatagtatt ttcctcaagt gaaagatctt      8520
catcaatgtt gtaatacagt gacatgtcat catcaagcct ggttagatct atcctcaaaa      8580
tctactccat aaatttaagg gccaattccc tgtatgccac tagaaaatat actcattcct      8640
tgtatgccac tgaccccaca tgtcatagac accaaaaaat atacctatat gccactcagt      8700
ggcacacaag gaatgagtat aaaatttgat ggcataccag gaattttctc taaatttaat      8760
ttagagtttc tagagtactt ctcttttaac ttcacctttt ttagctacac ttgtttggtt      8820
gaaatataga gccgcacagt cccaaacaaa ctctaaggat gagttgatgt atccccaagt      8880
atatcttaca aaaatgata taatgactct atttatctta tagggtattt gtgattatac      8940
cctctctggt cttgaaattg tgattttacc catcgttttt caactttgtg atattttatc      9000
ccttcatttt gaaacgaag agttgccata cccttgtgcc gttagatgca gttaacaatg      9060 ttaaattga tgcaaaagat aaaaatacc aagcaattta ttttgatttt accctcgtta      9120
tattatgtaa tagtgattc acccctatta ggttgtgcc cataaagaat agaaaaggt      9180 agtttgaacc tttcacccat ttattttctc atttttat tttaatcac taattctgat      9240 tttcactaac gatgttgaga gtgaagggca aatggtagct tcgtatttaa aacggaggtg      9300
taaaattaga aagttgaaaa tgcagagtaa atcacaatt gcaaggccaa cgaagggtat      9360
aatcacaatt atctcttatc ttactagtag taattattag attgtgagga ataaagtaat      9420
ggcagattat ttcattctat tttataaacc aaacaaaact tggaaaagta aaatatgat      9480 ggagtgtatg tggggtggt tagggaggaa aggcccaaaa caagggttt tcgaatctta      9540 cctaaataaa aatcatggca agctaaattg ctaaaacaag aatctaacgt gtttgtttgg      9600
```

```
cacttgcata aagatggtat ctttctatt aattatatgt ataaattctt agttactaat      9660
ggaattaatg ttttatgaat aatttggtgt ctaaagatac ctttaaagat aaaaatcttc      9720
atgtagttct ttcaaaaaaa gagggtcatt ctcacaatct cacaaaggt aattttatca      9780 aaaagaaatt gaaatagtga cacaacttgc tcttttgagc cacaaaccat ctgatacata      9840
ttttctttga gtgcacttat gctaggttac tatagagaga agtttatatt tttttttctc      9900
gaacacgcag gaaaactgcg catcattata ttgaaagaga gaaggtccg aaatggacca      9960 aagtacaaag ccaagcaggc aaaaaataaa aaggaaaaat agtacagcct catgcactag     10020
gaatagccct gatcctagca aaagcagcca gaag                                 10054

<210> SEQ ID NO 18
<211> LENGTH: 5714
<212> TYPE: DNA
<213> ORGANISM: Zea mays

<400> SEQUENCE: 18
atcacgcctc gcccgagcct agcctcgggc aagggcagcc gaccccgaag gggtttccgt       60
ctcgcccgag gccccccttc aacgcggac acatctccgg cttgcccgag gccttgcctt      120
cgctgagaag caaccctgac tgaatcgccg caccgaccgg ccaagtcgca ggagcattta      180
acgcaaagga aaccaggccc tgccaaaggc accataggaa actccgctcc gcccaaccca      240
gggctcggac tcgggcaaag ccccggaaga cggcgaactc cgctccgccc gacccagggc      300
tcggactcgg gctaagcccc ggaagacggc gaactccgct ccgccgacc cagggctcgg      360 actcgggcta agccccggaa gacggcgaac tccgctccgc cgaccaagg gctcggactc      420 gggctaagcc ccggaagacg gcgaactccg ctccgcccga ccaagggctc ggactcgggc      480
taagccccgg aagacggcga actccgctcc gcccgaccaa gggctcggac tcgggctaag      540
ccccggaaga cgacgaactc cgcctcgccc gacctagggg ctcggactcg gcctctgctg      600
acgaactctg cctcgcccga cccaggggct cggactcggc ctctgctgac gaactccgcc      660
tcgcccgacc caggggctcg gactcggcct ctgctgacga actccgcctc gcccgacccg      720
ggggctcgga ctcggcctct gctgacgacc tccgcctcgc cgacccagg ggctcggact      780 cggcttctgc tgacgacctc cgcctcgccc gacccagggg ctcggactcg gcctcggcca      840
tggaagacag actcgacccc ggcttcggag gagcctccac gtcgcccaac ctagggccca      900
ggccagccac gtcgacagga agcgccatca tcaccctacc ccgagccgac tcgggtcgca      960
gagaacaaga cctgtgtccc atctggctgg ctccgccaga taggcaatga tggcgccccg     1020
ctagccccgt gacgacggcg gctctcagct ctcttacgga agcagggcga cgtcagcaag     1080
gacacaaccg ttccaacagc tgtccctccg ccaggctccg ttgctcctcc gacagccacg     1140
acatcacgcc agcagggtgc caagatctct ccggctgcca tattggcatg tacttagggc     1200
actagctctc ccccgctag acacgtagca ctccgctaca ccccattgta cgcctggatc     1260
ctctccttac gcctataaaa ggaaggacca gggccttctt agagaaggtt ggccgcgcgg     1320
ggacgaggac gggacaggc actctcttgc ggccgctcgc ttccctcacc cgtgtggacg     1380
cttgtaaccc cctattgcaa gcgcaccga cctgggcgcg ggacgaacac gaaggccgcg     1440
ggattcccac ctctctctcg ccggactccg gcctcctcgc tcctttcccc cttcgcgctc     1500
gcccacgcgc tcgacccatc tgggctgggg cacgcagcac actcactcgt cggcttaggg     1560
accccccggt ctcgaaacgc cgacactact cttgaggaga ttattagatt atcataatct     1620
```

```
aggctttaga ttatataatc tgaacacata atctagttgt ttgtttatct aatggattat    1680
ttacgctaga ttatataatc tggagagatt ataatctgaa acaaacatgg ccttagtgat    1740
taaaaataaa aataaggggt aaaatcacaa ttgtaaagtg agagaaggct ataatcacaa    1800
ttaaccataa aaagtttaat attattttca ggttaatttt gagtatatcc ttctcttccc    1860
ttacagttat gattttaccc cttattttta attttgtaa tcaataattc acaaagttga     1920
aaacgtataa tcacagttgt ccttaaaatt aaatgtgctg cccaacaaaa tactctcgga    1980
ctgacagaca gtcgccagtc aagagcccct cgggcagcag gatcttcccc ctccccaaaa   2040
ccaaaccagc tgcctccgac agcatccacc ttttcctccc ccaaaccatg gacttctcca    2100
ccggcgggag cgtgagcggg ggcggcggag gcgccagcga cggccccgcg caggcggagc    2160
gctggctgga gatcgccgag aagctcctcg cggcgcgcga cctcgtcggc tgcaagcgct    2220
tcgcggagcg gtcggtggag gcgaacccgc tcctcgccgg cgttgacgaa ctcctcgccg    2280
tcgccgacgt cctcctcgct tcccagttca tgggcacctc gggccagccg gacccgctcg    2340
ccatcctcca gctgccgccc ggagtcagcc ccgaccaggc cgccgtgtcc cgcgccttcc    2400
gccgcctcgc gctcctcctc ggtcccagca acccgcaccc gggagccgag atggcgctcc    2460
gcctcgtcaa cgacgcctac gccttcctct cggatccctc tcgccgcccc ccgccgcccg    2520
ccgatcccgc cactggtacc ccttactcct cccagtatcc cgccgcggcc gctcccgcct    2580
ccgacacccc ggagttctgg acggcgtgcc ccttctgctg ctacgtgcac cagtacccgc    2640
gcagcctgat cgggcgcgcc ctcaagtgcc ccaacgcggg ctgccgccgc ggattcgtgg    2700
cttctgagct cccgaccccca cccacggttg tgccgggcac tgaaatgtac cactgcgcct    2760
gggggttctt ccccctcgga tttcccaacg cggccgacct gggtgccaac tggaagccat    2820
tctacaagat gttcccttgg aacacggctc ccagtggcca aggtggtggt ggtaggagtc    2880
acggaaacca tggtggtagg cagccacaga atgacagtgc tcgtggtggc tcttctagag    2940
gtaggatcaa gaagacgacg gcccgcaaga aggtcgggtg agggctcagg agacgttctc    3000
ttggtgtgga gagtggcatt gattcttcga tgctcgggca ggaaggctgg gctggggatg    3060
agaacgctgg agatggaagg gccgaggagg tgaggagaat taacataaat gaggcagcac    3120
atgctacaga tggcactggt agggttaatg ttagcggtgc tggcggagtt gaagatatcg    3180
gcaactttca tatcgatgtt gatgcatccg aggatatatt gggggaatttg cacaacatgc    3240 acttcttgag ggtggacaat cttggacgga tgatttaact gttgttatgg tttactgggg    3300
ctatgattag ccaggccgac tcttgctgtt caagtgttca tttgagtgta attgttccat    3360
ccctgttatg taatgttgta gttgtagact tgtagtctac ctggtacctg tagttactta    3420
acatcaggca gggaaaaatt tgtatgttca ttagatggag atacatgcca tttgccttag    3480
caaacacact ttgtggaggt ttccagtgat gggataatgc ttcgcagagg tgtggttgga    3540
ctggcaatgc ttaccatgcc acttctggtt tcttcctggc atggtgacac aaaatgttgt    3600
tgagatcaag taagtgaatt atgttctgct ttctgagttc ggtaaacttc tttggctaca    3660
aaaggactaa gcttagttat gctaacttgt tgatttggtt gtgatcattg catcattctg    3720
ctgtgtgaat tgatacttaa tacctctgat ttttatagc ctgcttacaa ttacatatgt     3780
tacctaatga gatatattcc attttccatt gattctgtta acaatattca taccactttg    3840
gtcgtgataa attcatttga ctattgtata gaagtcatat atgtctacat gtgaagtgaa    3900
tgatccatta tcagatacac atgaattctc atagtgttgc ttgatatgtc accgtttaag    3960
tttgctccta cagaagatag gattcgatga ttacatgtaa caaagattag ttgtgatttt    4020
```

```
gtctattaat tggatgagat attatcttga agcaaaaggt catcgagaac cataaaaaat    4080
gggttaatcc cacagcagac tagtactgtc cgctaaatac aagtgcttac ctttcctgga    4140
ccatttaatc tttgaaacac acgcagaact tgttatagat aatctttgtg atagcatgga    4200
atagaaatca ttgacttggg tgcctaacat agcaagcaat tgacgatttt gagttactca    4260
tgtccatttt tgctgagtat ccatattaat gcagacggcc atagttcatt ttcgtgtcgt    4320
tatttttcat tgagatagaa caaaacagcg acttctcttg gggagtacac ttattaccaa    4380
cgctggcatc ctgttatcta gtttaatctg aacctgttct tgaaaactgt gtttcagaaa    4440
gtcacttgcc ttggtttgtt ctataatatt cttctgtgct atgagctatg gtaagcaaaa    4500
tatttcgaat tttaaagcag ttttctaaat gatgcaaagg cagattggtt tgagattgca    4560
catctacaga attcttttga ctaacatctt atcttagcca agcagtagtt aagattaact    4620
gttttactca ccaagtagaa ctcttcaaag ctcagactaa gcattttgtg gtttcttact    4680
aactcctttg tttggcaacc cgcagtgggt tgtccatacc atgccctgaa tgaagcaaag    4740
tttcttggcc gattggccca gcttagtggg gatatcagca gccctagcct gaagggccaa    4800
ttccttttac tgtttttttt atccctattt tttgaggaag caaagttcca acaacaatgt    4860
tatgaatatg tttgaataaa tgatggagac acatgtgact ttccgattag aatatgacta    4920
cataaaaaaa ttagctttga gtctatggat aagatcacaa agggatctct taacatatgt    4980
ttttatggat gtagtgttag ttgatgaaag ctaagcacga gtaaatggaa aactagagtt    5040
gtcgtgggag attctagagt ttaaaggttt tggacgattt tggactcgat cagtagaact    5100
caaattgaat ataaagatg tgatttcaac actactacat atgaggaaag acatgttagt     5160
ttgaaaaatc aagtagtgtc cggaaggaca tctttagata tttagaatct atgctactac    5220
atatgaggaa agacatgtta gtttgaaaaa tcaagtagtg ttctgaaagg acatctttag    5280
atatttagga tctatgcata gatatttagg atctatgcat agatatttag gatctatgct    5340
acgaaaggct acgtagagat agtgataaag gtattagtca aaggatgagg tggcgccaaa    5400
catttgatgt tctatatgac aataggatac cacaaaagtt aaaaagaatc tttataggat    5460
gacaattcga tctgctatat tgttcggtgc agaatgttag tctaaaaaag acatgttcaa    5520
tacgtatgcg ctacagaaat gtatatgttg tgttggagtt tggccataaa aaaggatcga    5580
gtatgaaacg aggatacata tgatagacta gatgtaacat cggtgcgagt atgaaacgag    5640
gatacatatg atagactaga tgtaacatcg gtgcgaagaa aagctcatcc agcatcggtt    5700
aaaatggttt agac                                                     5714
```

<210> SEQ ID NO 19
<211> LENGTH: 577
<212> TYPE: DNA
<213> ORGANISM: Zea mays

<400> SEQUENCE: 19

```
actcgatcct tcctcttcct caaccgtgcg ggcgatcgat cgcaccgccc cctcgcccga      60
ccccatgcct tccacgtcgc ggtcggggta gggctcagga gacgttctct tggtgtggag     120
agtggcattg attcttcgat gctcgggcag gaaggctggg ctggggatga aacgctgga     180 gatggaaggg ccgaggaggt gaggagaatt aacataaatg aggcagcaca tgctacagat    240
ggcactggta gggttaatgt tagcggtgct ggcggagttg aagatatcgg caactttcat    300
atcgatgttg atgcatccga ggatatattg gggaatttgc acaacatgca cttcttgagg    360
```

```
gtggacaatc ttggacggat gatttaactg ttgttatggt ttactggggc tatgattagc      420
caggccgact cttgctgttc aagtgttcat ttgagtgtaa ttgttccatc cctgttatgt      480
aatgttgtag ttgtagactt gtagtctacc tggtacctgt agttacttaa catcaggcag      540
ggaaaaattt gtatgttcat taaaaaaaaa aaaaaaa                               577
```

<210> SEQ ID NO 20
<211> LENGTH: 4090
<212> TYPE: DNA
<213> ORGANISM: Zea mays

<400> SEQUENCE: 20

```
cacactcact cgtcggctta gggaccccccc ggtctcgaaa cgccgacact actcttgagg      60
agattattag attatcataa tctaggcttt agattatata atctgaacac ataatctagt     120
tgtttgttta tctaatggat tatttacgct agattatata atctggagag attataatct     180
gaaacaaaca tggccttagt gattaaaaat aaaataagg ggtaaaatca caattgtaaa      240
gtgagagaag gctataatca caattaacca taaaagtta atattatttt caggttaatt      300
ttgagtatat ccttctcttc ccttacagtt atgattttac cccttatttt taattttgt       360 aatcaataat tcacaaagtt gaaaacgtat aatcacagtt gtccttaaaa ttaaatgtgc     420
tgcccaacaa aatactctcg gactgacaga cagtcgccag tcaagagccc ctcgggcagc     480
aggatcttcc ccctccccaa aaccaaacca gctgcctccg acagcatcca ccttttcctc     540
ccccaaacca tggacttctc caccggcggg agcgtgagcg ggggcggcgg aggcgccagc     600
gacggccccg cgcaggcgga gcgctggctg gagatcgccg agaagctcct cgcggcgcgc     660
gacctcgtcg gctgcaagcg cttcgcggag cggtcggtgg aggcgaaccc gctcctcgcc     720
ggcgttgacg aactcctcgc cgtcgccgac gtcctcctcg cttcccagtt catgggcacc     780
tcgggccagc cggacccgct cgccatcctc cagctgccgc ccggagtcag ccccgaccag     840
gccgccgtgt cccgcgcctt ccgccgcctc gcgctcctcc tcgtcccag caacccgcac     900 ccgggagccg agatggcgct ccgcctcgtc aacgacgcct acgcttcct ctcggatccc     960 tctcgccgcc cccgccgcc cgccgatccc gccactggta ccccttactc ctcccagtat    1020
cccgccgcgg ccgctcccgc ctccgacacc ccggagttct ggacggcgtg cccttctgc      1080 tgctacgtgc accagtaccc gcgcagcctg atcgggcgcg ccctcaagtg ccccaacgcg    1140
ggctgccgcc gcggattcgt ggcttctgag ctcccgaccc cacccacggt tgtgccgggc    1200
actgaaatgt accactgcgc ctgggggttc ttcccccctcg gatttcccaa cgcggccgac    1260
ctgggtgcca actggaagcc attctacaag atgttcccctt ggaacacggc tcccagtggc    1320
caaggtggtg gtggtaggag tcacggaaac catggtggta ggcagccaca gaatgacagt    1380
gctcgtggtg gctcttctag aggtaggatc aagaagacga cggcccgcaa gaaggtcggg    1440
gtagggctca ggagacgttc tcttggtgtg gagagtggca ttgattcttc gatgctcggg    1500
caggaaggct gggctgggga tgagaacgct ggagatggaa gggccgagga ggtgaggaga    1560
attaacataa atgaggcagc acatgctaca gatggcactg gtagggttaa tgttagcggt    1620
gctggcggag ttgaagatat cggcaacttt catatcgatg ttgatgcatc cgaggatata    1680
ttggggaatt tgcacaacat gcacttcttg agggtggaca atcttggacg gatgatttaa    1740
ctgttgttat ggtttactgg ggctatgatt agccaggccg actcttgctg ttcaagtgtt    1800
catttgagtg taattgttcc atccctgtta tgtaatgttg tagttgtaga cttgtagtct    1860
acctggtacc tgtagttact taacatcagg caggaaaaaa tttgtatgtt cattagatgg    1920
```

```
agatacatgc catttgcctt agcaaacaca ctttgtggag gtttccagtg atgggataat    1980
gcttcgcaga ggtgtggttg gactggcaat gcttaccatg ccacttctgg tttcttcctg    2040
gcatggtgac acaaaatgtt gttgagatca agtaagtgaa ttatgttctg ctttctgagt    2100
tcggtaaact tctttggcta caaaaggact aagcttagtt atgctaactt gttgatttgg    2160
ttgtgatcat tgcatcattc tgctgtgtga attgatactt aatacctctg attttttata    2220
gcctgcttac aattacatat gttacctaat gagatatatt ccattttcca ttgattctgt    2280
taacaatatt cataccactt tggtcgtgat aaattcattt gactattgta tagaagtcat    2340
atatgtctac atgtgaagtg aatgatccat tatcagatac acatgaattc tcatagtgtt    2400
gcttgatatg tcaccgttta agtttgctcc tacagaagat aggattcgat gattacatgt    2460
aacaaagatt agttgtgatt ttgtctatta attggatgag atattatctt gaagcaaaag    2520
gtcatcgaga accataaaaa atgggttaat cccacagcag actagtactg tccgctaaat    2580
acaagtgctt acctttcctg gaccatttaa tctttgaaac acgcagaa cttgttatag      2640
ataatctttg tgatagcatg gaatagaaat cattgacttg ggtgcctaac atagcaagca    2700
attgacgatt ttgagttact catgtccatt tttgctgagt atccatatta atgcagacgg    2760
ccatagttca ttttcgtgtc gttattttc attgagatag aacaaacag cgacttctct      2820
tgggagtac acttattacc aacgctggca tcctgttatc tagtttaatc tgaacctgtt     2880
cttgaaaact gtgtttcaga aagtcacttg ccttggtttg ttctataata ttcttctgtg    2940
ctatgagcta tggtaagcaa atatttcga atttttaaagc agttttctaa atgatgcaaa    3000
ggcagattgg tttgagattg cacatctaca gaattctttt gactaacatc ttatcttagc    3060
caagcagtag ttaagattaa ctgtttact caccaagtag aactcttcaa agctcagact     3120
aagcattttg tggtttctta ctaactcctt tgtttggcaa cccgcagtgg gttgtccata    3180
ccatgccctg aatgaagcaa agtttcttgg ccgattggcc cagcttagtg gggatatcag    3240
cagccctagc ctgaagggcc aattccttt actgtttttt ttatccctat tttttgagga     3300
agcaaagttc caacaacaat gttatgaata tgtttgaata aatgatggag acacatgtga    3360
ctttccgatt agaatatgac tacataaaaa aattagcttt gagtctatgg ataagatcac    3420
aaagggatct cttaacatat gtttttatgg atgtagtgtt agttgatgaa agctaagcac    3480
gagtaaatgg aaaactagag ttgtcgtggg agattctaga gtttaaaggt tttgacgat    3540
tttggactcg atcagtagaa ctcaaattga atataaaaga tgtgatttca acactactac    3600
atatgaggaa agacatgtta gtttgaaaaa tcaagtagtg tccggaagga catctttaga    3660
tatttagaat ctatgctact acatatgagg aaagacatgt tagtttgaaa aatcaagtag    3720
tgttctgaaa ggacatcttt agatatttag gatctatgca tagatattta ggatctatgc    3780
atagatattt aggatctatg ctacgaaagg ctacgtagag atagtgataa aggtattagt    3840
caaaggatga ggtggcgcca aacatttgat gttctatatg acaataggat accacaaaag    3900
ttaaaaagaa tctttatagg atgacaattc gatctgctat attgttcggt gcagaatgtt    3960
agtctaaaaa agacatgttc aatacgtatg cgctacagaa atgtatatgt tgtgttggag    4020
tttggccata aaaaggatc gagtatgaaa cgaggataca tatgatagac tagatgtaac    4080
atcggtgcga                                                           4090
```

<210> SEQ ID NO 21
<211> LENGTH: 10452
<212> TYPE: DNA

<213> ORGANISM: Zea mays

<400> SEQUENCE: 21

| | | | | | |
|---|---|---|---|---|---|
| tgcggataga | cttcagagga | aaggactacc | gcacccggtg | gtttgtccat | tatgtgatca | 60 |
| agagcaggaa | actatcttgc | acctcttgtg | ctcttgcagt | ttcgctagac | aattttggca | 120 |
| tgttatattt | tcagctttga | ggatgggcca | tcttacgcct | actagagagg | cgggctcttt | 180 |
| tgtggattgg | tgggaaaagg | tgcataggag | agtccccaaa | catatcagaa | aaaggttttc | 240 |
| atagtctcat | tatcctaggg | gcctggtgtt | tatggctaca | tcgcaataag | gcggttttttg | 300 |
| atggtgtcaa | cccttcattg | agcaccattc | agaggctttt | catggatgag | gtggaatgct | 360 |
| ggtatatggc | tggtgcaaag | cagctcgaga | gtctcggact | tctggctgct | tttgctagga | 420 |
| tcagggctat | tcctagtgca | tgaggctgta | ctattttttcc | ttttttatttt | ttgcctgctt | 480 |
| ggctttgtac | tttggtccat | ttcggaccctt | tctctctttc | aatataatga | tgcgcagttt | 540 |
| tcctgcgtgt | tcgagaaaaa | aaatataaa | cttctctcta | tagtaaccta | gcataagtgc | 600 |
| actcaaagaa | aatatgtatc | agatggtttg | tggctcaaaa | gagcaagttg | tgtcactatt | 660 |
| tcaatttctt | tttgataaaa | ttaccttttg | tgagattgtg | agaatgaccc | tctttttttg | 720 |
| aaagaactac | atgaagattt | ttatcttttaa | aggtatcttt | agcaccaaa | ttattcataa | 780 |
| aacattaatt | ccattagtaa | ctaagaattt | atacatataa | ttaatagaaa | agataccatc | 840 |
| tttatgcaag | tgccaaacaa | acacgttaga | ttcttgtttt | agcaatttag | cttgccatga | 900 |
| tttttattta | ggtaagattc | gaaaaccctt | tgttttgggc | ctttcctccc | taaccacccc | 960 |
| cacatacact | ccatcatatt | tttacttttc | caagttttgt | ttggtttata | aaatagaatg | 1020 |
| aaataatctg | ccattacttt | attcctcaca | atctaataat | tactactagt | aagataagag | 1080 |
| ataattgtga | ttatacccctt | cgttggcctt | gcaattgtga | ttttactctg | cattttcaac | 1140 |
| tttctaattt | tacacctccg | ttttaaatac | gaagctacca | tttgcccttc | actctcaaca | 1200 |
| tcgttagtga | aaatcagaat | tagtgattaa | aaataaaaaa | atgagaaaat | aaatgggtga | 1260 |
| aaggttcaaa | ctacctttttt | ctattctttta | tgggcacaac | cctaataggg | gtgaaatcac | 1320 |
| tattacataa | tataacgagg | gtaaaatcaa | aataaattgc | ttgggtatt | ttatcttttg | 1380 |
| catcaaattt | aacattgtta | actgcatcta | acggcacaag | ggtatggcaa | ctcttcgttt | 1440 |
| tcaaaatgaa | gggataaaat | atcacaaagt | tgaaaaacga | tgggtaaaat | cacaatttca | 1500 |
| agaccagaga | gggtataatc | acaaatacc | tataagataa | atagagtcat | tatatcattt | 1560 |
| tttgtaagat | atacttgggg | atacatcaac | tcatccttag | agtttgtttg | ggactgtgcg | 1620 |
| gctctatatt | tcaaccaaac | aagtgtagct | aaaaaaggtg | aagttaaaag | agaagtactc | 1680 |
| tagaaactct | aaattaaatt | tagagaaaat | tcctggtatg | ccatcaaatt | ttatactcat | 1740 |
| tccttgtgtg | ccactgagtg | gcatataggt | atatttttttg | gtgtctatga | catgtggggt | 1800 |
| cagtggcata | caaggaatga | gtatatttttc | tagtggcata | cagggaattg | gcccttaaat | 1860 |
| ttatggagta | gattttgagg | atagatctaa | ccaggcttga | tgatgacatg | tcactgtatt | 1920 |
| acaacattga | tgaagatctt | tcacttgagg | aaaatactat | tgtgcaacca | acattctat | 1980 |
| acaatccaac | tatcaaaagt | cacaaaaata | tttaaaaaat | tatacatata | tattatttac | 2040 |
| tttatcaata | tatcatattt | aagatcctag | attgatttat | gctatgttaa | tatataattc | 2100 |
| attcatctta | tataacaagg | tatatatttt | tggtacagtc | tttggagcga | aactttgact | 2160 |
| atttgtttat | ttcaaaatat | gctatcaata | aaaacataac | gagcattaaa | ttaaagtaat | 2220 |
| ttttgaatac | aaatcaagta | tataacatgt | atatactaaa | atatatgctt | ttggctgaat | 2280 |

```
tactagtcaa aagttttaaa acattgagtc ttttttttt  aaaatgcagg ccttatttta   2340
cggaattgag ggaattttt  ttatctaatt gaatatattt tttcttttac tattgtataa   2400
atttaaactt aaaattttat aatctaataa agtaaacaat aaattatatt tatatatttt   2460
tagaattttt tatggttttt ggtagtccaa ttatacattg attgtatgca aaacttgctc   2520
tgcggtgggg cgctacaatg gtctggtatg tttgcatatg ggaaaactaa tagcccgttc   2580
ccttggtttt aattcgaaac ggcttttact atttctgtag tgttttggtc tctgtgaatt   2640
gcagctacaa taatctaaac aactgacttt aattcgaagc taacaggcta aagacgctc    2700 tccaacggat cctttcccct cccttcacg  acgtattcgg tgatttcgta catcgagaga   2760
gcttcaacag gtccctctcc tccctcttgt agggtgagag aaggaaaaca ccttgtaaaa   2820
cgagaaagat agaaccctac tcttcactaa ttagtgtttt taactataaa attaatctgc   2880
tataagtttg gttaagtgac aatgtgtatt atgatattat aaatattaaa aactctaaaa   2940
actgatgtag aaaagtcaaa tagcttagtt aaagggtaaa gggagagctg aatagaggga   3000
tgcttggaga ggaggtaaaa tagggaaata atagtgaaga tgaggatatt taaatatgaa   3060
tagaaagtcc aaatgtggga tttgagatgg agaatgattg gagagagcct aataaaatca   3120
agggataatt gtgattatac ccttttctaa tattttaatt gtgattttat cccttctttt   3180
ttaactttgt taccccctctg ttttgaaaac aaagccgttg tttgcaccgc cttatcaacg   3240
ttaataaaaa tcagaattag tgattaaaaa taaaataag  gggtaaaatc acaattgtaa   3300
agtgagagaa ggctataatc acaattaacc ataaaaagtt taatattatt ttcagattaa   3360
ttttgagtat atccttctct tcccttacaa ttatgatttt accctcatt  tttaattttc    3420 gtaatcaata attcacgaag ttgaaaacgt ataatcacag ttgtccttaa aataaatgtg   3480
ctgcccaaca aaatactctc ggactgacag acagtcgcca gtcaagagcc cctcgggcag   3540
caggatcttc cccctcccca aaaccaaacc agctgcctcc gacagcatcc acctttcct    3600 cccccaaacc atggacttct ccaccggcgg gagcgtgagc gggggcggcg gaggcgccag   3660
cgacggcccc gcgcaggcgg agcgctggct ggagatcgcc gagaagctcc tcgcggcgcg   3720
cgacctcgtc ggctgcaagc gcttcgcgga gcggtcgatg gaggcgaacc cgctcctcgc   3780
tggcgttgac gagctcctcg ccgtcgccga cgtcctcctc gcttcccagt tcatgggccc   3840
ctcgggccag ccggacccgc tcgccatcct ccagctgccg cccggagtca gccccgacca   3900
ggccgccgtg tcccgcgcct tccgccgcct cgcgctcctc ctcggcccca gcaacccgca   3960
cccgggagcc gagatggcgc tccgcctcgt caacgacgcc tacgccttcc tctcggatcc   4020
ctctcgccgc cccccgccgc ccgccgatcc cgccactggt accccttact cctcccagta   4080
tcccgccgcg gccgctcccg cctcggacac cccggagttc tggacggcgt gcccttctg    4140 ctgctacgtg caccagtacc cgcgcagcct gatcgggcgc gccctcaagt gccccaacgc   4200
gggctgccgc cgcggattcg tggcttctga gctcccgacc ccacccaccg ttgtgccggg   4260
cactgaaatg taccactgcg cctggggggtt cttcccccctc ggatttccca acgcggccga   4320
cctgggtgcc aactggaagc cattctacaa gatgttcct  tggaacacgg ctcccagtgg   4380
ccaaggtggt ggtggtagga gtcacggaaa ccatggtggt aggcagccac agaatgacag   4440
tgctcgtggt ggctcttcta gaggtaggat caagaagacg acggcccgca agaaggtcgg   4500
ggtagggctc aggagacgtt ctcttggtgt ggagagtggc attgattctt cgatgctcgg   4560
gcaggaaggc tgggctgggg atgagaacgc tggagatgga agggccgagg aggtgaggag   4620
```

```
aattaacata aatgaggcag cacatgctac agatggcact ggtagggtta atgttagcgg    4680
tgctggcgga gttgaagata tcagcaactt tcatatcgat gttgatgcat ctgaggatat    4740
attggggaat ttgcacaaca tgcacttctt gagggtggac aatcttggac ggatgattta    4800
actgttgtta tggtttactg gggctatgat tagccaggcc gaagcagatg tctcagagac    4860
tggctcttgc tgttcaagtg ttcatttgag tgtaattgtt ccatccctgt tatgtaatgt    4920
tgtagttgta gacttgtagt ctacctggta cctgtagtta cttaacatca ggcagggcaa    4980
aatttgtatg ttcattagat ggagatacat gccatttgcc ttagcaaaca cgctttgtgg    5040
aggtttccag tgatgggata atgcttcaca gaggtctggt tggactggca atgcttacca    5100
tgccacttct ggtttcttcc tggcatggtg acacaaaatg ttgttgagat caagtaagtg    5160
aattatgttc tgctttctga gttcggtaaa cttctttggc tacaaaagga ctaatcttag    5220
ttatgataac ttgttgactt ggttgtgatc attgcatcat tctgctgtct gaattgatac    5280
ttaataccct tgatttttta tagcctgctt acaattccat atgttaccta atgagatata    5340 ttccatttc  cattgattct gttaacaata ttcataccac ttttgtagtc atatatgtct    5400
acatgtgaag tgaatgatcc tttatcagat acacatgaat tctcatagtg ttgcttgata    5460
tgtcaccgtt taagtttgct cctacagaag ataggattcg atgatgacat gtaacaaaga    5520
ttacttgtga ttttgtctat taattggatc agatattatc ttgaagcaaa aggccatcga    5580
gaaccataaa aaatgggtta atcccacagc agactagtac tgtccgctaa atacaagtgc    5640
ttacctttca tggatcattt aatgtttgaa acacactcag aacttgttat agataatctt    5700
tgcgatatca tggaatataa atcattgact gggtgctta  acatagcaag cacttgacga    5760
ttttgagtta ctcatgtcca tttttgctgc gtatccatat taatgcagac ggccatagtt    5820 cattttgtg  tcgttatttt tcattgagaa agaacaaaac agtgacttct cttggggagt    5880
agacttatta ccaacgctgg catcctgtta tctagtttaa tctgaacctg ttcttgaaaa    5940
ctgtgtttca gaaagtcact tgccttggtt tgttctataa tattcttctg tgctatgagc    6000
tattgtaagc aaaatatttc gaattttaaa gcagttttct aaatgatgca aaggcagatt    6060
ggtttgagat tgcacatcta cagaattctt ttagctaaca tcttatctta gccaagcagt    6120
agttaagatt aactgtttta ctcaccaagt agaactcttc aaagctcaga ctaagcattt    6180
tgtggtttct tactaacttc tttgtttggc aatccgcagt gggttgtcca tatcatgccc    6240
tgaatgaagc aaagtttctt ggccgattgg cccagcttag tggggatatc agcagctcta    6300
gcctgaaggg ccaattcctt ttactgtttt ttatccctgt tttttgagga agcaaagttc    6360
caacaacaat gttatgaata tgtttgaata aatgatggag acacatgtga cttttcgatt    6420
agaatatgac tacataaaaa attagctgag tctatggata agatcacaaa gggatatctc    6480
ttaacatatg ttttttatgg atgtagtgtt agttgatgaa agctaagcac gagtaaatag    6540
aaaactagag ttgtggtggg agattctaga gtttaaaggt tttggacgat tttggactcg    6600
atcagtagaa ctcaaattga atataaaaga tgtgatttca acactactac atatgaggaa    6660
agacatgtta gtttgaaaaa tcaagtagtg tccaggaagg acatctttag atatttagga    6720
tctatgctac tacatattag gaaagacatg ttagtttgaa aaatcaagta gtgtccatga    6780
aggacatctt tagatatttta ggatctatgc tacgtagaga tattgataaa ggtattagtc    6840
aatggatgag gtagcgccaa acatttgata ttctatatga caataggata ccacaaaagt    6900 taaaagaag  ttttatagga tgacaattcg atctgctatg ttgttcggtg caaaatgtta    6960
gtctaaaaaa gacatgttca atacatatgc gctacagaaa tgcatatgtt gtgttggagt    7020
```

```
ttggccataa aaaaggatcg agtatgaaac gacgatacat atgatagact agatgtaaca   7080
ccggtgcgaa gaaaacctca tccaacatcg gttgaaatgg tttagacata tcaataaaga   7140
ctttcagatg caccaataat tccttcttcg ctttcctttc ttccttttt tatcacaaa    7200 caagttaaag aacacggctc tctttgatcc tctgtattga agctactagt ttgctacgaa   7260
aattgaaaag catcatataa acatgtatgc ttgcgacctt taggtacata agaatgcaac   7320
ctcaataata ccaaacgaat cgcctcacca atcaccacca ccacaggagc aaccagccaa   7380
acatttcttg cagcactctg ggcgacctgg aacgataatc ccggaatgca gcaaatggct   7440
gcttacgcga tacgaaggaa gcggtcctat ccaatgcttt gttctttaac aaattcaccc   7500
cattctaaat ttgtccagct acgccagcac gagcctgcag tgtctcggta cgtttgcttt   7560
tttccatttg ttccaccagc cagtctatgc cagatttgat cccctcctg caagagccgg    7620 tgtcacattt aaacaatata acagatcttt agaatatcat gcacccagga aacaatataa   7680
cagacgaatg tgtgaatttt tttgtatctt tgagtaaaat tgtcatttt ttcatggcga    7740 gtcaaatttc ctcaggaacc agttgagttt ctgcgctcac ccatcatatg cagatacagc   7800
ctgaaatgta tatgtcctct catccagttc tttatgcaga aatttagcca attcttcctc   7860
atcaatggct ccaggtaaat cctgccaaaa gaaatccaga agcaccctcc aaacatgaga   7920
acaagctaga ggtaaataat aaacaatttg atagaataat gtgtacccag cttaacagaa   7980
acagacagtg catgtagtca ttggtttcca tgtgatcttt tcaggaagtt ttaattgatt   8040
taaaaactac atctggtatt caacctcgca atggcgcata ggcgctttgc aacgtaggaa   8100
tttatatttg tatgcctcac agcatgtgca catgacaaaa acaaaatctt tattttaact   8160
acgatggcaa ctttattgta agcactaaat ctttcaatca taattatgta ctgtggtaca   8220
aaatatagaa agtggaagta aacccttcac ctgtttgttt gcaactatca agagtggtgc   8280
tcctctcaga tgttcatggc gaataacctt ctctgaagta agaaatttag gttaggttct   8340
ctagaatgag ttctcatccc atttaccaga gaggcattgc atcttctgga aagatctagc   8400
aatagaaaca aaccagtact ccctctgttc caagttataa gacgatgttt tagcttttct   8460
agatatattg ttttaactat gtaccaggac attatatata ttttaatat ttaagtccat    8520 agcaaaattt atttatctag aaaaaggcca aaatgtctta taatttggaa tggatggcgt   8580
agtttataat tgacacaaat aagaacctta cccaaagcag atttggaatc ttcaaatgac   8640
gatgctgtgg cagcgtcaat aacgtacatt atggcatggg cctcttcata gtatttctcc   8700
cagattgttc gtaggctaac ctgccaagca ggcaagtgtg taagaaatac tgaacttggc   8760
atggaagctt aattatcata ctagcaagca gtgatactga agttagtttt acactaattc   8820
ttataacata gcagagaagc tgatgctgtt ctactagcca cccaattcta ttgagtactg   8880
tgaatgttag ccaacagagc atatctttgc tttctgaaaa ttctattgag cattccatat   8940
aactagatta tatatattct gctggaacgc aaaaagatgc taggttaata actaaagcaa   9000
ccacatccta gtaatttgat tttatgacat gtatttccca ggcattagaa accctgatat   9060
agcaccaaac tgacaagact caaatatcaa cgatcgtagg gtggtgccac ggcaacagaa   9120
ggctcacttt actacgtacg taaacgttct tacctgacca cctagatccc agaaaacaag   9180
ttttgccttt gcgtcttcga tgcggccaat gttgagccca actgttggaa cgacacggtc   9240
aggcggaagt ccttccccct tgagatatat cgatttcaac ttctccagca aagtctatgg   9300
caacggttcc agaaacattg tgtacaggta agtttcatca atttctagtt cagaaaggga   9360
```

| | | |
|---|---|---|
| aatatatata tatgaaggct gggagctagc agctaccgtc ttgccagctc tgtcaacacc | 9420 | |
| aagaatcaga acacggaact cgtccttggc gaacacatac ttccacaggc catagaacaa | 9480 | |
| ggagaacatt tccgcttata tatatatatc cggcgataag caaccgccag cacgttacgt | 9540 | |
| cctgaaaaac gaatcatacg ttacaaacat tttctccgat cagtaacagt acgcagccaa | 9600 | |
| aagcatgtac gccccaaatt gccagacgca aaactaggaa ccatcctcat agtacagggc | 9660 | |
| cgcagcattt caatccacaa cgaaatggta tcgaccgagt aaaaataagg ggagaggata | 9720 | |
| taacttaact gaaccatcgg gcgggagagt acaactacag actacagagg ggagaggatg | 9780 | |
| ttgagatcta gatagctcac cggagcgctc gaaggctcct tgatcgcgcc gcttcagacg | 9840 | |
| acaccacccg ctcccgtgtg gactggagcg cgggaggctg agggcgggtt ttgagccgcg | 9900 | |
| cggcggtggg agcgcgccca ccggagttag gaactgggc actcgcctcg ccagtcgcca | 9960 | |
| cacggcttgg gttcggttga ctcgatgggc gtcacggtgg gcgacttgga actggaaccc | 10020 | |
| acgcaggagc aggacccgtg gggctatgat cggtgggtcc tgcaggattc tgggacggga | 10080 | |
| ggccctaccg ctcagtgagg ttatcgtact gccagtggga attcgtgatg tgactgtacc | 10140 | |
| agtggttgac ccggaaggaa ggcactggct ggcaggaggg ctttgccatt aataaaaaca | 10200 | |
| taaattattg catctgacaa gtttagtgga gagctaacgg tgccaaatgt tgcgcttgcc | 10260 | |
| tttctacctg cagtcagtcc tattcagccc agctcattta gcccggtctc ggactctcgg | 10320 | |
| cccacatggc agcccatacc atgacactct ccacctctcg aaatgtcagc ccataccatg | 10380 | |
| acattcactt aagggggtgtt tgaatgcact agagctaata gttagtagct aaaattagtt | 10440 | |
| gagacatcca aa | 10452 | |

<210> SEQ ID NO 22
<211> LENGTH: 6816
<212> TYPE: DNA
<213> ORGANISM: Zea mays

<400> SEQUENCE: 22

| | | |
|---|---|---|
| tgtcccgcgc ctcccgccgc ctcgcgctcc tcctcggccc cagcaacccg cacccgggag | 60 | |
| ccgagatggc gctccgcctc gtcaacgacg cctacgcctt cctctcggat ccctctcgcc | 120 | |
| gcccccgcc gcccgccgat cccgccactg gtaccccta ctcctcccag tatcccgccg | 180 | |
| cggccgctcc cgcctcggac acccggagt tctggacggc gtgccccttc tgctgctacg | 240 | |
| tgcaccagta cccgcgcagc ctgatcgggc gcgccctcaa gtgccccaac gcgggctgcc | 300 | |
| gccgcggatt cgtggcttct gcgacgcggg ctgccgccgc ggattcgtgg cttctgagct | 360 | |
| cccgacccca cccaccgttg tgccgggcac tgaaatgtac cactgcgcct gggggttctt | 420 | |
| ccccctcgga tttcccaacg cggccgacct gggtgccaac tggaagccat tctacaagat | 480 | |
| gtttccttgg aacacggctc ccagtggcca aggtggtggt ggtaggagtc acggaaacca | 540 | |
| tggtggtagg cagccacaga atgacagtgc tcgtggtggc tcttctagag gtaggatcaa | 600 | |
| gaagacgacg gcccgcaaga aggtcggggt agggctcagg agacgttctc ttggtgtgga | 660 | |
| gagtggcatt gattcttcga tgctcgggca ggaaggctgg gctggggatg agaacgctgg | 720 | |
| agatggaagg gccgaggagg tgaggagaat taacataaat gaggcagcac atgctacaga | 780 | |
| tggcactggt agggttaatg ttagcggtgc tggcggagtt gaagatatca gcaactttca | 840 | |
| tatcgatgtt gatgcatctg aggatatatt ggggaatttg cacaacatgc acttcttgag | 900 | |
| ggtggacaat cttggacgga tgatttaact gttgttatgg tttactgggg ctatgattag | 960 | |
| ccaggccgaa gcagatgtct cagagactgg ctcttgctgt tcaagtgttc atttgagtgt | 1020 | |

```
aattgttcca tccctgttat gtaatgttgt agttgtagac ttgtagtcta cctggtacct   1080
gtagttactt aacatcaggc agggcaaaat ttgtatgttc attagatgga gatacatgcc   1140
atttgcctta gcaaacacgc tttgtggagg tttccagtga tgggataatg cttcacagag   1200
gtctggttgg actggcaatg cttaccatgc cacttctggt ttcttcctgg catggtgaca   1260
caaaatgttg ttgagatcaa gtaagtgaat tatgttctgc tttctgagtt cggtaaactt   1320 cttggctac aaaaggacta atcttagtta tgataacttg ttgacttggt tgtgatcatt   1380
gcatcattct gctgtctgaa ttgatactta atacctctga ttttttatag cctgcttaca   1440
attccatatg ttacctaatg agatatattc cattttccat tgattctgtt aacaatattc   1500
ataccacttt tgtagtcata tatgtctaca tgtgaagtga atgatccttt atcagataca   1560
catgaattct catagtgttg cttgatatgt caccgtttaa gtttgctcct acagaagata   1620
ggattcgatg atgacatgta acaaagatta cttgtgattt tgtctattaa ttggatcaga   1680
tattatcttg aagcaaaagg ccatcgagaa ccataaaaaa tgggttaatc ccacagcaga   1740
ctagtactgt ccgctaaata caagtgctta cctttcatgg atcatttaat gtttgaaaca   1800
cactcagaac ttgttataga taatctttgc gatatcatgg aatataaatc attgacttgg   1860
gtgcttaaca tagcaagcac ttgacgattt tgagttactc atgtccattt tgctgcgta   1920 tccatattaa tgcagacggc catagttcat ttttgtgtcg ttattttca ttgagaaaga   1980 acaaaacagt gacttctctt ggggagtaga cttattacca acgctggcat cctgttatct   2040
agtttaatct gaacctgttc ttgaaaactg tgtttcagaa agtcacttgc cttggtttgt   2100
tctataatat tcttctgtgc tatgagctat tgtaagcaaa atatttcgaa ttttaaagca   2160
gttttctaaa tgatgcaaag gcagattggt ttgagattgc acatctacag aattctttta   2220
gctaacatct tatcttagcc aagcagtagt taagattaac tgttttactc accaagtaga   2280
actcttcaaa gctcagacta agcattttgt ggtttcttac taacttcttt gtttggcaat   2340
ccgcagtggg ttgtccatat catgccctga atgaagcaaa gtttcttggc cgattggccc   2400
agcttagtgg ggatatcagc agctctagcc tgaagggcca attccttta ctgttttta    2460 tccctgtttt ttgaggaagc aaagttccaa caacaatgtt atgaatatgt ttgaataaat   2520
gatggagaca catgtgactt ttcgattaga atatgactac ataaaaaatt agctgagtct   2580
atggataaga tcacaaaggg atatctctta acatatgttt tttatggatg tagtgttagt   2640
tgatgaaagc taagcacgag taaatagaaa actagagttg tggtgggaga ttctagagtt   2700
taaaggtttt ggacgatttt ggactcgatc agtagaactc aaattgaata taaagatgt    2760 gatttcaaca ctactacata tgaggaaaga catgttagtt tgaaaaatca agtagtgtcc   2820
aggaaggaca tctttagata tttaggatct atgctactac atattaggaa agacatgtta   2880
gtttgaaaaa tcaagtagtg tccatgaagg acatctttag atatttagga tctatgctac   2940
gtagagatat tgataaaggt attagtcaat ggatgaggta gcgccaaaca tttgatattc   3000
tatatgacaa taggatacca caaaagttaa aaagaagttt tataggatga caattcgatc   3060
tgctatgttg ttcggtgcaa aatgttagtc taaaaaagac atgttcaata catatgcgct   3120
acagaaatgc atatgttgtg ttggagtttg gccataaaaa aggatcgagt atgaaacgac   3180
gatacatatg atagactaga tgtaacaccg gtgcgaagaa aacctcatcc aacatcggtt   3240
gaaatggttt agacatatca ataaagactt tcagatgcac caataattcc ttcttcgctt   3300
tcctttcttc cttttttta tcacaaacaa gttaaagaac acggctctct ttgatcctct    3360
```

```
gtattgaagc tactagtttg ctacgaaaat tgaaaagcat catataaaca tgtatgcttg    3420
cgacctttag gtacataaga atgcaacctc aataatacca aacgaatcgc ctcaccaatc    3480
accaccacca caggagcaac cagccaaaca tttcttgcag cactctgggc gacctggaac    3540
gataatcccg gaatgcagca aatggctgct tacgcgatac gaaggaagcg gtcctatcca    3600
atgctttgtt ctttaacaaa ttcaccccat tctaaatttg tccagctacg ccagcacgag    3660
cctgcagtgt ctcggtacgt ttgcttttt ccatttgttc caccagccag tctatgccag     3720
atttgatccc cctcctgcaa gagccggtgt cacatttaaa caatataaca gatctttaga    3780
atatcatgca cccaggaaac aatataacag acgaatgtgt gaattttttt gtatctttga    3840
gtaaaattgt cattttttc atggcgagtc aaatttcctc aggaaccagt tgagtttctg     3900
cgctcaccca tcatatgcag atacagcctg aaatgtatat gtcctctcat ccagttcttt    3960
atgcagaaat ttagccaatt cttcctcatc aatggctcca ggtaaatcct gccaaaagaa    4020
atccagaagc accctccaaa catgagaaca agctagaggt aaataataaa caatttgata    4080
gaataatgtg tacccagctt aacagaaaca gacagtgcat gtagtcattg gtttccatgt    4140
gatcttttca ggaagtttta attgatttaa aaactacatc tggtattcaa cctcgcaatg    4200
gcgcataggc gctttgcaac gtaggaattt atatttgtat gcctcacagc atgtgcacat    4260
gacaaaaaca aaatctttat tttaactacg atggcaactt tattgtaagc actaaatctt    4320
tcaatcataa ttatgtactg tggtacaaaa tatagaaagt ggaagtaaac ccttcacctg    4380
tttgtttgca actatcaaga gtggtgctcc tctcagatgt tcatggcgaa taaccttctc    4440
tgaagtaaga aatttaggtt aggttctcta gaatgagttc tcatcccatt taccagagag    4500
gcattgcatc ttctggaaag atctagcaat agaaacaaac cagtactccc tctgttccaa    4560
gttataagac gatgttttag cttttctaga tatattgttt taactatgta ccaggacatt    4620
atatatattt ttaatattta agtccatagc aaaatttatt tatctagaaa aaggccaaaa    4680
tgtcttataa tttggaatgg atggcgtagt ttataattga cacaaataag aaccttaccc    4740
aaagcagatt tggaatcttc aaatgacgat gctgtggcag cgtcaataac gtacattatg    4800
gcatgggcct cttcatagta tttctcccag attgttcgta ggctaacctg ccaagcaggc    4860
aagtgtgtaa gaaatactga acttggcatg gaagcttaat tatcatacta gcaagcagtg    4920
atactgaagt tagttttaca ctaattctta taacatagca gagaagctga tgctgttcta    4980
ctagccaccc aattctattg agtactgtga atgttagcca acagagcata tctttgcttt    5040
ctgaaaattc tattgagcat tccatataac tagattatat atattctgct ggaacgcaaa    5100
aagatgctag gttaataact aaagcaacca catcctagta atttgatttt atgacatgta    5160
tttcccaggc attagaaacc ctgatatagc accaaactga caagactcaa atatcaacga    5220
tcgtagggtg gtgccacggc aacagaaggc tcactttact acgtacgtaa acgttcttac    5280
ctgaccacct agatcccaga aaacaagttt tgcctttgcg tcttcgatgc ggccaatgtt    5340
gagcccaact gttggaacga cacggtcagg cggaagtcct tcccccttga gatatatcga    5400
tttcaacttc tccagcaaag tctatggcaa cggttccaga acattgtgt acaggtaagt     5460 ttcatcaatt tctagttcag aaagggaaat atatatatat gaaggctggg agctagcagc    5520
taccgtcttg ccagctctgt caacaccaag aatcagaaca cggaactcgt ccttggcgaa    5580
cacatacttc cacaggccat agaacaagga gaacatttcc gcttatatat atatatccgg    5640
cgataagcaa ccgccagcac gttacgtcct gaaaacgaa tcatacgtta caaacatttt     5700
ctccgatcag taacagtacg cagccaaaag catgtacgcc ccaaattgcc agacgcaaaa    5760
```

```
ctaggaacca tcctcatagt acagggccgc agcatttcaa tccacaacga aatggtatcg    5820
accgagtaaa aataagggga gaggatataa cttaactgaa ccatcgggcg ggagagtaca    5880
actacagact acagagggga gaggatgttg agatctagat agctcaccgg agcgctcgaa    5940
ggctccttga tcgcgccgct tcagacgaca ccacccgctc ccgtgtggac tggagcgcgg    6000
gaggctgagg gcgggttttg agccgcgcgg cggtgggagc gcgcccaccg gagttaggaa    6060
ctggggcact cgcctcgcca gtcgccacac ggcttgggtt cggttgactc gatgggcgtc    6120
acggtgggcg acttggaact ggaacccacg caggagcagg acccgtgggg ctatgatcgg    6180
tgggtcctgc aggattctgg gacgggaggc cctaccgctc agtgaggtta tcgtactgcc    6240
agtgggaatt cgtgatgtga ctgtaccagt ggttgacccg aaggaaggc  actggctggc    6300 aggagggctt tgccattaat aaaaacataa attattgcat ctgacaagtt tagtggagag    6360
ctaacggtgc caaatgttgc gcttgccttt ctacctgcag tcagtcctat tcagcccagc    6420
tcatttagcc cggtctcgga ctctcggccc acatggcagc ccataccatg acactctcca    6480
cctctcgaaa tgtcagccca taccatgaca ttcacttaag gggtgtttga atgcactaga    6540
gctaatagtt agtagctaaa attagttgag acatccaaac actttagtta atagttcaac    6600
tattagctat ttttggtaaa ttagttaata gttagatagt tatttgttag ctagctaatt    6660
ccactaccaa tttttagcca actaactatt agttctagtg cattcaaaca ccccttagc    6720 ctggtcttaa cagagtagaa gagatgtcag caccgacaac ctgaaacctt tgctactcaa    6780
gtgcaattga tggacaagtg cttctccttgt tcttcg                             6816
```

<210> SEQ ID NO 23
<211> LENGTH: 3904
<212> TYPE: DNA
<213> ORGANISM: Zea mays

<400> SEQUENCE: 23

```
tgcggataga cttcagagga aaggactacc gcacccggtg gtttgtccat tatgtgatca      60
agagcaggaa actatcttgc acctcttgtg ctcttgcagt ttcgctagac aattttggca     120
tgttatattt tcagctttga ggatgggcca tcttacgcct actagagagg cgggctcttt     180
tgtggattgg tgggaaaagg tgcataggag agtccccaaa catatcagaa aaaggttttc     240
atagtctcat tatcctaggg gcctggtgtt tatggctaca tcgcaataag gcggttttttg    300 atggtgtcaa cccttcattg agcaccattc agaggctttt catggatgag gtggaatgct    360
ggtatatggc tggtgcaaag cagctcgaga gtctcggact tctggctgct tttgctagga    420
tcagggctat tcctagtgca tgaggctgta ctattttttcc tttttatttt ttgcctgctt    480
ggctttgtac tttggtccat ttcggacctt tctctctttc aatataatga tgcgcagttt    540
tcctgcgtgt tcgagaaaaa aaaatataaa cttctctcta tagtaaccta gcataagtgc    600
actcaaagaa aatatgtatc agatggtttg tggctcaaaa gagcaagttg tgtcactatt    660
tcaatttctt tttgataaaa ttaccttttg tgagattgtg agaatgaccc tcttttttg     720 aaagaactac atgaagattt ttatcttaaa aggtatcttt agacaccaaa ttattcataa    780
aacattaatt ccattagtaa ctaagaattt atacatataa ttaatagaaa agataccatc    840
tttatgcaag tgccaaacaa acacgttaga ttcttgtttt agcaatttag cttgccatga    900 tttttatttta ggtaagattc gaaaacccctt tgttttgggc ctttcctccc taaccacccc    960
cacatacact ccatcatatt tttactttc caagttttgt ttggtttata aaatagaatg    1020
```

```
aaataatctg ccattacttt attcctcaca atctaataat tactactagt aagataagag   1080
ataattgtga ttatacccct cgttggcctt gcaattgtga ttttactctg cattttcaac   1140
tttctaattt tacacctccg ttttaaatac gaagctacca tttgcccttc actctcaaca   1200
tcgttagtga aaatcagaat tagtgattaa aaataaaaaa atgagaaaat aaatgggtga   1260
aaggttcaaa ctacctttt ctattcttta tgggcacaac cctaataggg gtgaaatcac   1320
tattacataa tataacgagg gtaaaatcaa aataaattgc ttgggtattt ttatcttttg   1380
catcaaattt aacattgtta actgcatcta acggcacaag ggtatggcaa ctcttcgttt   1440
tcaaaatgaa gggataaaat atcacaaagt tgaaaacga tgggtaaaat cacaatttca   1500
agaccagaga gggtataatc acaaataccc tataagataa atagagtcat tatatcattt   1560
tttgtaagat atacttgggg atacatcaac tcatccttag agtttgtttg ggactgtgcg   1620
gctctatatt tcaaccaaac aagtgtagct aaaaaaggtg aagttaaaag agaagtactc   1680
tagaaactct aaattaaatt tagagaaaat tcctggtatg ccatcaaatt ttatactcat   1740
tccttgtgtg ccactgagtg gcatataggt atatttttg gtgtctatga catgtggggt   1800
cagtggcata caaggaatga gtatatttc tagtggcata cagggaattg gcccttaaat   1860
ttatggagta gattttgagg atagatctaa ccaggcttga tgatgacatg tcactgtatt   1920
acaacattga tgaagatctt tcacttgagg aaaatactat tgtgcaacca aacattctat   1980
acaatccaac tatcaaaagt cacaaaaata tttaaaaaat tatacatata tattatttac   2040
tttatcaata tatcatattt aagatcctag attgatttat gctatgttaa tatataattc   2100
attcatctta tataacaagg tatatatttt tggtacagtc tttggagcga aactttgact   2160
atttgtttat ttcaaaatat gctatcaata aaaacataac gagcattaaa ttaaagtaat   2220
ttttgaatac aaatcaagta tataacatgt atatactaaa atatatgctt ttggctgaat   2280
tactagtcaa aagttttaaa acattgagtc tttttttttt aaaatgcagg ccttatttta   2340
cggaattgag ggaatttttt ttatctaatt gaatatattt tttcttttac tattgtataa   2400
atttaaactt aaaattttat aatctaataa agtaaacaat aaattatatt tatatatttt   2460
tagaattttt tatggttttt ggtagtccaa ttatacattg attgtatgca aaacttgctc   2520
tgcggtgggg cgctacaatg gtctggtatg tttgcatatg ggaaaactaa tagcccgttc   2580
ccttggtttt aattcgaaac ggcttttact atttctgtag tgttttggtc tctgtgaatt   2640
gcagctacaa taatctaaac aactgacttt aattcgaagc taacaggcta aagacgctc    2700 tccaacggat cctttccct ccccttcacg acgtattcgg tgatttcgta catcgagaga   2760
gcttcaacag gtccctctcc tccctcttgt agggtgagag aaggaaaaca ccttgtaaaa   2820
cgagaaagat agaaccctac tcttcactaa ttagtgtttt taactataaa attaatctgc   2880
tataagtttg gttaagtgac aatgtgtatt atgatattat aaatattaaa aactctaaaa   2940
actgatgtag aaaagtcaaa tagcttagtt aaagggtaaa gggagagctg aatagaggga   3000
tgcttggaga ggaggtaaaa tagggaaata atagtgaaga tgaggatatt taaatatgaa   3060
tagaaagtcc aaatgtggga tttgagatgg agaatgattg gagagagcct aataaaatca   3120
agggataatt gtgattatac ccttttctaa tattttaatt gtgattttat cccttctttt   3180
ttaactttgt taccctctg ttttgaaaac aaagccgttg tttgcaccgc cttatcaacg    3240
ttaataaaaa tcagaattag tgattaaaaa taaaataag gggtaaaatc acaattgtaa   3300
agtgagagaa ggctataatc acaattaacc ataaaaagtt taatattatt ttcagattaa   3360
ttttgagtat atccttctct tcccttacaa ttatgatttt acccctcatt tttaattttc   3420
```

```
gtaatcaata attcacgaag ttgaaaacgt ataatcacag ttgtccttaa aataaatgtg    3480
ctgcccaaca aaatactctc ggactgacag acagtcgcca gtcaagagcc cctcgggcag    3540
caggatcttc cccctcccca aaaccaaacc agctgcctcc gacagcatcc acctttcct     3600 cccccaaacc atggacttct ccaccggcgg gagcgtgagc gggggcggcg gaggcgccag    3660
cgacggcccc gcgcaggcgg agcgctggct ggagatcgcc gagaagctcc tcgcggcgcg    3720
cgacctcgtc ggctgcaagc gcttcgcgga gcggtcgatg gaggcgaacc cgctcctcgc    3780
tggcgttgac gagctcctcg ccgtcgccga cgtcctcctc gcttcccagt tcatgggccc    3840
ctcgggccag ccggacccgc tcgccatcct ccagctgccg cccggagtca gccccgacca    3900
ggcc                                                                3904

<210> SEQ ID NO 24
<211> LENGTH: 1191
<212> TYPE: DNA
<213> ORGANISM: Zea mays

<400> SEQUENCE: 24
atggacttct ccaccggcgg gagcgtgagc gggggcggcg gaggcgccag cgacggcccc     60
gcgcaggcgg agcgctggct ggagatcgcc gagaagctcc tcgcggcgcg cgacctcgtc    120
ggctgcaagc gcttcgcgga gcggtcgatg gaggcgaacc cgctcctcgc tggcgttgac    180
gagctcctcg ccgtcgccga cgtcctcctc gcttcccagt tcatgggccc ctcgggccag    240
ccggacccgc tcgccatcct ccagctgccg cccggagtca gccccgacca ggccgccgtg    300
tcccgcgcct tccgccgcct cgcgctcctc ctcggcccca gcaacccgca cccgggagcc    360
gagatggcgc tccgcctcgt caacgacgcc tacgccttcc tctcggatcc ctctcgccgc    420 ccccgccgc ccgccgatcc cgccactggt accccttact cctcccagta tcccgccgcg    480
gccgctcccg cctcggacac cccggagttc tggacggcgt gccccttctg ctgctacgtg    540
caccagtacc cgcgcagcct gatcgggcgc gccctcaagt gccccaacgc gggctgccgc    600
cgcggattcg tggcttctga gctcccgacc ccacccaccg ttgtgccggg cactgaaatg    660
taccactgcg cctgggggtt cttccccctc ggatttccca acgcggccga cctggtgcc     720 aactggaagc cattctacaa gatgtttcct tggaacacgg ctcccagtgg ccaaggtggt    780
ggtggtagga gtcacggaaa ccatggtggt aggcagccac agaatgacag tgctcgtggt    840
ggctcttcta gaggtaggat caagaagacg acggcccgca agaaggtcgg ggtagggctc    900
aggagacgtt ctcttggtgt ggagagtggc attgattctt cgatgctcgg gcaggaaggc    960
tgggctgggg atgagaacgc tggagatgga agggccgagg aggtgaggag aattaacata   1020
aatgaggcag cacatgctac agatggcact ggtagggtta atgttagcgg tgctggcgga   1080
gttgaagata tcagcaactt tcatatcgat gttgatgcat ctgaggatat attggggaat   1140
ttgcacaaca tgcacttctt gagggtggac aatcttggac ggatgattta a             1191

<210> SEQ ID NO 25
<211> LENGTH: 5776
<212> TYPE: DNA
<213> ORGANISM: Zea mays

<400> SEQUENCE: 25
acctagaggg ggtaaataga tgatcctgca aaattagctt taaacaacac aaacttggtt     60
tgtaaaatat gttagtgaga actaaaacca agttaggtta cgaagagagg agaaaagaga    120
```

```
actcttcact tgattgctcc tttaaaataa gtattaaagt tagtagcaat attataaata    180
aatatgagaa ttaaatagat aataatcgca ataagcagaa tggtccctct caggccaacc    240
gttccatccg tatccatttc tatcacatca tctctcacgt ctgcatgaac atgtgcacat    300
ggtatttcct tctcaaattt aacccgcgat atgaaaaaca tcgttatcaa tctttcacat    360
ctcaaaataa ctctacataa attttagtat ttgttttatt tagttcaatg agaaaaagat    420
ttgattatat acattgtagt acacctcacg ttctgcttgg acacctctat atatcttcct    480
ctaggcccta tactccctgg cccaattaaa caacacggca tcatgcagta ccaaaagaca    540
aaaacaattt ctagtagtcg agtgcctcct ctctctcctc gataccacat aatatgatat    600
atcacatggc agacggtaga taaagtaggc ggactttgct gggcatagaa aaaaaaaagg    660
atcggcgcca attaccatgg caccgatctt ctgtcacgta gacgccagat cagcgtgaaa    720
gagtgagatc tcgacgccat cttatattgg cgcgcgagac atgcaaactc ggtactaata    780
ataatggcgc cggagtaaag gttcattttt tgaattgaaa cttaaaaaga cgtatttgta    840
ataatcttac aaaaaaatat caaaataaaa aaaagtcag cgaaacaacg cttcacctat    900
tttaaaacgg gcctcggcgc tcgccctctt ggccacagcg cgcctcacag cgacacccac    960
aagaccacgc cccggtcgt gcatcatcat catcgctcgc gtcttcgagt tcgaggacat    1020
ggagaggccg cgttgctact ctccgcttgc cctgcacctc ctcctctgcc tcttctcgct    1080
ccgcgcctgt tccgccgcgt ccatcacagc cggcaccccc gacgagtcgg agctgtgggg    1140
gtacgtcgag gtccggccaa gtacgtaaca accctcct atctcgttgc gcttcagagc    1200
ctctcctcgt cgaaggcgag gtgtcgccgt tgacgacgct tgccgccttt gtcgcagagg    1260
cgcacctgtt ctggtggtac tacaagagcc cgcagaagac gtcgacgccg tccaagccat    1320
ggcccacggt cctctggctg cagggcgcc cggtaggcag ctgctgcctc gttctctctt    1380
tccctcctca caccaccaca atttctcggc ttcggcacag gagggcatga tccggcctct    1440
gtgcttcatt acgggagcac ggtctagcta cctgatgagc gagagcgagt gatcaaccat    1500
ggttgttttg tccctctcgc agggcgcgtc cggggtcggg ctcggcaact tcctggagat    1560
ggggccgctg gacgtggacc tgaagccgcg caactcgacg tggctccaca aggccgacct    1620
catctttgtg gtcagaccag agagcgatag ctgatgcctg atggcggctc tcttctcctc    1680
tcttctgccc ccgctcttc tacaccttc gctgtcgtga tgtcctcgct gaccgacttc    1740
ttccatggcc gggcgcgcgc gcgcaggaca acccggtcgg cacagggtac agctacgtgg    1800
aggacgacag cctgttcgtg accagcgact ggcagcaggc cgcggacatg acgacggtgg    1860
tcagggcgct ggcgaaggag gtgcccaccc tggcgagcag cccgctgttc ctggtcgccg    1920
agtcctacgg cggcaagtac gccgccacgc tcggcgcgtc cattgccagg gccgtccgcg    1980
ctggcgagct caacgtcacg ctcggaggtt cgtaaggtta cttccgttcc atctccgggc    2040
tccgactcga tgaaccaaat cgacgttggg ggagcagagc agctgactcg atgaaattct    2100
cgttccctcc tgctgcaggt gtggcggttg agatagctg gatctcgccg gaggatttca    2160
cggtgaggtt gaccattcct agtttcgtta gtgcagaaat aaaccacgga cacattacag    2220
agctaatagt tacctgctaa aattagctaa atacatttag tctagctaat aatttaacta    2280
ttagctattt tagtaaacta gcgtatagcc tgtactaata tattatctag ccaaacaata    2340
atttatattg tttgtttacc ctttaactta tttaagtttg attatataat ctagaggata    2400
tccaaaccta taaaactaat agctagaagc taaaactagc tatctcaacc tagctaaaac    2460
cagctaataa gtgattggcg attaaattgc tccgaaccat ttctacctat tagcttatta    2520
```

```
gaaaaaggga cgtggatagc ttatcagaat aatctagggt attagcttta gatttagaac    2580
atcctcagct aataatagtt agccagtaac aattagttgt agaggtttgg cttcatctag    2640
actaatgcta ctaaccgaga ctaaattaga ccagtgattt tagtcttgtt ttccatctga    2700
tcgggactaa aagatgaaga cttgttctgt actagtgttc tcttggataa atcacaaatg    2760
atgaatacgc atgtgataat taaagtgagg cctgagtgct gctgcagctt cctacacac    2820 cgctgcttct gagcgtgtcg aggctggacg acaacgccgg cgacgaagca aacaagtaag    2880
gcagcaacaa cacgcacact gcaccaccac catttgcatg cataaatttc tcttgacgct    2940
tagcgcaccc ccatcacata tatgggcatg cgaatttgag ttcaggaagg cggagacggt    3000
gaaggagcaa atcgtggcgg ggcagtgggc cgcctcgcag aagtcatggg gcagcctgct    3060
agatttcatc gacacaaaga gcggcaacgt cgtaagacta gtttacttat cttcgttctt    3120
atattcaaac ttcactcttc gaacaatata atctacagtg caatctcttt tttttggcag    3180
gacgtttaca atttcatgct cgactccggc atggacccgg tggcactgcc cgtgggttct    3240
tcatcactga tgagcagctt gcaggcgatg aagtactcga cgtacggcca ggactcccag    3300
cctggctcca acaccattga cggcatcatg aatggggtca tcaagcaaaa gctcaagata    3360
atccccaaga acttcacgta tgtcagtcca tagcagtgct catatcgcat cacaagtcac    3420
agccggtttc ctgctgctaa tataatgctg cctgtgacgc tggctgcgct tccaaattaa    3480
acgtctacag gtgggggag caatccgact cggtctacaa cgcgctggtc aacgatttca    3540
tgaaaccgaa gatcgatgag gtaaacggat cgagcagatc aatgaaaagc gccctcgatc    3600
agtttctgaa atttatccct ctttgttttc ttattcagat tgatgagctg ctgtcttatg    3660
gcattaatgt gacggtgtac aatggccagg tcagtaacag tctgcaactt cttcttacga    3720
tccccagcag ctcaaaacta ctcggagctc gtcatcggtt tttactgcat gcatgcgttc    3780
tgttagttcg attagtatta cactgcctgg catcctatct gctataaagc cgtccactct    3840
ttgtaattaa aaaaaaaaca cagatcatga aaactagaag acagaccagg ataaggtcat    3900
tggatagtgg cttagtgaat gattggcatt gactataata atattcgaag ttgagattat    3960
tagcatttac taataagact gcattttttt cattactgaa cttgatatat acatgacttt    4020
tcctctatct gaagctcgac gtaatctgct cgaccaacgg agcagaagca tgggttcaga    4080
agctcaagta agttttttt tgcgacctat tcccttccct ccccttctct ggcaggattt    4140
caacgatgca tctggattgc tcgttttcag atgggatggt ctgaggacct tcctgagcct    4200
gccaaggcag cccctctact gtggcgccag caagggtacc aaggcctttg tcaggtccca    4260
caagaacctg catttctact ggatacttgg agcagggcac tatgtaagtc ccaagtctga    4320
accccaactg tgccgtctca tctgagatct gcttcccatg tctgtgagag tgtgaggttc    4380
ttaggtttgg atgaaccaaa taaaaccctta tttgttttct cgtgggatca tctctctgat    4440
tgcattgcag gtgcctgcag accagccctg catcgcgcta agcatgatca gcagcataac    4500
ccagtcgcca gcaagctagt tcactgactc tatgtggtgt atgccaagaa caaaggaggc    4560
gttgaagcag gtagcgcaag gtcccggagg accattcggc gttcttgaag tgcggtatag    4620
gttggatacc tgaaagacga tgcagttgac aaggacattt tttttacaga aaagatccg    4680 ataaaaacat atatgatcta cgtattacaa atattgtaa agaggccgga acttgttttt    4740
ttaataatag aaatgtatct ggcttcatcc tggtccaaat aacgtgccaa ataacgtgaa    4800
aaatacattg ccgcattctc tagcttgcgg aatgcctgca acatcggctc ctgctcctca    4860
```

```
gacattgtat ttgggcccaa gatccaagcc aatgcattcg actgaaaatg acatacaaga    4920
gattttggtc agcaaagttg tcaaattttg acagcttcgt ttcttgttag ctagatagat    4980
taacagatca cagacgtcat gtccataaaa aatggatctt tgtagggtat taatcattga    5040
aacagttttg gatattcagc ggcggagagg tcttcgtcag ggagaccctc tcttccctat    5100
gttgtttgtg ctgatcatgg acgtgcttag cagtcttttc aggactgctg aatgtagggg    5160
attgctgcac agtttggaaa gggcaagagt ccataacagg ctttctatct atgttgatga    5220
tgtggtcctt tttgttaaac ccattgagga agatctgaaa tgtgttagat tgattctgaa    5280
ttgttttggg tcggcctccg gattggttac caatatgaat aagagttatg ctattcctat    5340
cagatgtgag gagcatgtgg ttcaagaggg ctgcaatatg ctgaggtgca gtgtggcctc    5400
atttccttgt tcttacttgg gtctgccaat ctcagacagg aagctgaagc gagatgatct    5460
taagttgtgg atagataaaa ttgcagacag actccctaac tggaaggctc gtttattgaa    5520
cctagccggg aggacaacat tagtgcggtt tgtcttatcg gtcatcccaa tttatcttct    5580
tattgccatt aaaattccca atgggttat taaatcaatt gacaagattc gaagagagtt    5640
tctttggaaa gggtgaaagg aggtgaatgg tggaagttgt attgttccct gggaaactgt    5700
gacaaggcca taagtttagg gggtcttggt gttcctaatt tgcaattgaa gagttgggca    5760
ctgcaggcta agtggc                                                    5776

<210> SEQ ID NO 26
<211> LENGTH: 1653
<212> TYPE: DNA
<213> ORGANISM: Zea mays

<400> SEQUENCE: 26
gtcttcgagt tcgaggacat ggagaggccg cgttgctact ctccgcttgc cctgcacctc      60
ctcctctgcc tcttctcgct ccgcgcctgt tccgccgcgt ccatcacagc cggcaccccc     120
gacgagtcgg agctgtgggg gtacgtcgag gtccggccaa aggcgcacct gttctggtgg     180
tactacaaga gcccgcagaa gacgtcgacg ccgtccaagc catggcccac ggtcctctgg     240
ctgcagggcg gccgggcgc gtccggggtc gggctcggca acttcctgga gatggggccg     300
ctggacgtgg acctgaagcc gcgcaactcg acgtggctcc acaaggccga cctcatcttt     360
gtggacaacc cggtcggcac agggtacagc tacgtggagg acgacagcct gttcgtgacc     420
agcgactggc agcaggccgc ggacatgacg acggtggtca gggcgctggc gaaggaggtg     480 cccacccctgg cgagcagccc gctgttcctg gtcgccgagt cctacggcgg caagtacgcc     540
gccacgctcg gcgcgtccat tgccagggcc gtccgcgctg gcgagctcaa cgtcacgctc     600
ggaggtgtgg cggttggaga tagctggatc tcgccggagg atttcacgct ttcctacaca     660
ccgctgcttc tgagcgtgtc gaggctggac gacaacgccg gcgacgaagc aaacaagaag     720
gcggagacgg tgaaggagca aatcgtgcg gggcagtggg ccgcctcgca gaagtcatgg     780
ggcagcctgc tagatttcat cgacacaaag agcggcaacg tcgacgttta caatttcatg     840
ctcgactccg gcatggaccc ggtggcactg cccgtgggtt cttcatcact gatgagcagc     900
ttgcaggcga tgaagtactc gacgtacggc caggactccc agcctggctc caacaccatt     960
gacggcatca tgaatgggt catcaagcaa aagctcaaga taatccccaa gaacttcacg    1020 tgggggagc aatccgactc ggtctacaac gcgctggtca acgatttcat gaaaccgaag    1080
atcgatgaga ttgatgagct gctgtcttat ggcattaatg tgacggtgta caatggccag    1140
ctcgacgtaa tctgctcgac caacggagca gaagcatggg ttcagaagct caaatgggat    1200
```

```
ggtctgagga ccttcctgag cctgccaagg cagcccctct actgtggcgc cagcaagggt    1260
accaaggcct ttgtcaggtc ccacaagaac ctgcatttct actggatact tggagcaggg    1320
cactatgtgc ctgcagacca gccctgcatc gcgctaagca tgatcagcag cataacccag    1380
tcgccagcaa gctagttcac tgactctatg tggtgtatgc caagaacaaa ggaggcgttg    1440
aagcaggtag cgcaaggtcc cggaggacca ttcggcgttc ttgaagtgcg gtataggttg    1500 gataccctgaa agacgatgca gttgacaagg acatttttt tacagaaaaa gatccgataa    1560
aaacatatat gatctacgta ttacaaaata ttgtaaagag gccggaactt gttttttta    1620 taatagaaat gtatctggct tcatcctggt cca                                 1653

<210> SEQ ID NO 27
<211> LENGTH: 1800
<212> TYPE: DNA
<213> ORGANISM: Zea mays

<400> SEQUENCE: 27
acgtgggaga ccacgccccc ggtcgtgcat catcatcatc gctcgcgtct acgagttcga      60
ggacatggag aggccgcgtt gctactctcc gcttgccctg cacctcctcc tctgcctctt     120
ctcgctccgc gcctgttccg ccgcgtccat cacagccggc accccgacg agtcggagct      180 gtggggtac gtcgaggtcc ggccaaaggc gcacctgttc tggtggtact acaagagccc      240
gcagaagacg tcgacgccgt ccaagccatg gcccacggtc ctctggctgc agggcggccc     300
gggcgcgtcc ggggtcgggc tcggcaactt cctggagatg gggccgctgg acgtggacct     360
gaagccgcgc aactcgacgt ggctccacaa ggccgacctc atctttgtgg acaacccggt     420
cggcacaggg tacagctacg tggaggacga cagcctgttc gtgaccagcg actggcagca     480
ggccgcggac atgacgacgg tggtcagggc gctggcgaag gaggtgccca ccctggcgag     540
cagcccgctg ttcctggtcg ccgagtccta cggcggcaag tacgccgcca cgctcggcgc     600
gtccattgcc agggccgtcc gcgctggcga gctcaacgtc acgctcggag gtgtggcggt     660
tggagatagc tggatctcgc cggaggattt cacgctttcc tacacaccgc tgcttctgag     720
cgtgtcgagg ctggacgaca acgccggcga cgaagcaaac aagaaggcgg agacggtgaa     780
ggagcaaatc gtggcggggc agtgggccgc ctcgcagaag tcatgggca gcctgctaga     840 tttcatcgac acaaagagcg gcaacgtcga aggacaaatt caggctgagc agtgggccgc     900
ctcgcagaag tcaaacggca ccctgcgaac aatataatcg acacagcaag agcggcaacg     960
tggcaggacg tttacaattt catgctcgac tccggcatgg acccggtggc actgcccgtg    1020
ggttcttcat cactgatgag cagcttgcag gcgatgaagt actcgacgta cggccaggac    1080
tcccagcctg gctccaacac cattgacggc atcatgaatg gggtcatcaa gcaaaagctc    1140
aagataatcc ccaagaactt cacgtggggg gagcaatccg actcggtcta caacgcgctg    1200
gtcaacgatt tcatgaaacc gaagatcgat gagattgatg agctgctgtc ttatggcatt    1260
aatgtgacgg tgtacaatgg ccagctcgac gtaatctgct cgaccaacgg agcagaagca    1320
tgggttcaga agctcaaatg ggatggtctg aggaccttcc tgagcctgcc aaggcagccc    1380
ctctactgtg gcgccagcaa gggtaccaag gcctttgtca ggtccacaa gaacctgcat    1440 ttctactgga tacttggagc agggcactat gtgcctgcag accagccctg catcgcgcta    1500
agcatgatca gcagcataac ccagtcgcca gcaagctagt tcactgactc tatgtggtgt    1560
atgccaagaa caaaggaggc gttgaagcag gtagcgcaag gtcccggagg accattcggc    1620
```

| gttcttgaag tgcggtatag gttggatacc tgaaagacga tgcagttgac aaggacattt | 1680 |
| tttttttacag aaaaagatcc gataaaaaca tatatgatct acgtattaca aaatattgta | 1740 |
| aagaggccgg aacttgtttt tttaataata gaaatgtatc tggcttcatc ctggtccaaa | 1800 |

<210> SEQ ID NO 28
<211> LENGTH: 1150
<212> TYPE: DNA
<213> ORGANISM: Zea mays

<400> SEQUENCE: 28

| tcacaaatga tgaatacgca tgtgataatt aaagtgaggc ctgagtgctg ctgcagcttt | 60 |
| cctacacacc gctgcttctg agcgtgtcga ggctggacga caacgccggc gacgaagcaa | 120 |
| acaagaaggc ggagacggtg aaggagcaaa tcgtggcggg gcagtgggcc gcctcgcaga | 180 |
| agtcatgggg cagcctgcta gatttcatcg acacaaagag cggcaacgtc gtaagactag | 240 |
| tttacttatc ttcgttctta tattcaaact tcactcttcg aacaatataa tctacagtgc | 300 |
| aatctctttt ttttggcagg acgtttacaa tttcatgctc gactccggca tggacccggt | 360 |
| ggcactgccc gtgggttctt catcactgat gagcagcttg caggcgatga agtactcgac | 420 |
| gtacggccag gactcccagc ctggctccaa caccattgac ggcaccatga atggggtcat | 480 |
| caagcaaaag ctcaagataa tccccaagaa cttcacgtgg ggggagcaat ccgactcggt | 540 |
| ctacaacgcg ctggtcaacg atttcatgaa accgaagatc gatgagattg atgagctgct | 600 |
| gtcttatggc attaatgtga cggtgtacaa tggccagctc gacgtaatct gctcgaccaa | 660 |
| cggagcagaa gcatgggttc agaagctcaa atgggatggt ctgaggacct tcctgagcct | 720 |
| gccaaggcag cccctctact gtggcgccag caagggtacc aaggcctttg tcaggtccca | 780 |
| caagaacctg catttctact ggatacttgg agcagggcac tatgtgcctg cagaccagcc | 840 |
| ctgcatcgcg ctaagcatga tcagcagcat aacccagtcg ccagcaagct agttcactga | 900 |
| ctctatgtgg tgtatgccaa gaacaaagga ggcgttgaag caggtagcgc aaggtcccgg | 960 |
| aggaccattc ggcgttcttg aagtgcggta taggttggat acctgaaaga cgatgcagtt | 1020 |
| gacaaggaca ttttttttac agaaaaagat ccgataaaaa catatatgat ctacgtatta | 1080 |
| caaaatattg taaagaggcc ggaacttgtt ttttaataa tagaaatgta tctggcttca | 1140 |
| tcctggtcca | 1150 |

<210> SEQ ID NO 29
<211> LENGTH: 4215
<212> TYPE: DNA
<213> ORGANISM: Zea mays

<400> SEQUENCE: 29

| aaggacatat ttgtaataat ctttccaaaa aagtgtcaaa atacaaaaaa aaaagtcagc | 60 |
| gaaacaacgc ttcacctatt ttaaaacggg tctcggcgct cgccctcttg gccacaggcc | 120 |
| cacagcgcgc ctcacagcga cacccaccac gcccccggtc gtgcatcatc atcatcactc | 180 |
| gcgtcttcga gttcgaggac atggacaggc gcgttgcta ctccccgctt gccctgcacc | 240 |
| tcctcctctg cctcgtctcg ctccgcgcct gttccgccgc gtccatcact gccggcaccc | 300 |
| ccgacgagtc ggagctgtgg gggtacgtcg aggtccggcc aagtacgtaa cacccccctcc | 360 |
| ctagctcgtt gcgcttcaga gcctctcttc gtcgaaggcg aggtgtcgcc gttgacgacg | 420 |
| cttttgccgcc ttgtcgcaga ggcgcacctg ttctggtggt actacaagag cccgcagagg | 480 |
| acgtcgacgc cgtccaagcc atggcccacg gtcctctggc tgcagggcgg cccggtaggc | 540 |

-continued

```
agctgctgcc tcgttctctc tttccctcct cacaccacca caatttctcg gcttcggcac    600
aggaggacat gatccggcct ctgtgcttca ttacgggagc acggtctagc tacctgatga    660
gcaagagcga gtaatcaacc atggttgtct tgtccctctc gcagggcgcg tccggggtcg    720
ggctcggcaa cttcctggag atggggccgc tggacgtgga cctgaagccg cgcaactcga    780
cgtggctcca caaggccgac ctcatctttg tggtcagacc agagagcgat agctgatggc    840
ggctctcttc tccgatcctc tcttctgccc ccgctcttc ttctacacct ttcgctgtcg    900
tgatgtcctc actgaccgac ttcttccatg gccgggcgcg cgcgcaggac aacccggtcg    960
gcacagggta cagctacgtg gaggacgaca gcctgttcgt gaccagcgac tggcagcagg   1020
ccgcggacat gacgacggtg gtcagggcgc tggcgaagga ggtgcccacc ctggcgagca   1080
gcccgctgtt cctggtcgcc gagtcctacg cggcaagta cgccgccacg ctcggcgcgt    1140
ccatcgccag ggccgtccgc gctggcgagc tcaacgtcac gctcggaggt tcgtaaggtt   1200
gcttccgttc catctccggg ctccgactcg atgaaccaaa tcgacgttgg gggagcagag   1260
cagagcagag cagctgactc gatgaaattc tcgttccctc ctgctgcagg tgtggcggtt   1320
ggagatagct ggatctcgcc ggaggatttc acggtgaggt tgaccgttct tagtttcgtt   1380
agtgcagaaa taaactgcgg ctacgttgca gagctaatag ttagctgata aaattagcta   1440
aaaacattta aatagtctag ctaataattt aactattagc tatttagta aactagcgtg    1500 tagcatgtac taatatatta tctaaaagcc aaataataat ctatattgtt tgtttaccct   1560
ttaacttatt taagtttaat tatataatct agaggatatc caaacttata aaattaatag   1620
ctagaagcta aaactagcta tcccaaccta gctaaaacca gctaataagt gattgacgat   1680
taaattgctt cgaaccattt ctacctatta gcttattaga aaaagggacg tggatagctt   1740
atcagaataa tctagggtat tagctttaga tttagaacat cctcaactaa taatagttcc   1800
agtaacaatt agttctagag gtttggcttg atctagacta atgctactaa ccgagactaa   1860
attagaccag tgattttagt cttgtttggt agcttcaatc gagactaatg cttccatctg   1920
atcgggacta aaagatgaag acttgttctg tactagtgtt ctcttggata aatcacaaat   1980
gatgaatatg catgtgataa ttaaagtgag gcctgaatgc tgctgcagct ttcctacaca   2040
ccgctgcttc tgagcgtgtc gaggctggac gacaacgccg gcgacgaagc aaacaagtaa   2100
gggggtgttt ggtttctagg gactaatgtt tagtcccttc attttattcc ttttagtgt    2160 ataaattgat aaacatagaa attaaaataa agttttagtt tctatatttg gtaattttgg   2220
accaaaaatg gaataaaatc tagggactaa acattagtcc ctagaaacca aacaccctct   2280
aaggcagcaa caacacgcac actgcaccac caccatttgc atgcataaat ttctcttgac   2340
gcttagcgca cccccatcac atatatgggc atgcgaattt gagttcagga aggcggagac   2400
ggtgaaggag caaatcgtgg cggggcagtg ggccgcctcg cagaagtcat ggagcagcct   2460
gctagatttc atcgacacaa agagcggcaa cgtcgtaagg ctagtttact tatcttcatt   2520
cttatattta aacttcactc ttcgaacaat ataatctaca gtgcaatctc ttttttttgg   2580
caggacgttt acaatttcat gctcgactcc ggcatggacc cggtggcact gctgcccgtg   2640
ggttcttcat cactgatgag cagcttgcag gcgatgaaga agtactcgac gtacggccag   2700
gactcccagc ctggctccaa caccattgac ggcatcatga atggggtcat caagcaaaag   2760
ctcaagataa tccccaagaa cttcacgtat gtcagtccat agcagtgctc atatcgcatc   2820
acaagtcaca gccggtttcc tgctgctaat gtaatgctgc ctgtgacgct ggctgcgctt   2880
```

```
ccaaattaaa cgtctacagg tgggggcagc aatccgactc ggtctacaac gcgctggtca      2940
acgatttcat gaaaccgagg atcgatgagg taaactggtc gagcagataa atgaaaagcg      3000
ccctcgatca gtttctgaaa ttaatccctc ttcattttct cattcagatt gatgagctgc      3060
tgtcttatgg cattaatgtg acggtgtaca atggccaggt cagtaacagt ctgcaacttc      3120
aattcttacg atccccagca gctcaaaact actcggaaaa aaatttgctg cagcccggct      3180
gcaaaacagt atgtttacag cccctcacaa aaggaggag agatctctac tcttttttt        3240 ctcgaatata caggagacct gcatatctgt tagttcgatt agtattacac tgccatccta      3300
tctgctataa agccgtccac tctttgtaat taaaaaaaac acagatcatg aaaactagaa      3360
gacagaccag gataaggtca ttggatagtg gcttagtgaa tgattggcat tgactaataa      3420
tattcgaagt tgagattgag attattagca tttactaata agactgcatt ttttttcatta    3480 ctgaacttga tatatacatg acttttcctc tatctgaagc tcgacgtaat ctgctcgacc      3540
aacggagcag aagcatgggt tcagaagctc aagtaagttt ttttttttggc aacctattcc    3600 ctcccattct ctggcaggat ttcaacgatg catctgatt gctcgttttc agatgggatg      3660
gtctgaggac cttcctgagc ctgccaaggc agcccctcta ctgtggcgcc agcaagggca      3720
ccaaggcctt tgtcaggtcc cacaagaacc tgcatttcta ctggattctt ggagcagggc      3780
actatgtaag tcccaagtct gaaccctaac tgtgccgtct catctgagat ctgcttccca      3840
tgtctgtgag agtgggaggt tcttaggttt ggatgaacca aaaccttatt tgttttctcg      3900
tgggatcatc tctctgattg cattgcaggt gcctgcagac cagccctgca tcgcgctaag      3960
catgatcagc agcataaccc agtcgccagc aagctagttg actgactcta tgtggtgtat      4020
gccaaaaaca aaggaggcgt tgaagcaggt agcgcaaggt cccggaggac cattcggcgt      4080
tcttgaagtg cggtataggt tggatacctg aaaaaataca taagattata ttataaaaag     4140
gaagaatata cactaaatgg tagtataatt aattataaaa tgtttgtagt cctttttcttg    4200 cgaagaaaat cttt                                                       4215
```

<210> SEQ ID NO 30
<211> LENGTH: 5108
<212> TYPE: DNA
<213> ORGANISM: Zea mays

<400> SEQUENCE: 30

```
tataatccga ctacatttaa tacccggaac ggaggttcaa acattcgatg ggacagggac      60
taaattttag cggggtgtaa ccaaacaccc ccttagtagc aatattacaa gtgaatatga     120
gaacttaaga agacaataat cgcaataaga agaatggtcc ctctccggcc aaccgttcca     180
tccatatcca tttctatcac atcatctctc acgtctccat gaacatgtgc acatggtatt     240
tccttctcaa attttaccc gcgatatgaa aaacatcgtt atcaatcttt cacatctcaa     300 ataactcta ctataaattt ttagtatttg ttatatttag ttcaatgaga aaaggatttg     360
attatataca ttgtagtaca cgtcatgttc tgcttggaca cctctgtata tctccctcta     420
ggctctatac tccctgcccc aattaaacaa cacggcatca tgccaaaaac aatttctagt     480
agtcgagtgc ctactctctc tcctcgttct ctctccccag tggcatcgaa ggaaaagtat     540
atatgattgt acccatgatg tgatatacca tatgacagac ggtagataaa gcaggcggac     600
tttgatgggc atagaaaaca gggtcggcgc caattaccat ggcgccgatc tcatgtcaca     660
tagacgccac atcagcgtga gagagtgaga tctcgacagt cgacgccatc tatattgccg     720
cgcgagacgt gcaaactcgg tactaataat aatggcgccg ggtaaaggtc tattttttta     780
```

```
attgaaactt aaaaggacat atttgtaata atctttccaa aaaagtgtca aaatacaaaa    840
aaaaaagtca gcgaaacaac gcttcaccta ttttaaaacg ggtctcggcg ctcgccctct    900
tggccacagg cccacagcgc gcctcacagc gacacccacc acgccccggt tcgtgcatca    960
tcatcatcac tcgcgtcttc gagttcgagg acatggacag gccgcgttgc tactcccgc   1020
ttgccctgca cctcctcctc tgcctcgtct cgctccgcgc ctgttccgcc gcgtccatca   1080
ctgccggcac ccccgacgag tcggagctgt gggggtacgt cgaggtccgg ccaagtacgt   1140
aacaccccct ccctagctcg ttgcgcttca gagcctctct tcgtcgaagg cgaggtgtcg   1200
ccgttgacga cgctttgccg ccttgtcgca gaggcgcacc tgttctggtg gtactacaag   1260
agcccgcaga ggacgtcgac gccgtccaag ccatggccca cggtcctctg gctgcagggc   1320
ggcccggtag gcagctgctg cctcgttctc tctttccctc ctcacaccac cacaatttct   1380
cggcttcggc acaggaggac atgatccggc ctctgtgctt cattacggga gcacggtcta   1440
gctacctgat gagcaagagc gagtaatcaa ccatggttgt cttgtccctc tcgcagggcg   1500
cgtccggggt cgggctcggc aacttcctgg agatggggcc gctggacgtg gacctgaagc   1560
cgcgcaactc gacgtggctc cacaaggccg acctcatctt tgtggtcaga ccagagagcg   1620
atagctgatg gcggctctct tctccgatcc tctcttctgc cccccgctct tcttctacac   1680
cttcgctgt cgtgatgtcc tcactgaccg acttcttcca tggccgggcg cgcgcgcagg   1740
acaacccggt cggcacaggg tacagctacg tggaggacga cagcctgttc gtgaccagcg   1800
actggcagca ggccgcggac atgacgacgg tggtcagggc gctggcgaag gaggtgccca   1860
ccctggcgag cagcccgctg ttcctggtcg ccgagtccta cggcggcaag tacgccgcca   1920
cgctcggcgc gtccatcgcc agggccgtcc gcgctggcga gctcaacgtc acgctcggag   1980
gttcgtaagg ttgcttccgt tccatctccg ggctccgact cgatgaacca aatcgacgtt   2040
gggggagcag agcagagcag agcagctgac tcgatgaaat tctcgttccc tcctgctgca   2100
ggtgtggcgg ttggagatag ctggatctcg ccggaggatt tcacggtgag gttgaccgtt   2160
cttagtttcg ttagtgcaga aataaactgc ggctacgttg cagagctaat agttagctga   2220
taaaattagc taaaaacatt taaatagtct agctaataat ttaactatta gctattttag   2280
taaactagcg tgtagcatgt actaatatat tatctaaaag ccaataata atctatattg   2340
tttgtttacc ctttaactta tttaagttta attatataat ctagaggata tccaaactta   2400
taaaattaat agctagaagc taaaactagc tatcccaacc tagctaaaac cagctaataa   2460
gtgattgacg attaaattgc ttcgaaccat ttctacctat tagcttatta gaaaaggga   2520
cgtggatagc ttatcagaat aatctagggt attagcttta gatttagaac atcctcaact   2580
aataatagtt ccagtaacaa ttagttctag aggtttggct tgatctagac taatgctact   2640
aaccgagact aaattagacc agtgatttta gtcttgtttg gtagcttcaa tcgagactaa   2700
tgcttccatc tgatcgggac taaaagatga agacttgttc tgtactagtg ttctcttgga   2760
taaatcacaa atgatgaata tgcatgtgat aattaaagtg aggcctgaat gctgctgcag   2820
ctttcctaca caccgctgct tctgagcgtg tcgaggctgg acgacaacgc cggcgacgaa   2880
gcaaacaagt aaggggtgt ttggtttcta gggactaatg tttagtccct tcatttttatt   2940
ccttttttagt gtataaattg ataaacatag aaattaaaat aaagtttttag tttctatatt   3000
tggtaatttt ggaccaaaaa tggaataaaa tctagggact aaacattagt ccctagaaac   3060
caaacaccct ctaaggcagc aacaacacgc acactgcacc accaccattt gcatgcataa   3120
```

| | |
|---|---|
| atttctcttg acgcttagcg cacccccatc acatatatgg gcatgcgaat ttgagttcag | 3180 |
| gaaggcggag acggtgaagg agcaaatcgt ggcggggcag tgggccgcct cgcagaagtc | 3240 |
| atggagcagc ctgctagatt tcatcgacac aaagagcggc aacgtcgtaa ggctagttta | 3300 |
| cttatcttca ttcttatatt taaacttcac tcttcgaaca atataatcta cagtgcaatc | 3360 |
| tcttttttt ggcaggacgt ttacaatttc atgctcgact ccggcatgga cccggtggca | 3420 |
| ctgctgcccg tgggttcttc atcactgatg agcagcttgc aggcgatgaa gaagtactcg | 3480 |
| acgtacggcc aggactccca gcctggctcc aacaccattg acggcatcat gaatggggtc | 3540 |
| atcaagcaaa agctcaagat aatccccaag aacttcacgt atgtcagtcc atagcagtgc | 3600 |
| tcatatcgca tcacaagtca cagccggttt cctgctgcta atgtaatgct gcctgtgacg | 3660 |
| ctggctgcgc ttccaaatta aacgtctaca ggtgggggca gcaatccgac tcggtctaca | 3720 |
| acgcgctggt caacgatttc atgaaaccga ggatcgatga ggtaaactgg tcgagcagat | 3780 |
| aaatgaaaag cgccctcgat cagtttctga aattaatccc tcttcatttt ctcattcaga | 3840 |
| ttgatgagct gctgtcttat ggcattaatg tgacggtgta caatggccag gtcagtaaca | 3900 |
| gtctgcaact tcaattctta cgatccccag cagctcaaaa ctactcggaa aaaaatttgc | 3960 |
| tgcagcccgg ctgcaaaaca gtatgtttac agcccctcac aaaaaggagg atagatctct | 4020 |
| actctttttt ttctcgaata tacaggagac ctgcatatct gttagttcga ttagtattac | 4080 |
| actgccatcc tatctgctat aaagccgtcc actctttgta attaaaaaaa acacagatca | 4140 |
| tgaaaactag aagacagacc aggataaggt cattggatag tggcttagtg aatgattggc | 4200 |
| attgactaat aatattcgaa gttgagattg agattattag catttactaa taagactgca | 4260 |
| tttttttcat tactgaactt gatatataca tgactttcc tctatctgaa gctcgacgta | 4320 |
| atctgctcga ccaacggagc agaagcatgg gttcagaagc tcaagtaagt tttttttttg | 4380 |
| gcaacctatt ccctcccatt ctctggcagg atttcaacga tgcatctgga ttgctcgttt | 4440 |
| tcagatggga tggtctgagg accttcctga gcctgccaag gcagcccctc tactgtggcg | 4500 |
| ccagcaaggg caccaaggcc tttgtcaggt cccacaagaa cctgcatttc tactggattc | 4560 |
| ttggagcagg gcactatgta agtcccaagt ctgaacccta actgtgccgt tcatctgag | 4620 |
| atctgcttcc catgtctgtg agagtgggag gttcttaggt ttggatgaac caaaacctta | 4680 |
| tttgtttct cgtgggatca tctctctgat tgcattgcag gtgcctgcag accagccctg | 4740 |
| catcgcgcta agcatgatca gcagcataac ccagtcgcca gcaagctagt tgactgactc | 4800 |
| tatgtggtgt atgccaaaaa caaaggaggc gttgaagcag gtagcgcaag gtcccggagg | 4860 |
| accattcggc gttcttgaag tgcggtatag gttggatacc tgaaaaaata cataagatta | 4920 |
| tattataaaa aggaagaata tacactaaat ggtagtataa ttaattataa aatgtttgta | 4980 |
| gtccttttct tgcgaagaaa atcttttaaa tggcatttgt gtgaagcaca atgtttagag | 5040 |
| tcctaaaaat gcaattgtct ctgttgggga cttgctctca aatgctatga atcaagagca | 5100 |
| agacaaca | 5108 |

<210> SEQ ID NO 31
<211> LENGTH: 1659
<212> TYPE: DNA
<213> ORGANISM: Zea mays

<400> SEQUENCE: 31

| | |
|---|---|
| gtcttcgagt tcgaggacat ggacaggccg cgttgctact ctccgcttgc cctgcacctc | 60 |
| ctcctctgcc tcttctcgct ccgcgcctgt tccgccgcgt ccatcacagc cggcaccccc | 120 |

```
gacgagtcgg agctgtgggg gtacgtcgag gtccggccaa aggcgcacct gttctggtgg    180
tactacaaga gcccgcagaa gacgtcgacg ccgtccaagc catggcccac ggtcctctgg    240
ctgcagggcg gcccgggcgc gtccggggtc gggctcggca acttcctgga gatggggccg    300
ctggacgtgg aacctgaagcc gcgcaactcg acgtggctcc acaaggccga cctcatcttt    360
gtggacaacc cggtcggcac agggtacagc tacgtggagg acgacagcct gttcgtgacc    420
agcgactggc agcaggccgc ggacatgacg acggtggtca gggcgctggc gaaggaggtg    480
cccaccctgg cgagcagccc gctgttcctg gtcgccgagt cctacggcgg caagtacgcc    540
gccacgctcg gcgcgtccat tgccagggcc gtccgcgctg gcgagctcaa cgtcacgctc    600
ggaggtgtgg cggttggaga tagctggatc tcgccggagg atttcacgct ttcctacaca    660
ccgctgcttc tgagcgtgtc gaggctggac gacaacgccg cgacgaagc aaacaagaag    720
gcggagacgg tgaaggagca aatcgtggcg gggcagtggg ccgcctcgca gaagtcatgg    780
ggcagcctgc tagatttcat cgacacaaag agcggcaacg tcgacgttta caatttcatg    840
ctcgactccg gcatggaccc ggtggcactg ctgcccgtgg gttcttcatc actgatgagc    900
agcttgcagg cgatgaagaa gtactcgacg tacggccagg actcccagcc tggctccaac    960
accattgacg gcatcatgaa tggggtcatc aagcaaaagc tcaagataat ccccaagaac   1020
ttcacgtggg gggagcaatc cgactcggtc tacaacgcgc tggtcaacga tttcatgaaa   1080
ccgaagatcg atgagattga tgagctgctg tcttatggca ttaatgtgac ggtgtacaat   1140
ggccagctcg acgtaatctg ctcgaccaac ggagcagaag catgggttca gaagctcaaa   1200
tgggatggtc tgaggacctt cctgagcctg ccaaggcagc ccctctactg tggcgccagc   1260
aagggtacca aggcctttgt caggtcccac aagaacctgc atttctactg gatacttgga   1320
gcagggcact atgtgcctgc agaccagccc tgcatcgcgc taagcatgat cagcagcata   1380
acccagtcgc cagcaagcta gttcactgac tctatgtggt gtatgccaag aacaaaggag   1440
gcgttgaagc aggtagcgca aggtcccgga ggaccattcg gcgttcttga agtgcggtat   1500
aggttggata cctgaaagac gatgcagttg acaaggacat ttttttttaca gaaaaagatc   1560
cgataaaaac atatatgatc tacgtattac aaaatattgt aaagaggccg gaacttgttt   1620
ttttaataat agaaatgtat ctggcttcat cctggtcca                          1659
```

<210> SEQ ID NO 32
<211> LENGTH: 1795
<212> TYPE: DNA
<213> ORGANISM: Zea mays

<400> SEQUENCE: 32

```
agttcatcac taatcacact tattgtgccc tcgacgagta tctatagcta gctcattaat     60
cgattcgggg gtgtgttgtc gaaggcggca atggcgagct actcgtcgcg gcgtccatgc    120
aatacctgta gcacgaaggc gatggccggg agcgtggtcg gcgagcccgt cgtgctgggg    180
cagagggtga cggtgctgac ggtggacggc ggcggcgtcc ggggtctcat cccgggaacc    240
atcctcgcct tcctggaggc caggctgcag gagctggacg gaccggaggc gaggctggcg    300
gactacttcg actacatcgc cggaaccagc accggcggtc tcatcaccgc catgctcacc    360
gcgcccggca aggacaagcg gcctctctac gctgccaagg acatcaacca ctttttacatg    420
cagaactgcc cgcgcatctt tcctcagaag tgagtccgat gctgccgcca ttgttcttgc    480
atccatccag catcgtacgt acgtcctcta tacatctgcg gatcatcatg tgcgcatgtt    540
```

-continued

```
tgtggcatgc atgcatgcat gtgagcagga gcaggcttgc ggccgccatg tccgcgctga      600
ggaagccaaa gtacaacggc aagtgcatgc gcagcctgat taggagcatc ctcggcgaga      660
cgagggtaag cgagacgctg accaacgtca tcatccctgc cttcgacatc aggctgctgc      720
agcctatcat cttctctacc tacgacgtac gtacgtcgtc acgaatgatt catctgtacg      780
tcgtcgcatg cgaatggctg cctacgtacg ccgtgcgcta acatactcag ctctttccta      840
tctgctgcgc caatttgcag gccaagagca cgcctctgaa gaacgctctg ctctcggacg      900
tgtgcattgg cacgtccgcc gcgccgacct acctcccggc gcactacttc cagactgaag      960
acgccaacgg caaggagcgc gaatacaacc tcatcgacgg cggtgtggcg gccaacaacc     1020
cggtaactga ctagctaact ggaaaacgga cgcacagact ccatgtccat ggcggcccac     1080
aaggtcgatg ctaattgttg cttatgtatg tcgcccgatt gcacatgcgt agacgatggt     1140
tgcgatgacg cagatcacca aaaagatgct tgccagcaag acaaggccg aggagctgta      1200 cccagtgaag ccgtcgaact gccgcaggtt cctggtgctg tccatcggga cggggtcgac     1260
gtccgagcag ggcctctaca cggcgcgcca gtgctcccgg tggggtatct gccggtggct     1320
ccgcaacaac ggcatggccc ccatcatcga catcttcatg gcggccagct cggacctggt     1380
ggacatccac gtcgccgcga tgttccagtc gctccacagc gacggcgact acctgcgcat     1440
ccaggacaac tcgctccgtg gcgccgcggc caccgtggac gcggcgacgc cggagaacat     1500
gcggacgctc gtcgggatcg gggagcggat gctggcacag agggtgtcca gggtcaacgt     1560
ggagacaggg aggtacgaac cggtgactgg cgaaggaagc aatgccgatg ccctcggtgg     1620
gctcgctagg cagctctccg aggagaggag aacaaggctc gcgcgccgcg tctctgccat     1680
caacccaaga ggctctagat gtgcgtcgta cgatatctaa gacaagtggc tttactgtca     1740
gtcacatgct tgtaaataag tagactttat tttaataaaa cataaaaata tatat          1795
```

<210> SEQ ID NO 33
<211> LENGTH: 1452
<212> TYPE: DNA
<213> ORGANISM: Zea mays

<400> SEQUENCE: 33

```
agttcatcac taatcacact tattgtgccc tcgacgagta tctatagcta gctcattaat       60
cgattcgggg gtgtgttgtc gaaggcggca atggcgagct actcgtcgcg gcgtccatgc      120
aatacctgta gcacgaaggc gatggccggg agcgtggtcg gcgagcccgt cgtgctgggg      180
cagagggtga cggtgctgac ggtggacggc ggcggcgtcc ggggtctcat cccgggaacc      240
atcctcgcct tcctggaggc caggctgcag gagctggacg gaccggaggc gaggctggcg      300
gactacttcg actacatcgc cggaaccagc accggcggtc tcatccaccgc catgctcacc      360 gcgcccggca aggacaagcg gcctctctac gctgccaagg acatcaacca cttttacatg      420
cagaactgcc cgcgcatctt tcctcagaag agcaggcttg cggccgccat gtccgcgctg      480
aggaagccaa agtacaacgg caagtgcatg cgcagcctga ttaggagcat cctcggcgag      540
acgagggtaa gcgagacgct gaccaacgtc atcatccctg ccttcgacat caggctgctg      600
cagcctatca tcttctctac ctacgacgcc aagagcacgc ctctgaagaa cgctctgctc      660
tcggacgtgt gcattggcac gtccgccgcg ccgacctacc tcccggcgca ctacttccag      720
actgaagacg ccaacggcaa ggagcgcgaa tacaacctca tcgacggcgg tgtggcggcc      780
aacaacccga cgatggttgc gatgacgcag atcaccaaaa agatgcttgc cagcaaggac      840
aaggccgagg agctgtaccc agtgaagccg tcgaactgcc gcaggttcct ggtgctgtcc      900
```

```
atcgggacgg ggtcgacgtc cgagcagggc ctctacacgg cgcggcagtg ctcccggtgg    960
ggtatctgcc ggtggctccg caacaacggc atggccccca tcatcgacat cttcatggcg   1020
gccagctcgg acctggtgga catccacgtc gccgcgatgt ccagtcgct ccacagcgac    1080 ggcgactacc tgcgcatcca ggacaactcg ctccgtggcg ccgcggccac cgtggacgcg   1140
gcgacgccgg agaacatgcg gacgctcgtc gggatcgggg agcggatgct ggcacagagg   1200
gtgtccaggt caacgtgga cagggagg tacgaaccgg tgactggcga aggaagcaat      1260
gccgatgccc tcggtgggct cgctaggcag ctctccgagg agaggagaac aaggctcgcg   1320
cgccgcgtct ctgccatcaa cccaagaggc tctagatgtg cgtcgtacga tatctaagac   1380
aagtggcttt actgtcagtc acatgcttgt aaataagtag actttatttt aataaaacat   1440
aaaaatatat at                                                       1452

<210> SEQ ID NO 34
<211> LENGTH: 4564
<212> TYPE: DNA
<213> ORGANISM: Zea mays

<400> SEQUENCE: 34
aaggaaaggt cacacatcct agctagcttc actggttcta gctccttcca attttgcaaa     60
aaagtcacaa aggataagcc attttttccaa atgatttgtg aaatgcctat gctaaaaagc   120
ctacttttcc gaaaaaccag agctagagcc attttttgaca agtcagaacc ctaccaaata   180
gtccctcagt ttaagcaaag tgaggccata ctgaagctaa attatgccaa attgggccta   240
catctccata ttttcaacca aatgctttag ggtttcttgt aatcgacatg atttgtttct   300
tcataaatag tatatggacc gctccaaaat actccatccg tttcaattta tatttcgttt   360
gatcttttta ccctaaattt gatcgactcg tcttattaaa aaagttcat aactattaat    420 aatcttact gtgatatcat ttagcatata atatacttta attgtggctt tgattttttt   480
ccgcaaaaat taaatgaaac gacccaatca aacttgataa aaaagtaaaa ctaattataa   540
atttggacag aaggagtagg agggtgtttg aatacactag agttaatagt tagttgcctt   600
aaaatttgct agtacaatta gctagctaac aaatatttag gtaactatta gctaatttgc   660
taaaaacagc taatagttaa actattagct agactgtttg gatgtattca gctaattta    720 gcagctaact attagctata gtataatatt caaacacctc ctaattaaaa tggacaaata   780
tctcttccct tggtcccttg cgttagattt ccatatctcc ttatttagta taaaagaat    840 catcaaaaag tggacaaccc ctagtggaac accattttag tagtggttgc atgaaacctt   900
tcgcgcatca gttactatgt gtcactctaa aaatggggca gcatgtacgc agtgcctata   960
tttatacaag gcatctatcg ttgcctcctc agttcatcac taatcacact tattgttccc  1020
tcgacgagta tctagctagc tcattaatcg atcaatcggg gtgtgcggtc gaaggcggca  1080
atggcgagct actcgtcgcg gcgtccatgc aatacctgta gcacgaaggc gatggccggg  1140
agcgtggtcg gcgagcccgt cgtgctgggg cagagggtga cggtgctgac ggtggacggc  1200
ggcggcgtcc ggggtctcat cccgggaacc atcctcgcct tcctcgaggc caggctgcag  1260
gagctggacg gaccggaggc gaggctggcg gactacttcg actacatcgc cggaaccagc  1320
accggcggtc tcatcaccgc catgctcacc gcgcccggca aggacaagcg gcctctctac  1380
gctgccaagg acatcaacca ctttttacatg gagaactgcc gcgcatctt ccctcagaag   1440 tgagtccgat gctgccgcca ttgttcttgc atccatgcat ccagcatcgt acgtcctcta  1500
```

-continued

```
tacatctgcg gatgatcatt tgcgcatgtt tgtggcatgc atgcatgtga tgtgagcagg   1560
agcaggcttg cggccgccat gtccgcgctg aggaagccaa agtacaacgg caagtgcatg   1620
cgcagcctga ttaggagcat cctcggcgag acgagggtaa gcgagacgct gaccaacgtc   1680
atcatccctg ccttcgacat caggctgctg cagcctatca tcttctctac ctacgacgta   1740
cgtacgtcgt cacgaatgat tcatctgtac gtcgtcgcat gcgaatggct gcctacgtac   1800
gccgtgcgct aacatactca gctctttcct atctgctgcg ccaatttgca ggccaagagc   1860
acgcctctga agaacgctct gctctcggac gtgtgcattg gcacgtccgc cgcgccgacc   1920
tacctcccgg cgcactactt ccagactgaa gacgccaacg gcaaggagcg cgaatacaac   1980
ctcatcgacg gcggtgtggc ggccaacaac ccggtaactg actagctaac tggaaaacgg   2040
acgcacagac tccatgtcca tggcggccca aaggtcgat gctaattgtt gcttatgtat    2100
gtcgcccgat tgcacatgcg tagacgatgg ttgcgatgac gcagatcacc aaaaagatgc   2160
ttgccagcaa ggacaaggcc gaggagctgt acccagtgaa gccgtcgaac tgccgcaggt   2220
tcctggtgct gtccatcggg acgggtcga cgtccgagca gggcctctac acggcgcggc    2280
agtgctcccg gtggggtatc tgccggtggc tccgcaacaa cggcatggcc cccatcatcg   2340
acatcttcat ggcggccagc tcggacctgg tggacatcca cgtcgccgcg atgttccagt   2400
cgctccacag cgacggcgac tacctgcgca tccaggacaa ctcgctccgt ggcgccgcgg   2460
ccaccgtgga cgcggcgacg ccggagaaca tgcggacgct cgtcgggatc ggggagcgga   2520
tgctggcaca gagggtgtcc agggtcaacg tggagacagg gaggtacgaa ccggtgactg   2580
gcgaaggaag caatgccgat gccctcggtg ggctcgctag gcagctctcc gaggagagga   2640
gaacaaggct cgcgcgccgc gtgtctgcca tcaacccaag aggctctaga tgtgcgtcgt   2700
acgatatcta agacaagtgg ctttactgtc agtcacatgc ttgtaaataa gtagacttta   2760
ttttaataaa acataaaaat atatatatgt tcttgaatat aaaattgata accaaaattc   2820
gaaccatcac ttatacataa ttttacttta tttttttataa aacgtgaacg ggaaggacta  2880
ccatgaatga ctatagaacc aatcatacta gtataaaata tatgatgaca ctacgagaga   2940
gacaaacttt gtctggcgct aaatatttg ccgagtgtga attcacgggc actaggcaaa    3000
gatcttcttt gccgagtgtt acgctgggca aagtaagaca ctaggtaaat cagtcatttg   3060
ccgagtgtcc gccactaggc aaagcaaaac actggcaaat caaagtttta cctagtgcca   3120
gacactaggc aaaaaaaaac gctcggcaaa tcggaagttt ccctagtgcc agacactaga   3180
caaagaaaaa cacttgataa actagcgtcg tcagctaaca ccatccacca accgttaacg   3240
ttgccgagta tctgacttcg acactcggca aagaaggtct ctttgcctag tgtcggtctg   3300
gaacactagg caaagaggca ctttacctag tgtcgtattt tgacactcag taaaataatt   3360
tttttcttt ctgcttccaa acttttatg atgtgttcct atagcaccta gaactacatg     3420
tcaagttttg gtaaaatttt tgaagttttt gctatattta cttaatttat tttatttaat   3480
tgaatttctt ttgataattc aaatttgaac tcggcaaggt aagaagcgag ggtagcctgg   3540
aaacacactt tgcctagtgt tacactcggt acaggagcct cccctgccta gtgctgcact   3600
cgacaaaaga ttcgcctttg cctagcgctg cactcggcac aggagtcgcc tttgcctagt   3660
gctgcactag gcaaagcctc cgttaccgtg ccttccatcg tcatggaaac ttttcttcgc   3720
cgagtgacgt gtggcactag gcaaagtttt tgccgagtgc ccgagaaatg gcactcggca   3780
aggactcttt gtcgatccct tcgttgccga cttcttttg ccgagtgcaa cactaggcaa    3840
accatttgcc gagtgtaaaa gaggctttgc ctagtgtctg tggcactagg caaagaagac   3900
```

-continued

| gagtcctgta gtgaacctag taggccagtg cgggaccatt ccaaaaaata cctataaaaa | 3960 |
| taaatttaat attaaattaa acatatggtc cacgtaccaa gatattaaac tcaaaagaac | 4020 |
| aattattaca atttatctta gctaaaaggc cgagaaaagt atatgttaaa aaggagtgtg | 4080 |
| atcccatttt tatagctcgc tcggtcgatc gcccgtccac ttttaggtaa cgaggtggta | 4140 |
| ccatgtagga gtgttgcgtt gcgtgcgact tcctatcatg ttgggcttag gtggcttctc | 4200 |
| acgacccaat gataggcgag aagtgtggaa gatgaacaaa cctacttgtt tcgtgcacga | 4260 |
| cgcatgtgtt tgaacaacga gttagattag aaaaaaaata taatgacttt ttttttgcaa | 4320 |
| aagtgaggat aatgaaaacc agaaaaactg gtgcttcata agagtagaga tttgatggta | 4380 |
| aatatagtag taatgcaatg gctatactac acgcgagagt ccaatggcaa gccggtgtgt | 4440 |
| tggggcgaag cgaagacgc taccctttcgc tccaggcctt tgtcaactcg ctgcaccaac | 4500 |
| agaggcaaga tgaccggcgc ggcccaccct tcgtcctctt cactgcaaga cgaaggccta | 4560 |
| cgac | 4564 |

<210> SEQ ID NO 35
<211> LENGTH: 2089
<212> TYPE: DNA
<213> ORGANISM: Zea mays

<400> SEQUENCE: 35

| caccggcggt ctcatcaccg ccatgctcac cgcgcccggc aaggacaagc ggcctctcta | 60 |
| cgctgccaag gacatcaact acttttacat ggagaactgc ccgcgcatct tccctcagaa | 120 |
| gtgagtccga tgctgccgcc attgttctcg catccatcca gcatcgtacg tcctctatac | 180 |
| atctgcggat gatcatttgc gcatgtttgt ggcatgcatg tgagcaggag caggcttgcg | 240 |
| gccgccatgt ccgcgctgag gaagccaaag tacaacggca agtgcatgcg cagcctgatt | 300 |
| aggagcatcc tcggcgagac gagggtaagc gagacgctga ccaacgtcat catccctgcc | 360 |
| ttcgacatca ggctgctgca gcctatcatc ttctctacct acgacgtacg tacgtcgtca | 420 |
| cgaatgattc atctgtacgt cgtcgcatgc gaatggctgc ctacgccgtg cgctaacata | 480 |
| ctcagctctt tccgatctgc tgcgccaatt tgcaggccaa gagcacgcct ctgaagaacg | 540 |
| cgctgctctc ggacgtgtgc attggcacgt ccgccgcgcc gacctacctc ccggcgcact | 600 |
| acttccagac tgaagacgcc aacggcaagg agcgcgaata caacctcatc gacggcggtg | 660 |
| tggcggccaa caacccggta actgactagc taactgcaaa acgaacgcac agactccatg | 720 |
| tccatggcgg cccacaaggt cgatgctaat tgttgcttat gtatgtcgcc cgattgcaca | 780 |
| tgcgtagacg atggttgcga tgacgcagat caccaaaaag atgcttgcca gcaaggacaa | 840 |
| ggccgaggag ctgtacccag tgaacccgtc gaactgccgc aggttcctgg tgctgtccat | 900 |
| cgggacgggg tcgacgtccg agcagggcct ctacacggcg cggcagtgct cccggtgggg | 960 |
| catctgccgg tggctccgca caacggcat ggccccatc atcgacatct tcatggcggc | 1020 |
| cagctcggac ctggtggaca tccacgtcgc cgcgatgttc cagtcgctcc acagcgacgg | 1080 |
| cgactaccta cgcatccagg acaactcgct ccgtggcgcc gcggcaaccg tggacgcggc | 1140 |
| gacgccggag aacatgcgga cgctcgtcgg gatcggggag cggatgctgg cacagcgggt | 1200 |
| gtccagggtc aacgtggaga cagggagcga ggtacgaacc ggtgaccgga gaaggaagca | 1260 |
| atgccgatgc cctcggtggg ctcgctaggc agctctccga ggagaggaga acaaggctcg | 1320 |
| cgcgccgcgt ctctgccatc aaccccagaa gctctagatg tgcgccctac gatatctaag | 1380 |

| | |
|---|---|
| acaagtggct ttactgtcaa tcacatgctt gtaaataagt agactttatt ttaataaaat | 1440 |
| ataaatatat atatattctg ataaccaaga ttcgaaccct cacttataca caattttatc | 1500 |
| ttatttttta taaaatgaga atggaaagga ctaccgtgaa cgactataga accaatcata | 1560 |
| ctagtttaaa atgctcgtaa gctatgacga acctagtagg ccggtgctgg accattccaa | 1620 |
| aaaacctata aaaataaatt taatattaaa ttaaacatat ggtctatata tcagatatta | 1680 |
| aactcaaaag aataattatt ataatttatc ttagctaaaa ggttgagaaa ggtatgcgtt | 1740 |
| aaaaaagagt tttaacccat ttttatagct tatttgatcg cccgtccact tttagggagc | 1800 |
| gaggtggtac tatgcagaag tgttgcgctg tgtgcgactt actatcatgt tgggtttagg | 1860 |
| tggattctca cgacccaatg atagacgaga agtgtgggag atgaacaaac ctacgcattt | 1920 |
| cgcgtacgac acatgtgttt gaacaacgag ttagattgga aaaatataa tgacctttt | 1980 |
| tgcaaaaatg actacaatga aaaccaggaa aaccggtgct tcataggagt agagatttga | 2040 |
| cggtaaattg ttacgatcta ctggtatttg ctgcgaggat gtattcgct | 2089 |

<210> SEQ ID NO 36
<211> LENGTH: 3557
<212> TYPE: DNA
<213> ORGANISM: Zea mays

<400> SEQUENCE: 36

| | |
|---|---|
| tgacgtttgg taaaacgact tcttccgaaa aacacccaaa aacccaagat atttatact | 60 |
| acgaaggaaa ggtcacacat cctagttagc ttcactggtt ctagctcctt ccaattttgc | 120 |
| aaaaaagtca caaggataa gccatttttt caaatgattt gtgaaatgcc tacgctaaaa | 180 |
| agtctacttt tccaaaaaaa ctagagctag agccgttttt ggcaagtcag aaccctacca | 240 |
| aatagtccct cagtttaagc aaagtgaggc tatactgaag ctaaattatg ccaaattggg | 300 |
| cctacatctc catattttca accaaatgct ttagggtttc ttgtaatcga catgatttgt | 360 |
| ttcttcataa atagtatatg gaccgctcca aaatactcca tccgtttcaa tttatattac | 420 |
| gtttgatctt tttaccctaa atttgatcga ctcgtcttat taaaaaagtt cataactatt | 480 |
| aataatcttt actgtgatat catttagcat ataaatact ttaagtgtag cttttgatttt | 540 |
| tttttttgcaa aaattaaatg aaacgaccca atcaaacttg ataaaaagt aaaactaatt | 600 |
| ataaatttgg acataaggag taggagggtg tttgaataca ctagagttaa tagttagttg | 660 |
| tcttaaaatt tgctagtaca attagctagc taacaaatat ttaggtaact attagctaat | 720 |
| ttgctaaaaa cagctaatag ttgaactatt agttgaacta ttagctagac tgtttggatg | 780 |
| tattcaacta attttagcag ctaactatta gttatagtat aatattcaaa cacctcctaa | 840 |
| ttaaaatgga caaatatcta ttcccttggt cccttgcgtt agattttcca tatatcctca | 900 |
| tttagtataa aagaatcat caaaaagtgg acaaccccta gtggaacacc atttagtag | 960 |
| tggttgcatg aaacctttcg cgcatcagtt actatgtgtc actctaaaaa tgggcagca | 1020 |
| tgtacgcagt gcctatattt atacaaggca tctatcgttg cctcctcagt tcatcactaa | 1080 |
| tcacacttat tgtgccctcg acgagtatct agctagctca ttaatcgatc aatcggggtg | 1140 |
| tgcggtcgaa ggcggcaatg gcgagctact cgtcgcggcg tccatgcaat acctgtagca | 1200 |
| cgaaggcgat ggccgggagc gtggtcggcg agcccgtcgt gctggggcag agggtgacgg | 1260 |
| tgctgacggt ggacggcggc ggcgtccggg gtctcatccc gggaaccatc ctcgccttcc | 1320 |
| tggaggccag gctgcaggag ctggacggac cggaggcgag gctggcggac tacttcgact | 1380 |
| acatcgccgg aaccagcacc ggcggtctca tcaccgccat gctcaccgcg cccggcaagg | 1440 |

```
acaagcggcc tctctacgct gccaaggaca tcaactactt ttacatggag aactgcccgc   1500
gcatcttccc tcagaagtga gtccgatgct gccgccattg ttctcgcatc catccagcat   1560
cgtacgtcct ctatacatct gcggatgatc atttgcgcat gtttgtggca tgcatgtgag   1620
caggagcagg cttgcggccg ccatgtccgc gctgaggaag ccaaagtaca acggcaagtg   1680
catgcgcagc ctgattagga gcatcctcgg cgagacgagg gtaagcgaga cgctgaccaa   1740
cgtcatcatc cctgccttcg acatcaggct gctgcagcct atcatcttct ctacctacga   1800
cgtacgtacg tcgtcacgaa tgattcatct gtacgtcgtc gcatgcgaat ggctgcctac   1860
gccgtgcgct aacatactca gctctttccg atctgctgcg ccaatttgca ggccaagagc   1920
acgcctctga agaacgcgct gctctcggac gtgtgcattg gcacgtccgc cgcgccgacc   1980
tacctcccgg cgcactactt ccagactgaa gacgccaacg gcaaggagcg cgaatacaac   2040
ctcatcgacg gcggtgtggc ggccaacaac ccggtaactg actagctaac tgcaaaacga   2100
acgcacagac tccatgtcca tggcggccca caaggtcgat gctaattgtt gcttatgtat   2160
gtcgcccgat tgcacatgcg tagacgatgg ttgcgatgac gcagatcacc aaaaagatgc   2220
ttgccagcaa ggacaaggcc gaggagctgt acccagtgaa cccgtcgaac tgccgcaggt   2280
tcctggtgct gtccatcggg acggggtcga cgtccgagca gggcctctac acggcgcggc   2340
agtgctcccg gtggggcatc tgccggtggc tccgcaacaa cggcatggcc ccatcatcg    2400 acatcttcat ggcggccagc tcggacctgg tggacatcca cgtcgccgcg atgttccagt   2460
cgctccacag cgacggcgac tacctacgca tccaggacaa ctcgctccgt ggcgccgcgg   2520
caaccgtgga cgcggcgacg ccggagaaca tgcggacgct cgtcgggatc ggggagcgga   2580
tgctggcaca gcgggtgtcc agggtcaacg tggagacagg gagcgaggta cgaaccggtg   2640
accggagaag gaagcaatgc cgatgccctc ggtgggctcg ctaggcagct ctccgaggag   2700
aggagaacaa ggctcgcgcg ccgcgtctct gccatcaacc ccagaagctc tagatgtgcg   2760
ccctacgata tctaagacaa gtggctttac tgtcaatcac atgcttgtaa ataagtagac   2820 tttatttttaa taaatataaa atatatatat attctgataa ccaagattcg aaccctcact   2880
tatacacaat tttatcttat tttttataaa atgagaatgg aaaggactac cgtgaacgac   2940
tatagaacca atcatactag tttaaaatgc tcgtaagcta tgacgaacct agtaggccgg   3000
tgctggacca ttccaaaaaa cctataaaaa taaatttaat attaaattaa acatatggtc   3060
tatatatcag atattaaact caaaagaata attattataa tttatcttag ctaaaaggtt   3120
gagaaaggta tgcgttaaaa aagagttttta acccattttt atagcttatt tgatcgcccg   3180 tccacttttta gggagcgagg tggtactatg cagaagtgtt gcgctgtgtg cgacttacta   3240
tcatgttggg tttaggtgga ttctcacgac ccaatgatag acgagaagtg tgggagatga   3300
acaaacctac gcatttcgcg tacgacacat gtgtttgaac aacgagttag attggaaaaa   3360
atataatgac cttttttgca aaaatgacta caatgaaaac caggaaaacc ggtgcttcat   3420
aggagtagag atttgacggt aaattgttac gatctactgg tatttgctgc gaggatgtat   3480
tcgcttggtg aaaacagaat tacagagtag cagtagcagg gaagacagta gcgagaggag   3540
aagaagaaac ttgagga                                                 3557
```

<210> SEQ ID NO 37
<211> LENGTH: 1382
<212> TYPE: DNA
<213> ORGANISM: Zea mays

<400> SEQUENCE: 37

```
agttcatcac taatcacact tattgtgccc tcgacgagta tctagctagc tcattaatcg    60
atcaatcggg gtgtgcggtc gaaggcggca atggcgagct actcgtcgcg gcgtccatgc   120
aataccctgta gcacgaaggc gatggccggg agcgtggtcg gcgagcccgt cgtgctgggg   180
cagagggtga cggtgctgac ggtggacggc ggcggcgtcc ggggtctcat cccgggaacc   240
atcctcgcct tcctggaggc caggctgcag gagctggacg gaccggaggc gaggctggcg   300
gactacttcg actacatcgc cggaaccagc accggcggtc tcatcaccgc catgctcacc   360
gcgcccggca aggacaagcg gcctctctac gctgccaagg acatcaacta cttttacatg   420
gagaactgcc cgcgcatctt ccctcagaag agcaggcttg cggccgccat gtccgcgctg   480
aggaagccaa agtacaacgg caagtgcatg cgcagcctga ttaggagcat cctcggcgag   540
acgagggcca agagcacgcc tctgaagaac gcgctgctct cggacgtgtg cattggcacg   600
tccgccgcgc cgacctacct cccggcgcac tacttccaga ctgaagacgc caacggcaag   660
gagcgcgaat acaacctcat cgacggcggt gtggcggcca caacccgac gatggttgcg    720
atgacgcaga tcaccaaaaa gatgcttgcc agcaaggaca aggccgagga gctgtaccca   780
gtgaacccgt cgaactgccg caggttcctg gtgctgtcca tcgggacggg gtcgacgtcc   840
gagcagggcc tctacacggc gcggcagtgc tcccggtggg gcatctgccg gtggctccgc   900
aacaacggca tggcccccat catcgacatc ttcatggcgg ccagctcgga cctggtggac   960
atccacgtcg ccgcgatgtt ccagtcgctc cacagcgacg gcgactacct acgcatccag  1020
gacaactcgc tccgtggcgc cgcggcaacc gtggacgcgg cgacgccgga gaacatgcgg  1080
acgctcgtcg ggatcgggga gcggatgctg gcacagcggg tgtccagggt caacgtggag  1140
acagggagcg aggtacgaac cggtgaccgg agaaggaagc aatgccgatg ccctcggtgg  1200
gctcgctagg cagctctccg aggagaggag aacaaggctc gcgcgccgcg tctctgccat  1260
caaccccaga agctctagat gtgcgcccta cgatatctaa gacaagtggc tttactgtca  1320
atcacatgct tgtaaataag tagactttat tttaataaaa tataaatata tatatattct  1380
ga                                                                  1382
```

<210> SEQ ID NO 38
<211> LENGTH: 10843
<212> TYPE: DNA
<213> ORGANISM: Zea mays

<400> SEQUENCE: 38

```
cgcacacact gtctttctct gcctttcttt ccctagcgcc gcgccggcgc cgccattcga    60
tcaggccgct tcgccggcga cagcatattc caggtatgcc gtcccttctg ctccttctgc   120
gagaattcaa acaccccgaa ctccccaaat ctagtatttg tattcggatc tgaccatttt   180
tcactgggcc cgccccctgat tcgcaggtcg gttggttttg gcacttcgga ccggcggcca   240
tggcttccga cggcatcggc cccagaggta taactgtttc atctcttctt tgtgttcaaa   300
cagacagacg tcaaaccgcc gagaggaggt acaaatatag attttgggct atgagcacgc   360
cattgcgctt ccagcgatct gacatattgg gaattcttgt ttttttttttg ggtaccttgc   420
aaggccgaaa tttgacgctt ttctgtttaa ttctagtgcc tgtctgcatc cattagggca   480
tcctagctgc tccatgctcg tgatctcgtc cgtttgcttg attgaatcca ttgttttcca   540
aagttcattg ctactgcgaa atacgttat atgattacca caattgtgt tttgcctttt    600
tcgggttgca cagagggtac tgccatcatt gttgttttag cgccatttgg aacaagtgat   660
```

```
tcactggtac tagtacagta tgtgcttttc atgtgtgttt ggtttgtacc atcagatgga      720
attttgagcg cggtttacaa attagtacta tagatatact gtgaggtgca cactagatgg      780
ttctgctttg ttctacagtc agtaactttt tcttccttgc tcacagatgt atgtgttgtt      840
ggggttgcac gcaccccaat gggcggtttc cttggtgcct tgtctccctt gcctgctacg      900
aaacttggct ctatagtaat tcaaggtgag atccgaatct tctctgcatt tacatccgag      960
ctctgaacat ggtcatggct gggggctgtt agctgctctg aaagagcaa acgtggatcc      1020 agccctcgtg caggaggtct actttggaaa cgtcttgagt gctaatttgg ggcaagctcc     1080
tgcaaggcaa gctgctctgg gtgccggat accaaactct gttgtttgca ccactgttaa      1140
caaagtctgt gcatctggca tgaaaggttt gaatcgaatt tatctgtctg tccttgtgta     1200
ctctgctcag agttcacaga agtgagagat tacctgacca tgctcttgtt ttccttttcct    1260 atatgcagct actatgtttg cagcacagtc aattcaattg ggtatcaatg atattgttgt    1320
ggctggtggc atggaaagca gtccaatgc cccaaagtac attgctgaag ctaggtatgc      1380
aattattact tggtggatat attcaatatc gagctgcata aaccaaatga tagtcttaag    1440
ttatttggta gatacatgca tgcttactta tcttcattgc attttctaaa tttgtttgta    1500
agaaatgttg attcaccagc agcgaggcta ttaacgaagt ggccagtttt gttgtgaaag    1560
tatattctgt tcatgtttaa agtgcatttc aactgcttat aagcttgcta attacaattg    1620
caggaagggg tctcgttttg gtcatgacac acttgttgat gccatgctta aggatgggct    1680
ttgggatgta tacaatgatt gtgccatggg aatgtgtgcc gagctttgtg ctgacaacca    1740
tgccctcaca agagaagacc aggtctctta atacagatag cagtaaatgc tgtttgttat    1800
aatattccca tattttcaa gatataagtt gtgctataca acatgtcaat gctggcaatt     1860
cttttgagac tgccctggaa tcttcgtgct ttatcttggt catcatcata aatggtctag    1920
agactctaga ccagcatctg cattccttgt ctgatgaact agtaacttgg atcctttcta    1980
gcaatgattt tctgttatgt tgtgacatga ttgatagggt gggcttttat gcatgctctg    2040
ggtctgtgaa ctgaccattc atctgcttcc agagatgaaa gtagatgtgc cacacaaaaa    2100
tgagcactct tttgtattcc tgttagagct atacaagtat aatctcttaa aagctgctca    2160
tcagtacatg acactagtac cttgatgatt ttactgtatc tgtttatgta atttttttct    2220
taataaattt gatatagtat aattaaaatt gagttgcctt ttaattttca cttatatgtt    2280
gcaatttatt tttgtctata ttgcaataaa tatatttcca atttctggta tatttaattt    2340
tacttattct tgaataggat gcatttgcta tccaaagcaa cgagcgtgga attgctgctc    2400
gtgacagtgg tgcttttgca tgggagatta ttccggtaat tttctccctc attgatgata    2460
ctagacatgc ttttcttggt tttctgatgg tcagtgttgt cacccaggtt caagttcctg    2520
ttggtagagg aaaaccccca acattaattg agagagatga aagcctggat aaggtatttt    2580
ttctgacgtg acaaaatatt tttaacaaaa taaagcttgt agttgatcaa aggcaaaaag    2640
actggcaggc actttgattt attgttcttg cttcctccaa atgcaacgtt ccttgcataa    2700
tgagctttgc tagcagttat ttgtaagatc aatgcatgac agtttttattt atgtcttgtg    2760 ctattccttt tgtgtcttag tttgacccag taaaactaaa gaaacttcgc ccaagtttca    2820
aggagaatgg tggtacagtt acagctggaa atgcttctag tataaggtag ctgcttgaaa    2880
tatttctgag gccttttgtc ctacaaagtc tttctgagac cttgttttttc ggccatatgt    2940 tgtttagctg acagatatga aggacaacct atttcattgt tgacagttaa attatattat    3000
```

```
tgtattatgc atgcattttt aactgatata ttatgcttgc attttgtcaa cttcattgtt    3060
tctctatttg tttttagact gcttgggtat gctctactcc gttaaataga tggtaatttt    3120
ttctttagat ttggtaccca attggtgtga atgatttatc acaatatcac ataagaaagt    3180
aaaaacattt taaatgcctt attatgccca ttcaaacaac aaaagttgcc ctaccttttta   3240 aatttcttca tggttgccct agaccttgtt tgtctcactt tgtactgtgt ctatttttag    3300
ctgacaagta ctgtccggtg tactgcctac tatggcttgt gtagccttct gcaaccagtc    3360
atctaatttg ttttatatgg atcagtgatg gagctgctgc attagtttta gtgagtgggc    3420
agaaggctca agagcttggc cttcaagtcc ttgcaaggat caaaggttat gctgatgcag    3480
ctcaagtaag ccacagaaac aattgttagc tctcctaaga gtagaatgcg cttattctaa    3540
tttacactgt gatctaaata ttttaggata taggaagtta ttttatctg gaacgatttt     3600 atgttactat tttagatatc gaaatttatc aactattgga acttgtgatc tggaatatta    3660
ttttgtaatg tggatgctgt ttatacaggc tccggagctt tttacaacca ctccagcact    3720
tgcaatacca aaggctatcg caaatgctgg attagagtca tcccgtgttg atttctatga    3780
gattaatgaa gccttttcgg tatgcattga gtttcttta ctcacatttt ttgtaagcct      3840
tttgttatgc attgagagtt tattttactt attactttt ttgtaataat gtcttttta     3900 cttgtcaata taggctgttg cgcttgcaaa tcaaaaactt cttggaattc cttcagtaag    3960
tgtcacctgt attaaactgc cattctttgt ggattttaga agtaaacaa tcactttcag     4020 aaagtacata ttgtctcttt tttgttattt gctatgcagc agcaacgtgt aattgcatta    4080
taacagtatt atctgtacta acagcatatg tgtttgcagg aaaagattaa tgttcatgga    4140
ggagctgtat ccttaggaca tcctctcggg tgcagtggtg ctcgcatttt ggttacccTT    4200
attggtgtaa gttctatctt aagatgcttg ttttaccttt tgagttacaa tccctttgt     4260 ttaaaaaaaa tgtgcaatgt ttttctagta aaaaataga tggtctttga gtaaataatg     4320
aattctgaca tatgttacca tatcatcata gggttcgtga tgaacagtaa gcatcttcac    4380
tattgctact aggtctactt cctctatccc aaattataag acgtcttggg atgttggcat    4440
tgttagattt atagctttta ctacgtgtac tgagacataa tgtttatcgc aataaaaact    4500
acaaatctag aaaaagtaaa aacatcttat aatttgaaac atagggagta tgttggatca    4560
agccacccca tccctgcacc aaacactacc ttaggccatg ttcggttaca agtggttcga    4620
gggggattga aggggattaa atccccttct agttaaaatt gaataggagg ggatttaatc    4680
cccctcaatc ccctccaatc ctctcgcaac cgaacaagcc cttagtgatt tccaatgtgc    4740
aaattatctg caaatagaat cttgtataaa gctgcaaatg tagagtttca cattgatatc    4800
ggctcatccc ttgtttcact tgttgctggt gatcaatagt ttcttttct cttcattttc     4860 tttaagcaaa acgttgggca caatatagtg ccatcatgtt gggacatcaa aatatattgt    4920
gcttgacccT cctaatcatt gtttcttgtt aacaggttct cagggcgaag agtggcaaga    4980
tcggagttgc tggtgtctgc aacggtggag gcggagcatc agctcttgtt ctggagctcg    5040
cataagaaat ctagaccttg taagactcaa acaccgaat atatctcaac tcaaattgat     5100
tcttttacta gctggcagta ggagctaacc agtataaggt gctattatca aactgtaata    5160
tggtcgcata ttcagctagg cctaattaag ttgtatttt tccttttaca actgttgtgc     5220
aatttgacta actgctgcac cttgatattg caggtagtta gcaaaagctc cctgaggtga    5280
tcttgtagtc ttattttccg ttgtagtagt cccatagaac atttcttaat ttaatttggc    5340
aataaagcaa aagctccctg aggagatatt gcttctgttg gttgcatagt agagtatcat    5400
```

```
gtaataagag ctacagaaat attttgata tatttgtgag gatactacag aaatatttta     5460
tatatttgtg atgtgtcttg tacatttatc taggtcacat caactatcct gccgcccggg     5520
atctggaact ccgacagccc gatttcaaat agtttgaaag aacatcagca aacacccaag     5580
gcaaatacaa agatcagaga agctggaggg ttagttacag gagcatcagg ttaccgagaa     5640
tgcaaccatg cacggcaaaa ggcgcctacc ccgcatcaaa atttctgcca gaaacaaaca     5700
agaaacgaaa gaatcacacg cacactatct acatccagaa acgtgatgtt atactagata     5760
gtcagcggca ttcaggaagc cctcgtactg ggtaccgttg agggcgctgt agacctcgtc     5820
ccagttctcg atctgctccg acagcggctt cgtgtgtatc ttcacgtgcc ggctcaccag     5880
cttcctcctc ggcactccga ggaaatccag gacatccaag agcttctgca gtgcagcagc     5940
gatggtaagc gacacaacca acggaaggga acagacaagg gaagggcatc agcgagaacg     6000
cactgttctg ttgcggacga cgtcctcgta gtagacgctc atgtgccggg tgttgtttag     6060
gttctcaaga gcgtcgcgag tgtactcgtc agctcgtttc agctgccata tcagtgacgt     6120
cgtgttgagc ctgggcctgt atcttgccag tatatgggcc tgtggagcga gaacgaacga     6180
cacgtcaaac acagagagag atcagatcag ctcagagact tgctgccata tccgtttctt     6240
agctagcatt actaacctca cgcttcgtgt ggacatgggc cttgtgcgtt ccgtttagtt     6300
gcttaagtaa cctgtcgtgg ttgttcgcta cctgtgatac caactggcgg agcaggttcc     6360
ttctgaaaag aaatatcgca gagactcctc ttcggttgaa gtagtcgact acgtccgcat     6420
ggtttgccac gaggccctga aaacatacac cccaaccccg ttcagaagaa atgctccttt     6480
gtttccactc tctagctaca atgcctgttt tgtttccagt ctctaaacct atgtttggcc     6540
aatattcatg gtttggttag gcaatctgtc taccaggaaa aaagttcgtt ctcgcacaaa     6600
ttagatgaag ccctgaaaca aacatgcttg acatgtagat tataatcagt ctactggaca     6660
cactacagaa tctatcaaat attactccat atgcatttgc agttctcatg catgttcgag     6720
agagagaaaa tttgtctaaa atgcaggatc tgacagcaag tcagaaaact aaactagcta     6780
ccgacagttc cataaggcct tgttcggtta ttcgcatccc acatggattg aagagattg      6840
gaaaatttta agaaggattt tgacttctta tggatttaaa ctcatccaat ctcgtccaat     6900
ccacatggat tggcactaaa acgagcaagc cctaaagtgg attcccaaaa aaaaatagtt     6960
acatggactt gaggaaagtt tggcgcaata tgcaataaca tttagcatct acagttgaga     7020
acatgtaggc cgtttaggag actacacata ctaataattg aaacatactg gaactaaatg     7080
gaaaaataaa tgaaaaagga tcatccaaat aaattatcta tactgcatgt tttagtccgc     7140
acctgattta gcatccactt gaagccaata gctgcagtgc actcattctt ggaagcgcta     7200
ctgttccagt ccaaattgta cactttatcc agggtatcta ttatagagga aatgttactc     7260
ctcctttctt ttctagagaa aatttcacca ttggagctaa cattcatgtg ctgttaaga      7320
agtgtttcaa accagccact tccagatcgc tgcgatgata taattgcaaa ggaccggaca     7380
gcattgcact tgcattcctc cctagaaata aaaaattatg cattaggcat taaacaaacg     7440
agattgctca atcttaccac agtgcagatc tcacctgctg taaatatagg aagttatttt     7500
tatctggaac gattttatgt tactatttta gatatcgaaa tttatcaact attggaactt     7560
gtgatctgga atattatttt gtaatgtgga tgctgtttat acaggctccg gagctttta     7620
caaccactcc agcacttgca ataccaaagg ctatcgcaaa tgctggatta gagtcatccc     7680
gtgttgattt ctatgagatt aatgaagcct ttcggtatg cattgagttt cttttactca     7740
```

```
cattttttgt aagccttttg ttatgcattg agagtttatt ttacttatta ctttttttgt   7800
aataatgtct tttttacttg tcaatatagg ctgttgcgct tgcaaatcaa aaacttcttg   7860
gaattccttc agtaagtgtc acctgtatta aactgccatt ctttgtggat tttagaagtt   7920
aaacaatcac tttcagaaag tacatattgt ctcttttttg ttatttgcta tgcagcagca   7980
acgtgtaatt gcattataac agtattatct gtactaacag catatgtgtt tgcaggaaaa   8040
gattaatgtt catggaggag ctgtatcctt aggacatcct ctcgggtgca gtggtgctcg   8100
cattttggtt acccttattg gtgtaagttc tatcttaaga tgcttgtttt acctttttgag  8160
ttacaatccc ttttgtttaa aaaaaatgtg caatgttttt ctagtaaaaa aatagatggt   8220
ctttgagtaa ataatgaatt ctgacatatg ttaccatatc atcatagggt tcgtgatgaa   8280
cagtaagcat cttcactatt gctactaggt ctacttcctc tatcccaaat tataagacgt   8340
cttgggatgt tggcattgtt agatttatag cttttactac gtgtactgag acataatgtt   8400
tatcgcaata aaaactacaa atctagaaaa agtaaaaaca tcttataatt tgaaacatag   8460
ggagtatgtt ggatcaagcc accccatccc tgcaccaaac actaccttag gccatgttcg   8520
gttacaagtg gttcgagggg gattgaaggg gattaaatcc ccttctagtt aaaattgaat   8580
aggaggggat ttaatccccc tcaatcccct ccaatcctct cgcaaccgaa caagcccttta  8640
gtgatttcca atgtgcaaat tatctgcaaa tagaatcttg tataaagctg caaatgtaga   8700
gtttcacatt gatatcggct catcccttgt ttcacttgtt gctggtgatc aatagtttct   8760
ttttctcttc attttctttta agcaaaacgt tgggcacaat atagtgccat catgttggga  8820
catcaaaata tattgtgctt gaccctccta atcattgttt cttgttaaca ggttctcagg   8880
gcgaagagtg gcaagatcgg agttgctggt gtctgcaacg gtggaggcgg agcatcagct   8940
cttgttctgg agctcgcata agaaatctag accttgtaag actcaaaaca ccgaatatat   9000
ctcaactcaa attgattctt ttactagctg gcagtaggag ctaaccagta taaggtgcta   9060
ttatcaaact gtaatatggt cgcatattca gctaggccta attaagttgt attttttcct   9120
tttacaactg ttgtgcaatt tgactaactg ctgcaccttg atattgcagg tagttagcaa   9180
aagctccctg aggtgatctt gtagtcttat tttccgttgt agtagtccca tagaacattt   9240
cttaatttaa tttggcaata aagcaaaagc tccctgagga gatattgctt ctgttggttg   9300
catagtagag tatcatgtaa taagagctac agaaatattt ttgatatatt tgtgaggata   9360
ctacagaaat attttatata tttgtgatgt gtcttgtaca tttatctagg tcacatcaac   9420
tatcctgccg cccgggatct ggaactccga cagcccgatt tcaaatagtt tgaaagaaca   9480
tcagcaaaca cccaaggcaa atacaaagat cagagaacgr mmgtgagcat caggttaccg   9540
agaatgcaac catgcacggc aaaaggcgcc taccccgcat caaaatttct gccagaaaca   9600
aacaagaaac gaaagaatca cacgcacact atctacatcc agaaacgtga tgttatacta   9660
gatagtcagc ggcattcagg aagccctcgt actgggtacc gttgagggcg ctgtagacct   9720
cgtcccagtt ctcgatctgc tccgacagcg gcttcgtgtg tatcttcacg tgccggctca   9780
ccagcttcct cctcggcact ccgaggaaat ccaggacatc aagagcttc tgcagtgcag    9840
cagcgatggt aagcgacaca accaacggaa gggaacagac aagggaaggg catcagcgag   9900
aacgcactgt tctgttgcgg acgacgtcct cgtagtagac gctcatgtgc cgggtgttgt   9960
ttaggttctc aagagcgtcg cgagtgtact cgtcagctcg tttcagctgc catatcagtg   10020
acgtcgtgtt gagcctgggc ctgtatcttg ccagtatatg ggcctgtgga gcgagaacga   10080
acgacacgtc aaacacagag agagatcaga tcagctcaga gacttgctgc catatccgtt   10140
```

```
tcttagctag cattactaac ctcacgcttc gtgtggacat gggccttgtg cgttccgttt    10200
agttgcttaa gtaacctgtc gtggttgttc gctacctgtg ataccaactg gcggagcagg    10260
ttccttctga aaagaaatat cgcagagact cctcttcggt tgaagtagtc gactacgtcc    10320
gcatggtttg ccacgaggcc ctgaaaacat acaccccaac cccgttcaga agaaatgctc    10380
ctttgtttcc actctctagc tacaatgcct gttttgtttc cagtctctaa acctatgttt    10440
ggccaatatt catggtttgg ttaggcaatc tgtctaccag gaaaaagtt cgttctcgca     10500 caaattagat gaagccctga acaaacatg cttgacatgt agattataat cagtctactg      10560
gacacactac agaatctatc aaatattact ccatatgcat ttgcagttct catgcatgtt    10620
cgagagagag aaaatttgtc taaaatgcag gatctgacag caagtcagaa aactaaacta    10680
gctaccgaca gttccataag gccttgttcg gttattcgca tcccacatgg attggaagag    10740
attggaaaat tttaagaagg attttgactt cttatggatt taaactcatc caatctcgtc    10800
caatccacat ggattggcac taaaacgagc aagccctaaa gtg                       10843

<210> SEQ ID NO 39
<211> LENGTH: 1704
<212> TYPE: DNA
<213> ORGANISM: Zea mays

<400> SEQUENCE: 39
gtgttgcgtt ccctacttgc tcttttcttc ctccgcttca acctgtcccg agcgcccccc      60
gcgcacacac tgtctttctc tgcctttctt tccctagcgc cgcgccggcg ccgccattcg    120
atcaggccgc ttcgccggcg acagcatatt ccaggtcggt tggttttggc acttcggacc    180
ggcggccatg gcttccgacg gcatcggccc cagagatgta tgtgttgttg gggttgcacg    240 cacccccaatg ggcggttttcc ttggtgcctt gtctcccttg cctgctacga aacttggctc   300
tatagtaatt caaggtgaga tccgaatctt ctctgcattt acatccgagc tctgaacatg    360
gtcatggctg ggggctgtta gctgctctgg aaagagcaaa cgtggatcca gccctcgtgc    420
aggaggtcta ctttggaaac gtcttggagtg ctaatttggg gcaagctcct gcaaggcaag    480
ctgctctggg tgccgggata ccaaactctg ttgtttgcac cactgttaac aaagtctgtg    540
catctggcat gaaagctact atgtttgcag cacagtcaat tcaattgggt atcaatgata    600
ttgttgtggc tggtggcatg gaaagcatgt ccaatgcccc aaagtacatt gctgaagcta    660 ggaagggtc tcgttttggt catgacacac ttgttgatgc catgcttaag gatgggcttt     720
gggatgtata caatgattgt gccatgggaa tgtgtgccga gctttgtgct gacaaccatg    780
ccctcacaag agaagaccag gatgcatttg ctatccaaag caacgagcgt ggaattgctg    840
ctcgtgacag tggtgctttt gcatgggaga ttattccggt tcaagttcct gttggtagag    900
gaaaaccccc aacattaatt gagagagatg aaagcctgga taagtttgac ccagtaaaac    960
taaagaaact tcgcccaagt ttcaaggaga atggtggtac agttacagct ggaaatgctt    1020
ctagtataag tgatggagct gctgcattag ttttagtgag tgggcagaag gctcaagagc    1080
ttggccttca gtccttgca aggatcaaag gttatgctga tgcagctcaa gctccggagc    1140 ttttttacaac cactccagca cttgcaatac caaaggctat cgcaaatgct ggattagagt    1200
catcccgtgt tgatttctat gagattaatg aagccttttc ggctgttgcg cttgcaaatc    1260
aaaaacttct tggaattcct tcagaaaaga ttaatgttca tggaggagct gtatccttag    1320
gacatcctct cggggtgcagt ggtgctcgca ttttggttac ccttattggt gttctcaggg    1380
```

```
cgaagagtgg caagatcgga gttgctggtg tctgcaacgg tggaggcgga gcatcagctc    1440
ttgttctgga gctcgcataa gaaatctaga ccttgtagtt agcaaaagct ccctgaggtg    1500
atcttgtagt cttattttcc gttgtagtag tcccatagaa catttcttaa tttaatttgg    1560
caataaagca aaagctccct gaggagatat tgcttctgtt ggttgcatag tagagtatca    1620
tgtaataaga gctacagaaa tattttgat atatttgtga ggatactaca gaaatatttt    1680
atatatttgt gatgtgtctt gtac                                           1704

<210> SEQ ID NO 40
<211> LENGTH: 1637
<212> TYPE: DNA
<213> ORGANISM: Zea mays

<400> SEQUENCE: 40
gtgttgcgtt ccctacttgc tcttttcttc ctccgcttca acctgtcccc agcgcccccc      60
gcgcacacac tgtctttctc tgcctttctt tccctagcgc cgcgccggcg ccgccattcg     120
atcaggccgc ttcgccggcg acagcatatt ccaggtcggt tggttttggc acttcggacc     180
ggcggccatg gcttccgacg gcatcggccc cagagatgta tgtgttgttg gggttgcacg     240 cacccccaatg ggcggtttcc ttggtgcctt gtctcccttg cctgctacga aacttggctc     300
tatagtaatt caagctgctc tggaaagagc aaacgtggat ccagccctcg tgcaggaggt     360
ctactttgga aacgtcttga gtgctaattt ggggcaagct cctgcaaggc aagctgctct     420
gggtgccggg ataccaaact ctgttgtttg caccactgtt aacaaagtct gtgcatctgg     480
catgaaagct actatgtttg cagcacagtc aattcaattg ggtatcaatg atattgttgt     540
ggctggtggc atggaaagca tgtccaatgc cccaaagtac attgctgaag ctaggaaggg     600
gtctcgtttt ggtcatgaca cacttgttga tgccatgctt aaggatgggc tttgggatgt     660
atacaatgat tgtgccatgg gaatgtgtgc cgagctttgt gctgacaacc atgccctcac     720
aagagaagac caggatgcat ttgctatcca agcaacgag cgtggaattg ctgctcgtga     780
cagtggtgct tttgcatggg agattattcc ggttcaagtt cctgttggta gaggaaaacc     840
cccaacatta attgagagag atgaaagcct ggataagttt gacccagtaa aactaaagaa     900
acttcgccca gtttcaagg agaatggtgg tacagttaca gctggaaatg cttctagtat     960
aagtgatgga gctgctgcat tagttttagt gagtgggcag aaggctcaag agcttggcct    1020
tcaagtcctt gcaaggatca aaggttatgc tgatgcagct caagctccgg agcttttttac    1080 aaccactcca gcacttgcaa taccaaaggc tatcgcaaat gctggattag agtcatcccg    1140
tgttgatttc tatgagatta tgaagccttt tcggctgtt gcgcttgcaa atcaaaaact    1200
tcttggaatt ccttcagaaa agattaatgt tcatggagga gctgtatcct taggacatcc    1260 tctcggggtgc agtggtgctc gcattttggt taccttatt ggtgttctca gggcgaagag    1320
tggcaagatc ggagttgctg gtgtctgcaa cggtggaggc ggagcatcag ctcttgttct    1380
ggagctcgca taagaaatct agaccttgta gttagcaaaa gctccctgag gtgatcttgt    1440
agtcttattt tccgttgtag tagtcccata gaacatttct taatttaatt tggcaataaa    1500
gcaaaagctc cctgaggaga tattgcttct gttggttgca tagtagagta tcatgtaata    1560
agagctacag aaatattttt gatatatttg tgaggatact acagaaatat tttatatatt    1620
tgtgatgtgt cttgtac                                                   1637

<210> SEQ ID NO 41
<211> LENGTH: 1780
```

```
<212> TYPE: DNA
<213> ORGANISM: Zea mays

<400> SEQUENCE: 41
cagagcacca gctcaccgcc ccaccgattc aaaggcgctc ggatcctctg acgtcgacgt      60
tccctgccag ctcccggctg ccgccctcgc tccttccgcc atctgcgctg ctctgcggcg     120
ccagagccgg cgcccgcccg ctgccgccct cgacggaccg ggacacgggg ccccaccgtt     180
ctctttcctg cgctgcgctg cgcggcggct gtgctgctga tcagttaatg tgcctgtgag     240
gctgtgacag gcggcgtcga gcgagtccga ggcgggctaa ctaaaccgc cgtctctcga      300
ggcggcgccc gcggagggcc aggtggaggg ccgaggaagg tggaggcggt gaggcgatgg     360
ggggcgccaa gcggaggac aagcccgccg ccgccaccgc tgaagacgat tggtgttacc      420
agtttggaaa caagaatgcg tttgactcga aggccccgaa aaaatcacca cttgcattga     480
gagtggttgt ctttgccatg actgtgttat gtgggatatc tatttggtca atgtgtatga     540
agcagctagg gagtgatggc tggtcaagaa tagtgaagat cgaagttgtg gaacaaccat     600
gtaataagtc tacagttcct ccttctgagg ttcaatttgc gcattaccct caaccgacaa     660
cttacagcag ggaggaatgc aagtgcaatg ctgtccggtt ctttgcgatt atatcatcac     720
agcgatctgg aagtggctgg tttgaaaccc ttcttaacag ccacatgaat gttagctcca     780
acggtgaaat tttctctaga aagaaagga gaagtaacat ttcctctata atagataccc      840
tggataaagt gtacaatttg gactggaaca gtagcgcttc aagaatgag tgcactgcag      900
ctattggctt caagtggatg ctaaatcagg gcctcgtggc aaaccatgcg gacgtagtcg     960
actacttcaa ccgaagagga gtctctgcga tatttctttt cagaaggaac ctgctccgcc    1020
agttggtatc acaggtagcg aacaaccacg acaggttact taagcaacta aacgaacgc     1080
acaaggccca tgtccacacg aagcgtgagg cccatatact ggcaagatac aggcccaggc    1140
tcaacacgac gtcactgata tggcagctga acgagctga cgagctgagtacact cgcgacgctc   1200
ttgagaacct aaacaacacc cggcacatga gcgtctacta cgaggacgtc gtccgcaaca    1260
gaacaaagct cttggatgtc ctggatttcc tcggagtgcc gaggaggaag ctggtgagcc    1320
ggcacgtgaa gatacacacg aagccgctgt cggagcagat cgagaactgg gacgaggtct    1380
acagcgccct caacggtacc cagtacgagg gcttcctgaa tgccgctgac tatctagtat    1440
aacatcacgt ttctggatgt agatagtgtg cgtgtgattc tttcgtttct tgtttgtttc    1500
tggcagaaat tttgatgcgg ggtaggcgcc ttttgccgtg catggttgca ttctcggtaa    1560
cctgatgctc ctgtaactaa ccctccagct tctctgatct ttgtatttgc cttgggtgtt    1620
tgctgatgtt ctttcaaact atttgaaatc gggctgtcgg agttccagat cccgggcggc    1680
aggatagttg atgtgaccta gataaatgta caagacacat cacaaatata taaaatattt    1740
ctgtagtatc ctcaaaaaaa aaaaaaaaa aaaaaaaag                             1780

<210> SEQ ID NO 42
<211> LENGTH: 11900
<212> TYPE: DNA
<213> ORGANISM: Zea mays

<400> SEQUENCE: 42
aacgccatgg agaaatcaca catgagacac caattactca aggagtttac ttaattatat      60
tttacttaaa ttgagtatag gattcatcgt actaccaagg ggatccaaaa ataaggttgg     120
tgtttgccaa agctcaagcc tctatattca aaagctattt tttgaaaatc aaaaatctct     180
```

```
ttaaaattct atggttgact atggttaggt ttgagaaacc tagagtgttt ttgttgaaaa      240
gcagctgagc ttttcagctg aactaaactt cagctgagtt gagcttcttc agctgcagtt      300
gagcttttca gctgagctaa acttcagctg tgtcgagctt tctcaactcc agttgaactt      360
caacttcaac tggggtccag tcaagttcaa ccggggtcca ggcaggttca accgggtcc       420 aaggcaagtt caaccggggt ccagagaggt tcaactgggg tccaggaaaa gttcaaccgg      480
ggtttagaga ggttcaacca gggatgggct gtacgcaacg cgtctaagaa ttgtacgtgt      540
gttctctcgt aaccagaagc agcctcacct cctttgtata tataaacgag cagagggagg      600
cgaacggata gtaacggtca ccatcagagc tatcattaca gccagccaga aacgacgcc       660 attagtgacg tccgttaata gctgacaagc attataactc gttcgttact atccataaca      720
taggaaacga ccaataacgt acaacagtaa tggacggtca tcactttagg caaaatgtgc      780
aaccgttagg aaggaatatt cggaccaagg tccgatctac cacggccacg gcccggcggc      840
gcgcgcgtgt ggcagtcctt catcattttc tcaacttctc actagatgca ccaaagatcc      900
gcctatttaa gttgattgaa ttgtcccttg tacttccggt atggtactaa agtactagta      960
caccgtagca ttaaagtggg cctttagcat tgactattat tgaatattaa tttgggttag     1020
gccctcatta attcaacagt agcttctagg cctaaccatc ccaccccca aactaagcat      1080 agatgaacta tgtttaggtt gctacaaaaa tattccaaaa ataattccc tccgtcctaa      1140 aatactaacc gttttagcat tttaatagat tcataaaaat atgtcagatc cacaagtcat     1200
acgaggcaac tgtctcgagc atgatggatg gagaaccaat atccccttg taaaatgtct      1260 tcttcctcca cttccaatgc atgcaatcta tactcaatat cataatagaa atcccctttt     1320
ccacctcctt agctaagata agcctaagtc attgacaatg gcatgataat tgtactccgc      1380
cctgaaacat gcaataccac ctctacagaa tagaccaaaa actccactcg tagggggaaat    1440 actgccccca cggtaagaag aagcttaatc ggagccctga tcgagaaagg tcacgaaaga      1500
tgtacccctc ccccccatgca acatgagagt ccgcccccta taggccagat ctttactcgt    1560
gctttgagcc ctactagccc ttacacgagg atccgcccca taggtcagcc atctcatgt       1620 gcacacaact agggaaacta gtgagtgacc ttgttaacct cagcctaaaa ttcgctccca     1680
ccgggattca aacttaggac ctgaggagtg ctactcagac gacctaacca acttaactag     1740
ggaccctttc acacagaata gtccaaggca ctctgaggtg gaactttcct cattttgatg     1800
tactcatcga tggagtcagc aatgctacag tacgcaagca tgcttaggcc aattgtgcac     1860
ttctggtggg ggaggaaaca ctgcggttga atgcatcggt tcaaaaagtg aagtatggga     1920
agtgctcacc caatctctct aagatatgaa ggaagagact tctctagatg cggtaacttt    1980
gacaaaagta gagcagtggg tagacacaca ggtcgttgaa atggtcttgc attaaccggt    2040
cgtatgcaac tacatagtcg cagtcaatgt atctctgatg ttgccttggc cacctcatcg   2100
acctaggaga ctcggatcca agctctgacg cctgttgcat tatattttgt tgtaataact   2160
tgaataactc ttttcagtca tattgatgtc caagctgaac gaaaacatca caacaatgct   2220
tgatttgatt gaaacgagtg taagaggatt ataaggggtg gtagagaaat ttgaagtgtg   2280
ggttgtgtga atgagatcaa acactcctct atttatagac caagttctag ttttttttatt  2340 tttgaaaaaa aatcaaaata aagcgaagca attagaacct gccacatggc aagaggcgat   2400
cgttatcgac atggccgcaa tagctgttca gtaccaacca gtcagtatcg accgacgcgg   2460
tcccaacacg gtcaatagta accctggcgg ccgatcagta gcctcgacaa ccacaagcga   2520
ggctattagt gctggcacca tgtcgggtga tactgaccat ttggttgtgc cacatgggtg   2580
```

```
ggcgggcagt agagccaagc gccggcactc gcctaacatg atctaaaaca atcgataaaa    2640
ctgacagatt ggttgcggtt catgactacc tagacctggt cgaccacaag tagaaaatga    2700
gtcgagccga gcttgactcg gctcgtccat ttcacgagct agagagttag gctcggctca    2760
gctcgaagtc ggctcgcgag ctacaccccg atatatatta tttcattata tagtaaatta    2820
ttaatatata aacataaaat ataaaaatat tattcaccat tatgaattat cttatattta    2880
tcatcaaagg ctaagaaata agccgactat ctataaatta tctaatatct atcattattc    2940
tacatattga ttaatttggt acaactagct cgctcgcaga cgctccgaac ttgatctgac    3000
tcgtgagcct caagtttttt ttctagcctt aaccacatgc ccgcgaggat gattgttcga    3060
ggtgattagc aaacgcaaac gatatcaatt gacattttt attagtttca ttaggtttag    3120
agataaaatt atatcatgta tgtcactcgt ctagtatctt atttgttatc ataaatgttc    3180
taatcctttt tacgtcaccc gaatacaatt ttttactctt tcatgtcata gtaagggact    3240
aagacataca acattttaca tttaacattt ggccacgaca tgtaagagtg agatattgaa    3300
ttcgagtaac atacgaggta cgatgaataa ggtattacac aaaattacag tggcatatag    3360
tgaattgaat tgttctattt ttactttttt tttgcctaac ataaagccta ttttatttag    3420
tactttctct gattcagctt taattttat gatttattaa ttttattata tatctatata    3480
ttgtatagat taaaaaataa aataaattat agatttagga aaaattacat tcgggtgatt    3540
tggctgttgg gtgttgcgtt ccctacttgc tcttttcttc ctccgcttca acctgtcccc    3600
agcgccccc gcgcacacac tgtctttctc tgcctttctt tccctagcgc cgcgccggcg    3660
ccgccattcg atcaggccgc ttcgccggcg acagcatatt ccaggtatgc cgtcccttct    3720
gctccttctg cgagaattca aacaccccga actccccaaa tctagtattt gtattcggat    3780
ctgaccattt ttcactgggc ccgcccctga ttcgcaggtc ggttggtttt ggcacttcgg    3840
accggcggcc atggcttccg acggcatcgg ccccagaggt ataactgttt catctcttct    3900
ttgtgttcaa acagacagac gtcaaaccgc cgagaggagg tacaaatata gattttgggc    3960
tatgagcacg ccattgcgct tccagcgatc tgacatattg ggaattcttg tttttttttt    4020
gggtaccttg caaggccgaa atttgacgct tttctgttta attctagtgc ctgtctgcat    4080
ccattagggc atcctagctg ctccatgctc gtgatctcgt ccgtttgctt gattgaatcc    4140
attgttttcc aaagttcatt gctactgcga aatacgttta tatgattacc acaatttgtg    4200
ttttttgcctt ttcgggttgc acagagggta ctgccatcat tgttgtttta gcgccatttg    4260
gaacaagtga ttcactggta ctagtacagt atgtgctttt catgtgtgtt tggtttgtac    4320
catcagatgg aattttgagc gcggtttaca aattagtact atagatatac tgtgaggtgc    4380
acactagatg gttctgcttt gttctacagt cagtaacttt ttcttccttg ctcacagatg    4440
tatgtgttgt tggggttgca cgcacccaa tgggcggttt ccttggtgcc ttgtctccct    4500
tgcctgctac gaaacttggc tctatagtaa ttcaaggtga gatccgaatc ttctctgcat    4560
ttacatccga gctctgaaca tggtcatggc tggggggctgt tagctgctct ggaaagagca    4620
aacgtggatc cagccctcgt gcaggaggtc tactttggaa acgtcttgag tgctaatttg    4680
gggcaagctc ctgcaaggca agctgctctg ggtgccggga taccaaactc tgttgtttgc    4740
accactgtta acaaagtctg tgcatctggc atgaaaggtt tgaatcgaat ttatctgtct    4800
gtccttgtgt actctgctca gagttcacag aagtgagaga ttacctgacc atgctccttgt    4860
tttcctttcc tatatgcagc tactatgttt gcagcacagt caattcaatt gggtatcaat    4920
```

```
gatattgttg tggctggtgg catggaaagc atgtccaatg ccccaaagta cattgctgaa    4980
gctaggtatg caattattac ttggtggata tattcaatat cgagctgcat aaaccaaatg    5040
atagtcttaa gttatttggt agatacatgc atgcttactt atcttcattg cattttctaa    5100
atttgtttgt aagaaatgtt gattcaccag cagcgaggct attaacgaag tggccagttt    5160
tgttgtgaaa gtatattctg ttcatgttta aagtgcattt caactgctta taagcttgct    5220
aattacaatt gcaggaaggg gtctcgtttt ggtcatgaca cacttgttga tgccatgctt    5280
aaggatgggc tttgggatgt atacaatgat tgtgccatgg gaatgtgtgc cgagctttgt    5340
gctgacaacc atgccctcac aagagaagac caggtctctt aatacagata gcagtaaatg    5400
ctgtttgtta taatattccc atattttca agatataagt tgtgctatac aacatgtcaa    5460
tgctggcaat tcttttgaga ctgccctgga atcttcgtgc tttatcttgg tcatcatcat    5520
aaatggtcta gagactctag accagcatct gcattccttg tctgatgaac tagtaacttg    5580
gatcctttct agcaatgatt ttctgttatg ttgtgcatg attgataggg tgggctttta    5640
tgcatgctct gggtctgtga actgaccatt catctgcttc cagagatgaa agtagatgtg    5700
ccacacaaaa atgagcactc ttttgtattc ctgttagagc tatacaagta taatctctta    5760
aaagctgctc atcagtacat gacactagta ccttgatgat tttactgtat ctgtttatgt    5820
aattttttc ttaataaatt tgatatagta taattaaaat tgagttgcct tttaattttc    5880
acttatatgt tgcaatttat ttttgtctat attgcaataa atatatttcc aatttctggt    5940
atatttaatt ttacttattc ttgaatagga tgcatttgct atccaaagca acgagcgtgg    6000
aattgctgct cgtgacagtg gtgcttttgc atgggagatt attccggtaa ttttctccct    6060
cattgatgat actagacatg cttttcttgg ttttctgatg gtcagtgttg tcacccaggt    6120
tcaagttcct gttggtagag gaaaaccccc aacattaatt gagagagatg aaagcctgga    6180
taaggtattt tttctgacgt gacaaaatat ttttaacaaa ataaagcttg tagttgatca    6240
aaggcaaaaa gactggcagg cactttgatt tattgttctt gcttcctcca aatgcaacgt    6300
tccttgcata atgagctttg ctagcagtta tttgtaagat caatgcatga cagttttatt    6360
tatgtcttgt gctattcctt ttgtgtctta gtttgaccca gtaaaactaa agaaacttcg    6420
cccaagtttc aaggagaatg gtggtacagt tacagctgga aatgcttcta gtataaggta    6480
gctgcttgaa atatttctga ggccttttgt cctacaaagt ctttctgaga ccttgttttt    6540
cggccatatg ttgtttagct gacagatatg aaggacaacc tatttcattg ttgacagtta    6600
aattatatta ttgtattatg catgcatttt taactgatat attatgcttg cattttgtca    6660
acttcattgt ttctctattt gttttagac tgcttgggta tgctctactc cgttaaatag    6720
atggtaattt tttctttaga tttggtaccc aattggtgtg aatgatttat cacaatatca    6780
cataagaaag taaaaacatt ttaaatgcct tattatgccc attcaaacaa caaaagttgc    6840
cctacctttt aaatttcttc atggttgccc tagaccttgt ttgtctcact ttgtactgtg    6900
tctatttta gctgacaagt actgtccggt gtactgccta ctatggcttg tgtagccttc    6960
tgcaaccagt catctaattt gttttatatg gatcagtgat ggagctgctg cattagtttt    7020
agtgagtggg cagaaggctc aagagcttgg ccttcaagtc cttgcaagga tcaaggtta    7080
tgctgatgca gctcaagtaa gccacagaaa caattgttag ctctcctaag agtagaatgc    7140
gcttattcta atttacactg tgatctaaat attttaggat ataggaagtt attttatct    7200
ggaacgattt tatgttacta ttttagatat cgaaatttat caactattgg aacttgtgat    7260
ctggaatatt attttgtaat gtggatgctg tttatacagg ctccggagct ttttacaacc    7320
```

```
actccagcac ttgcaatacc aaaggctatc gcaaatgctg gattagagtc atcccgtgtt    7380
gatttctatg agattaatga agccttttcg gtatgcattg agtttctttt actcacattt    7440
tttgtaagcc ttttgttatg cattgagagt ttattttact tattactttt tttgtaataa    7500 tgtcttttt  acttgtcaat ataggctgtt gcgcttgcaa atcaaaaact tcttggaatt    7560
ccttcagtaa gtgtcacctg tattaaactg ccattctttg tggatttag  aagttaaaca    7620 atcactttca gaaagtacat attgtctctt ttttgttatt tgctatgcag cagcaacgtg    7680
taattgcatt ataacagtat tatctgtact aacagcatat gtgtttgcag gaaaagatta    7740
atgttcatgg aggagctgta tccttaggac atcctctcgg gtgcagtggt gctcgcattt    7800
tggttaccct tattggtgta agttctatct taagatgctt gttttacctt ttgagttaca    7860
atcccttttg tttaaaaaaa atgtgcaatg ttttctagt  aaaaaaatag atggtctttg    7920
agtaaataat gaattctgac atatgttacc atatcatcat agggttcgtg atgaacagta    7980
agcatcttca ctattgctac taggtctact tcctctatcc caaattataa gacgtcttgg    8040
gatgttggca ttgttagatt tatagctttt actacgtgta ctgagacata atgtttatcg    8100
caataaaaac tacaaatcta gaaaagtaa  aaacatctta taatttgaaa catagggagt    8160
atgttggatc aagccacccc atccctgcac caaacactac cttaggccat gttcggttac    8220
aagtggttcg aggggattg  aaggggatta atccccttc  tagttaaaat tgaataggag    8280
gggatttaat ccccctcaat cccctccaat cctctcgcaa ccgaacaagc ccttagtgat    8340
ttccaatgtg caaattatct gcaaatagaa tcttgtataa agctgcaaat gtagagtttc    8400
acattgatat cggctcatcc cttgtttcac ttgttgctgg tgatcaatag tttcttttc    8460 tcttcatttt ctttaagcaa aacgttgggc acaatatagt gccatcatgt tgggacatca    8520
aaatatattg tgcttgaccc tcctaatcat tgtttcttgt taacaggttc tcagggcgaa    8580
gagtggcaag atcggagttg ctggtgtctg caacggtgga ggcggagcat cagctcttgt    8640
tctggagctc gcataagaaa tctagacctt gtaagactca aaacaccgaa tatatctcaa    8700
ctcaaattga ttcttttact agctggcagt aggagctaac cagtataagg tgctattatc    8760
aaactgtaat atggtcgcat attcagctag gcctaattaa gttgtatttt ttccttttac    8820
aactgttgtg caatttgact aactgctgca ccttgatatt gcaggtagtt agcaaaagct    8880
ccctgaggtg atcttgtagt cttatttcc  gttgtagtag tcccatagaa catttcttaa    8940
tttaatttgg caataaagca aaagctccct gaggagatat tgcttctgtt ggttgcatag    9000
tagagtatca tgtaataaga gctacagaaa tattttgat  atatttgtga ggatactaca    9060
gaaatatttt atatatttgt gatgtgtctt gtacatttat ctaggtcaca tcaactatcc    9120
tgccgcccgg gatctggaac tccgacagcc cgatttcaaa tagtttgaaa gaacatcagc    9180
aaacacccaa ggcaaataca aagatcagag aagctggagg gttagttaca ggagcatcag    9240
gttaccgaga atgcaaccat gcacggcaaa aggcgcctac cccgcatcaa aatttctgcc    9300
agaaacaaac aagaaacgaa agaatcacac gcacactatc tacatccaga aacgtgatgt    9360
tatactagat agtcagcggc attcaggaag ccctcgtact gggtaccgtt gagggcgctg    9420
tagacctcgt cccagttctc gatctgctcc gacagcggct tcgtgtgtat cttcacgtgc    9480
cggctcacca gcttcctcct cggcactccg aggaaatcca ggacatccaa gagcttctgc    9540
agtgcagcag cgatggtaag cgacacaacc aacggaaggg aacagacaaa gggcatcagc    9600
gagaacgcac tgttctgttg cggacgacat cctcgtagta gacgctcatg tgccgggtgt    9660
```

```
tgtttaggtt ctcaagagcg tcgcgagtgt actcgtcagc tcgtttcagc tgccatatca    9720
gtgacgtcgt gttgagcctg ggcctgtatc ttgccagtat atgggcctgt ggagcgagaa    9780
cgaacgacac gtcaaacaca gacagagatc agctcagctc agagacttgc tgtgagagtg    9840
agacattagc cgcgaacacg tttcttagct agcattacta acctcacgct tcgtgtggac    9900
atgggccttg tgcgttccgt ttagttgctt aagtaacctg tcgtgattgt tcgctacttg    9960
tgataccaac tggcggagca ggttccttct gaaaagaaat attgcagaga ctcctcttcg   10020
attgaagtag tcgactacgt ccgcatggtt tgccacgagg ccctgaaaac atacacccca   10080
accccaaccc cgttcagaag aaatgctcct ttgtttccac tctctagcta cagtgcctgt   10140 tttgttttcca gtctctaact ctatgtttgg ccaacattca tggtttggtt aggcaatctg   10200
tctaccagga aaaagtttg ttctcacaca aattagatga agccctgaaa caaacatgct   10260
tgacatgtag attataatca gtctactgga cacactacag aatctatcaa atattactcc   10320
atatgcattt gcagttctca tgcacgttcg agagaaaaaa attgtctaaa atgcaggatc   10380
tgacagcaag tcacaaaact aaactagcta tccgacagtc ccataaggtt attcgcatcc   10440
cacatagatt ggaagggatt ggaaaatttt aagaaggatt ttgacttctt acggatttaa   10500
acccgttcaa tctcgtccaa tccacatgga ttggcactaa gacgagcaag ccctaaagtg   10560
gattcccaaa aaaaaatagt tccatggact tgaggaaagt ttggagcaat atgcaatact   10620
ggaactaaat ggaaaaataa atgaaaaagg gtcatccaaa taaatctata ctgcatgttt   10680
tagtccgcac ctgatttagc atccacttga agccaatagc tgcagtgcac tcattcttgg   10740
aagcgctact gttccagtcc aaattgtaca ctttatccag ggtatctatt atagaggaaa   10800
tgttactcct cctttctttt ctagagaaaa tttcaccatt ggagctaaca ttcatgtggc   10860
tgttaagaag agtttcaaac cagccacttc cagatcgctg cgatgatata attgcaaagg   10920
accggacagc attgcacttg cattcctccc tagaaattaa aaattatgta ttaggcatta   10980
aacaaacgag attgctcaat cttaccacag ttgcagatct cacctgctgt aagttatcgg   11040
ttgaggatag cgcacaaatt gagcctccga agaggagca atggacttat tacatggttg   11100
tcccacaact tcaatcttga caactcttga ccagccatca ctccctagtt gcttcatgca   11160
cattgagcaa atagatatcc cgcataacat agtcatagca aagacaaccg ttctcaacgc   11220
gatcggtgat ttttcgggg gcttcaagtc aaatgcatcc tgcaaacaga tccgaccagt   11280
acaaaaccaa tcagcaggtt gcactgcgca tacgcggttc agtgccagta tatatacatt   11340
gcagcccttt tttgaggtaa gatctgttat tttgtaacct tctgctacag taaaaaaacc   11400
tttcagcaaa caacacaaac attaatgttc aatgtgagct gagaagcatc catttggcta   11460
catctatata agcagaaata aaagaaata aacaaataa acttcaaggt ctatctagtc   11520
ctcagggaag ttaaaatgag cacgtactat tcaattcagc tactagcctt tttaccaaca   11580
tggaagacac ggcaagggat gaaaaggccc ttttttgata agttcaagta cattcccata   11640
tattctgtcg cccagctgcc ttaggggcg tttggttgcc ttctccagtg gtgcagctgc   11700
atctacacat gcaaaaagta gtgtttgttt ggttcgttgt atcgcacgag acaggctagc   11760
acggaactta aagcgccgcg agccaggccc ggcagaaacg catcgcgcga ccgcacgcgc   11820
gcggccaggc tccgctcagc cagctctta ctcgtgcacg catatcgaga cacgttttta   11880
attggttttt tcattatatc                                               11900
```

<210> SEQ ID NO 43
<211> LENGTH: 1411

```
<212> TYPE: DNA
<213> ORGANISM: Zea mays

<400> SEQUENCE: 43
gtgttgcgtt ccctacttgc tcttttcttc ctccgcttca acctgtcccc agcgcccccc      60
gcgcacacac tgtctttctc tgcctttctt tccctagcgc cgcgccggcg ccgccattcg     120
atcaggccgc ttcgccggcg acagcatatt ccaggtcggt tggttttggc acttcggacc     180
ggcggccatg gcttccgacg gcatcggccc cagaggatgt atgtgttgtt ggggttgcac     240
gcaccccaat gggcggtttc cttggtgcct tgtctccctt gcctgctacg aaacttggct     300
ctatagtaat tcaagctgct ctggaaagag caaacgtgga tccagccctc gtgcaggagg     360
tctactttgg aaacgtcttg agtgctaatt ggggcaagc tcctgcaagg caagctgctc      420
tgggtgccgg gataccaaac tctgttgttt gcaccactgt taacaaagtc tgtgcatctg     480
gcatgaaagc tactatgttt gcagcacagt caattcaatt gggtatcaat gatattgttg     540
tggctggtgg catggaaagc atgtccaatg ccccaaagta cattgctgaa gctaggaagg     600
ggtctcgttt tggtcatgac acacttgttg atgccatgct taaggatggg ctttgggatg     660
tatacaatga ttgtgccatg ggaatgtgtg ccgagctttg tgctgacaac catgccctca     720
caagagaaga ccaggatgca tttgctatcc aaagcaacga gcgtggaatt gctgctcgtg     780
acagtggtgc ttttgcatgg agattattc cggttcaagt tcctgttggt agaggaaaac     840
ccccaacatt aattgagaga gatgaaagcc tggataagtt tgacccagta aaactaaaga    900
aacttcgccc aagtttcaag gagaatggtg gtacagttac agctgaaat gcttctagta     960
taagtgatgg agctgctgca ttagttttag tgagtgggca gaaggctcaa gagcttggcc    1020
ttcaagtcct tgcaaggatc aaaggttatg ctgatgcagc tcaagctccg gagcttttta    1080
caaccactcc agcacttgca ataccaaagg ctatcgcaaa tgctggatta gagtcatccc    1140
gtgttgattt ctatgagatt aatgaagcct tttcggctgt tgcgcttgca aatcaaaaac    1200
ttcttggaat tccttcagaa aagattaatg ttcatggagg agctgtatcc ttaggacatc    1260
ctctcgggtg cagtggtgct cgcatttttg ttacccttat tggtgttctc agggcgaaga    1320
gtggcaagat cggagttgct ggtgtctgca acggtggagg cggagcatca gctcttgttc    1380
tggagctcgc ataagaaatc tagaccttgt a                                   1411

<210> SEQ ID NO 44
<211> LENGTH: 5790
<212> TYPE: DNA
<213> ORGANISM: Zea mays

<400> SEQUENCE: 44
gggggcagtc tatactgccc ccttaatagt tagtagagat ttggtacaac tcacgagcta      60
gctcgctcgc agacgctccg aacttgatct gactcgtgag cctcaagttt ttttctagc     120
cttaaccaca tgcccacgag gatgattgtt cgaggtgatt agcaaacgca aacgatatca     180
attgacattt tttattagtt tcattaggtt tagagataaa attatatcat gtatgtcact     240
catctagtat cttatttgtt atcataaatg ttctaatcct ttttacgtca cccgaataca     300
atttttact ctttcatgtc atcgttgatg acatagtaag ggactaagac atacaacatt      360
ttacatttaa catttggcca cgacatgtaa gagtgagata ttgaattcga gtaacatacg     420
aggtacgatg aataaggtat tacacaaaat tacagtggca tatagtgaat tgaattgttc    480
tatttttact ttttttttgc ctaacataaa gcctatttta tttagtactt tctctgattc     540
```

```
agctttaatt tttatgattt attaatttta ttatatatct atatattgta tagattaaaa    600
aataaaatag attatagatt taggaaaaat tacattcggg tgatttggct gttgggtgtt    660
gcgttcccta cttgctcttt tcttcctccg cttcaacctg tccccagcgc ccccgcgca     720
cacactgtct ttctctgcct ttctttccct agcgccgcgc cggcgacgcc attcgatcag    780
gccgcttcgc cggcgacagc atattccagg tatgccgtcc cttctgctcc ttctgcgaga    840
attcaaacac cccgaactcc ccaaatctag tatttgtatt cggatctgac cattttcac    900
tgggcccgcc cctgattcgc aggtcggttg gttttggcac ttcggaccgg cggccatggc    960
ttccgacggc atcggcccca gaggtattac tgtttcatct cttcttgtgt caaacagac    1020
agacgtcaag ccgccgagag gaggtacaaa tatagatttt gggtaatgag cacgccattg    1080
cgcttccagc gatctgacat attgggaatt cttgcttttt tttgggtacc ttgcaaggcc    1140
gaaatttgac gcttttctgt ttaattctag tgcctgtctg catccattag gcatcctag    1200
ctgctccatg ctcgtgatct cgtccgtttg cttgattgaa tccattgttt tccaaagttc    1260
attgctactg cgaaatacgt ttatatgatt accacaagtt gtgttttttc cttttcgggt    1320
tgcacagagg gtactgccat cattgttgtt atagcgccat ttggaacaag tgattcactg    1380
gtactagtac agtatgtgct tttcatgtgt gtttggtttg taccatcaga tggaattttg    1440
agcgcggttt acaaattagt actatagata tactgtgagg tgcacactag atggttctgc    1500
tttgttctac agtcagtaac ttttttcttcc ttgctcacag atgtatgtgt gttggggtt    1560
gcacgcaccc caatgggcgg tttccttggt gccttgtctc ccttgcctgc tacgaaactt    1620
ggctctatag taattcaagg tgagatccga atcttctctg catttacatc cgagctctga    1680
acatggtcat ggctggggc tgttagctgc tctggaaaga gcaaacgtgg atccagccct     1740
cgtgcaggag gtctactttg gaaacgtctt gagtgctaat ttggggcaag cgcctgcaag    1800
gcaagctgct ctgggtgccg ggataccaaa ctctgttgtt tgcaccactg ttaacaaagt    1860
ctgtgcatct ggcatgaaag gtttgaatcg aatttatctg tctgtccttg tgtactctgc    1920
tcagagttca cagaagtgag agattacctg accatgctct tgtttccctt tcctatatgc    1980
agctactatg tttgcagcac agtcaattca attgggtatc aatgatattg ttgtggctgg    2040
tggcatggaa agcatgtcca atgccccaaa gtacattgct gaagctaggt atgcaattat    2100
tacttggtgg atatattcaa tatcgagctg cataaaccaa atgatagtct taagttattt    2160
ggtagataca tgcatgctta cttatcttca ttgcattttc taaatttgtt tgtaagaaat    2220
gttgattcac cagcagcgag gctattaacg aagtggccag ttttgttgtg aaagtatatt    2280
ctgttcatgt ttaaagtgca tttcaactgc tttaatccaa taagcttgct acttacaatt    2340
gcaggaaggg gtctcgtttt ggtcatgaca cacttgttga tgccatgctt aaggatgggc    2400
tttgggatgt atacaatgat tgtgccatgg gaatgtgtgc cgagctttgt gctgacaatc    2460
atgccctcac aagagaagac caggtctctt aatacagata gcagtaaatg ctgtttgtta    2520
taatattccc atattttca agatataagt tgtgctatac aacatgtcaa tgctggcaat    2580
tattttgaga gtgccctgga atcttcgtgc tttatcttgg ttatcatcat aaatggtcta    2640
gagactctag accagcatct gcattccttg tccgatgaac tagtaacttg gatcctttct    2700
ggcaatgatt ttctgttagg ttgtgacatg attgataggg tgggcttatg catgctctgg    2760
gtctgtgaac tgaccattca tttgcttcca gagatgaaag tagatgtgcc acacaaaaat    2820
gagcactctt ttgcattctt gttagagcta tacaagtata atctcttaaa agctgctcat    2880
cagtacatga cactagtacc ttgatgattt tactgtatct gtttatgtaa ttttttcttt    2940
```

```
aataaatttg atatagtata attaaaattg agttgccttt gaattttcac ttatatgttg    3000
caatgtattt ttgtctatat tgcaataaat atattcccaa tttctggtat atttacttat    3060
tcttgaatag gatgcatttg ctatccaaag caatgagcgt ggaattgctg ctcgtgacag    3120
tggtgctttt gcatgggaga ttattccggt aattttctcc ctcattgatg atactagaca    3180
tgcttttctt ggttttctga tggtcaatgt tgtcgcccag gttcaagttc ctgttggtag    3240
aggaaaaccc ccaacattaa ttgagagaga tgaaagcctg gataaggttt tttttctgat    3300
ttgacaaaat attttttaaca aaataaagct tgtagttgat caaaggcaaa aagactggca    3360
ggcactttga tttattgttc ttgcttcctc caaatgcaac gttcctcgca taatgagctt    3420
tgctagcagt tatttgtaag atcaatgcat gacagtttta tttatgtctt gtgctattcc    3480
ttttgtgtct tagtttgacc cagtaaaact aaagaaactt cgcccaagtt tcaaggagaa    3540
tgatggtaca gttacagctg gaaatgcttc tagtataagg tagctgcttg aaatatttct    3600
gagacctttt tgtcctacaa agtctttctg agaccttgtt tttcggccat atgttgttta    3660
gctgacagat atgaaggaca acctatttca ttgttgacag ttaaattata ttattgtatt    3720
atgcatgcat ttttaactga tatattatgc ttgcatttg tcaacttcat tgtttctcta     3780
tttgttttta gactgcttgg gtatgctcta ctctgtgaaa tagatggtaa tttttttcttt   3840 agaattggta cccaatcgat gtgaatgatt tatcacataa gaaagtaaaa acatttttaaa   3900 tgccttatta tgcccattca aacaacaaaa gttgccctag accttgtctg tctcactttg    3960
tactgtgtct attttttagct gaccagtact gtccggtgta ctgcctacta tggcttgtct   4020
agccttctgc aaccagtcat atctaatttg ttttatatgg atcagtgatg gagctgctgc    4080
attagttttg gtgagtgggc agaaggctca agagcttggc cttcaagtcc ttgcaaggat    4140
caaaggttat gctgatgcag ctcaagtaag ccacagtaac aattgttagc tctcctaaga    4200
gtagaatgcg cttattctaa ttcacattgt gatctaaata ttttaggata taggaagtta    4260
tttttatctg gaacgattt atgttactat tttagatatc gaaatttatc aactattgga    4320
acttgtgatc tggaatatta ttttgtaatg tggatgctgt ttatacaggc tccggagctt    4380
tttacaacca ctccagcact tgcaatacca aaggctatcg caaatgctgg attagagtca    4440
tcccatgttg atttctatga gattaatgaa gccttttcgg tatgcattgg gtttctttat    4500
ttgtaagcct tttgttatgc attgagagct tatttttactt attactttttt tttttgtaata  4560 atgtctttt tacttatcaa tataggctgt tgcacttgca aatcaaaagc ttcttggaat      4620
tccttcagta agtgtcacct gtattaaact gccattcttt gtgcattta gaagttaaaa     4680 catcactttc agaaagtaca tattggcact ttttttgttat ttgctatgca gcagcaacat   4740
gtaattgcat tataacagca ttatatgtac taacaacata tgtgtttgca ggaaaagatt    4800
aatgttcatg gaggagctgt atcttaggga catcctctcg ggtgcagtgg tgctcgcatt    4860
ttggttaccc ttattggtgt aagttctatc ttaagatgct tgtttatct tttgagttac     4920 aatccctttt gtttaaaaaa atgtgcaatg ttttttctagt aaaaaaatag atgatggtct   4980
ttgagtaatt tgatgaattct gacatatgtt accgtatcat catagggttc gtgatgaaca   5040
gtaagcatct tcactattgc tactaagtct acttccttag tgttttccaa tgtgcaatgt    5100
ttttcttgta taaagctgca aatgtagagt ttcacttgtt gctggtgatc agtagtttct    5160
cttcattttc tttaagcaaa accttgagaa caatatggtg ccatcatgtt gggacatcaa    5220
atatatggtg cttgacccctc ctaatcattg tttcttgtta acaggttctc agggcgaaga   5280
```

-continued

| | |
|---|---|
| gtggcaagat cggagttgct ggtgtctgca acggtggagg cggagcatca gctcttgttc | 5340 |
| tggagctcgc ataagaaatc tagaccttgt aaggctcaaa acaccgaata tatctcaact | 5400 |
| caaattgatt cttttactag ctggcaggag ctaaccagta taaggtgcta ttactgttgt | 5460 |
| gcaatttgac taactgctgc aactgatatt gcaggtattt agcaaaagtt ccctgaggtg | 5520 |
| atcttgtagt cttattttcc gttgtagtag tcccatagaa catttcttaa tttaatttgg | 5580 |
| caataaagcg aagtcgtgct tctgttggtt gcatagtaga gtatcatgta ataagagcaa | 5640 |
| tggggatgtt tcatagatat ttttgaggat gctacagaaa tattttatat actagtgagt | 5700 |
| gctcgtgcgt tgcaacggga atatataatt ctatgataac ttatatacaa aatgtgtgct | 5760 |
| acattgttat aagaaaatgt ttcataatct | 5790 |

<210> SEQ ID NO 45
<211> LENGTH: 5881
<212> TYPE: DNA
<213> ORGANISM: Zea mays

<400> SEQUENCE: 45

| | |
|---|---|
| gggcagtcta tactgccccc ttaatagtta gtagagattt ggtacaactc acgagctagc | 60 |
| tcgctcgcag acgctccgaa cttgatctga ctcgtgagcc tcaagttttt tttctagcct | 120 |
| taaccacatg cccacgagga tgattgttcg aggtgattag caaacgcaaa cgatatcaat | 180 |
| tgacattttt tattagtttc attaggttta gagataaaat tatatcatgt atgtcactca | 240 |
| tctagtatct tatttgttat cataaatgtt ctaatccttt ttacgtcacc cgaatacaat | 300 |
| tttttactct ttcatgtcat cgttgatgac atagtaaggg actaagacat acaacatttt | 360 |
| acatttaaca tttggccacg acatgtaaga gtgagatatt gaattcgagt aacatacgag | 420 |
| gtacgatgaa taaggtatta cacaaaatta cagtggcata tagtgaattg aattgttcta | 480 |
| tttttacttt tttttttgcct aacataaagc ctattttatt tagtactttc tctgattcag | 540 |
| ctttaatttt tatgatttat taatttttatt atatatctat atattgtata gattaaaaaa | 600 |
| taaaatagat tatagattta ggaaaaatta cattcgggtg atttggctgt tgggtgttgc | 660 |
| gttccctact tgctctttttc ttcctccgct tcaacctgtc cccagcgccc ccgcgcaca | 720 |
| cactgtcttt ctctgccttt ctttccctag cgccgcgccg gcgacgccat tcgatcaggc | 780 |
| cgcttcgccg gcgacagcat attccaggta tgccgtccct tctgctcctt ctgcgagaat | 840 |
| tcaaacaccc cgaactcccc aaatctagta tttgtattcg gatctgacca tttttcactg | 900 |
| ggcccgcccc tgattcgcag gtcggttggt tttggcactt cggaccggcg gccatggctt | 960 |
| ccgacggcat cggccccaga ggtattactg tttcatctct tcttgtgttc aaacagacag | 1020 |
| acgtcaagcc gccgagagga ggtacaaata tagattttgg gtaatgagca cgccattgcg | 1080 |
| cttccagcga tctgacatat tgggaattct tgcttttttt tgggtacctt gcaaggccga | 1140 |
| aatttgacgc ttttctgttt aattctagtg cctgtctgca tccattaggg catcctagct | 1200 |
| gctccatgct cgtgatctcg tccgtttgct tgattgaatc cattgttttc caaagttcat | 1260 |
| tgctactgcg aaatacgttt atatgattac cacaagttgt gttttttcct tttcgggttg | 1320 |
| cacagagggt actgccatca ttgttgttat agcgccattt ggaacaagtg attcactggt | 1380 |
| actagtacag tatgtgcttt tcatgtgtgt ttggtttgta ccatcagatg gaattttgag | 1440 |
| cgcggtttac aaaattagtac tatagatata ctgtgaggtg cacactagat ggttctgctt | 1500 |
| tgttctacag tcagtaactt tttcttcctt gctcacagat gtatgtgttg ttggggttgc | 1560 |
| acgcaccccca atgggcggtt tccttggtgc cttgtctccc ttgcctgcta cgaaacttgg | 1620 |

```
ctctatagta attcaaggtg agatccgaat cttctctgca tttacatccg agctctgaac    1680
atggtcatgg ctgggggctg ttagctgctc tggaaagagc aaacgtggat ccagccctcg    1740
tgcaggaggt ctactttgga aacgtcttga gtgctaattt ggggcaagcg cctgcaaggc    1800
aagctgctct gggtgccggg ataccaaact ctgttgtttg caccactgtt aacaaagtct    1860
gtgcatctgg catgaaaggt ttgaatcgaa tttatctgtc tgtccttgtg tactctgctc    1920
agagttcaca gaagtgagag attacctgac catgctcttg tttccctttc ctatatgcag    1980
ctactatgtt tgcagcacag tcaattcaat gggtatcaa tgatattgtt gtggctggtg      2040
gcatggaaag catgtccaat gccccaaagt acattgctga agctaggtat gcaattatta    2100
cttggtggat atattcaata tcgagctgca taaaccaaat gatagtctta agttatttgg    2160
tagatacatg catgcttact tatcttcatt gcattttcta aatttgtttg taagaaatgt    2220
tgattcacca gcagcgaggc tattaacgaa gtggccagtt tgttgtgaa agtatattct      2280
gttcatgttt aaagtgcatt tcaactgctt taatccaata agcttgctac ttacaattgc    2340
aggaagggt ctcgttttgg tcatgacaca cttgttgatg ccatgcttaa ggatgggctt      2400
tgggatgtat acaatgattg tgccatggga atgtgtgccg agctttgtgc tgacaatcat    2460
gccctcacaa gagaagacca ggtctcttaa tacagatagc agtaaatgct gtttgttata    2520
atattcccat atttttcaag atataagttg tgctatacaa catgtcaatg ctggcaatta    2580
ttttgagagt gccctggaat cttcgtgctt tatcttggtt atcatcataa atggtctaga    2640
gactctagac cagcatctgc attccttgtc cgatgaacta gtaacttgga tcctttctgg    2700
caatgatttt ctgttaggtt gtgacatgat tgatagggtg ggcttatgca tgctctgggt    2760
ctgtgaactg accattcatt tgcttccaga gatgaaagta gatgtgccac acaaaaatga    2820
gcactctttt gcattcttgt tagagctata caagtataat ctcttaaaag ctgctcatca    2880
gtacatgaca ctagtacctt gatgatttta ctgtatctgt ttatgtaatt tttttcttaa    2940
taaatttgat atagtataat taaaattgag ttgcctttga attttcactt atatgttgca    3000
atgtattttt gtctatattg caataaatat attcccaatt tctggtatat ttacttattc    3060
ttgaatagga tgcatttgct atccaaagca atgagcgtgg aattgctgct cgtgacagtg    3120
gtgcttttgc atgggagatt attccggtaa ttttctccct cattgatgat actagacatg    3180
cttttcttgg ttttctgatg gtcaatgttg tcgcccaggt tcaagttcct gttggtagag    3240
gaaacccccc aacattaatt gagagagatg aaagcctgga taaggttttt tttctgattt    3300
gacaaaatat ttttaacaaa ataaagcttg tagttgatca aaggcaaaaa gactggcagg    3360
cactttgatt tattgttctt gcttcctcca aatgcaacgt tcctcgcata atgagctttg    3420
ctagcagtta tttgtaagat caatgcatga cagtttatt tatgtcttgt gctattcctt      3480
ttgtgtctta gtttgaccca gtaaaactaa agaaacttcg cccaagtttc aaggagaatg    3540
atggtacagt tacagctgga aatgcttcta gtataaggta gctgcttgaa atatttctga    3600
gacctttttg tcctacaaag tctttctgag accttgtttt tcggccatat gttgtttagc    3660
tgacagatat gaaggacaac ctatttcatt gttgacagtt aaattatatt attgtattat    3720
gcatgcattt ttaactgata tattatgctt gcattttgtc aacttcattg tttctctatt    3780
tgttttttaga ctgcttgggt atgctctact ctgtgaaata gatggtaatt ttttctttag    3840
aattggtacc caatcgatgt gaatgattta tcacataaga aagtaaaaac attttaaatg    3900
ccttattatg cccattcaaa caacaaaagt tgccctagac cttgtctgtc tcactttgta    3960
```

```
ctgtgtctat ttttagctga ccagtactgt ccggtgtact gcctactatg gcttgtctag    4020
ccttctgcaa ccagtcatat ctaatttgtt ttatatggat cagtgatgga gctgctgcat    4080
tagttttggt gagtgggcag aaggctcaag agcttggcct tcaagtcctt gcaaggatca    4140
aaggttatgc tgatgcagct caagtaagcc acagtaacaa ttgttagctc tcctaagagt    4200
agaatgcgct tattctaatt cacattgtga tctaaatatt ttaggatata ggaagttatt    4260
tttatctgga acgattttat gttactattt tagatatcga aatttatcaa ctattggaac    4320
ttgtgatctg gaatattatt ttgtaatgtg gatgctgttt atacaggctc cggagctttt    4380
tacaaccact ccagcacttg caataccaaa ggctatcgca aatgctggat tagagtcatc    4440
ccatgttgat ttctatgaga ttaatgaagc ttttcggta tgcattgggt ttctttattt    4500
gtaagccttt tgttatgcat tgagagctta ttttacttat tactttttt ttgtaataat    4560 gtcttttta cttatcaata taggctgttg cacttgcaaa tcaaaagctt cttggaattc    4620
cttcagtaag tgtcacctgt attaaactgc cattctttgt gcattttaga agttaaaaca    4680
tcactttcag aaagtacata ttggcccttt tttgttattt gctatgcagc agcaacatgt    4740
aattgcatta taacagcatt atatgtacta acaacatatg tgtttgcagg aaaagattaa    4800
tgttcatgga ggagctgtat cttaggaca tcctctcggg tgcagtggtg ctcgcatttt    4860 ggttacccctt attggtgtaa gttctatctt aagatgcttg ttttatcttt tgagttacaa    4920
tcccttttgt ttaaaaaaat gtgcaatgtt tttctagtaa aaaaatagat gatggtcttt    4980
gagtaattga tgaattctga catatgttac cgtatcatca tagggttcgt gatgaacagt    5040
aagcatcttc actattgcta ctaagtctac ttccttagtg ttttccaatg tgcaatgttt    5100
ttcttgtata aagctgcaaa tgtagagttt cacttgttgc tggtgatcag tagtttctct    5160 tcatttctt taagcaaaac cttgagaaca atatggtgcc atcatgttgg gacatcaaat    5220
atatggtgct tgaccctcct aatcattgtt tcttgttaac aggttctcag ggcgaagagt    5280
ggcaagatcg gagttgctgg tgtctgcaac ggtggaggcg gagcatcagc tcttgttctg    5340
gagctcgcat aagaaatcta gaccttgtaa ggctcaaaac accgaatata tctcaactca    5400
aattgattct tttactagct ggcaggagct aaccagtata aggtgctatt actgttgtgc    5460
aatttgacta actgctgcaa ctgatattgc aggtatttag caaaagttcc ctgaggtgat    5520
cttgtagtct tattttccgt tgtagtagtc ccatagaaca tttcttaatt taatttggca    5580
ataaagcgaa gtcgtgcttc tgttggttgc atagtagagt atcatgtaat aagagcaatg    5640
gggatgtttc atagatattt ttgaggatgc tacagaaata ttttatatac tagtgagtgc    5700
tcgtgcgttg caacgggaat atataattct atgataactt atatacaaaa tgtgtgctac    5760
attgttataa gaaatgtttt cataatctat acacaaagat gagatttctg caaagaatac    5820
catgccacat cactaaaata tgaatggctc acttatccct tataacagca gccttgtctt    5880
t                                                                    5881
```

<210> SEQ ID NO 46
<211> LENGTH: 1628
<212> TYPE: DNA
<213> ORGANISM: Zea mays

<400> SEQUENCE: 46

```
gtgttgcgtt ccctacttgc tctttctt ctccgcttca acctgtcccc agcgccccc       60 gcgcacacac tgtctttctc tgcctttctt tccctagcgc cgcgccggcg acgccattcg     120
atcaggccgc ttcgccggcg acagcatatt ccaggtcggt tggttttggc acttcggacc    180
```

-continued

| | |
|---|---|
| ggcggccatg gcttccgacg gcatcggccc cagagatgta tgtgttgttg gggttgcacg | 240 |
| caccccaatg ggcggtttcc ttggtgcctt gtctcccttg cctgctacga aacttggctc | 300 |
| tatagtaatt caagctgctc tggaaagagc aaacgtggat ccagccctcg tgcaggaggt | 360 |
| ctactttgga aacgtcttga gtgctaattt ggggcaagcg cctgcaaggc aagctgctct | 420 |
| gggtgccggg ataccaaact ctgttgtttg caccactgtt aacaaagtct gtgcatctgg | 480 |
| catgaaagct actatgtttg cagcacagtc aattcaattg ggtatcaatg atattgttgt | 540 |
| ggctggtggc atggaaagca tgtccaatgc cccaaagtac attgctgaag ctaggaaggg | 600 |
| gtctcgtttt ggtcatgaca cacttgttga tgccatgctt aaggatgggc tttgggatgt | 660 |
| atacaatgat tgtgccatgg gaatgtgtgc cgagctttgt gctgacaatc atgccctcac | 720 |
| aagagaagac caggatgcat tgctatccaa agcaatgagc gtggaattg ctgctcgtga | 780 |
| cagtggtgct tttgcatggg agattattcc ggttcaagtt cctgttggta gaggaaaacc | 840 |
| cccaacatta attgagagag atgaaagcct ggataagttt gacccagtaa aactaaagaa | 900 |
| acttcgccca gtttcaagg agaatgatgg tacagttaca gctggaaatg cttctagtat | 960 |
| aagtgatgga gctgctgcat tagttttggt gagtgggcag aaggctcaag agcttggcct | 1020 |
| tcaagtcctt gcaaggatca aaggttatgc tgatgcagct caagctccgg agcttttac | 1080 |
| aaccactcca gcacttgcaa taccaaaggc tatcgcaaat gctggattag agtcatccca | 1140 |
| tgttgatttc tatgagatta tgaagccctt tcggctgtt gcacttgcaa atcaaaagct | 1200 |
| tcttggaatt ccttcagaaa agattaatgt tcatggagga gctgtatctt taggacatcc | 1260 |
| tctcggtgc agtggtgctc gcattttggt taccttatt ggtgttctca gggcgaagag | 1320 |
| tggcaagatc ggagttgctg gtgtctgcaa cggtggaggc ggagcatcag ctcttgttct | 1380 |
| ggagctcgca taagaaatct agaccttgta tttagcaaaa gttccctgag gtgatcttgt | 1440 |
| agtcttattt tccgttgtag tagtcccata gaacatttct taatttaatt tggcaataaa | 1500 |
| gcgaagtcgt gcttctgttg gttgcatagt agagtatcat gtaataagag caatggggat | 1560 |
| gtttcataga tatttttgag gatgctacag aaatatttta tatactagtg agtgctcgtg | 1620 |
| cgttgcaa | 1628 |

<210> SEQ ID NO 47
<211> LENGTH: 1714
<212> TYPE: DNA
<213> ORGANISM: Zea mays

<400> SEQUENCE: 47

| | |
|---|---|
| aagagcccct cgggcagcag gatcttcccc ctccccaaaa ccaaaccagc tgcctccgac | 60 |
| agcatccacc ttttcctccc ccaaaccatg gacttctcca ccggcgggag cgtgagcggg | 120 |
| ggcggcggag gcgccagcga cggccccgcg caggcggagc gctggctgga gatcgccgag | 180 |
| aagctcctcg cggcgcgcga cctcgtcggc tgcaagcgct tcgcggagcg gtcggtggag | 240 |
| gcgaacccgc tcctcgccgg cgttgacgaa ctcctcgccg tcgccgacgt cctcctcgct | 300 |
| tcccagttca tgggcacctc gggccagccg gaccgctcg ccatcctcca gctgccgccc | 360 |
| ggagtcagcc ccgaccaggc cgccgtgtcc cgcgccttcc gccgctcgc gctcctcctc | 420 |
| ggtcccagca acccgcaccc gggagccgag atggcgctcc gcctcgtcaa cgacgcctac | 480 |
| gccttcctct cggatccctc tcgccgcccc ccgccgccg ccgatcccgc cactggtacc | 540 |
| ccttactcct cccagtatcc cgccgcggcc gctcccgcct ccgacacccc ggagttctgg | 600 |

| | |
|---|---|
| acggcgtgcc ccttctgctg ctacgtgcac cagtacccgc gcagcctgat cgggcgcgcc | 660 |
| ctcaagtgcc ccaacgcggg ctgccgccgc ggattcgtgg cttctgagct cccgacccca | 720 |
| cccacggttg tgccgggcac tgaaatgtac cactgcgcct gggggttctt cccctcgga | 780 |
| tttcccaacg cggccgacct gggtgccaac tggaagccat tctacaagat gttcccttgg | 840 |
| aacacggctc ccagtggcca aggtggtggt ggtaggagtc acggaaacca tggtggtagg | 900 |
| cagccacaga atgacagtgc tcgtggtggc tcttctagag gtaggatcaa gaagacgacg | 960 |
| gcccgcaaga aggtcggggt agggctcagg agacgttctc ttggtgtgga gagtggcatt | 1020 |
| gattcttcga tgctcgggca ggaaggctgg gctggggatg agaacgctgg agatggaagg | 1080 |
| gccgaggagg tgaggagaat taacataaat gaggcagcac atgctacaga tggcactggt | 1140 |
| agggttaatg ttagcggtgc tggcggagtt gaagatatcg gcaactttca tatcgatgtt | 1200 |
| gatgcatccg aggatatatt ggggaatttg cacaacatgc acttcttgag ggtggacaat | 1260 |
| cttggacgga tgatttaact gttgttatgg tttactgggg ctatgattag ccaggccgac | 1320 |
| tcttgctgtt caagtgttca tttgagtgta attgttccat ccctgttatg taatgttgta | 1380 |
| gttgtagact tgtagtctac ctggtacctg tagttactta acatcaggca gggaaaaatt | 1440 |
| tgtatgttca ttagatggag atacatgcca tttgccttag caaacacact ttgtggaggt | 1500 |
| ttccagtgat gggataatgc ttcgcagagg tgtggttgga ctggcaatgc ttaccatgcc | 1560 |
| acttctggtt tyttcctggc atggtgacac aaaatgttgt tgagatcaag taagtgaatt | 1620 |
| atgttctgct ttctgagttc ggtaaacttc tttggctaca aaaggactaa gcttagttat | 1680 |
| gctaacttgt tgatttggtt gtgatcattg catc | 1714 |

<210> SEQ ID NO 48
<211> LENGTH: 9828
<212> TYPE: DNA
<213> ORGANISM: Zea mays

<400> SEQUENCE: 48

| | |
|---|---|
| tggcctcagc atgtttgcaa aatgaatcag taaggaaaaa gaacacggct gcatcatcta | 60 |
| tatgataccT ccaagtgaac ataaaggaca acatcatcga ccaatttaat ataaatccaa | 120 |
| agcaaaccac atgaaaatca aactcgcagc aggtataaca tgaacaacac actgtaccaa | 180 |
| accctaactc atgaagcatg aaccagaaaa tagaacgatt gggggttgat ttcaccttgg | 240 |
| ggtcaaggtc gtagcaacgg agacggagca gacctagaag tataggaagc aaatcgacca | 300 |
| gagacgaagc gacgaagcag atgcccaacg ccacggagtc ctggcaccag gcggagctgg | 360 |
| acgcagccgc gacgcacagc cactcgccgc cggtctctca cgagggaggg aggggtgga | 420 |
| agaagaacga gcagcgagag gaggggaaaa ggagggtgca ccgtcgccat atatagccgc | 480 |
| aagaggattc accggagcgc tccttcccgc gcgcgcgaaa acctcaccat tcccgcgcga | 540 |
| gcccgcgcga gctcccgcca gccacctcgc ccgccgccac attccgccag tgcgccgcgc | 600 |
| gcagccgagc tcccaggaaa cgaaccctag ccgcgtttcc tgggagccac ccaggaaaca | 660 |
| ggctgttttc agccaggctg cgaaacgggc caaccttgca aacaaggtta gttgtagccc | 720 |
| acgggcacaa tcgggctact gggccatcct ccgaaacacg cccttggtga tctctggtgg | 780 |
| cgaagcgata cgatacgatg gccggccgta gtacgtcccg tgggtggccg ctgacgtgac | 840 |
| gagaaacagt cggtcggcgg ccagccagta acgtgacact cgccatctgc ttccatcttt | 900 |
| tgtggttttt tcttctctag acttgactgc atgcagccaa gaaccagaaa ccggacgacc | 960 |
| gaccgacgac ggcgacgggt cgtcgtgcac cgccacacgg gggtcatacg atacgacacg | 1020 |

```
acacgttccg ccgcgagatc gaggtcgatg agtccgaggc tctcggctcc caagtcccaa    1080
caagctgcac cggctcgacg aggacgacgt actgtacgaa cagaacaaca gccagaggcc    1140
ggccggccgg acgaccgacg gtcgccgtcg tgcaccgtgc acggtgcacc acgtctcatg    1200
ccgtctggcg tgtgggtgac gaatcactga aactgaaagg gtaggcagca cagcacatcc    1260
acacacatgt tctttgccta tcacacgctc tttgtaaaat tttagtacac tggtgacaat    1320
aggcggaccg agtccaacat caacaaaaaa atatatatat actggacgtt cgttagccgg    1380
gaccattttt cccccaaaag gaaccaacta cagcaggctg aaataaacgt tcctccctct    1440
atgccaaaat aaaattcgta ttagtaaatt agtggttcat ataacatttg atgtatgtgt    1500
tttgtatata tatacatgcc tatatttatt aacatttatt tgaatataga tataaaaaca    1560
cagagctaaa acgattacta ataaagttaa cttgacgctg cagtgttgtt ttttttata     1620 aactctgttc aagttagaga aatctgattt gtagcagctc ttgacttcaa cagagggatc    1680
agaataacta taaagctcca gtaaatagat tacagaatac agcttccctg tttctttcaa    1740
caatacggca gtttagaatt ttttatgtaa caaagctaga gagtttgtgt tttatgtaac    1800
taagccaaag tgtgggtaag tgatatacga taaagtagca tgacacacgg aagttccact    1860
catggaatgg ctttgttcgt ttacaccaat cccgctctag attagcatgg attggaatta    1920
aatccatgcc tcaatccatg ccccaaaata atccatgact acttaatttt ttttattcgg    1980
ttaaacccat catggaatat aacccaaagg tttgggaatt ttttaaacta tggaagacat    2040
ggattctatc catagcccat taggtatgga acaaatccat gagatattgc acaagtttac    2100
attagaattc atggatcaaa agaataacta gctttgaaag tcacatggat ttgttgatgg    2160
atttaatccc accatgggat taggtgtgag atatggattc acccaatcca tacccagatt    2220
aaatccatgg tgggattata tcccatataa ccgaacaaga ccttatgtgg aaatataact    2280
aaataggagg acaacaagct tacttctatt caagcacagc tctagcaagg gactatgaca    2340
atacagataa accaagatat agtaaggtag gacacaatag cattccaggg tgcaccacga    2400
gcgctatgct ttaacaaata gacctaacat catggagtac atagattagg gataaaaaca    2460
ggtacccgaa ctcttaaaac aaatctaata ttttaaaata gatatgtata aaatttaatc    2520
ataatctttc cttctgttat aagcacacta ttatatataa gaataaattt tacatagatt    2580
gttttataca ttatttactc tttacaacaa aaagatgaaa aaatgtttgt atccgtatcc    2640
gaatgctacc caaattttat atctatcatt ttaaaaaata tgataaattt gatgtttatt    2700
ttttataaat cttacaagt tcaatgctaa aaacaagaat attaatttgt ctagcagatt     2760
ctatatcata tttattcact atcaaagaaa aaaataccaa aaaactggta tgcgaatagg    2820
tacccgtttt catccctaca taggatggac atggttgtca ccaccttcca actatcatta    2880
actatttaga ggcctaacca cattccggta cccggtagag taaacaccac tgaaaggccc    2940
tagtttgatt ttggtaaccg agtgacaacc taggtggact aatatatttt ctatgttgag    3000
atacacaggt gattagtcca caagtagact agtttgagat acttaaatca tgatggtgaa    3060
atgcttggat ttattgtaaa cctcaactag gtgtatgtga gacatcacat ggtgtcttgt    3120
ggataggtgc aggcagtggc ggagccagga tttctgtaag tgtagggcca atataacact    3180
aacaaatatt tatatcagct agaaaatctt aaatcatgca aatgtataga taatgacaca    3240
tatgaccatg aacggattat acaaattctc tcattccttc agaacatatt tgggtcccta    3300
gcaatttttc ggctcaagag tagggcccaa gccctaatgg ccctatgcct gtctccgcca    3360
```

```
ctgggtgtag gatatcaaga gacatggttt gggtatgaag gactgattgt aaaagtgatt    3420
gacaagttag atactttgag gcgatggacc acatgtggca gagaagcttg agcaaggact    3480
tggcaccgat cgaccaagga aacaataaag accaaatgaa gttgcgataa ataaagtaat    3540
gaggccacaa tggtaacatg aagtggacca tatcattcaa agaagatcaa gccaattgtt    3600
tattcatgtt gatggtcaag tggcttgatg aagtatgatg gaggaacttc atgatatggt    3660
taatgatcaa aggtagcatg gttggctaca tctatggatg atcattgccc atcatgtgat    3720
gaggttggat gcttgtataa catcatcaac attaagatga aatggaatgt gcaagacaaa    3780
ggtattgtcc aagattgttc tgtagtgatt atgcaggtat gtcacgagat cgagagcata    3840
gtgattatgt aggtatttca cgagatcgat agcatatata gtgattatac gggatatgtc    3900
atgggatcga gagctaaagg ttagggcatg agagacatga ggatttatac atgtttggac    3960
tctcaatgtc agacaatact ttttgtcttg tgtgtgttgt tatatgttcg gaacgatcac    4020
agagttttcc cgtccctctt tttatattct aaggagggat agatgttaca cggtaagcat    4080
agagccgatt atcaagttca tgatggaatc aagtcaattg ccaagttgta cacaagtcca    4140
atttacggct tatctcatat tcagttgaga tctttaaaat ctatcctagt ttaatcattg    4200
attctttgga cttatggccg gacgcatagg tccttctgct tagcctcttc tttataaagc    4260
ttgatttagg tactcatgca tattattgac aatagcttca gactttgttt gacgataaaa    4320
aagactctct atatatgaga gcatccatac aaggttttga ccactttagg acgaaacttg    4380
aagatggaga gatatgagaa aatacaatgt cgtttccatc tctactcaca gccgtgagtc    4440
catacacgag ttgttttttat gttcaatttc cacggtcatg tccctgtatt taatgataa    4500
aaaaactaaa attatattta aatataagat atgacatatg gatgttggct ataaacctat    4560
attcacacac ctaactcatg gttctatagt cgtcgtgcat caccottetc attcccgttt    4620
atgcaaaaat aaagagaaaa tatgcatgat tggggatttg aactttagtt gtaggatcta    4680
agttcatacc ctcctatcca acagagcaca tatattttta tgtttcatta aaacaaagt    4740
atactcatgt cttatataaa aaccgtttca acgaatgaac atctcattag tgatatttaa    4800
aaactatagc aatgcataag caactaacta ctcaaaaaaa tgcaacctga atacttcctt    4860
tgcttctcca cacatgaaat gaaagaaact gaaataagaa acgggcaaac ggcgctgcaa    4920
aagcgggaaa tccctttttcc ttgctgatag tgatacccgg tcaaaaccca ccgagacggc    4980
gagacgcggg gagcgggtac atacacactg acacacctca cgcgagccga gacgcccagc    5040
tcaccgcccc accgagtccc acagtctcag aggccacctc gagcccccccc tgccccgcaa    5100
gccgcacccg ccgctccctc cgccatctgc gctgcgctgc tctgctctgc ggtgccaggc    5160
tgccagccag tgccggcgcg cgcccgctgc cgccccgacg ggcccaccgt tctcttctct    5220
ccgcgctgcg cgccggctgg gctgcaggtc agttaatgcg cccgtgacag gcggcgtcgg    5280
ggaggccaag ggcggtgccg ggttaatccc gccgtctctc gaggcggcgc ccgcggagga    5340
ccaggcggga gggggagacg gtgaggcgcg gccatggggg gcgccaaggc ggaggacaaa    5400
cccgccgccg ccgctgcaga agattggtgc taccaatttg gaaacaaggt tcgatttctt    5460
caccatttgc actcctctgc aagactggga cacgttccg ggtttcgttc tgcctgggcg    5520
gcgacaaatc tcatggcaaa ttgcctttgt ggggctcatt ccctgggttc acactccaaa    5580
tccttccttg cgaccttctc tcagccgtcg cgctttccgt ggcaagcctt ttggaaccct    5640
gatctgaagt gtcactcaga tcaatgcagt cgcattgatt ctattcgttt cctgtttccg    5700
tttcccccctt ttaacgtgtc tgctagttcc aagtcccgag cgttttccgt tctctgtttc    5760
```

```
agaattgaag cttgttaagt tctgtttttt ttacaatcct tcgttttgt cccagtcctt    5820
tctattcctg gagaagttag gaatctgttg ttctcctgtt ccatttctcc tttctattcc    5880
tggagaagtt aggaatctgt tgttctcctg ttccatttct cggtgcagta ttagttgcag    5940
aacaggaatc cacttgattt gtcagtttaa ttatgcttgt gtcacctcag atgtgtcata    6000
ttgattatga ctgcatttt gtcagctgta atatgcgtgt tggcttgcat ttgtttctct    6060
ctttattagt actaccagca tttcggtca gtatttttg tcttccttgc tgaagaatga    6120
gaaggaaagc tgtcatactc ctcgtcggga tagcttcatt tattaaggca gctgggcgac    6180
agaatatatg ggaatgtact tgaacttcac aaaaaagggc ctttcatcc cttgccgtgt    6240
cttccatgtt ggtaaaaagg ctagtagctg aattgaatag tacgtgctca ttttaactac    6300
cctgaggact agatagatct tgaagtttta tttgtttatt tctttttatt tctgcttata    6360
tagatgtagg atgtagccaa atggatgctt ctcagctcac attgaacatt aatgtttgtg    6420
ttgtttgctg aaaggttttt tactgtagca gaaggttaca aaataacaga tcttacctca    6480
aaaaagggct gcaatgtata tatactggca ctgaaccgcg tatgcgcagt gcaacctgct    6540
gattggtttt gtactggtcg gatctgtttg caggatgcat ttgacttgaa gcccccgaaa    6600
aaatcaccga tcgcgttgag aacggttgtc ttcgctatga ctatgttatg cgggatatct    6660
atttgctcaa tgtgcatgaa gcaactaggg agtgatggct ggtcaagagt tgtcaagatt    6720
gaagttgtgg aacaaccatg taataagtcc attgctcctc tttcggaggc tcaatttgtg    6780
cgctatcctc aaccgataac ttacagcagg tgagatctgc actgtggtaa gattgagcaa    6840
tctcgtttgt ttaatgccta atgcataatt tttatttct agggaggaat gcaagtgcaa    6900
tgctgtccgg tcctttgcaa ttatatcatc gcagcgatct ggaagtggct ggtttgaaac    6960
acttcttaac agccacatga atgttagctc caatggtgaa attttctcta gaaaagaaag    7020
gaggagtaac atttcctcta taatagatac cctggataaa gtgtacaatt tggactggaa    7080
cagtagcgct tccaagaatg agtgcactgc agctattggc ttcaagtgga tgctaaatca    7140
ggtgcggact aaaacatgca gtatagataa tttatttgga tgatcctttt tcatttattt    7200
ttccatttag ttccagtatg tttcaattat tagtatgtgt agtctcctaa acggcctaca    7260
tgttctcaac tgtagatgct aaatgttatt gcatattgcg ccaaactttc ctcaagtcca    7320
tgtaactatt ttttttggg aatccacttt agggcttgct cgttttagtg ccaatccatg    7380
tggattggac gagattggat gagtttaaat ccataagaag tcaaaatcct tcttaaaatt    7440
ttccaatctc ttccaatcca tgtgggatgc gaataaccga acaaggcctt atggaactgt    7500
cggtagctag tttagttttc tgacttgctg tcagatcctg cattagac aaattttctc    7560
tctctcgaac atgcatgaga actgcaaatg catatgagt aatatttgat agattctgta    7620
gtgtgtccag tagactgatt ataatctaca tgtcaagcat gtttgtttca gggcttcatc    7680
taatttgtgc gagaacgaac tttttcctg gtagacagat tgcctaacca aaccatgaat    7740
attggccaaa cataggttta gagactggaa acaaaacagg cattgtagct agagagtgga    7800
aacaaaggag catttcttct gaacggggtt ggggtgtatg ttttcagggc ctcgtggcaa    7860
accatgcgga cgtagtcgac tacttcaacc gaagaggagt ctctgcgata tttcttttca    7920
gaaggaacct gctccgccag ttggtatcac aggtagcgaa caaccacgac aggttactta    7980
agcaactaaa cggaacgcac aaggcccatg tccacacgaa gcgtgaggtt agtaatgcta    8040
gctaagaaac ggatatggca gcaagtctct gagctgatct gatctctctc tgtgtttgac    8100
```

```
gtgtcgttcg ttctcgctcc acaggcccat atactggcaa gatacaggcc caggctcaac      8160
acgacgtcac tgatatggca gctgaaacga gctgacgagt acactcgcga cgctcttgag      8220
aacctaaaca acacccggca catgagcgtc tactacgagg acgtcgtccg caacagaaca      8280
gtgcgttctc gctgatgccc ttcccttgtc tgttcccttc cgttggttgt gtcgcttacc      8340
atcgctgctg cactgcagaa gctcttggat gtcctggatt tcctcggagt gccgaggagg      8400
aagctggtga gccggcacgt gaagatacac acgaagccgc tgtcggagca gatcgagaac      8460
tgggacgagg tctacagcgc cctcaacggt acccagtacg agggcttcct gaatgccgct      8520
gactatctag tataacatca cgtttctgga tgtagatagt gtgcgtgtga ttctttcgtt      8580
tcttgtttgt ttctggcaga aattttgatg cggggtaggc gccttttgcc gtgcatggtt      8640
gcattctcgg taacctgatg ctcctgtaac taaccctcca gcttctctga tctttgtatt      8700
tgccttgggt gtttgctgat gttctttcaa actatttgaa atcgggctgt cggagttcca      8760
gatcccgggc ggcaggatag ttgatgtgac ctagataaat gtacaagaca catcacaaat      8820
atataaaata tttctgtagt atcctcacaa atatatcaaa aatatttctg tagctcttat      8880
tacatgatac tctactatgc aaccaacaga agcaatatct cctcagggag cttttgcttt      8940
attgccaaat taaattaaga aatgttctat gggactacta caacgaaaaa taagactaca      9000
agatcacctc agggagcttt tgctaactac ctgcaatatc aaggtgcagc agttagtcaa      9060
attgcacaac agttgtaaaa ggaaaaaata caacttaatt aggcctagct gaatatgcga      9120
ccatattaca gtttgataat agcaccttat actggttagc tcctactgcc agctagtaaa      9180
agaatcaatt tgagttgaga tatattcggt gttttgagtc ttacaaggtc tagatttctt      9240
atgcgagctc cagaacaaga gctgatgctc cgcctccacc gttgcagaca ccagcaactc      9300
cgatcttgcc actcttcgcc ctgagaacct gttaacaaga acaatgatt aggagggtca      9360 agcacaatat attttgatgt cccaacatga tggcactata ttgtgcccaa cgttttgctt      9420
aaagaaaatg aagagaaaaa gaaactattg atcaccagca acaagtgaaa caagggatga      9480
gccgatatca atgtgaaact ctacatttgc agctttatac aagattctat ttgcagataa      9540
tttgcacatt ggaaatcact aagggcttgt tcggttgcga gaggattgga ggggattgag      9600
ggggattaaa tcccctccta ttcaatttta actagaaggg gatttaatcc ccttcaatcc      9660
ccctcgaacc acttgtaacc gaacatggcc taaggtagtg tttggtgcag ggatggggtg      9720
gcttgatcca acatactccc tatgtttcaa attataagat gttttttactt tttctagatt      9780 tgtagttttt attgcgataa acattatgtc tcagtacacg tagtaaaa            9828
```

<210> SEQ ID NO 49
<211> LENGTH: 11900
<212> TYPE: DNA
<213> ORGANISM: Zea mays

<400> SEQUENCE: 49

```
gatataatga aaaaaccaat taaaaacgtg tctcgatatg cgtgcacgag taaagagctg       60
gctgagcgga gcctggccgc gcgcgtgcgg tcgcgcgatg cgtttctgcc gggcctggct      120
cgcggcgctt taagttccgt gctagcctgt ctcgtgcgat acaacgaacc aaacaaacac      180 tacttttgc atgtgtagat gcagctgcac cactggagaa ggcaaccaaa cgcccctaa       240 ggcagctggg cgacagaata tatgggaatg tacttgaact tatcaaaaaa gggccttttc      300
atcccttgcc gtgtcttcca tgttggtaaa aaggctagta gctgaattga atagtacgtg      360 ctcatttta acttccctgag gactagatag accttgaagt tttatttgtt tatttctttt      420
```

```
tatttctgct tatatagatg tagccaaatg gatgcttctc agctcacatt gaacattaat    480
gtttgtgttg tttgctgaaa ggttttttta ctgtagcaga aggttacaaa ataacagatc    540
ttacctcaaa aaagggctgc aatgtatata tactggcact gaaccgcgta tgcgcagtgc    600
aacctgctga ttggttttgt actggtcgga tctgtttgca gratgcattt gacttgaagc    660
ccccgaaaaa atcaccgatc gcgttgagaa cggttgtctt tgctatgact atgttatgcg    720
ggatatctat ttgctcaatg tgcatgaagc aactagggag tgatggctgg tcaagagttg    780
tcaagattga agttgtggaa caaccatgta ataagtccat tgctcctctt tcggaggctc    840
aatttgtgcg ctatcctcaa ccgataactt acagcaggtg agatctgcaa ctgtggtaag    900
attgagcaat ctcgtttgtt taatgcctaa tacataattt ttaatttcta gggaggaatg    960
caagtgcaat gctgtccggt cctttgcaat tatatcatcg cagcgatctg gaagtggctg   1020
gtttgaaach cttcttaaca gccacatgaa tgttagctcc aatggtgaaa ttttctctag   1080
aaaagaaagg aggagtaaca tttcctctat aatagatacc ctggataaag tgtacaattt   1140
ggactggaac agtagcgctt ccaagaatga gtgcactgca gctattggct tcaagtggat   1200
gctaaatcag gtgcggacta aaacatgcag tatagattta tttggatgac ccttttttcat  1260 ttatttttcc atttagttcc agtattgcat attgctccaa actttcctca agtccatgga   1320 actattttttt tttgggaatc cactttaggg cttgctcgtc ttagtgccaa tccatgtgga   1380
ttggacgaga ttgaacgggt ttaaatccgt aagaagtcaa aatccttctt aaaattttcc   1440
aatcccttcc aatctatgtg ggatgcgaat aaccttatgg gactgtcgga tagctagttt   1500
agttttgtga cttgctgtca gatcctgcat tttagacaat ttttttctct cgaacgtgca   1560
tgagaactgc aaatgcatat ggagtaatat ttgatagatt ctgtagtgtg tccagtagac   1620
tgattataat ctacatgtca agcatgtttg tttcagggct tcatctaatt tgtgtgagaa   1680
caaacttttt tcctggtaga cagattgcct aaccaaacca tgaatgttgg ccaaacatag   1740
agttagagac tggaaacaaa acaggcactg tagctagaga gtggaaacaa aggagcattt   1800
cttctgaacg gggttggggt tggggtgtat gttttcaggg cctcgtggca aaccatgcgg   1860
acgtagtcga ctacttcaac cgaagaggag tctctgcgat atttcttttc agaaggaacc   1920
tgctccgcca gttggtatca caggtagcga acaaccacga caggttactt aagcaactaa   1980
acggaacgca caaggcccat gtccacacga agcgtgaggt tagtaatgct agctaagaaa   2040
cgtgttcgcg gctaatgtct cactctcaca gcaagtctct gagctgagct gatctctgtc   2100
tgtgtttgac gtgtcgttcg ttctcgctcc acaggcccat atactggcaa gatacaggcc   2160
caggctcaac acgacgtcac tgatatggca gctgaaacga gctgacgagt acactcgcga   2220
cgctcttgag aacctaaaca acacccggca catgagcgtc tactacgagg acgtcgtccg   2280
caacagaaca gtgcgttctc gctgatgccc tttgtctgtt cccttccgtt ggttgtgtcg   2340
cttaccatcg ctgctgcact gcagaagctc tggatgtcc tggatttcct cggagtgccg    2400
aggaggaagc tggtgagccg gcacgtgaag atacacacga agccgctgtc ggagcagatc   2460
gagaactggg acgaggtcta cagcgccctc aacggtaccc agtacgaggg cttcctgaat   2520
gccgctgact atctagtata acatcacgtt tctggatgta gatagtgtgc gtgtgattct   2580
ttcgtttctt gtttgtttct ggcagaaatt ttgatgcggg gtaggcgcct tttgccgtgc   2640
atggttgcat tctcggtaac ctgatgctcc tgtaactaac cctccagctt ctctgatctt   2700
tgtatttgcc ttgggtgttt gctgatgttc tttcaaacta tttgaaatcg ggctgtcgga   2760
```

```
gttccagatc ccgggcggca ggatagttga tgtgacctag ataaatgtac aagacacatc    2820
acaaatatat aaaatatttc tgtagtatcc tcamaaatat atcaaaaata tttctgtagc    2880
tcttattaca tgatactcta ctatgcaacc aacagaagca atatctcctc agggagcttt    2940
tgctttattg ccaaattaaa ttaagaaatg ttctatggga ctactacaac ggaaaataag    3000
actacaagat cacctcaggg agcttttgct aactacctgc aatatcaagg tgcagcagtt    3060
agtcaaattg cacaacagtt gtaaaaggaa aaaatacaac ttaattaggc ctagctgaat    3120
atgcgaccat attacagttt gataatagca ccttatactg gttagctcct actgccagct    3180
agtaaaagaa tcaatttgag ttgagatata ttcggtgttt tgagtcttac aaggtctaga    3240
tttcttatgc gagctccaga acaagagctg atgctccgcc tccaccgttg cagacaccag    3300
caactccgat cttgccactc ttcgccctga gaacctgtta acaagaaaca atgattagga    3360
gggtcaagca caatatattt tgatgtccca acatgatggc actatattgt gcccaacgtt    3420
ttgcttaaag aaaatgaaga gaaaagaaa ctattgatca ccagcaacaa gtgaaacaag    3480
ggatgagccg atatcaatgt gaaactctac atttgcagct ttatacaaga ttctatttgc    3540
agataatttg cacattggaa atcactaagg gcttgttcgg ttgcgagagg attggagggg    3600
attgaggggg attaaatccc ctcctattca attttaacta gaaggggatt taatccccctt    3660 caatccccct cgaaccactt gtaaccgaac atggcctaag gtagtgtttg gtgcagggat    3720
ggggtggctt gatccaacat actccctatg tttcaaatta agatgtttt ttactttttc    3780 tagatttgta gttttattg cgataaacat tatgtctcag tacacgtagt aaaagctata    3840
aatctaacaa tgccaacatc ccaagacgtc ttataatttg ggatagagga agtagaccta    3900
gtagcaatag tgaagatgct tactgttcat cacgaaccct atgatgatat ggtaacatat    3960
gtcagaattc attatttact caaagaccat ctatttttt actagaaaaa cattgcacat    4020 ttttttaaa caaagggat tgtaactcaa aaggtaaaac aagcatctta agatagaact    4080
tacaccaata agggtaacca aaatgcgagc accactgcac ccgagaggat gtcctaagga    4140
tacagctcct ccatgaacat taatctttc ctgcaaacac atatgctgtt agtacagata    4200
atactgttat aatgcaatta cacgttgctg ctgcatagca aataacaaaa aagagacaat    4260
atgtactttc tgaaagtgat tgtttaactt ctaaaatcca caagaatgg cagtttaata    4320 caggtgacac ttactgaagg aattccaaga agtttttgat ttgcaagcgc aacagcctat    4380
attgacaagt aaaaaagaca ttattacaaa aaaagtaata agtaaaataa actctcaatg    4440
cataacaaaa ggcttacaaa aaatgtgagt aaaagaaact caatgcatac cgaaaaggct    4500
tcattaatct catagaaatc aacacgggat gactctaatc cagcatttgc gatagccttt    4560
ggtattgcaa gtgctggagt ggttgtaaaa agctccggag cctgtataaa cagcatccac    4620
attacaaaat aatattccag atcacaagtt ccaatagttg ataaatttcg atatctaaaa    4680
tagtaacata aaatcgttcc agataaaaat aacttcctat atcctaaaat atttagatca    4740
cagtgtaaat tagaataagc gcattctact cttaggagag ctaacaattg tttctgtggc    4800
ttacttgagc tgcatcagca taaccttga tccttgcaag gacttgaagg ccaagctctt    4860
gagccttctg cccactcact aaaactaatg cagcagctcc atcactgatc catataaaac    4920
aaattagatg actggttgca gaaggctaca caagccatag taggcagtac accggacagt    4980
acttgtcagc taaaaataga cacagtacaa agtgagacaa acaaggtcta gggcaaccat    5040
gaagaaattt aaaaggtagg gcaacttttg ttgtttgaat gggcataata aggcatttaa    5100
aatgttttta ctttcttatg tgatattgtg ataaatcatt cacaccaatt gggtaccaaa    5160
```

```
tctaaagaaa aaattaccat ctatttaacg gagtagagca tacccaagca gtctaaaaac   5220
aaatagagaa acaatgaagt tgacaaaatg caagcataat atatcagtta aaaatgcatg   5280
cataatacaa taatataatt taactgtcaa caatgaaata ggttgtcctt catatctgtc   5340
agctaaacaa catatggccg aaaaacaagg tctcagaaag actttgtagg acaaaaggcc   5400
tcagaaatat ttcaagcagc taccttatac tagaagcatt tccagctgta actgtaccac   5460
cattctcctt gaaacttggg cgaagtttct ttagttttac tgggtcaaac taagacacaa   5520
aaggaatagc acaagacata aataaaactg tcatgcattg atcttacaaa taactgctag   5580
caaagctcat tatgcaagga acgttgcatt tggaggaagc aagaacaata aatcaaagtg   5640
cctgccagtc tttttgcctt tgatcaacta caagctttat tttgttaaaa atattttgtc   5700
acgtcagaaa aaatacctta tccaggcttt catctctctc aattaatgtt ggggttttc    5760 ctctaccaac aggaacttga acctgggtga caacactgac catcagaaaa ccaagaaaag   5820
catgtctagt atcatcaatg agggagaaaa ttaccggaat aatctcccat gcaaaagcac   5880
cactgtcacg agcagcaatt ccacgctcgt tgctttggat agcaaatgca tcctattcaa   5940
gaataagtaa aattaaatat accagaaatt ggaaatatat ttattgcaat atagacaaaa   6000
ataaattgca acatataagt gaaaattaaa aggcaactca attttaatta tactatatca   6060
aatttattaa gaaaaaaatt acataaacag atacagtaaa atcatcaagg tactagtgtc   6120
atgtactgat gagcagcttt taagagatta tacttgtata gctctaacag gaatacaaaa   6180
gagtgctcat ttttgtgtgg cacatctact ttcatctctg gaagcagatg aatggtcagt   6240
tcacagaccc agagcatgca taaaagccca ccctatcaat catgtcacaa cataacagaa   6300
aatcattgct agaaaggatc caagttacta gttcatcaga caaggaatgc agatgctggt   6360
ctagagtctc tagaccattt atgatgatga ccaagataaa gcacgaagat tccagggcag   6420
tctcaaaaga attgccagca ttgacatgtt gtatagcaca acttatatct tgaaaaatat   6480
gggaatatta taacaaacag catttactgc tatctgtatt aagagacctg gtcttctctt   6540
gtgagggcat ggttgtcagc acaaagctcg gcacacattc ccatggcaca atcattgtat   6600
acatcccaaa gcccatcctt aagcatggca tcaacaagtg tgtcatgacc aaaacgagac   6660
cccttcctgc aattgtaatt agcaagctta taagcagttg aaatgcactt taaacatgaa   6720
cagaatatac tttcacaaca aaactggcca cttcgttaat agcctcgctg ctggtgaatc   6780
aacatttctt acaaacaaat ttagaaaatg caatgaagat aagtaagcat gcatgtatct   6840
accaaataac ttaagactat catttggttt atgcagctcg atattgaata tccaccaa    6900 gtaataattg catacctagc ttcagcaatg tactttgggg cattggacat gctttccatg   6960
ccaccagcca caacaatatc attgataccc aattgaattg actgtgctgc aaacatagta   7020
gctgcatata ggaaaggaaa acaagagcat ggtcaggtaa tctctcactt ctgtgaactc   7080
tgagcagagt acacaaggac agacagataa attcgattca aacctttcat gccagatgca   7140
cagactttgt taacagtggt gcaaacaaca gagtttggta tcccggcacc cagagcagct   7200
tgccttgcag gagcttgccc caaattagca ctcaagacgt ttccaaagta gacctcctgc   7260
acgagggctg gatccacgtt tgctctttcc agagcagcta acagccccca gccatgacca   7320
tgttcagagc tcggatgtaa atgcagagaa gattcggatc tcaccttgaa ttactataga   7380
gccaagtttc gtagcaggca agggagacaa ggcaccaagg aaaccgccca ttggggtgcg   7440 tgcaaccccca acaacacata catctgtgag caaggaagaa aaagttactg actgtagaac   7500
```

-continued

```
aaagcagaac catctagtgt gcacctcaca gtatatctat agtactaatt tgtaaaccgc    7560
gctcaaaatt ccatctgatg gtacaaacca acacacatg aaaagcacat actgtactag     7620
taccagtgaa tcacttgttc caaatggcgc taaaacaaca atgatggcag taccctctgt    7680
gcaacccgaa aaggcaaaaa cacaaattgt ggtaatcata taaacgtatt tcgcagtagc    7740
aatgaacttt ggaaaacaat ggattcaatc aagcaaacgg acgagatcac gagcatggag    7800
cagctaggat gccctaatgg atgcagacag gcactagaat aaacagaaa agcgtcaaat     7860
ttcggccttg caaggtaccc aaaaaaaaaa caagaattcc caatatgtca gatcgctgga    7920
agcgcaatgg cgtgctcata gcccaaaatc tatatttgta cctcctctcg gcggtttgac    7980
gtctgtctgt ttgaacacaa agaagagatg aaacagttat acctctgggg ccgatgccgt    8040
cggaagccat ggccgccggt ccgaagtgcc aaaaccaacc gacctgcgaa tcagggggcgg   8100
gcccagtgaa aaatggtcag atccgaatac aaatactaga tttggggagt tcggggtgtt   8160
tgaattctcg cagaaggagc agaagggacg gcatacctgg aatatgctgt cgccggcgaa   8220
gcggcctgat cgaatggcgg cgccggcgcg gcgctaggga agaaaggca gagaaagaca    8280
gtgtgtgcgc ggggggcgct ggggacaggt tgaagcggag gaagaaaga gcaagtaggg    8340
aacgcaacac ccaacagcca aatcacccga atgtaatttt tcctaaatct ataatttatt   8400
ttattttta atctatacaa tatatagata tataataaaa ttaataaaatc ataaaaatta   8460
aagctgaatc agagaaagta ctaaataaaa taggctttat gttaggcaaa aaaaaagtaa   8520
aaatagaaca attcaattca ctatatgcca ctgtaatttt gtgtaatacc ttattcatcg   8580
tacctcgtat gttactcgaa ttcaatatct cactcttaca tgtcgtggcc aaatgttaaa   8640
tgtaaaatgt tgtatgtctt agtcccttac tatgacatga aagagtaaaa aattgtattc   8700
gggtgacgta aaaaggatta gaacatttat gataacaaat aagatactag acgagtgaca   8760
tacatgatat aattttatct ctaaacctaa tgaaactaat aaaaaatgtc aattgatatc   8820
gtttgcgttt gctaatcacc tcgaacaatc atcctcgcgg gcatgtggtt aaggctagaa   8880
aaaaaacttg aggctcacga gtcagatcaa gttcggagcg tctgcgagcg agctagttgt   8940
accaaattaa tcaatatgta gaataatgat agatattaga taatttatag atagtcggct   9000
tatttcttag cctttgatga taaatataag ataattcata atggtgaata atatttttat   9060
attttatgtt tatatattaa taatttacta tataatgaaa taatatatat cggggtgtag   9120
ctcgcgagcc gacttcgagc tgagccgagc ctaactctct agctcgtgaa atggacgagc   9180
cgagtcaagc tcggctcgac tcattttcta cttgtggtcg accaggtcta ggtagtcatg   9240
aaccgcaacc aatctgtcag ttttatcgat tgttttagat catgttaggc gagtgccggc   9300
gcttggctct actgcccgcc cacccatgtg gcacaaccaa atggtcagta tcacccgaca   9360
tggtgccagc actaatagcc tcgcttgtgg ttgtcgaggc tactgatcgg ccgccagggt   9420
tactattgac cgtgttggga ccgcgtcggt cgatactgac tggttggtac tgaacagcta   9480
ttgcggccat gtcgataacg atcgcctctt gccatgtggc aggttctaat tgcttcgctt   9540
tatttttgatt ttttttcaaa aataaaaaaa ctagaacttg gtctataaat agaggagtgt  9600
ttgatctcat tcacacaacc cacacttcaa atttctctac caccccttat aatcctctta   9660
cactcgtttc aatcaaatca agcattgttg tgatgttttc gttcagcttg acatcaata    9720
tgactgaaaa gagttattca agttattaca acaaaatata atgcaacagg cgtcagagct   9780
tggatccgag tctcctaggt cgatgaggtg gccaaggcaa catcagagat acattgactg   9840
cgactatgta gttgcatacg accggttaat gcaagaccat ttcaacgacc tgtgtgtcta   9900
```

```
cccactgctc tactttttgtc aaagttaccg catctagaga agtctcttcc ttcatatctt    9960
agagagattg ggtgagcact tcccatactt cacttttga accgatgcat tcaaccgcag    10020
tgtttcctcc cccaccagaa gtgcacaatt ggcctaagca tgcttgcgta ctgtagcatt    10080
gctgactcca tcgatgagta catcaaaatg aggaaagttc cacctcagag tgccttggac    10140
tattctgtgt gaaagggtcc ctagttaagt tggttaggtc gtctgagtag cactcctcag    10200
gtcctaagtt tgaatcccgg tgggagcgaa ttttaggctg aggttaacaa ggtcactcac    10260
tagtttccct agttgtgtgc acatgagatg ggctgaccta tggggcggat cctcgtgtaa    10320
gggctagtag ggctcaaagc acgagtaaag atctggccta taggggcgg actctcatgt    10380
tgcatggggg gagggtaca tctttcgtga cctttctcga tcagggctcc gattaagctt    10440
cttcttaccg tgggggcagt atttccccta cgagtggagt ttttggtcta ttctgtagag    10500
gtggtattgc atgtttcagg gcggagtaca attatcatgc cattgtcaat gacttaggct    10560
tatcttagct aaggaggtgg aaaggggatt ttctattatg atattgagta tagattgcat    10620
gcattggaag tggaggaaga agacatttta caagggggat attggttctc catccatcat    10680
gctcgagaca gttgcctcgt atgacttgtg gatctgacat attttatga atctattaaa    10740
atgctaaaac ggttagtatt ttaggacgga gggaattatt ttttggaata tttttgtagc    10800
aacctaaaca tagttcatct atgcttagtt tgggggggtgg gatggttagg cctagaagct    10860
actgttgaat taatgagggc ctaacccaaa ttaatattca ataatagtca atgctaaagg    10920
cccactttaa tgctacggtg tactagtact ttagtaccat accggaagta caagggacaa    10980
ttcaatcaac ttaaataggc ggatctttgg tgcatctagt gagaagttga gaaaatgatg    11040
aaggactgcc acacgcgcgc gccgccgggc cgtggccgtg gtagatcgga ccttggtccg    11100
aatattcctt cctaacggtt gcacattttg cctaaagtga tgaccgtcca ttactgttgt    11160
acgttattgg tcgtttccta tgttatggat agtaacgaac gagttataat gcttgtcagc    11220
tattaacgga cgtcactaat ggcgtccgtt tctggctggc tgtaatgata gctctgatgg    11280
tgaccgttac tatccgttcg cctccctctg ctcgtttata tatacaaagg aggtgaggct    11340
gcttctggtt acgagagaac acacgtacaa ttcttagacg cgttgcgtac agcccatccc    11400
tggttgaacc tctctaaacc ccggttgaac ttttcctgga ccccagttga acctctctgg    11460
accccggttg aacttgcctt ggaccccggt tgaacctgcc tggaccccgg ttgaacttga    11520
ctggacccca gttgaagttg aagttcaact ggagttgaga agctcgaca cagctgaagt    11580
ttagctcagc tgaaaagctc aactgcagct gaagaagctc aactcagctg aagtttagtt    11640
cagctgaaaa gctcagctgc ttttcaacaa aaacactcta ggtttctcaa acctaaccat    11700
agtcaaccat agaattttaa agagattttt gattttcaaa aaatagcttt tgaatataga    11760
ggcttgagct ttggcaaaca ccaaccttat ttttggatcc ccttggtagt acgatgaatc    11820
ctatactcaa tttaagtaaa atataattaa gtaaactcct tgagtaattg gtgtctcatg    11880
tgtgatttct ccatggcgtt                                                11900
```

<210> SEQ ID NO 50
<211> LENGTH: 3571
<212> TYPE: DNA
<213> ORGANISM: Zea mays
<220> FEATURE:
<221> NAME/KEY: misc_feature
<222> LOCATION: (1933)..(1933)
<223> OTHER INFORMATION: n is a, c, g, or t

```
<400> SEQUENCE: 50
ggagggggag acggtgaggc gcggccatgg ggggcgccaa ggcggaggac aaaccggccg        60
ccgctgcaga agattggtgc taccaatttg gaaacaaggt tcgatttctt caccatttgc       120
actcctctgc aagactggga cacgtttccg ggtttcgttc tgcctgggcg gcgacaaatc       180
tcatggcaaa ttgcctttgg ggggctcatt ccctgggttc acactccaaa tccttccttg       240
cgaccttctc tcagccgtcg cgcttttccgt ggcaagcctt ttggaaccct gatctgaagt       300
gtcactcaga tcaatgcagt cgcattgatt ctattcgttt cctgtttccg tttccccctt       360
ttaacgtgtc tgctagttcc aagtcccgag cgttttccgt tctctgtttc agaattgaag       420
cttgttaagt tctgttttt tttacaatcc ttcgttttg tcccagtcct ttctattcct         480
ggagaagtta ggaatctgtt gttctcctgt tccattctc ggtgcagtat tagttgcaga        540
acaggaatcc acttgatttg tcagtttaat tatgcttgtg tcacctcaga tgtgtcatat       600
tgatgatgac tgcattttt tttcagctgt aatatgcgtg ttggcttgca tttgtttctc        660
tctttattag tactaccagc atttttcggtc agtattttt gtcttccttg ctgaagaatg       720
agaaggaaag ctgtcatact cctcgtcggg atagcttcat ttattatggc agctgggcga       780
cagaatatat gggaatgtac ttgaacttca caaaaaaggg ccttttcatc ccttgccgtg       840
tcttccatgt tggtaaaaag gctagtagct gaattgaata gtacgtgctc attttaacta      900
ccctgaggac tagatagatc ttgaagtttt atttgtttat ttcttttttac ttctgcttat     960 atagatgtag ccaaatatat gcttcttcag ctcacgttga acattaatgt ttgtgttgtt     1020
tgctgaaagg ttttttactg tagcagaagg ttacaaaata acagatctta cctcaaaaaa      1080
gggctgcaat gcatatatac tggcactgaa ccgcgtatgc gcagtgcaac ctgctgattg      1140
gttttgtact ggtcggatct gtttgcagga tgcatttgac ttgaagcccc cgaaaaaatc     1200
accgatcgcg ttgagaacgg ttgtctttgc tatgactatg ttatgcggga tatctatttg     1260
ctcaatgtgc atgaagcaac tagggagtga tggctggtca agagttgtca agattgaagt     1320
tgtggaacaa ccatgtaata agtccattgc tcctctttcg gaggctcaat ttgtgcgcta     1380
tcctcaaccg ataacttaca gcaggtgaga tttgcactgt ggtaagattg agcaatctcg     1440
tttgtttaat gcctaatata taattttttaa tttctaggga ggaatgcaag tgcaatgctg     1500
tccggtcctt tgcaattata tcatcgcagc gatctggaag tggctggttt gaaacacttc     1560
ttaacagcca catgaatgtt agctccaatg gtgaaatttt ctctagaaaa gaaaggagga     1620 gtaacattc ctctatagta gatacccctgg ataaagtgta caatttggac tggaatagta     1680
gtgcttccaa gaatgagtgc actgcagcta ttggcttcaa gtggatgctg aatcaggtgc     1740
ggactaaaac atgcagtata gataattat ttggatgatc cttttcatt tattgttcca      1800 tttagttcca gtatgtttca attattacta tctgtagtct cctaaacggc ctacatgttc     1860
tcaactgtag atgctagatg ttattgcata ttgcgccaaa cttcctcaa gaccatggaa     1920 cttttttttt ttntttttt ttttggaaac cacttaggg cttgttcgtt ttagtgccaa      1980
tccatatgga ttggatgggt ttaaatacat aagaagtcaa atccttctt aaaatttttc      2040 aatctcttcc aatccatgtg ggtgggatgc gattccaatc catgtgggat gcgaataacc     2100
gaacaaggcc ttataggact gtcgaatagc tagtttagtt ttctgacttg ctgtcagatc     2160
ctgcatttta gacaatttct ctctctcgaa catgcatgag aactgcaaat gcatatggag     2220
taatatttga tagattctgt agtgtgtcca gtagactgat tataatctac atgtcaagca     2280
tgtttgtttc agggcttcat ctaatttgtg cgagaacaaa ctttttttcct ggtagacaga     2340
```

```
ttgcctaacc aaaccatgaa tattggccaa acagagagtt agagactgga aacaaaacag    2400
gcactctagc tagggagtgg aaacaaagga gcatttcttc tgaacggggt tggggttggg    2460
gtgtatgttt tcagggcctc gtggcaaacc atgcggacgt agtcgactac ttcaaccgaa    2520
gaggagtctc tgcaatattt cttttcagaa ggaacctgct ccgtcagttg gtatcacaag    2580
tagcgaacaa tcacgacagg ttacttaagc aactaaacgg aacgcacaag gcccatgtcc    2640
acacgaagcg tgaggttagt aatgctagct aagaaacgtg ttcgcggcta atgtctcact    2700
ctcacagcaa gtctctgagc tgagctgatc tctgtctgtg tttgacgtgt cgttcgttct    2760
cgctccacag gcccatatac tggcaagata caggcccagg ctcaacacga cgtcactgat    2820
atggcagctg aaacgagctg acgagtacac tcgcgacgct cttgagaacc taaacaacac    2880
ccggcacatg agcgtctact acgaggacgt cgtccgcaac agaacagtgc gttctcgctg    2940
atgccctttg tctgttccct tccgttggtt gtatcgctta ccatcgctgc tgcactgcag    3000
aagctcttgg atgtcctgga tttcctcgga gtgccgagga ggaagctggt gagccggcac    3060
gtgaagatac acacgaagcc gctgtcggag cagatcgaga actgggacga ggtctacagc    3120
gccctcaacg gtacccagta cgagggcttc ctgaatgccg ctgactatct agtataacat    3180
cacgtttctg gatgtagata gtgtgcgtgt gattcttttcg tttcttgttt gtttctggca    3240
gaaattttga tgcggggtag gcgccttttg ccgtgcatgg ttgcattctc ggtaacctga    3300
tgctcctgta actaaccctc cagcttctct ggtctttgta tttgccttgg gtgtttgctg    3360
atgttctttc aaactatttg aaatcgggct gtcggagttc cagatcacgg gcggcaggat    3420
aggtgatgtg acctagataa atgtacgaga cacatgacaa atctatacta cttattaaaa    3480
gtgtaatagc agtctgccgt tctgccatcc tgcaacctca accgtccatt ccattgttct    3540
gcaatttcaa ccgttcgatc ccacccacca g                                   3571
```

<210> SEQ ID NO 51
<211> LENGTH: 1896
<212> TYPE: DNA
<213> ORGANISM: Zea mays

<400> SEQUENCE: 51

```
ccaaggcgga ggacaaaccg gccgccgctg cagaagattg gtgctaccaa tttggaaaca     60
aggttcgatt tcttcaccat ttgcactcct ctgcaagact gggacacgtt tccgggtttc    120
gttctgcctg ggcggcgaca aatctcatgg caaattgcct ttgggggggct cattccctgg    180 gttcacactc caaatccttc cttgcgacct tctctcagcc gtcgcgcttt ccgtggcaag    240
ccttttggaa ccctgatctg aagtgtcact cagatcaatg cagtcgcatt gattctattc    300
gtttcctgtt tccgtttccc ccttttaacg tgtctgctag ttccaagtcc cgagcgtttt    360
ccgttctctg tttcagaatt gaagcttgtt aagttctgtt tttttttaca atccttcgtt    420
tttgtcccag tcctttctat tcctggagaa gttaggaatc tgttgttctc ctgttccatt    480
tctcggtgca gtattagttg cagaacagga atccacttga tttgtcagtt taattatgct    540
tgtgtcacct cagatgtgtc atattgatga tgactgcatt ttttttttcag ctgtaatatg    600 cgtgttggct tgcatttgtt tctctctttta ttagtactac cagcatttc ggtcagtatt     660 ttttgtcttc cttgctgaag aatgagaagg aaagctgtca tactcctcgt cgggatagct    720
tcatttatta tggcagctgg gcgacagaat atatgggaat gtacttgaac ttcacaaaaa    780
agggcctttt catcccttgc cgtgtcttcc atgttggtaa aaaggctagt agctgaattg    840
```

```
aatagtacgt gctcatttta actaccctga ggactagata gatcttgaag ttttatttgt    900
ttatttcttt ttacttctgc ttatatagat gtagccaaat atatgcttct tcagctcacg    960
ttgaacatta atgtttgtgt tgtttgctga aaggttttt actgtagcag aaggttacaa   1020
aataacagat cttacctcaa aaagggctg caatgcatat atactggcac tgaaccgcgt   1080
atgcgcagtg caacctgctg attggttttg tactggtcgg atctgtttgc aggatgcatt   1140
tgacttgaag cccccgaaaa aatcaccgat cgcgttgaga acggttgtct ttgctatgac   1200
tatgttatgc gggatatcta tttgctcaat gtgcatgaag caactaggga gtgatggctg   1260
gtcaagagtt gtcaagattg aagttgtgga acaaccatgt aataagtcca ttgctcctct   1320
ttcggaggct caatttgtgc gctatcctca accgataact tacagcaggt gagatttgca   1380
ctgtggtaag attgagcaat ctcgtttgtt taatgcctaa tatataattt ttaatttcta   1440
gggaggaatg caagtgcaat gctgtccggt cctttgcaat tatatcatcg cagcgatctg   1500
gaagtggctg gtttgaaaca cttcttaaca gccacatgaa tgttagctcc aatggtgaaa   1560
ttttctctag aaaagaaagg aggagtaaca tttcctctat agtagatacc ctggataaag   1620
tgtacaattt ggactggaat agtagtgctt ccaagaatga gtgcactgca gctattggct   1680
tcaagtggat gctgaatcag gtgcggacta aaacatgcag tatagataat ttatttggat   1740
gatccttttt catttattgt tccatttagt tccagtatgt ttcaattatt actatctgta   1800
gtctcctaaa cggcctacat gttctcaact gtagatgcta gatgttattg catattgcgc   1860
caaactttcc tcaagaccat ggaactttt tttttt                             1896

<210> SEQ ID NO 52
<211> LENGTH: 1371
<212> TYPE: DNA
<213> ORGANISM: Zea mays

<400> SEQUENCE: 52
agttcatcac taatcacact tattgtgccc tcgacgagta tctatagcta gctcattaat     60
cgattcgggg gtgtgttgtc gaaggcggca atggcgagct actcgtcgcg cgtccatgc    120
aatacctgta gcacgaaggc gatggccggg agcgtggtcg gcgagcccgt cgtgctgggg    180
cagagggtga cggtgctgac ggtggacggc ggcggcgtcc ggggtctcat cccgggaacc    240
atcctcgcct tcctggaggc caggctgcag gagctggacg gaccggaggc gaggctggcg    300
gactacttcg actacatcgc cggaaccagc accggcggtc tcatcaccgc catgctcacc    360
gcgcccggca aggacaagcg gcctctctac gctgccaagg acatcaacca cttttacatg    420
cagaactgcc cgcgcatctt tcctcagaag agcaggcttg cggccgccat gtccgcgctg    480
aggaagccaa agtacaacgg caagtgcatg cgcagcctga ttaggagcat cctcggcgag    540
acgagggcca agagcacgcc tctgaagaac gctctgctct cggacgtgtg cattggcacg    600
tccgccgcgc cgacctacct cccggcgcac tacttccaga ctgaagacgc caacggcaag    660
gagcgcgaat acaacctcat cgacggcggt gtggcggcca caacccgac gatggttgcg    720
atgacgcaga tcaccaaaaa gatgcttgcc agcaaggaca aggccgagga gctgtaccca    780
gtgaagccgt cgaactgccg caggttcctg gtgctgtcca tcgggacggg gtcgacgtcc    840
gagcagggcc tctacacggc gcggcagtgc tcccggtggg gtatctgccg gtggctccgc    900
aacaacggca tggcccccat catcgacatc ttcatggcgg ccagctcgga cctggtggac    960
atccacgtcg ccgcgatgtt ccagtcgctc cacagcgacg cgactacct gcgcatccag   1020
gacaactcgc tccgtggcgc cgcggccacc gtggacgcgg cgacgccgga gaacatgcgg   1080
```

```
acgctcgtcg ggatcgggga gcggatgctg gcacagaggg tgtccagggt caacgtggag    1140
acagggaggt acgaaccggt gactggcgaa ggaagcaatg ccgatgccct cggtgggctc    1200
gctaggcagc tctccgagga gaggagaaca aggctcgcgc gccgcgtctc tgccatcaac    1260
ccaagaggct ctagatgtgc gtcgtacgat atctaagaca agtggcttta ctgtcagtca    1320
catgcttgta aataagtaga ctttatttta ataaaacata aaaatatata t             1371

<210> SEQ ID NO 53
<211> LENGTH: 1458
<212> TYPE: DNA
<213> ORGANISM: Zea mays

<400> SEQUENCE: 53
agttcatcac taatcacact tattgtgccc tcgacgagta tctagctagc tcattaatcg      60
atcaatcggg gtgtgcggtc gaaggcggca atggcgagct actcgtcgcg gcgtccatgc     120
aatacctgta gcacgaaggc gatggccggg agcgtggtcg gcgagcccgt cgtgctgggg     180
cagagggtga cggtgctgac ggtggacggc ggcggcgtcc ggggtctcat cccgggaacc     240
atcctcgcct tcctggaggc caggctgcag gagctggacg gaccggaggc gaggctggcg     300
gactacttcg actacatcgc cggaaccagc accggcggtc tcatcaccgc catgctcacc     360
gcgcccggca aggacaagcg gcctctctac gctgccaagg acatcaacta cttttacatg     420
gagaactgcc gcgcatcttt ccctcagaag agcaggcttg cggccgccat gtccgcgctg     480
aggaagccaa agtacaacgg caagtgcatg cgcagcctga ttaggagcat cctcggcgag     540
acgagggtaa gcgagacgct gaccaacgtc atcatccctg ccttcgacat caggctgctg     600
cagcctatca tcttctctac ctacgacgcc aagagcacgc tctgaagaa cgcgctgctc     660 tcggacgtgt gcattggcac gtccgccgcg ccgacctacc tcccggcgca ctacttccag     720
actgaagacg ccaacggcaa ggagcgcgaa tacaacctca tcgacggcgg tgtggcggcc     780
aacaacccga cgatggttgc gatgacgcag atcaccaaaa agatgcttgc cagcaaggac     840
aaggccgagg agctgtaccc agtgaacccg tcgaactgcc gcaggttcct ggtgctgtcc     900
atcgggacgg ggtcgacgtc cgagcagggc ctctacacgg cgcggcagtg ctcccggtgg     960
ggcatctgcc ggtggctccg caacaacggc atggccccca tcatcgacat cttcatggcg    1020
gccagctcgg acctggtgga catccacgtc gccgcgatgt tccagtcgct ccacagcgac    1080
ggcgactacc tacgcatcca ggacaactcg ctccgtggcg ccgcggcaac cgtggacgcg    1140
gcgacgccgg agaacatgcg gacgctcgtc gggatcgggg agcggatgct ggcacagcgg    1200
gtgtccaggg tcaacgtgga gacagggagc gaggtacgaa ccggtgaccg gagaaggaag    1260
caatgccgat gccctcggtg ggctcgctag gcagctctcc gaggagagga gaacaaggct    1320
cgcgcgccgc gtctctgcca tcaaccccag aagctctaga tgtgcgccct acgatatcta    1380
agacaagtgg cttactgtc aatcacatgc ttgtaaataa gtagacttta ttttaataaa    1440
atataaatat atatatat                                                    1458

<210> SEQ ID NO 54
<211> LENGTH: 401
<212> TYPE: PRT
<213> ORGANISM: Zea mays

<400> SEQUENCE: 54

Met Ala Ser Tyr Ser Ser Arg Arg Pro Cys Asn Thr Cys Ser Thr Lys
1               5                   10                  15
```

```
Ala Met Ala Gly Ser Val Val Gly Glu Pro Val Val Leu Gly Gln Arg
         20                  25                  30

Val Thr Val Leu Thr Val Asp Gly Gly Val Arg Gly Leu Ile Pro
         35                  40                  45

Gly Thr Ile Leu Ala Phe Leu Glu Ala Arg Leu Gln Glu Leu Asp Gly
 50                  55                  60

Pro Glu Ala Arg Leu Ala Asp Tyr Phe Asp Tyr Ile Ala Gly Thr Ser
 65                  70                  75                  80

Thr Gly Gly Leu Ile Thr Ala Met Leu Thr Ala Pro Gly Lys Asp Lys
                 85                  90                  95

Arg Pro Leu Tyr Ala Ala Lys Asp Ile Asn His Phe Tyr Met Gln Asn
             100                 105                 110

Cys Pro Arg Ile Phe Pro Gln Lys Ser Arg Leu Ala Ala Ala Met Ser
             115                 120                 125

Ala Leu Arg Lys Pro Lys Tyr Asn Gly Lys Cys Met Arg Ser Leu Ile
130                 135                 140

Arg Ser Ile Leu Gly Glu Thr Arg Ala Lys Ser Thr Pro Leu Lys Asn
145                 150                 155                 160

Ala Leu Leu Ser Asp Val Cys Ile Gly Thr Ser Ala Ala Pro Thr Tyr
                 165                 170                 175

Leu Pro Ala His Tyr Phe Gln Thr Glu Asp Ala Asn Gly Lys Glu Arg
             180                 185                 190

Glu Tyr Asn Leu Ile Asp Gly Gly Val Ala Ala Asn Asn Pro Thr Met
             195                 200                 205

Val Ala Met Thr Gln Ile Thr Lys Lys Met Leu Ala Ser Lys Asp Lys
210                 215                 220

Ala Glu Glu Leu Tyr Pro Val Lys Pro Ser Asn Cys Arg Arg Phe Leu
225                 230                 235                 240

Val Leu Ser Ile Gly Thr Gly Ser Thr Ser Glu Gln Gly Leu Tyr Thr
                 245                 250                 255

Ala Arg Gln Cys Ser Arg Trp Gly Ile Cys Arg Trp Leu Arg Asn Asn
             260                 265                 270

Gly Met Ala Pro Ile Ile Asp Ile Phe Met Ala Ala Ser Ser Asp Leu
             275                 280                 285

Val Asp Ile His Val Ala Ala Met Phe Gln Ser Leu His Ser Asp Gly
290                 295                 300

Asp Tyr Leu Arg Ile Gln Asp Asn Ser Leu Arg Gly Ala Ala Ala Thr
305                 310                 315                 320

Val Asp Ala Ala Thr Pro Glu Asn Met Arg Thr Leu Val Gly Ile Gly
                 325                 330                 335

Glu Arg Met Leu Ala Gln Arg Val Ser Arg Val Asn Val Glu Thr Gly
             340                 345                 350

Arg Tyr Glu Pro Val Thr Gly Glu Gly Ser Asn Ala Asp Ala Leu Gly
             355                 360                 365

Gly Leu Ala Arg Gln Leu Ser Glu Glu Arg Thr Arg Leu Ala Arg
370                 375                 380

Arg Val Ser Ala Ile Asn Pro Arg Gly Ser Arg Cys Ala Ser Tyr Asp
385                 390                 395                 400

Ile

<210> SEQ ID NO 55
<211> LENGTH: 428
<212> TYPE: PRT
```

-continued

<213> ORGANISM: Zea mays

<400> SEQUENCE: 55

Met Ala Ser Tyr Ser Ser Arg Arg Pro Cys Asn Thr Cys Ser Thr Lys
1               5                   10                  15

Ala Met Ala Gly Ser Val Val Gly Glu Pro Val Val Leu Gly Gln Arg
            20                  25                  30

Val Thr Val Leu Thr Val Asp Gly Gly Val Arg Gly Leu Ile Pro
        35                  40                  45

Gly Thr Ile Leu Ala Phe Leu Glu Ala Arg Leu Gln Glu Leu Asp Gly
    50                  55                  60

Pro Glu Ala Arg Leu Ala Asp Tyr Phe Asp Tyr Ile Ala Gly Thr Ser
65                  70                  75                  80

Thr Gly Gly Leu Ile Thr Ala Met Leu Thr Ala Pro Gly Lys Asp Lys
                85                  90                  95

Arg Pro Leu Tyr Ala Ala Lys Asp Ile Asn His Phe Tyr Met Gln Asn
                100                 105                 110

Cys Pro Arg Ile Phe Pro Gln Lys Ser Arg Leu Ala Ala Ala Met Ser
            115                 120                 125

Ala Leu Arg Lys Pro Lys Tyr Asn Gly Lys Cys Met Arg Ser Leu Ile
    130                 135                 140

Arg Ser Ile Leu Gly Glu Thr Arg Val Ser Glu Thr Leu Thr Asn Val
145                 150                 155                 160

Ile Ile Pro Ala Phe Asp Ile Arg Leu Leu Gln Pro Ile Ile Phe Ser
                165                 170                 175

Thr Tyr Asp Ala Lys Ser Thr Pro Leu Lys Asn Ala Leu Leu Ser Asp
            180                 185                 190

Val Cys Ile Gly Thr Ser Ala Ala Pro Thr Tyr Leu Pro Ala His Tyr
    195                 200                 205

Phe Gln Thr Glu Asp Ala Asn Gly Lys Glu Arg Glu Tyr Asn Leu Ile
    210                 215                 220

Asp Gly Gly Val Ala Ala Asn Asn Pro Thr Met Val Ala Met Thr Gln
225                 230                 235                 240

Ile Thr Lys Lys Met Leu Ala Ser Lys Asp Lys Ala Glu Glu Leu Tyr
                245                 250                 255

Pro Val Asn Pro Ser Asn Cys Arg Arg Phe Leu Val Leu Ser Ile Gly
            260                 265                 270

Thr Gly Ser Thr Ser Glu Gln Gly Leu Tyr Thr Ala Arg Gln Cys Ser
    275                 280                 285

Arg Trp Gly Ile Cys Arg Trp Leu Arg Asn Asn Gly Met Ala Pro Ile
    290                 295                 300

Ile Asp Ile Phe Met Ala Ala Ser Ser Asp Leu Val Asp Ile His Val
305                 310                 315                 320

Ala Ala Met Phe Gln Ser Leu His Ser Asp Gly Asp Tyr Leu Arg Ile
                325                 330                 335

Gln Asp Asn Ser Leu Arg Gly Ala Ala Ala Thr Val Asp Ala Ala Thr
            340                 345                 350

Pro Glu Asn Met Arg Thr Leu Val Gly Ile Gly Glu Arg Met Leu Ala
    355                 360                 365

Gln Arg Val Ser Arg Val Asn Val Glu Thr Gly Arg Tyr Glu Pro Val
    370                 375                 380

Thr Gly Glu Gly Ser Asn Ala Asp Ala Leu Gly Gly Leu Ala Arg Gln
385                 390                 395                 400

-continued

Leu Ser Glu Glu Arg Arg Thr Arg Leu Ala Arg Val Ser Ala Ile
            405                 410                 415

Asn Pro Arg Gly Ser Arg Cys Ala Ser Tyr Asp Ile
            420                 425

<210> SEQ ID NO 56
<211> LENGTH: 372
<212> TYPE: PRT
<213> ORGANISM: Zea mays

<400> SEQUENCE: 56

Met Ala Ser Tyr Ser Ser Arg Arg Pro Cys Asn Thr Cys Ser Thr Lys
1               5                   10                  15

Ala Met Ala Gly Ser Val Val Gly Glu Pro Val Val Leu Gly Gln Arg
            20                  25                  30

Val Thr Val Leu Thr Val Asp Gly Gly Val Arg Gly Leu Ile Pro
            35                  40                  45

Gly Thr Ile Leu Ala Phe Leu Glu Ala Arg Leu Gln Glu Leu Asp Gly
    50                  55                  60

Pro Glu Ala Arg Leu Ala Asp Tyr Phe Asp Tyr Ile Ala Gly Thr Ser
65                  70                  75                  80

Thr Gly Gly Leu Ile Thr Ala Met Leu Thr Ala Pro Gly Lys Asp Lys
                85                  90                  95

Arg Pro Leu Tyr Ala Ala Lys Asp Ile Asn Tyr Phe Tyr Met Gln Asn
            100                 105                 110

Cys Pro Arg Ile Phe Pro Gln Lys Ser Arg Leu Ala Ala Ala Met Ser
        115                 120                 125

Ala Leu Arg Lys Pro Lys Tyr Asn Gly Lys Cys Met Arg Ser Leu Ile
    130                 135                 140

Arg Ser Ile Leu Gly Glu Thr Arg Ala Lys Ser Thr Pro Leu Lys Asn
145                 150                 155                 160

Ala Leu Leu Ser Asp Val Cys Ile Gly Thr Ser Ala Ala Pro Thr Tyr
                165                 170                 175

Leu Pro Ala His Tyr Phe Gln Thr Glu Asp Ala Asn Gly Lys Glu Arg
            180                 185                 190

Glu Tyr Asn Leu Ile Asp Gly Gly Val Ala Ala Asn Pro Thr Met
        195                 200                 205

Val Ala Met Thr Gln Ile Thr Lys Lys Met Leu Ala Ser Lys Asp Lys
    210                 215                 220

Ala Glu Glu Leu Tyr Pro Val Asn Pro Ser Asn Cys Arg Arg Phe Leu
225                 230                 235                 240

Val Leu Ser Ile Gly Thr Gly Ser Thr Ser Glu Gln Gly Leu Tyr Thr
                245                 250                 255

Ala Arg Gln Cys Ser Arg Trp Gly Ile Cys Arg Trp Leu Arg Asn Asn
            260                 265                 270

Gly Met Ala Pro Ile Ile Asp Ile Phe Met Ala Ala Ser Ser Asp Leu
        275                 280                 285

Val Asp Ile His Val Ala Ala Met Phe Gln Ser Leu His Ser Asp Gly
    290                 295                 300

Asp Tyr Leu Arg Ile Gln Asp Asn Ser Leu Arg Gly Ala Ala Ala Thr
305                 310                 315                 320

Val Asp Ala Ala Thr Pro Glu Asn Met Arg Thr Leu Val Gly Ile Gly
                325                 330                 335

Glu Arg Met Leu Ala Gln Arg Val Ser Arg Val Asn Val Glu Thr Gly
            340                 345                 350

```
Ser Glu Val Arg Thr Gly Asp Arg Arg Lys Gln Cys Arg Cys Pro
        355                 360                 365

Arg Trp Ala Arg
    370

<210> SEQ ID NO 57
<211> LENGTH: 399
<212> TYPE: PRT
<213> ORGANISM: Zea mays

<400> SEQUENCE: 57

Met Ala Ser Tyr Ser Arg Arg Pro Cys Asn Thr Cys Ser Thr Lys
1               5                   10                  15

Ala Met Ala Gly Ser Val Val Gly Glu Pro Val Val Leu Gly Gln Arg
            20                  25                  30

Val Thr Val Leu Thr Val Asp Gly Gly Val Arg Gly Leu Ile Pro
            35                  40                  45

Gly Thr Ile Leu Ala Phe Leu Glu Ala Arg Leu Gln Glu Leu Asp Gly
    50                  55                  60

Pro Glu Ala Arg Leu Ala Asp Tyr Phe Asp Tyr Ile Ala Gly Thr Ser
65                  70                  75                  80

Thr Gly Gly Leu Ile Thr Ala Met Leu Thr Ala Pro Gly Lys Asp Lys
                85                  90                  95

Arg Pro Leu Tyr Ala Ala Lys Asp Ile Asn Tyr Phe Tyr Met Gln Asn
            100                 105                 110

Cys Pro Arg Ile Phe Pro Gln Lys Ser Arg Leu Ala Ala Ala Met Ser
            115                 120                 125

Ala Leu Arg Lys Pro Lys Tyr Asn Gly Lys Cys Met Arg Ser Leu Ile
        130                 135                 140

Arg Ser Ile Leu Gly Glu Thr Arg Val Ser Glu Thr Leu Thr Asn Val
145                 150                 155                 160

Ile Ile Pro Ala Phe Asp Ile Arg Leu Leu Gln Pro Ile Ile Phe Ser
                165                 170                 175

Thr Tyr Asp Ala Lys Ser Thr Pro Leu Lys Asn Ala Leu Leu Ser Asp
            180                 185                 190

Val Cys Ile Gly Thr Ser Ala Ala Pro Thr Tyr Leu Pro Ala His Tyr
        195                 200                 205

Phe Gln Thr Glu Asp Ala Asn Gly Lys Glu Arg Glu Tyr Asn Leu Ile
    210                 215                 220

Asp Gly Gly Val Ala Ala Asn Asn Pro Thr Met Val Ala Met Thr Gln
225                 230                 235                 240

Ile Thr Lys Lys Met Leu Ala Ser Lys Asp Lys Ala Glu Glu Leu Tyr
                245                 250                 255

Pro Val Asn Pro Ser Asn Cys Arg Arg Phe Leu Val Leu Ser Ile Gly
            260                 265                 270

Thr Gly Ser Thr Ser Glu Gln Gly Leu Tyr Thr Ala Arg Gln Cys Ser
        275                 280                 285

Arg Trp Gly Ile Cys Arg Trp Leu Arg Asn Asn Gly Met Ala Pro Ile
    290                 295                 300

Ile Asp Ile Phe Met Ala Ser Ser Asp Leu Val Asp Ile His Val
305                 310                 315                 320

Ala Ala Met Phe Gln Ser Leu His Ser Asp Gly Asp Tyr Leu Arg Ile
                325                 330                 335

Gln Asp Asn Ser Leu Arg Gly Ala Ala Ala Thr Val Asp Ala Ala Thr
```

```
              340                 345                 350
Pro Glu Asn Met Arg Thr Leu Val Gly Ile Gly Glu Arg Met Leu Ala
        355                 360                 365

Gln Arg Val Ser Arg Val Asn Val Glu Thr Gly Ser Glu Val Arg Thr
    370                 375                 380

Gly Asp Arg Arg Lys Gln Cys Arg Cys Pro Arg Trp Ala Arg
385                 390                 395

<210> SEQ ID NO 58
<211> LENGTH: 2088
<212> TYPE: DNA
<213> ORGANISM: Zea mays

<400> SEQUENCE: 58
tatttgtact cattccatgt ctcataaact ttgggcacca tccatccaac acatccaatc      60
taaacacacc aaacgatggg gaatggaaag agcagtattc gattcaacaa tggcaaacaa     120
atatcactga attagaccaa gaataaacct aattagacaa cgacctccca accatcattc     180
gtcaggctgt aaagaagata aagctgcctt ggggcatgga tcaagcagaa caccagagat     240
gaatccaaac acacagaaaa tcacgcgcgc tgtctacaat gacaacaagc cccacatttc     300
attgcagtac actgggctac aaaggcacgt acaacaaaga gctagggaaa cattgcggag     360
ggcacgagag agcagctaac ttgacaatat agcagactga gcttgcactg ttagcaggcg     420
aggaagggaa tcatggggac ggagaatggg gtccatgccc gcgaaggaga aggcggacgc     480
cgccacggtg gcaccggcgc acgcgcacac agggaacccg cacaggcagc caaggatgct     540
gcctcgccat tgcgccggtc gtctctgcca cgctcctctc tctctcccgc tgcatcgccg     600
tggatggggc aagcagagag cagggactgc gacgatctgg gcggaggact cgccttggag     660
agcgcggacg cagacgggat tctagggaga gagcgaagac ggggcgcgcg cggcgctcgc     720
gcggcgtggt ggcggcgaga ttagcggggg tgggggagg gcggagccgt ggtgagggtg     780
tggacgccct ccttacccte ttaagtagta gtagagatat aatccgttcc aaaatatcca     840
tccgttcaat ttatatttcg tttgatcttt ttaccctaaa tttgattgac tcatcttatt     900
aaaaaagttc ataactatta ttaatctttta ttgagatatc atttagcata taatatactt     960
taagtgtggt tttagatttt ttttaaaaaa aaaattcgc aaaaattaaa tgaaacgacc    1020
caatcaaact tgaaaagtaa aactaattat aaatttgaac ggaaggagta agaggatgtt    1080
tgaatgtact agagctaata gttggttgct ttaaaatttg ctagtagaat tagctagcta    1140
ataaatatct agataactat tagctaattt gctaaaacag ctaatagttg aactattagc    1200
tagattgttt ggatgtattc ggctaatttt aatggctaac tattagctat agtacaatat    1260
tcaaacacct cctaattaaa atggacaaat atctcttctt ttggtccctt gcgttagatt    1320
tttcatatct ccttatttag tataaaagaa tcatcaaaaa gtggacaacc cctagtggaa    1380
caccatttta gtagtggttg catgaaacct ttcgcgcacc agtttctatg tgtcactcta    1440
aaaatgggac agcatgtacg tagtgcctat atatatacaa gtcatctatc gttgcctcct    1500
cagttcatca ctaatcacac ttattgtgcc ctcgacgagt atctatagct agctcattaa    1560
tcgattcggg ggtgtgttgt cgaaggcgg attggcgagc tactcgtcgc ggcgtccaag    1620
caataccggt agcacgaagg cgatcgccgg gagcgtggtc ggcgagcccg tcgtgctggg    1680
gcagagggtg acggtgctga cggtggacgg cggcggcgtc cggggtctca tcccgggaac    1740
catcctcgcc ttcctggagg ccaggctgca ggagctggac gcaccggagg cgaggctggc    1800
```

| ggactacttc gactacatcg ccggaaccag caccggcggt ctcatcaccg ccttgctgac | 1860 |
| cgcgcccggc aaggacaagc ggcctctcta ggctgccaag gacatcaacc acttttacat | 1920 |
| ccataactgc ccgcgcatct ttcctcagaa gtgagtccga tgctgccgcc attgttcttg | 1980 |
| catccatcca gcatcgtacg tacgtcctct atacatctgc ggatcatcat gtgcgcatgt | 2040 |
| ttgtggcatg catgcatgca tgtgagcagg agcaggcttg cgaaaacc | 2088 |

<210> SEQ ID NO 59
<211> LENGTH: 1089
<212> TYPE: DNA
<213> ORGANISM: Artificial Sequence
<220> FEATURE:
<223> OTHER INFORMATION: Synthetic

<400> SEQUENCE: 59

| ttgcgatggc gcagatcacc aaaaagatgc ttgccaacaa ggacaaggcc gaggagctgt | 60 |
| acccagtgaa gccgtcgaac tgccgcaggt tcctggtgct gtccatcggg acggggtcga | 120 |
| cgtccgagca gggcctctac acggcgcggc agtgctcccg gtggggtatc tgccggtggc | 180 |
| tccgcgtcga ctcgggagca tgcccttttgt gcttatgcct ccgttctgcc ttctgacgaa | 240 |
| tttggtactg gaagcagatg agttttggtt cactatcatt ctgaatttac acctgcgctt | 300 |
| gctgtcagac taggcaacca agtgactttt gtgactttga tcatgttcag tgtgtttcca | 360 |
| agtcctaatc aatcaaaaag aaaaacagtt tgttaacgat tgtttgccat gtctatataa | 420 |
| taaagttgct tttatagtag cttagaattc aatcggccaa ctttatctcg tacgctgaca | 480 |
| gtaaaggtac atttaaaagg tgacaatgga tagtctaata cttgaactga caatagagac | 540 |
| acattacatg tcagttgatt aagtttgtaa cagaaaaata aacaatacta cataattgca | 600 |
| aagtttcttt gatgtctttc tttcaagaaa cacaaatata tcaatgctac agtattgctg | 660 |
| atgaatttat ccatgttgag atgttttttct ggtttctgat ctgatcagtc tcaattggtg | 720 |
| tgctgtttca ttttcatttg ctgatgatcg tccgagtagt taattcttac taatatttag | 780 |
| ataatttggc atacaagcga atcacgtaga acatgatact tttgaatgaa tttatcaaag | 840 |
| ttttatcact tggtgagttg tttcatggtt ttcctactga tgtctcttct tcagatttct | 900 |
| cgaggcggag ccaccggcag atacccccacc gggagcactg ccgcgccgtg tagaggccct | 960 |
| gctcggacgt cgacccccgtc ccgatggaca gcaccaggaa cctgcggcag ttcgacggct | 1020 |
| tcactgggta cagctcctcg gccttgtcct tgctggcaag catcttttttg gtgatctgcg | 1080 |
| tcatcgcaa | 1089 |

<210> SEQ ID NO 60
<211> LENGTH: 915
<212> TYPE: DNA
<213> ORGANISM: Artificial Sequence
<220> FEATURE:
<223> OTHER INFORMATION: Synthetic

<400> SEQUENCE: 60

| gaacaggctt gcggccgccg tgtccgcgct gaggaagcca agtacaacg gcaagtgcat | 60 |
| gcgcagcctg attaggagca tcctcggcga gacgaggggt cgactcggga gcatgcccctt | 120 |
| tgtgcttatg cctccgttct gccttctgac gaatttggta ctggaagcag atgagttttg | 180 |
| gttcactatc attctgaatt tacacctgcg cttgctgtca gactaggcaa ccaagtgact | 240 |
| tttgtgactt tgatcatgtt cagtgtgttt ccaagtccta atcaatcaaa agaaaaaca | 300 |
| gtttgttaac gattgtttgc catgtctata taataaagtt gcttttatag tagcttagaa | 360 |

```
ttcaatcggc caactttatc tcgtacgctg acagtaaagg tacatttaaa aggtgacaat      420
ggatagtcta atacttgaac tgacaataga dacacattac atgtcagttg attaagtttg      480
taacagaaaa ataaacaata ctacataatt gcaaagtttc tttgatgtct ttctttcaag      540
aaacacaaat atatcaatgc tacagtattg ctgatgaatt tatccatgtt gagatgtttt      600
tctggtttct gatctgatca gtctcaattg gtgtgctgtt tcattttcat ttgctgatga      660
tcgtccgagt agttaattct tactaatatt tagataattt ggcatacaag cgaatcacgt      720
agaacatgat acttttgaat gaatttatca agttttatc acttggtgag ttgtttcatg      780
gttttcctac tgatgtctct tcttcagatt tctcgagccc tcgtctcgcc gaggatgctc      840
ctaatcaggc tgcgcatgca cttgccgttg tactttggct tcctcagcgc ggacatggcg      900
gccgcaagcc tgctc                                                       915

<210> SEQ ID NO 61
<211> LENGTH: 1452
<212> TYPE: DNA
<213> ORGANISM: Zea mays

<400> SEQUENCE: 61
atatatattt ttatgtttta ttaaaataaa gtctacttat ttacaagcat gtgactgaca       60
gtaaagccac ttgtcttaga tatcgtacga cgcacatcta gagcctcttg ggttgatggc      120
agagacgcgg cgcgcgagcc ttgttctcct ctcctcggag agctgcctag cgagcccacc      180
gagggcatcg gcattgcttc cttcgccagt caccggttcg tacctcccctg tctccacgtt      240 gaccctggac accctctgtg ccagcatccg ctccccgatc ccgacgagcg tccgcatgtt      300
ctccggcgtc gccgcgtcca cggtggccgc ggcgccacgg agcgagttgt cctggatgcg      360
caggtagtcg ccgtcgctgt ggagcgactg gaacatcgcg gcgacgtgga tgtccaccag      420
gtccgagctg gccgccatga agatgtcgat gatgggggcc atgccgttgt tgcggagcca      480
ccggcagata ccccaccggg agcactgccg cgccgtgtag aggccctgct cggacgtcga      540
ccccgtcccg atggacagca ccaggaacct gcggcagttc gacggcttca ctgggtacag      600
ctcctcggcc ttgtccttgc tggcaagcat ctttttggtg atctgcgtca tcgcaaccat      660
cgtcgggttg ttggccgcca caccgccgtc gatgaggttg tattcgcgct ccttgccgtt      720
ggcgtcttca gtctggaagt agtgcgccgg gaggtaggtc ggcgcggcgg acgtgccaat      780
gcacacgtcc gagagcagag cgttcttcag aggcgtgctc ttggcgtcgt aggtagagaa      840
gatgataggc tgcagcagcc tgatgtcgaa ggcagggatg atgacgttgg tcagcgtctc      900
gcttaccctc gtctcgccga ggatgctcct aatcaggctg cgcatgcact gccgttgta       960 ctttggcttc ctcagcgcgg acatggcggc cgcaagcctg ctcttctgag gaaagatgcg     1020
cgggcagttc tgcatgtaaa agtggttgat gtccttggca gcgtagagag gccgcttgtc     1080
cttgccgggc gcggtgagca tggcggtgat gagaccgccg gtgctggttc cggcgatgta     1140
gtcgaagtag tccgccagcc tcgcctccgg tccgtccagc cctgcagcc tggcctccag      1200 gaaggcgagg atggttcccg ggatgagacc ccggacgccg ccgccgtcca ccgtcagcac     1260
cgtcaccctc tgccccagca cgacgggctc gccgaccacg ctcccggcca tcgccttcgt     1320
gctacaggta ttgcatggac gccgcgacga gtagctcgcc attgccgcct tcgacaacac     1380 accccgaat cgattaatga gctagctata gatactcgtc gagggcacaa taagtgtgat      1440
tagtgatgaa ct                                                         1452
```

<210> SEQ ID NO 62
<211> LENGTH: 1382
<212> TYPE: DNA
<213> ORGANISM: Zea mays

<400> SEQUENCE: 62

```
tcagaatata tatatattta tattttatta aaataaagtc tacttattta caagcatgtg      60
attgacagta aagccacttg tcttagatat cgtagggcgc acatctagag cttctggggt     120
tgatggcaga gacgcggcgc gcgagccttg ttctcctctc ctcggagagc tgcctagcga     180
gcccaccgag ggcatcggca ttgcttcctt ctccggtcac cggttcgtac ctcgctccct     240
gtctccacgt tgaccctgga cacccgctgt gccagcatcc gctccccgat cccgacgagc     300
gtccgcatgt tctccggcgt cgccgcgtcc acggttgccg cggcgccacg gagcgagttg     360
tcctggatgc gtaggtagtc gccgtcgctg tggagcgact ggaacatcgc ggcgacgtgg     420
atgtccacca ggtccgagct ggccgccatg aagatgtcga tgatggggc catgccgttg      480
ttgcggagcc accggcagat gccccaccgg gagcactgcc gcgccgtgta gaggccctgc     540
tcggacgtcg accccgtccc gatggacagc accaggaacc tgcggcagtt cgacgggttc     600
actgggtaca gctcctcggc cttgtccttg ctggcaagca tcttttttggt gatctgcgtc     660
atcgcaacca tcgtcgggtt gttggccgcc acaccgccgt cgatgaggtt gtattcgcgc     720
tccttgccgt tggcgtcttc agtctggaag tagtgcgccg ggaggtaggt cggcgcggcg     780
gacgtgccaa tgcacacgtc cgagagcagc gcgttcttca gaggcgtgct cttggccctc     840
gtctcgccga ggatgctcct aatcaggctg cgcatgcact gccgttgta ctttggcttc      900
ctcagcgcgg acatggcggc cgcaagcctg ctcttctgag ggaagatgcg cgggcagttc     960
tccatgtaaa agtagttgat gtccttggca gcgtagagag gccgcttgtc cttgccgggc    1020
gcggtgagca tggcggtgat gagaccgccg gtgctggttc cggcgatgta gtcgaagtag    1080
tccgccagcc tcgcctccgg tccgtccagc tcctgcagcc tggcctccag gaaggcgagg    1140
atggttcccg ggatgagacc ccggacgccg ccgccgtcca ccgtcagcac cgtcaccctc    1200
tgccccagca cgacgggctc gccgaccacg ctccccgcca tcgccttcgt gctacaggta    1260
ttgcatggac gccgcgacga gtagctcgcc attgccgcct tcgaccgcac acccccgattg   1320
atcgattaat gagctagcta gatactcgtc gagggcacaa taagtgtgat tagtgatgaa    1380
ct                                                                  1382
```

<210> SEQ ID NO 63
<211> LENGTH: 19
<212> TYPE: DNA
<213> ORGANISM: Zea mays

<400> SEQUENCE: 63

```
tacgccgtgc gctaacata                                                  19
```

<210> SEQ ID NO 64
<211> LENGTH: 20
<212> TYPE: DNA
<213> ORGANISM: Zea mays

<400> SEQUENCE: 64

```
gtacctcgct ccctgtctcc                                                 20
```

<210> SEQ ID NO 65
<211> LENGTH: 18

```
<212> TYPE: DNA
<213> ORGANISM: Zea mays

<400> SEQUENCE: 65
gtacgccgtg cgctaaca                                          18

<210> SEQ ID NO 66
<211> LENGTH: 20
<212> TYPE: DNA
<213> ORGANISM: Zea mays

<400> SEQUENCE: 66
tcgtacctcc ctgtctccac                                        20
```